US009205253B2

(12) United States Patent
Olsen et al.

(10) Patent No.: US 9,205,253 B2
(45) Date of Patent: Dec. 8, 2015

(54) SHIELDING AN IMPLANTABLE MEDICAL LEAD

(75) Inventors: James M. Olsen, Plymouth, MN (US); Michael R. Klardie, Plymouth, MN (US); Richard T. Stone, Minneapolis, MN (US); Chad Q. Cai, Woodbury, MN (US); Spencer M. Bondhus, Columbia Heights, MN (US); Mark J. Conroy, St. Louis Park, MN (US); Timothy R. Abraham, Lino Lakes, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 143 days.

(21) Appl. No.: 13/264,067

(22) PCT Filed: Apr. 27, 2010

(86) PCT No.: PCT/US2010/032543

§ 371 (c)(1), (2), (4) Date: Oct. 12, 2011

(87) PCT Pub. No.: WO2010/126877

PCT Pub. Date: Nov. 4, 2010

(65) Prior Publication Data

US 2012/0046722 A1 Feb. 23, 2012

Related U.S. Application Data

(60) Provisional application No. 61/174,204, filed on Apr. 30, 2009, provisional application No. 61/174,216, (Continued)

(51) Int. Cl.
*A61N 1/05* (2006.01)
*A61N 1/08* (2006.01)
(Continued)

(52) U.S. Cl.
CPC ............. *A61N 1/08* (2013.01); *A61M 25/0152* (2013.01); *A61N 1/05* (2013.01); *A61N 1/056* (2013.01);
(Continued)

(58) Field of Classification Search
CPC ....... A61N 1/056; A61N 1/05; A61N 1/3718; A61N 1/3752; A61N 1/08; A61N 1/0152; A61N 1/0551; A61N 1/49227; A61N 1/4921; A61N 1/49117; A61N 1/49826; A61N 1/54
USPC .................................................. 607/116–118
See application file for complete search history.

(56) References Cited

U.S. PATENT DOCUMENTS

| | | | |
|---|---|---|---|
| 2,433,480 | A | 12/1947 | Rendich |
| 2,487,038 | A | 11/1949 | Jasper |

(Continued)

FOREIGN PATENT DOCUMENTS

| | | |
|---|---|---|
| EP | 0617978 | 10/1994 |
| EP | 0624383 | 11/1994 |

(Continued)

OTHER PUBLICATIONS

Baker et al., "Evaluation of Specific Absorption Rates as a Dosimeter of MRI-Related Implant Heating", Journal of Magnetic Resonance Imaging 20:315-320 (2004).

(Continued)

*Primary Examiner* — Amanda Patton
(74) *Attorney, Agent, or Firm* — Withers & Keys, LLC

(57) ABSTRACT

Implantable medical leads are shielded with a braided shield that surrounds an inner layer of insulation. An outer layer of insulation may also surround the shield. The shield is designed with parameters that limit the passage of radio frequency energy, particularly in the magnetic resonance imaging spectrum, to filars that are surrounded by the inner layer of insulation. The braided shield has a plurality of parameters and corresponding ranges. The parameters include one or more of braid angle, wire size, number of wires wound per direction, number of wires in a bundle, wire spacing in an axial dimension, ultimate tensile strength, cross-sectional wire shape, material, and distance from termination to a nearest electrode. Additional parameters of the lead related to the shielding also include one or more of inner insulation thickness, and outer insulation thickness.

60 Claims, 83 Drawing Sheets

Related U.S. Application Data filed on Apr. 30, 2009, provisional application No. 61/174,224, filed on Apr. 30, 2009, provisional application No. 61/174,234, filed on Apr. 30, 2009, provisional application No. 61/174,247, filed on Apr. 30, 2009, provisional application No. 61/174,254, filed on Apr. 30, 2009, provisional application No. 61/174,262, filed on Apr. 30, 2009, provisional application No. 61/174,276, filed on Apr. 30, 2009, provisional application No. 61/174,287, filed on Apr. 30, 2009, provisional application No. 61/174,296, filed on Apr. 30, 2009.

(51) Int. Cl.

*A61N 1/37* (2006.01)
*A61N 1/375* (2006.01)
*A61M 25/01* (2006.01)
*A61B 19/00* (2006.01)

(52) U.S. Cl.

CPC ............ *A61N 1/0551* (2013.01); *A61N 1/3718* (2013.01); *A61N 1/3752* (2013.01); *A61B 19/54* (2013.01); *A61N 2001/058* (2013.01); *A61N 2001/0582* (2013.01); *A61N 2001/086* (2013.01); *Y10T 29/4921* (2015.01); *Y10T 29/49117* (2015.01); *Y10T 29/49227* (2015.01); *Y10T 29/49826* (2015.01)

(56) References Cited

U.S. PATENT DOCUMENTS 3,788,329 A 1/1974 Friedman
3,842,485 A 10/1974 Bement
3,915,174 A 10/1975 Preston
4,033,355 A 7/1977 Amundson
4,038,990 A 8/1977 Thompson
4,214,804 A 7/1980 Little
4,220,813 A 9/1980 Kyle
4,280,507 A 7/1981 Rosenberg
4,320,763 A 3/1982 Money
4,350,169 A 9/1982 Dutcher
4,383,225 A 5/1983 Mayer
4,403,824 A 9/1983 Scott
4,441,498 A 4/1984 Nordling
4,628,942 A 12/1986 Sweeney et al.
4,683,895 A 8/1987 Pohndorf
4,711,027 A 12/1987 Harris
4,726,379 A 2/1988 Altman et al.
4,852,585 A 8/1989 Heath
4,906,241 A 3/1990 Noddin et al.
4,920,980 A 5/1990 Jackowski
4,922,607 A 5/1990 Doan et al.
4,934,380 A 6/1990 De Toledo
4,947,866 A 8/1990 Lessar et al.
4,951,672 A 8/1990 Buchwald et al.
4,991,583 A 2/1991 Silvian
5,003,992 A 4/1991 Holleman
5,005,587 A * 4/1991 Scott ............................ 607/122
5,012,045 A 4/1991 Sato
5,018,523 A 5/1991 Bach, Jr. et al.
5,020,544 A 6/1991 Dahl et al.
5,020,545 A 6/1991 Soukup
5,036,862 A 8/1991 Pohndorf
5,040,544 A 8/1991 Lessar et al.
5,063,932 A 11/1991 Dahl et al.
5,197,468 A 3/1993 Proctor et al.
5,213,111 A 5/1993 Cook et al.
5,217,010 A 6/1993 Tsitlik et al.
5,231,078 A 7/1993 Riebman et al.
5,243,996 A 9/1993 Hall
5,246,438 A 9/1993 Langberg
5,260,128 A 11/1993 Ishii et al.
5,265,608 A 11/1993 Lee et al.
5,265,623 A 11/1993 Kroll et al.
5,271,417 A 12/1993 Swanson et al.
5,308,664 A 5/1994 House et al.
5,314,459 A 5/1994 Swanson et al.
5,323,776 A 6/1994 Blakeley et al.
5,335,657 A 8/1994 Terry, Jr. et al.
5,349,133 A 9/1994 Rogers
5,360,441 A 11/1994 Otten
5,366,496 A 11/1994 Dahl et al.
5,370,644 A 12/1994 Langberg
5,374,286 A 12/1994 Morris
5,374,778 A 12/1994 Hashimoto et al.
5,417,719 A 5/1995 Hull et al.
5,456,705 A 10/1995 Morris
5,458,629 A 10/1995 Baudino et al.
5,458,631 A * 10/1995 Xavier ......................... 607/117
5,466,252 A 11/1995 Soukup et al.
5,473,812 A 12/1995 Morris et al.
5,476,496 A 12/1995 Strandberg et al.
5,485,667 A 1/1996 Kleshinski
5,500,013 A 3/1996 Buscemi et al.
5,504,274 A 4/1996 McCabe et al.
5,514,172 A 5/1996 Mueller
5,515,848 A 5/1996 Corbett, III et al.
5,523,534 A 6/1996 Meister et al.
5,523,578 A 6/1996 Herskovic
5,527,348 A 6/1996 Winkler et al.
5,534,018 A 7/1996 Wahlstrand et al.
5,552,565 A 9/1996 Cartier et al.
5,571,157 A 11/1996 McConnell
5,572,594 A 11/1996 DeVoe et al.
5,591,218 A 1/1997 Jacobson
5,594,304 A 1/1997 Graber
5,606,981 A 3/1997 Tartacower et al.
5,609,622 A 3/1997 Soukup et al.
5,628,780 A 5/1997 Helland et al.
5,629,622 A 5/1997 Scampini
5,643,254 A 7/1997 Scheldrup et al.
5,649,965 A 7/1997 Pons et al.
5,662,697 A 9/1997 Li et al.
5,676,659 A 10/1997 McGurk
5,676,694 A 10/1997 Boser et al.
5,683,435 A 11/1997 Truex et al.
5,683,444 A 11/1997 Huntley et al.
5,697,909 A 12/1997 Eggers et al.
5,697,958 A 12/1997 Paul et al.
5,702,437 A 12/1997 Baudino
5,706,826 A 1/1998 Schwager
5,722,998 A 3/1998 Prutchi et al.
5,727,552 A 3/1998 Ryan
5,751,539 A 5/1998 Stevenson et al.
5,766,232 A 6/1998 Grevious et al.
5,782,241 A 7/1998 Felblinger et al.
5,795,341 A 8/1998 Samson
5,807,258 A 9/1998 Cimochowski et al.
5,814,076 A 9/1998 Brownlee
5,827,997 A 10/1998 Chung et al.
5,830,136 A 11/1998 Delonzor et al.
5,842,966 A 12/1998 Markoll
5,842,986 A 12/1998 Avrin et al.
5,851,226 A 12/1998 Skubitz et al.
5,897,584 A 4/1999 Herman
5,905,627 A 5/1999 Brendel et al.
5,927,345 A 7/1999 Samson
5,931,861 A 8/1999 Werner et al.
5,954,760 A 9/1999 Jarl
5,964,705 A 10/1999 Truwit et al.
5,968,087 A 10/1999 Hess et al.
5,970,429 A 10/1999 Martin
6,004,269 A 12/1999 Crowley
6,016,447 A 1/2000 Juran et al.
6,024,703 A 2/2000 Zanelli et al.
6,032,063 A 2/2000 Hoar et al.
6,033,408 A 3/2000 Gage et al.
6,055,457 A 4/2000 Bonner
6,101,417 A 8/2000 Vogel et al.
6,103,037 A 8/2000 Wilson
6,108,582 A 8/2000 Fischer, Sr.
6,132,390 A 10/2000 Cookston et al.

(56) References Cited

U.S. PATENT DOCUMENTS 6,141,593 A 10/2000 Patag
6,143,013 A * 11/2000 Samson et al. ................ 606/192
6,152,746 A 11/2000 Brown
6,156,029 A 12/2000 Mueller
6,195,267 B1 2/2001 MacDonald et al.
6,198,807 B1 3/2001 DeSena
6,198,972 B1 3/2001 Hartlaub et al.
6,209,764 B1 4/2001 Hartlaub et al.
6,240,322 B1 5/2001 Peterfeso
6,258,071 B1 7/2001 Brookes
6,265,466 B1 7/2001 Glatkowski et al.
6,269,148 B1 7/2001 Jessop et al.
6,284,971 B1 9/2001 Atalar et al.
6,302,740 B1 10/2001 Holmstrom
6,348,070 B1 2/2002 Teissl et al.
6,424,234 B1 7/2002 Stevenson
6,471,699 B1 10/2002 Fleischman et al.
6,488,704 B1 12/2002 Connelly et al.
6,494,916 B1 12/2002 Babalola et al.
6,501,991 B1 12/2002 Honeck et al.
6,503,648 B1 1/2003 Wang
6,506,972 B1 1/2003 Wang
6,529,774 B1 3/2003 Greene
6,538,191 B1 3/2003 MacDonald
6,583,361 B2 6/2003 Clouet
6,606,521 B2 8/2003 Paspa et al.
6,640,137 B2 10/2003 MacDonald
6,648,690 B2 11/2003 Saito et al.
6,660,116 B2 12/2003 Wolf et al.
6,671,544 B2 12/2003 Baudino
6,671,554 B2 12/2003 Gibson et al.
6,673,999 B1 1/2004 Wang et al.
6,675,033 B1 1/2004 Lardo et al.
6,689,835 B2 2/2004 Amarasekera et al.
6,695,761 B2 2/2004 Oschman et al.
6,708,051 B1 3/2004 Durousseau
6,711,440 B2 3/2004 Deal et al.
6,712,844 B2 3/2004 Pacetti et al.
6,713,671 B1 3/2004 Wang et al.
6,718,203 B2 4/2004 Weiner et al.
6,718,207 B2 4/2004 Connelly
6,725,092 B2 4/2004 MacDonald et al.
6,735,471 B2 5/2004 Hill et al.
6,741,892 B1 5/2004 Meadows et al.
6,743,055 B1 6/2004 Flynn
6,750,055 B1 6/2004 Connelly et al.
6,757,566 B2 6/2004 Weiner et al.
6,760,628 B2 7/2004 Weiner et al.
6,763,268 B2 7/2004 MacDonald et al.
6,765,144 B1 7/2004 Wang et al.
6,768,053 B1 7/2004 Wang et al.
6,778,856 B2 8/2004 Connelly et al.
6,792,316 B2 9/2004 Sass
6,793,642 B2 9/2004 Connelly et al.
6,795,730 B2 9/2004 Connelly et al.
6,795,736 B2 9/2004 Connelly et al.
6,799,067 B2 9/2004 Pacetti
6,799,069 B2 9/2004 Weiner et al.
6,815,609 B1 11/2004 Wang et al.
6,819,954 B2 11/2004 Connelly
6,819,958 B2 11/2004 Weiner et al.
6,844,492 B1 1/2005 Wang et al.
6,845,259 B2 1/2005 Pacetti et al.
6,845,267 B2 1/2005 Harrison et al.
6,846,985 B2 1/2005 Wang et al.
6,850,805 B2 2/2005 Connelly et al.
6,852,091 B2 2/2005 Edwards et al.
6,863,653 B1 3/2005 Zanelli et al.
6,864,418 B2 3/2005 Wang
6,869,683 B2 3/2005 Sakurai et al.
6,871,091 B2 3/2005 Wilkinson et al.
6,872,882 B2 3/2005 Fritz
6,875,180 B2 4/2005 Weiner et al.
6,879,861 B2 4/2005 Benz et al.
6,882,519 B2 4/2005 Uzawa et al.
6,895,280 B2 5/2005 Meadows et al.
6,901,287 B2 5/2005 Davis et al.
6,901,290 B2 5/2005 Foster et al.
6,906,256 B1 6/2005 Wang
6,920,361 B2 7/2005 Williams
6,922,590 B1 7/2005 Whitehurst
6,925,328 B2 8/2005 Foster
6,930,242 B1 8/2005 Helfer
6,937,906 B2 8/2005 Terry et al.
6,944,489 B2 9/2005 Zeijlemaker et al.
6,949,929 B2 9/2005 Gray et al.
6,954,674 B2 10/2005 Connelly
6,968,235 B2 11/2005 Belden et al.
6,968,236 B2 11/2005 Hagele
6,971,391 B1 12/2005 Wang et al.
6,980,865 B1 12/2005 Wang et al.
6,982,378 B2 1/2006 Dickson
6,985,775 B2 1/2006 Reinke et al.
6,993,387 B2 1/2006 Connelly et al.
6,999,818 B2 2/2006 Stevenson et al.
6,999,821 B2 2/2006 Jenney et al.
7,001,369 B2 2/2006 Griffin et al.
7,013,174 B2 3/2006 Connelly et al.
7,013,180 B2 3/2006 Villaseca et al.
7,015,392 B1 3/2006 Dickenson
7,015,393 B2 3/2006 Weiner
7,047,084 B2 5/2006 Erickson
7,050,855 B2 5/2006 Zeijlemaker et al.
7,058,192 B2 6/2006 Muller et al.
7,076,283 B2 7/2006 Cho et al.
7,076,302 B2 7/2006 Scheiner
7,082,328 B2 7/2006 Funke
7,082,337 B2 7/2006 Sommer et al.
7,103,413 B2 9/2006 Swanson
7,113,827 B2 9/2006 Silvestri
7,115,134 B2 10/2006 Chambers
7,118,693 B2 10/2006 Glatkowski et al.
7,123,013 B2 10/2006 Gray
7,125,409 B2 10/2006 Truckai et al.
7,162,302 B2 1/2007 Wang et al.
7,174,219 B2 2/2007 Wahlstrand et al.
7,187,980 B2 3/2007 Osypka et al.
7,233,825 B2 6/2007 Jorgenson et al.
7,257,449 B2 8/2007 Bodner
7,282,260 B2 10/2007 LeGrande et al.
7,286,871 B2 10/2007 Cohen
7,286,882 B2 10/2007 Cole
7,292,894 B2 11/2007 Belden
7,294,785 B2 11/2007 Uutela et al.
7,319,901 B2 1/2008 Dublin et al.
7,363,090 B2 4/2008 Halperin
7,389,148 B1 6/2008 Morgan
7,540,865 B2 6/2009 Griffin et al.
7,548,788 B2 6/2009 Chinn et al.
7,591,831 B2 9/2009 Parsonage et al.
7,674,972 B2 3/2010 Gladd et al.
7,711,436 B2 5/2010 Stone
7,729,777 B2 6/2010 Gray et al.
7,738,942 B2 6/2010 Weiner
7,813,811 B2 10/2010 Wingeier et al.
7,819,826 B2 10/2010 Diederich et al.
7,822,484 B1 10/2010 Zhao et al.
7,828,833 B2 11/2010 Haverkost
7,844,343 B2 11/2010 Wahlstrand
7,844,344 B2 11/2010 Wahlstrand
7,853,332 B2 12/2010 Olsen
7,877,150 B2 1/2011 Hoegh et al.
7,904,178 B2 3/2011 Williams
7,917,213 B2 3/2011 Bulkes
7,933,652 B2 4/2011 Phillips
8,007,440 B2 8/2011 Magnin et al.
8,027,736 B2 9/2011 Wahlstrand
8,036,756 B2 10/2011 Swoyer et al.
8,048,060 B2 11/2011 Griffin et al.
8,055,351 B2 11/2011 Atalar et al.
8,106,657 B2 1/2012 Sakellariou et al.
8,170,691 B2 5/2012 Eckerdal
8,202,259 B2 6/2012 Evans et al.
8,246,643 B2 8/2012 Nita

(56) References Cited

U.S. PATENT DOCUMENTS

| | | | |
|---|---|---|---|
| 8,275,464 | B2 | 9/2012 | Li et al. |
| 8,280,526 | B2 | 10/2012 | Wahlstrand |
| 8,483,842 | B2 | 7/2013 | Alexander et al. |
| 8,620,455 | B2 | 12/2013 | Alexander et al. |
| 8,676,340 | B2 | 3/2014 | Wahlstrand |
| 8,744,598 | B2 | 6/2014 | Alexander et al. |
| 8,788,061 | B2 | 7/2014 | Mehdizadeh |
| 8,805,534 | B2 | 8/2014 | Olsen |
| 8,903,504 | B2 | 12/2014 | Hegland |
| 9,002,474 | B2 | 4/2015 | Olsen |
| 9,037,263 | B2 | 5/2015 | Marshall |
| 9,044,593 | B2 | 6/2015 | Li |
| 2001/0044646 | A1 | 11/2001 | Marshall et al. |
| 2002/0032468 | A1 | 3/2002 | Hill |
| 2002/0038135 | A1 | 3/2002 | Connelly et al. |
| 2002/0058978 | A1 | 5/2002 | Sass |
| 2002/0082673 | A1 | 6/2002 | Benz et al. |
| 2002/0106918 | A1 | 8/2002 | Saito et al. |
| 2002/0111659 | A1 | 8/2002 | Davis et al. |
| 2002/0111663 | A1 | 8/2002 | Dahl et al. |
| 2002/0116028 | A1 | 8/2002 | Greatbatch et al. |
| 2002/0116029 | A1 | 8/2002 | Miller et al. |
| 2002/0116033 | A1 | 8/2002 | Greatbatch et al. |
| 2002/0116034 | A1 | 8/2002 | Miller et al. |
| 2002/0128689 | A1 | 9/2002 | Connelly et al. |
| 2002/0128691 | A1 | 9/2002 | Connelly |
| 2002/0133086 | A1 | 9/2002 | Connelly et al. |
| 2002/0133199 | A1 | 9/2002 | MacDonald et al. |
| 2002/0133200 | A1 | 9/2002 | Weiner et al. |
| 2002/0133201 | A1 | 9/2002 | Connelly et al. |
| 2002/0133202 | A1 | 9/2002 | Connelly et al. |
| 2002/0133208 | A1 | 9/2002 | Connelly |
| 2002/0133211 | A1 | 9/2002 | Weiner et al. |
| 2002/0133216 | A1 | 9/2002 | Connelly et al. |
| 2002/0138102 | A1 | 9/2002 | Weiner et al. |
| 2002/0138107 | A1 | 9/2002 | Weiner et al. |
| 2002/0138108 | A1 | 9/2002 | Weiner et al. |
| 2002/0138110 | A1 | 9/2002 | Connelly et al. |
| 2002/0138112 | A1 | 9/2002 | Connelly et al. |
| 2002/0143377 | A1 | 10/2002 | Wessman et al. |
| 2002/0183438 | A1 | 12/2002 | Amarasekera et al. |
| 2002/0183740 | A1 | 12/2002 | Edwards et al. |
| 2002/0183822 | A1 | 12/2002 | Bodner |
| 2002/0188345 | A1 | 12/2002 | Pacetti |
| 2003/0009207 | A1 | 1/2003 | Paspa et al. |
| 2003/0014080 | A1 | 1/2003 | Baudino |
| 2003/0036776 | A1 | 2/2003 | Foster et al. |
| 2003/0044623 | A1 | 3/2003 | Sakurai et al. |
| 2003/0045920 | A1 | 3/2003 | Belden et al. |
| 2003/0060732 | A1 | 3/2003 | Jacobsen et al. |
| 2003/0083570 | A1 | 5/2003 | Cho et al. |
| 2003/0083723 | A1 | 5/2003 | Wilkinson et al. |
| 2003/0083726 | A1 | 5/2003 | Zeijlemaker et al. |
| 2003/0093107 | A1 | 5/2003 | Parsonage et al. |
| 2003/0109901 | A1 | 6/2003 | Greatbatch |
| 2003/0117787 | A1 | 6/2003 | Nakauchi |
| 2003/0120148 | A1 | 6/2003 | Pacetti |
| 2003/0120197 | A1 | 6/2003 | Kaneko et al. |
| 2003/0135114 | A1 | 7/2003 | Pacetti et al. |
| 2003/0139794 | A1 | 7/2003 | Jenney et al. |
| 2003/0139806 | A1 | 7/2003 | Haverkost et al. |
| 2003/0140931 | A1 | 7/2003 | Zeijlemaker |
| 2003/0144704 | A1 | 7/2003 | Terry |
| 2003/0144705 | A1 | 7/2003 | Funke |
| 2003/0144716 | A1 | 7/2003 | Reinke et al. |
| 2003/0144717 | A1 | 7/2003 | Hagele |
| 2003/0144718 | A1 | 7/2003 | Zeijlemaker |
| 2003/0144719 | A1 | 7/2003 | Zeijlemaker |
| 2003/0144720 | A1 | 7/2003 | Villaseca et al. |
| 2003/0144721 | A1 | 7/2003 | Villaseca et al. |
| 2003/0167052 | A1 | 9/2003 | Lee et al. |
| 2003/0204217 | A1 | 10/2003 | Greatbatch |
| 2003/0225331 | A1 | 12/2003 | Diederich et al. |
| 2004/0020674 | A1 | 2/2004 | McFadden et al. |
| 2004/0024442 | A1 | 2/2004 | Sowinski et al. |
| 2004/0028859 | A1 | 2/2004 | LeGrande et al. |
| 2004/0068307 | A1 | 4/2004 | Goble |
| 2004/0071949 | A1 | 4/2004 | Glatkowski et al. |
| 2004/0088012 | A1 | 5/2004 | Kroll et al. |
| 2004/0106958 | A1 | 6/2004 | Mathis et al. |
| 2004/0162600 | A1 | 8/2004 | Williams |
| 2004/0167443 | A1 | 8/2004 | Shireman et al. |
| 2004/0173368 | A1 | 9/2004 | Dickson |
| 2004/0199069 | A1 | 10/2004 | Connelly et al. |
| 2004/0220549 | A1 | 11/2004 | Dittman et al. |
| 2004/0249428 | A1 | 12/2004 | Wang et al. |
| 2004/0251042 | A1 | 12/2004 | Weiner et al. |
| 2004/0263172 | A1 | 12/2004 | Gray et al. |
| 2004/0263173 | A1 | 12/2004 | Gray |
| 2004/0263174 | A1 | 12/2004 | Gray et al. |
| 2004/0267328 | A1 | 12/2004 | Duffin |
| 2005/0065587 | A1 | 3/2005 | Gryzwa |
| 2005/0070972 | A1 | 3/2005 | Wahlstrand |
| 2005/0080471 | A1 | 4/2005 | Chitre et al. |
| 2005/0113876 | A1 | 5/2005 | Weiner |
| 2005/0115624 | A1 | 6/2005 | Walak |
| 2005/0137664 | A1 | 6/2005 | Sommer et al. |
| 2005/0145307 | A1 | 7/2005 | Shireman et al. |
| 2005/0159661 | A1 | 7/2005 | Connelly et al. |
| 2005/0182471 | A1 | 8/2005 | Wang |
| 2005/0222642 | A1 | 10/2005 | Przybyszewski |
| 2005/0222647 | A1 | 10/2005 | Wahlstrand |
| 2005/0222656 | A1 | 10/2005 | Wahlstrand |
| 2005/0222657 | A1 | 10/2005 | Wahlstrand |
| 2005/0222658 | A1 | 10/2005 | Hoegh et al. |
| 2005/0222659 | A1 | 10/2005 | Olsen |
| 2006/0030918 | A1 | 2/2006 | Chinn et al. |
| 2006/0036306 | A1 | 2/2006 | Heist et al. |
| 2006/0079926 | A1 | 4/2006 | Desai et al. |
| 2006/0089680 | A1 | 4/2006 | Bruchmann et al. |
| 2006/0095078 | A1 | 5/2006 | Tronnes |
| 2006/0135962 | A1 | 6/2006 | Kick et al. |
| 2006/0155270 | A1 | 7/2006 | Hancock |
| 2006/0167522 | A1 | 7/2006 | Malinowski |
| 2006/0167527 | A1 | 7/2006 | Femano et al. |
| 2006/0200218 | A1 | 9/2006 | Wahlstrand |
| 2006/0224207 | A1 | 10/2006 | Dublin |
| 2006/0247747 | A1 | 11/2006 | Olsen et al. |
| 2006/0247748 | A1 | 11/2006 | Wahlstrand |
| 2007/0021811 | A1 | 1/2007 | D'Aquanni et al. |
| 2007/0106332 | A1 | 5/2007 | Denker |
| 2007/0123805 | A1 | 5/2007 | Shireman et al. |
| 2007/0129779 | A1 | 6/2007 | Ayre |
| 2007/0168008 | A1 | 7/2007 | Olsen |
| 2007/0185556 | A1 | 8/2007 | Williams |
| 2007/0208383 | A1 | 9/2007 | Williams |
| 2007/0293924 | A1 | 12/2007 | Belden et al. |
| 2008/0033497 | A1 | 2/2008 | Bulkes |
| 2008/0039709 | A1 | 2/2008 | Karmarkar |
| 2008/0058715 | A1 | 3/2008 | Houser et al. |
| 2008/0154326 | A1 | 6/2008 | Clyne |
| 2008/0183263 | A1 | 7/2008 | Alexander |
| 2008/0195186 | A1 | 8/2008 | Li |
| 2008/0195187 | A1 | 8/2008 | Li |
| 2008/0215008 | A1 | 9/2008 | Nance et al. |
| 2008/0242944 | A1 | 10/2008 | Sharma |
| 2008/0243081 | A1 | 10/2008 | Nance et al. |
| 2008/0243218 | A1 | 10/2008 | Bottomley |
| 2008/0262582 | A1 | 10/2008 | Alexander |
| 2008/0262584 | A1 | 10/2008 | Bottomley |
| 2008/0269863 | A1 | 10/2008 | Alexander |
| 2008/0287804 | A1 | 11/2008 | Nita |
| 2009/0204192 | A1 | 8/2009 | Carlton |
| 2009/0221970 | A1 | 9/2009 | Spinoza |
| 2009/0228074 | A1 | 9/2009 | Edgell et al. |
| 2009/0234402 | A1 | 9/2009 | Marshall |
| 2009/0240235 | A1 | 9/2009 | Murata |
| 2009/0259272 | A1 | 10/2009 | Reddy |
| 2009/0270956 | A1 | 10/2009 | Vase |
| 2009/0287189 | A1 | 11/2009 | Suwito |
| 2010/0069743 | A1 | 3/2010 | Sheetz et al. |
| 2010/0100164 | A1 | 4/2010 | Johnson et al. |
| 2010/0137957 | A1 | 6/2010 | Eckerdal |
| 2010/0145426 | A1 | 6/2010 | Stone |

(56) References Cited

U.S. PATENT DOCUMENTS

| | | | |
|---|---|---|---|
| 2010/0198327 | A1 | 8/2010 | Helland |
| 2010/0256528 | A1 | 10/2010 | Lippert et al. |
| 2010/0256604 | A1 | 10/2010 | Lippert et al. |
| 2010/0268310 | A1 | 10/2010 | Bonde et al. |
| 2010/0331938 | A1 | 12/2010 | Sommer |
| 2011/0015713 | A1 | 1/2011 | Min |
| 2011/0034983 | A1 | 2/2011 | Min |
| 2011/0071599 | A1 | 3/2011 | Olsen |
| 2011/0071604 | A1 | 3/2011 | Wahlstrand |
| 2011/0071605 | A1 | 3/2011 | Wahlstrand |
| 2011/0112615 | A1 | 5/2011 | Hoegh et al. |
| 2011/0230943 | A1 | 9/2011 | Johnson et al. |
| 2011/0251487 | A1 | 10/2011 | Magnin et al. |
| 2011/0319905 | A1 | 12/2011 | Palme et al. |
| 2012/0010689 | A1 | 1/2012 | Wahlstrand |
| 2012/0035616 | A1 | 2/2012 | Olsen et al. |
| 2012/0035694 | A1 | 2/2012 | Olsen |
| 2012/0035695 | A1 | 2/2012 | Olsen |
| 2012/0035696 | A1 | 2/2012 | Kern |
| 2012/0035697 | A1 | 2/2012 | Stone |
| 2012/0035951 | A1 | 2/2012 | Goetz |
| 2012/0041528 | A1 | 2/2012 | Mehdizadeh |
| 2012/0041529 | A1 | 2/2012 | Olsen |
| 2012/0046722 | A1 | 2/2012 | Olsen |
| 2012/0053664 | A1 | 3/2012 | Hegland |
| 2012/0059467 | A1 | 3/2012 | Drew |
| 2012/0130461 | A1 | 5/2012 | Olsen |
| 2012/0330383 | A1 | 12/2012 | Wahlstrand |
| 2013/0296991 | A1 | 11/2013 | Alexander et al. |
| 2014/0107746 | A1 | 4/2014 | Alexander et al. |
| 2014/0200643 | A1 | 7/2014 | Wahlstrand |
| 2014/0288626 | A1 | 9/2014 | Alexander et al. |
| 2014/0345132 | A1 | 11/2014 | Mehdizadeh et al. |
| 2014/0350654 | A1 | 11/2014 | Olsen et al. |
| 2015/0082618 | A1 | 3/2015 | Hegland |

FOREIGN PATENT DOCUMENTS

| | | |
|---|---|---|
| EP | 0713714 | 5/1996 |
| EP | 0760196 | 5/1997 |
| EP | 0920239 | 2/1999 |
| EP | 1273922 | 8/2003 |
| EP | 1424095 | 2/2004 |
| EP | 1466576 | 10/2004 |
| EP | 1625875 | 2/2006 |
| EP | 1632265 | 3/2006 |
| EP | 1632265 | 8/2006 |
| EP | 1935449 | 6/2008 |
| GB | 2429154 | 2/2007 |
| JP | 07/255863 | 10/1995 |
| JP | 11/086641 | 3/1999 |
| WO | WO95/32673 | 12/1995 |
| WO | WO96/16694 | 6/1996 |
| WO | WO96/28951 | 9/1996 |
| WO | WO97/41923 | 11/1997 |
| WO | WO98/48896 | 11/1998 |
| WO | WO99/10035 | 3/1999 |
| WO | WO99/19020 | 4/1999 |
| WO | WO99/60370 | 11/1999 |
| WO | WO00/27279 | 5/2000 |
| WO | WO01/80940 | 11/2001 |
| WO | WO02/00292 | 1/2002 |
| WO | WO02/083236 | 10/2002 |
| WO | WO03/037429 | 5/2003 |
| WO | WO03/061755 | 7/2003 |
| WO | WO03/063946 | 8/2003 |
| WO | WO03/063948 | 8/2003 |
| WO | WO03/063952 | 8/2003 |
| WO | WO03/063953 | 8/2003 |
| WO | WO03/063954 | 8/2003 |
| WO | WO03/063955 | 8/2003 |
| WO | WO03/063956 | 8/2003 |
| WO | WO03/063957 | 8/2003 |
| WO | WO03/075797 | 9/2003 |
| WO | WO03/092326 | 11/2003 |
| WO | WO03/095022 | 11/2003 |
| WO | WO2004/012809 | 2/2004 |
| WO | WO2004/052448 | 6/2004 |
| WO | WO2004/073040 | 8/2004 |
| WO | WO2005/030322 | 4/2005 |
| WO | WO2005/032654 | 4/2005 |
| WO | WO2005/102444 | 11/2005 |
| WO | WO2005/102445 | 11/2005 |
| WO | WO2005/102446 | 11/2005 |
| WO | WO2005/102447 | 11/2005 |
| WO | WO2006/031317 | 3/2006 |
| WO | WO2006/093685 | 9/2006 |
| WO | WO2006/093686 | 9/2006 |
| WO | WO2006/118640 | 11/2006 |
| WO | WO2006/118641 | 11/2006 |
| WO | WO2007/047966 | 4/2007 |
| WO | WO2007/124273 | 11/2007 |
| WO | WO2007/126657 | 11/2007 |
| WO | WO2007/149757 | 12/2007 |
| WO | WO2008/088568 | 7/2008 |
| WO | WO2008/100839 | 8/2008 |
| WO | WO2008/100840 | 8/2008 |
| WO | WO2008/111986 | 9/2008 |
| WO | WO2008/130409 | 10/2008 |
| WO | WO2008-134196 | 11/2008 |
| WO | WO2008/134196 | 11/2008 |
| WO | WO2008/140376 | 11/2008 |
| WO | WO2009/011440 | 9/2009 |
| WO | WO2009/134901 | 11/2009 |
| WO | WO2010/062988 | 6/2010 |
| WO | WO2010/126871 | 11/2010 |
| WO | WO2010/126877 | 11/2010 |
| WO | WO2010/126884 | 11/2010 |
| WO | WO2010/126887 | 11/2010 |
| WO | WO2010/126935 | 11/2010 |
| WO | WO2010/126939 | 11/2010 |
| WO | WO2010/126943 | 11/2010 |
| WO | WO2010/126946 | 11/2010 |
| WO | WO2010/126949 | 11/2010 |
| WO | WO2010/126975 | 11/2010 |
| WO | WO2010/135440 | 11/2010 |
| WO | WO2011/019416 | 2/2011 |
| WO | WO2012/103419 | 8/2012 |
| WO | WO2013/158189 | 10/2013 |

OTHER PUBLICATIONS

Baker, K., et al., "Neurostimulation Systems: Assessment of Magnetic Field Interactions Associated with 1.5 and 3-Tesla MR Systems", J. Magn. Reson. Imaging, Jan. 2005, 21(1);72-7.

Chung, D.D.L., "Carbon Fiber Composites", 1994, chapter 1, p. 8, table 1.2, Elsevier, ISBN: 978-0-7506-9169-7.

Chung, D.D.L., Comparison of Submicron-Diameter Carbon Filaments and Conventional Carbon Fibers as Fillers in Composite Materials, Carbon 39 (2001) pp. 1119-1125, Elsevier Science Ltd.

Chung, D.D.L., Electromagnetic Interference Shielding Effectiveness of Carbon Materials, Carbon 29 (2001) pp. 279-285, Elsevier Science Ltd.

Finelli, D., et al., "MRI Imaging-Related Heating of Deep Brain Stimulation Electrodes: In Vitro Study", AJNR Am. J. Neuroadiol 23:1, Nov./Dec. 2002.

Jou, W.S. "A Novel Structure of Woven Continuous-Carbon Fiber Composites with High Electromagnetic Shielding", Journal of Electronic Materials, vol. 33, No. 3, Mar. 1, 2004, pp. 162-170(9), Minerals, Metals and Materials Society, http://findarticles.com/p/articles/mi_qu3776/is_200403/ai_n9405_582/print.

Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.

Kolin, et al., "An Electromagnetic Intravascular Blood-Flow Sensor", Department of Biophysics, University of California School of Medicine (Los Angeles), Mar. 20, 1967, Proc. N.A.S., vol. 57, pp. 1331-1337.

(56) References Cited

OTHER PUBLICATIONS

Kolin, et al., "Miniaturization of the Electromagnetic Blood Flow Meter and Its Use for the Recording of Circulatory Responses of Conscious Animals to Sensory Stimuli", Department of Biophysics, University of California at Los Angeles, Aug. 1959, Proc. N.A.S. vol. 45(8), pp. 1312-1321.
Medtronic Activa Product Family and Procedure Solution Brochure.
Medtronic Neurostimulation Systems Brochure.
Quick et al., "Endourethral MRI", Magnetic Resonance in Medicine, 45:138-146, 2001.
Rezai, A., et al., "Neurostimulation System Used for Deep Brain Stimulation (DBS): MR Safety Issues and Implications of Failing to Follow Safety Recommendations" Investigative Radiology, May 2004, vol. 39, Issue 5, pp. 300-303.
Rezai, A., et al., "Neurostimulation Systems for Deep Brain Stimulation In Vitro Evaluation of Magnetic Resonance Imaging-Related Healing at 1.5 Tesla", Journal of Magnetic Reson. Imaging 2002; 15:241-50.
PCT/US2004/042081: Search Report and Written Opinion.
PCT/US2005/000322: Search Report and Written Opinion.
PCT/US2008/053540: Search Report and Written Opinion.
PCT/US2008/053541: Search Report and Written Opinion.
PCT/US2008/059358: Search Report and Written Opinion.
PCT/US2009/036461: Search Report and Written Opinion.
PCT/US2010/032516: Search Report and Written Opinion.
PCT/US2010/032526: Search Report and Written Opinion.
PCT/US2010/032543: Search Report and Written Opinion.
PCT/US2010/032560: Search Report and Written Opinion.
PCT/US2010/032567: Search Report and Written Opinion.
PCT/US2010/032666: Search Report and Written Opinion.
PCT/US2010/032671: Search Report and Written Opinion.
PCT/US2010/032675: Search Report and Written Opinion.
PCT/US2010/032682: Search Report and Written Opinion.
PCT/US2010/032719: Search Report and Written Opinion.
PCT/US2013/023637: Search Report and Written Opinion.
Engdahl, Tomi, "Ground Loop Basics." Web Jan. 4, 2009, ePanorama.net www.epanorama.net/documents/groundloop/basics.html.

* cited by examiner

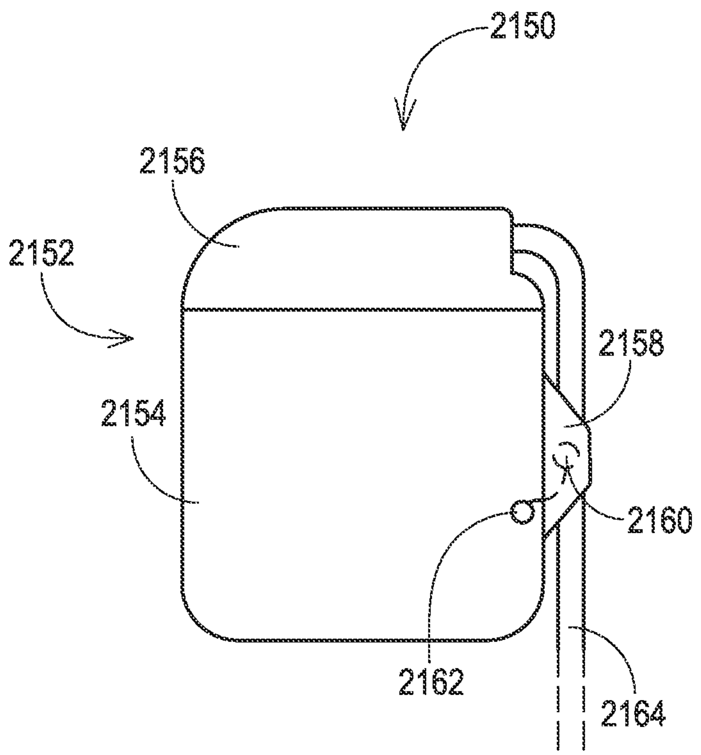
FIG. 5A
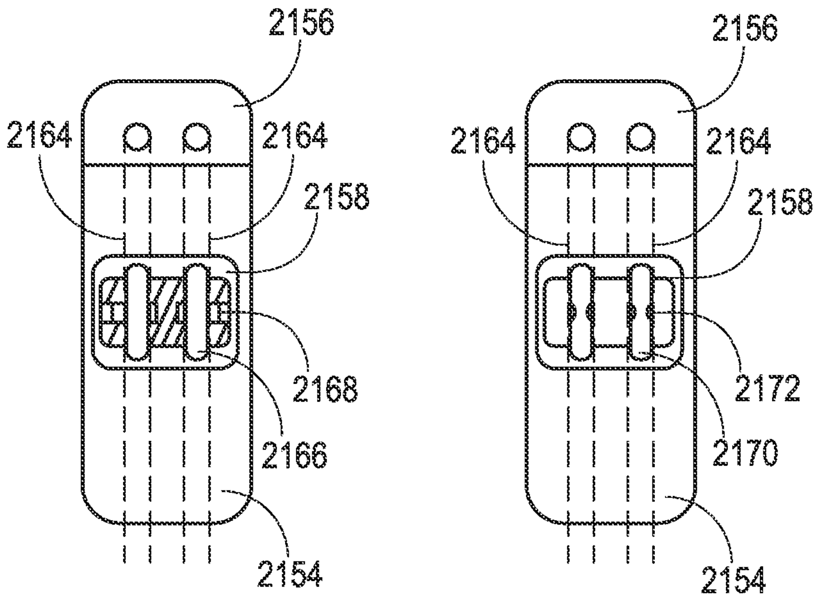
FIG. 5B
FIG. 5C
FIG. 6

SHIELDING AN IMPLANTABLE MEDICAL LEAD

RELATED CASES

The present application claims priority to and incorporates by reference the following, each as if rewritten herein in its entirety: U.S. Provisional Application 61/174,204 filed on Apr. 30, 2009; U.S. Provisional Application 61/174,216 filed on Apr. 30, 2009; U.S. Provisional Application 61/174,224 filed on Apr. 30, 2009; U.S. Provisional Application 61/174,234 filed on Apr. 30, 2009; U.S. Provisional Application 61/174,247 filed on Apr. 30, 2009; U.S. Provisional Application 61/174,254 filed on Apr. 30, 2009; U.S. Provisional Application 61/174,262 filed on Apr. 30, 2009; U.S. Provisional Application 61/174,276 filed on Apr. 30, 2009; U.S. Provisional Application 61/174,287 filed on Apr. 30, 2009; and U.S. Provisional Application 61/174,296 filed on Apr. 30, 2009.

TECHNICAL FIELD

Embodiments relate to implantable medical leads. More particularly, embodiments relate to implantable medical leads containing a shield.

BACKGROUND

Implantable medical systems including implantable medical devices (IMD) and associated implantable medical leads provide functions such as stimulation of muscle or neurological tissue and/or sensing of physiological occurrences within the body of a patient. Typically, the IMD is installed in a subcutaneous location that is accommodating and relatively accessible for implantation. For instance, to provide stimulation near the spine or pelvis, the IMD may be installed in a pocket located on the abdomen or upper buttocks region of the patient. The implantable medical lead is installed, either through a percutaneous procedure or a surgical procedure, depending upon the type of lead that is necessary.

Once installed, the lead extends from the stimulation site to the location of the IMD. The separation of the stimulation site to the location of the IMD varies, but may typically range from about 20 cm to about 100 cm. For relatively lengthy separation, if a lead of adequate length is unavailable then a lead extension may be implanted to span from the IMD to a proximal end of the implantable lead.

The implantable medical lead includes connector rings on a proximal end and electrodes on a distal end, and conductive filars interconnecting the electrodes at the proximal end connector rings to the electrodes at a distal end. The lead includes a jacket, often made of a flexible but biocompatible polymer, and the filars are insulated from the body tissue by the jacket. However, the filars are not insulated by the jacket from the presence of electromagnetic radiation. Electromagnetic radiation in the radio frequency (RF) spectrum induces currents into the filars and thus presents current at the electrode that is unintended. In the patient's normal daily experience, the level of RF radiation that is encountered is at a negligible level, and there is no danger of heating of tissue by the unintended current that may result.

RF radiation poses a risk to tissue in contact with the electrodes when the intensity is significantly higher than the background levels. The surface area of each electrode is relatively small so that a small amount of tissue must dissipate a potentially large amount of induced current. In particular, if the patient is exposed to the RF radiation from a magnetic resonance imaging (MRI) scan, there is a high probability that tissue damage at the stimulation site(s) can occur. This tissue damage may be very dangerous, particularly so for neurological tissue. Therefore, patients with IMDs are typically not permitted to have a body coil MRI scan for at least these reasons.

SUMMARY

Embodiments address issues such as these and others by providing an implantable lead that includes a shield within the jacket that may reduce the amount of RF current induced on the filars within the lead. The shield may have several parameters that fall within ranges suitable for providing RF protection while maintaining mechanical properties that are beneficial for implantation.

Embodiments provide an implantable medical lead that includes an inner layer of insulation establishing an axial dimension, the inner layer surrounding at least one conductive filar. A shield is provided over the inner layer of insulation, and the shield includes a plurality of metal wires forming a braid about the inner layer of insulation, a first set of the plurality being coiled in first direction and a second set of the plurality being coiled in a second direction, the metal wires each having a dimension that faces outward from the inner layer within a range from 0.5 to 2.5 mils. The braid has a braid angle less than 60 degrees when measured transversely from the axial dimension. An outer layer of insulation is provided over the shield with the outer layer of insulation being adhered to the inner layer of insulation through openings within the braid formed by the metal wires. At least one proximal electrode is on a proximal end of the inner layer of insulation and at least one distal electrode is on a distal end of the inner layer of insulation, with the at least one conductive filar establishing an electrical pathway between the at least one proximal electrode and the at least one distal electrode.

Embodiments provide an implantable medical lead that includes an inner layer of insulation establishing an axial dimension, the inner layer surrounding at least one conductive filar. A shield is provided over the inner layer of insulation, and the shield includes at least six metal wires forming a braid about the inner layer of insulation with at least three of the at least six wires forming a first set being coiled in the first direction and at least three of the at least six wires forming a second set being coiled in the second direction. The braid has a braid angle less than 60 degrees when measured transversely from the axial dimension. An outer layer of insulation is provided over the shield with the outer layer of insulation being adhered to the inner layer of insulation through openings within the braid formed by the metal wires. At least one proximal electrode is on a proximal end of the inner layer of insulation and at least one distal electrode is on a distal end of the inner layer of insulation, with the at least one conductive filar establishing an electrical pathway between the at least one proximal electrode and the at least one distal electrode.

Embodiments provide an implantable medical lead that includes an inner layer of insulation establishing an axial dimension, the inner layer surrounding at least one conductive filar. A shield is provided over the inner layer of insulation, and the shield includes at least six metal wires forming a braid about the inner layer of insulation with at least three of the at least six wires being coiled in the first direction and at least three of the at least six wires being coiled in the second direction. The metal wires each have a dimension that faces outward from the inner layer within a range from 0.5 to 2.5 mils. An outer layer of insulation is provided over the shield with the outer layer of insulation being adhered to the inner layer of insulation through openings within the braid formed by the metal wires. At least one proximal electrode is on a proximal end of the inner layer of insulation and at least one distal electrode is on a distal end of the inner layer of insulation, with the at least one conductive filar establishing an electrical pathway between the at least one proximal electrode and the at least one distal electrode.

Embodiments provide an implantable medical lead that includes an inner layer of insulation establishing an axial dimension, the inner layer surrounding at least one conductive filar. A shield is provided over the inner layer of insulation, and the shield includes a plurality of metal wires forming a braid about the inner layer of insulation, a first set of the plurality being coiled in a first direction and a second set of the plurality being coiled in a second direction, wherein spacing in the axial dimension between adjacent wires coiled in the first direction is no greater than a lead diameter and spacing in the axial dimension between adjacent wires coiled in the second direction is no greater than the lead diameter. An outer layer of insulation is provided over the shield with the outer layer of insulation being adhered to the inner layer of insulation through openings within the braid formed by the metal wires, a diameter of the outer layer establishing the lead diameter. At least one proximal electrode is on a proximal end of the inner layer of insulation and at least one distal electrode is on a distal end of the inner layer of insulation, with the at least one conductive filar establishing an electrical pathway between the at least one proximal electrode and the at least one distal electrode.

Embodiments provide an implantable medical lead that includes an inner layer of insulation establishing an axial dimension, the inner layer being a biocompatible material and surrounding at least one conductive filar and having a thickness of at least 2 mils. A shield is provided over the inner layer of insulation, and the shield includes at least six metal wires forming a braid about the inner layer of insulation with at least three of the at least six wires being coiled in a first direction and at least three of the at least six wires being coiled in a second direction. The braid has a braid angle less than 60 degrees when measured transversely from the axial dimension, and a spacing in the axial dimension between adjacent wires coiled in the first direction being no greater than a lead diameter. The metal wires each have a dimension that faces outward from the inner layer within a range from 0.5 to 2.5 mils, and the metal wires each have an ultimate tensile strength of at least 150 ksi. The metal wires have a cross-section in the shape of round, oval, or rectangular, and the metal wires are a biocompatible material. A biocompatible outer layer of insulation is provided over the shield with the outer layer of insulation being adhered to the inner layer of insulation through openings within the braid formed by the metal wires. The outer layer has a thickness over the metal wires of no greater than 4 mils, and a diameter of the outer layer establishes the lead diameter. At least one proximal electrode is on a proximal end and at least one distal electrode is on a distal end, with the at least one conductive filar establishing an electrical pathway between the at least one proximal electrode and the at least one distal electrode, the shield ending within 0.5 millimeters to 10 centimeters of a nearest edge of the at least one distal electrode.

Embodiments provide an implantable medical lead that includes an inner layer of insulation establishing an axial dimension, and the inner layer surrounds at least one conductive filar. A shield is provided over the inner layer of insulation, and the shield includes a plurality of metal wires forming a braid about the inner layer of insulation, a first set of the plurality being coiled in a first direction and a second set of the plurality being coiled in a second direction. An outer layer of insulation is provided over the shield with the outer layer of insulation being adhered to the inner layer of insulation through openings within the braid formed by the metal wires such that the shield is entirely surrounded by a combination of the outer layer of insulation and inner layer of insulation. At least one proximal electrode is on a proximal end of the inner layer of insulation and at least one distal electrode is on a distal end of the inner layer of insulation, with the at least one conductive filar establishing an electrical pathway between the at least one proximal electrode and the at least one distal electrode.

DESCRIPTION OF THE DRAWINGS

FIG. 5A shows a side view of an embodiment of an implantable medical system where the shield of the lead is grounded to a can of the IMD.

FIG. 5B shows an end view of the embodiment where the lead passes through a connection block having a set screw to ground the shield to the can.

FIG. 5C shows an end view of the embodiment where the lead passes through a connection block having a spring loaded connector to ground the shield to the can.

FIG. 6 shows an example of a spring loaded connector.

FIG. 74C shows an embodiment of an implantable lead with the shield having the axial cut but with the edges of the slot brought into an overlapping configuration to close the slot.

FIG. 74D shows an embodiment of an implantable lead with the shield having the axial cut but with a shield patch applied across the slot.

FIG. 75A shows the embodiment of the implantable lead of FIG. 74A in cross-section to reveal the shield and filars.

FIG. 75B shows the embodiment of the implantable lead of FIG. 74B in cross-section to reveal the shield and the slot.

FIG. 75C shows the embodiment of the implantable lead of FIG. 74C in cross-section to reveal the shield having the overlapping edges.

FIG. 75D shows the embodiment of the implantable lead of FIG. 74D in cross-section to reveal the shield and the shield patch.

FIG. 76A shows an embodiment of the shield as an equivalent tube to reveal a linear axial cut that produces a linear slot.

FIG. 76B shows the embodiment of the shield as an equivalent tube to reveal the edges of the slot that overlap to close the slot.

FIG. 76C shows the embodiment of the shield as an equivalent tube to reveal the shield patch that closes the slot.

FIG. 76D shows an embodiment of the shield as an equivalent tube to reveal a helical axial cut forming a helical slot.

FIG. 77 shows an embodiment of an implantable medical system that includes an implantable medical device (IMD) coupled to a lead containing a shield.

FIG. 78A shows an embodiment of an implantable lead with the shield revealed.

Figure 78A:
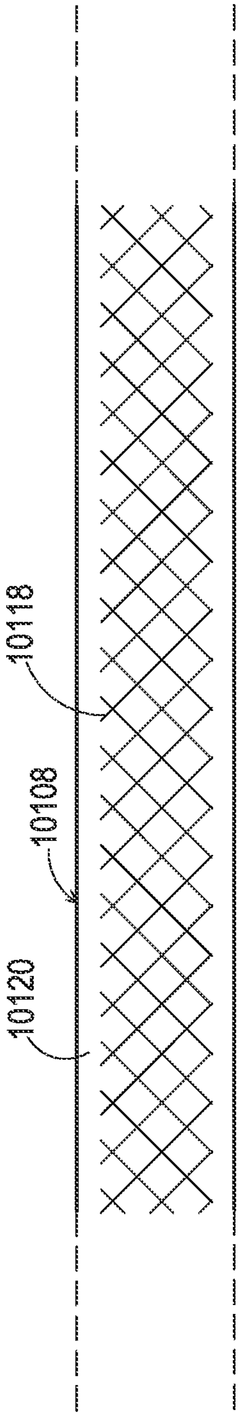
Figure 78B:
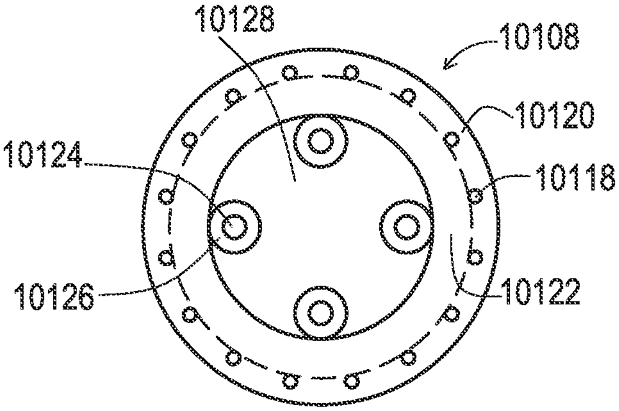

FIG. 78B shows the embodiment of the implantable lead of FIG. 78A in cross-section to reveal the shield and filars.

Figure 79A:
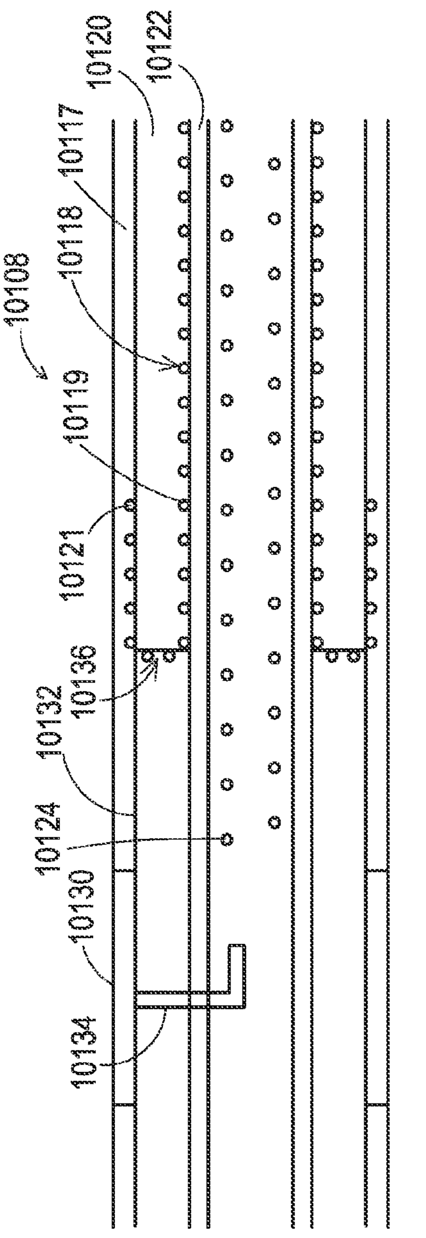

FIG. 79A shows one embodiment of a guard at the termination of the shield.

Figure 79B:
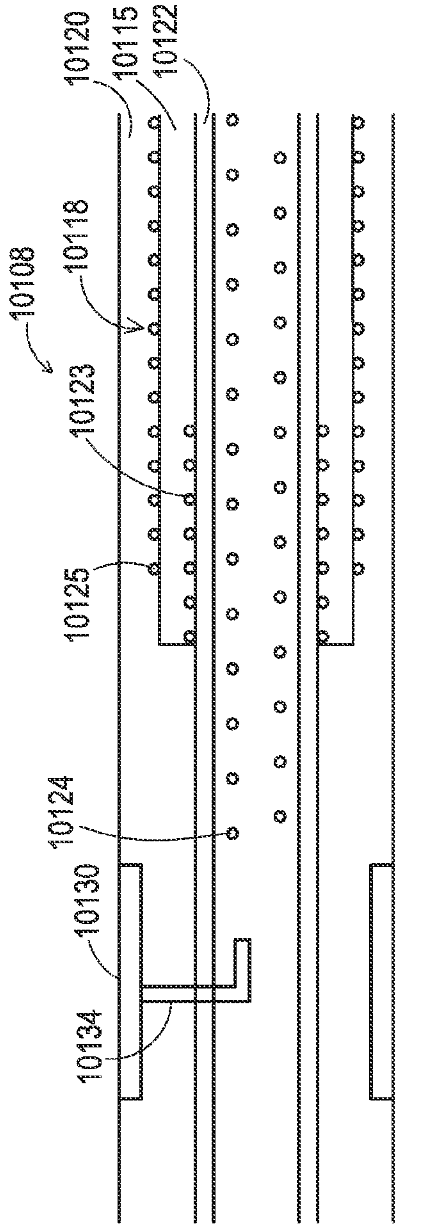

FIG. 79B shows another embodiment of a guard at the termination of the shield.

Figure 79C:
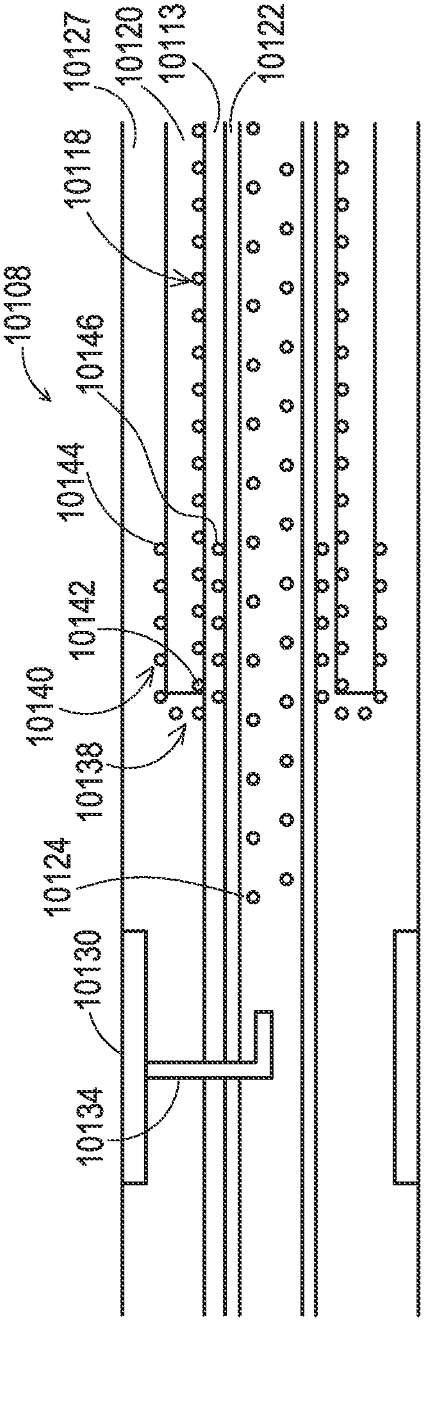

FIG. 79C shows another embodiment of a guard at the termination of the shield.

Figure 80A:
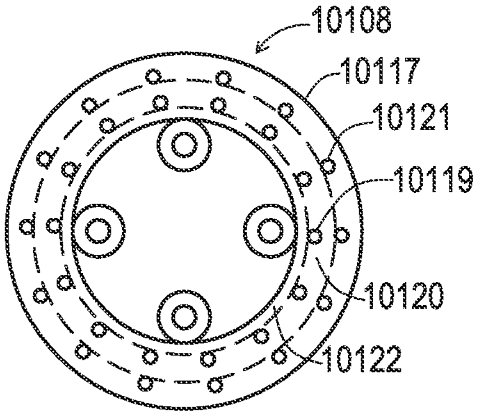

FIG. 80A shows the embodiment of FIG. 79A in cross-section to reveal first and second portions of the continuous shield forming a guard at the termination of the shield.

Figure 80B:
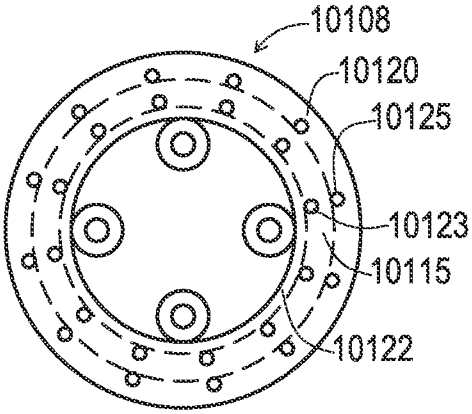

FIG. 80B shows the embodiment of FIG. 79B in cross-section to reveal first and second portions of the two-piece shield forming a guard at the termination of the shield.

Figure 80C:
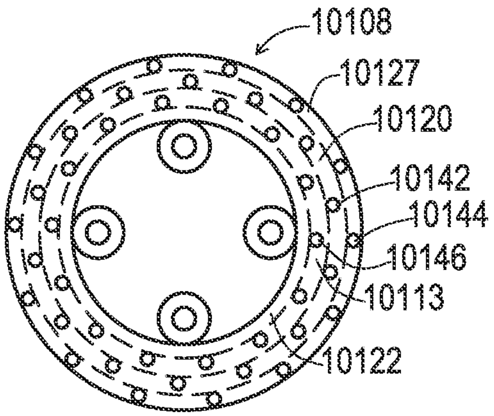

FIG. 80C shows the embodiment of FIG. 79C in cross-section to reveal a first portion including first and second sub-portions and a second portion at the termination of the two-piece shield.

DETAILED DESCRIPTION

Embodiments of implantable medical leads that include shields are disclosed herein. Ten primary subject matter topics are presented, where each new topic begins with reference to FIGS. 1, 3, 11, 16, 18, 30, 49, 59, 73, and 77. However, this detailed description should be read as a whole whereby subject matter of embodiments corresponding to one particular topic is applicable to embodiments corresponding to other topics.

Figure 1:
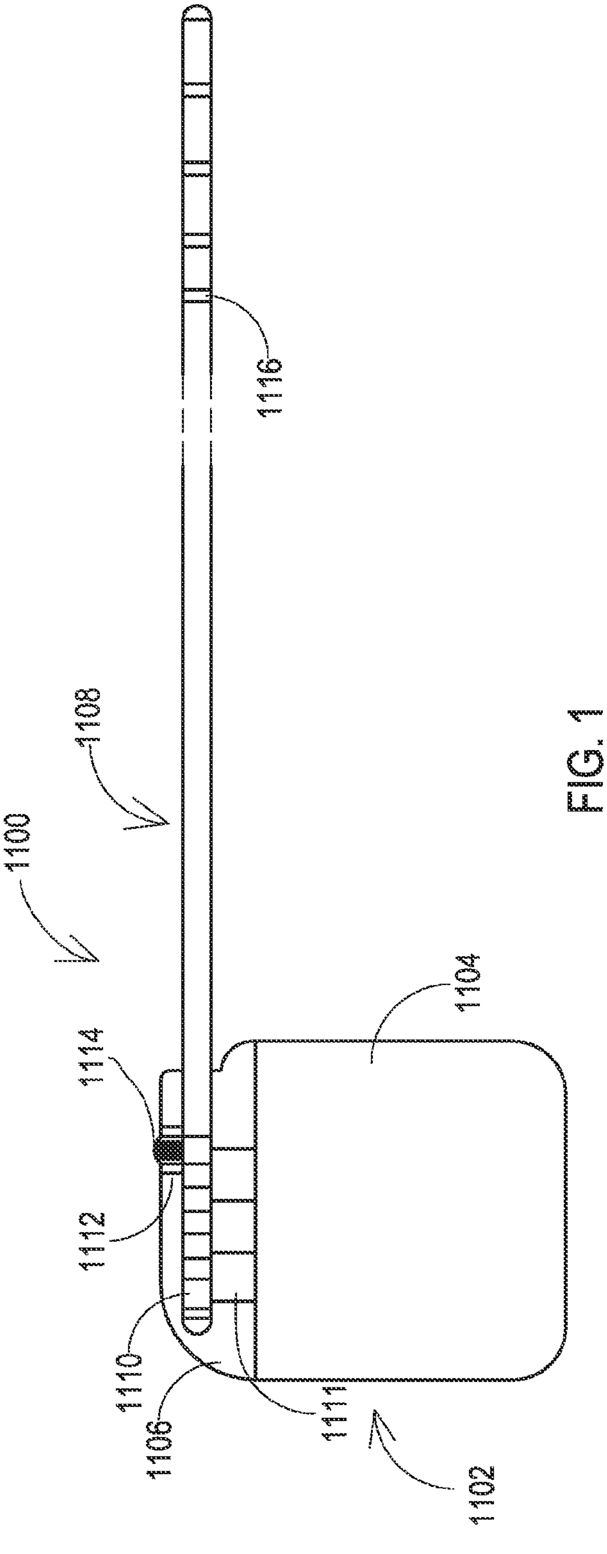
FIG. 1 shows an embodiment of an implantable medical system that includes an implantable medical device (IMD) coupled to a lead containing a shield.
Figure 2A:
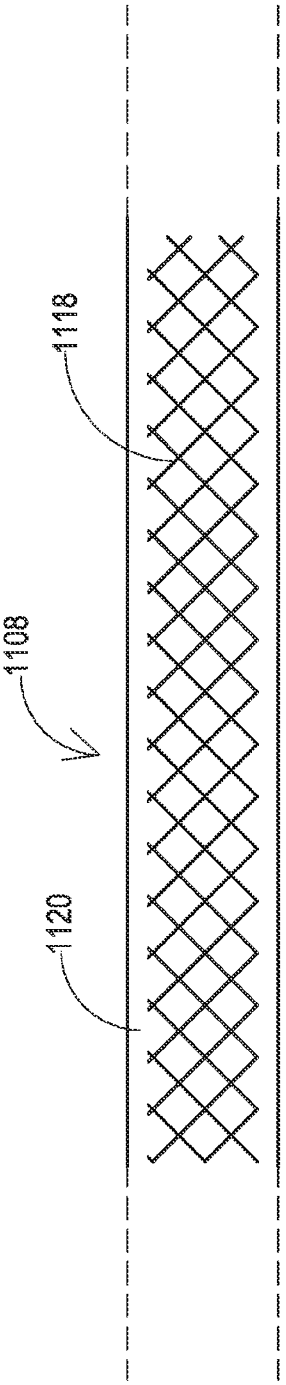
FIG. 2A shows an embodiment of an implantable lead with the shield revealed.
Figure 2B:
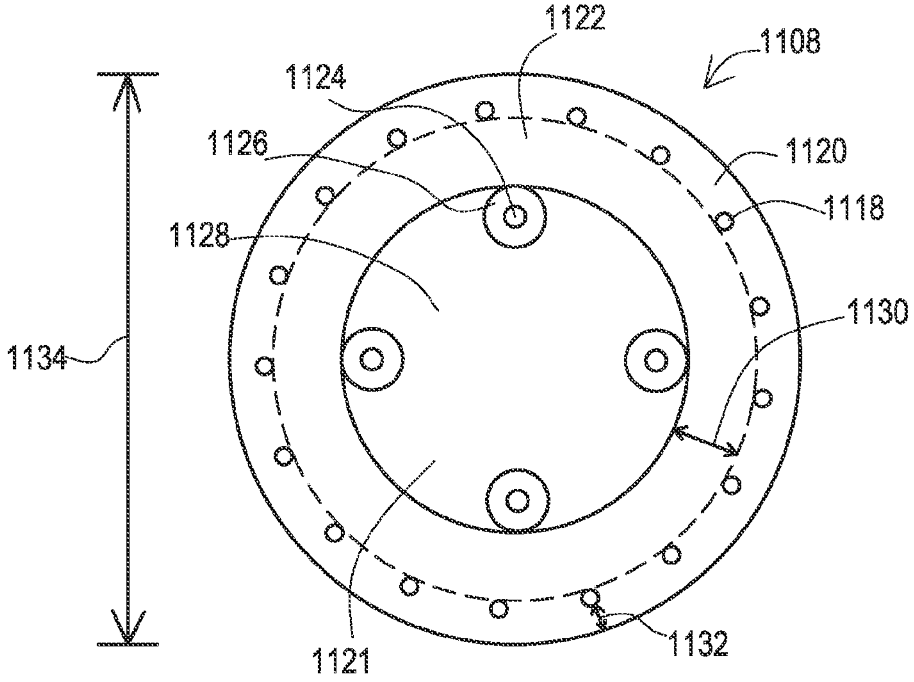
FIG. 2B shows the embodiment of the implantable lead in cross-section to reveal the shield and filars.
Figure 2C:
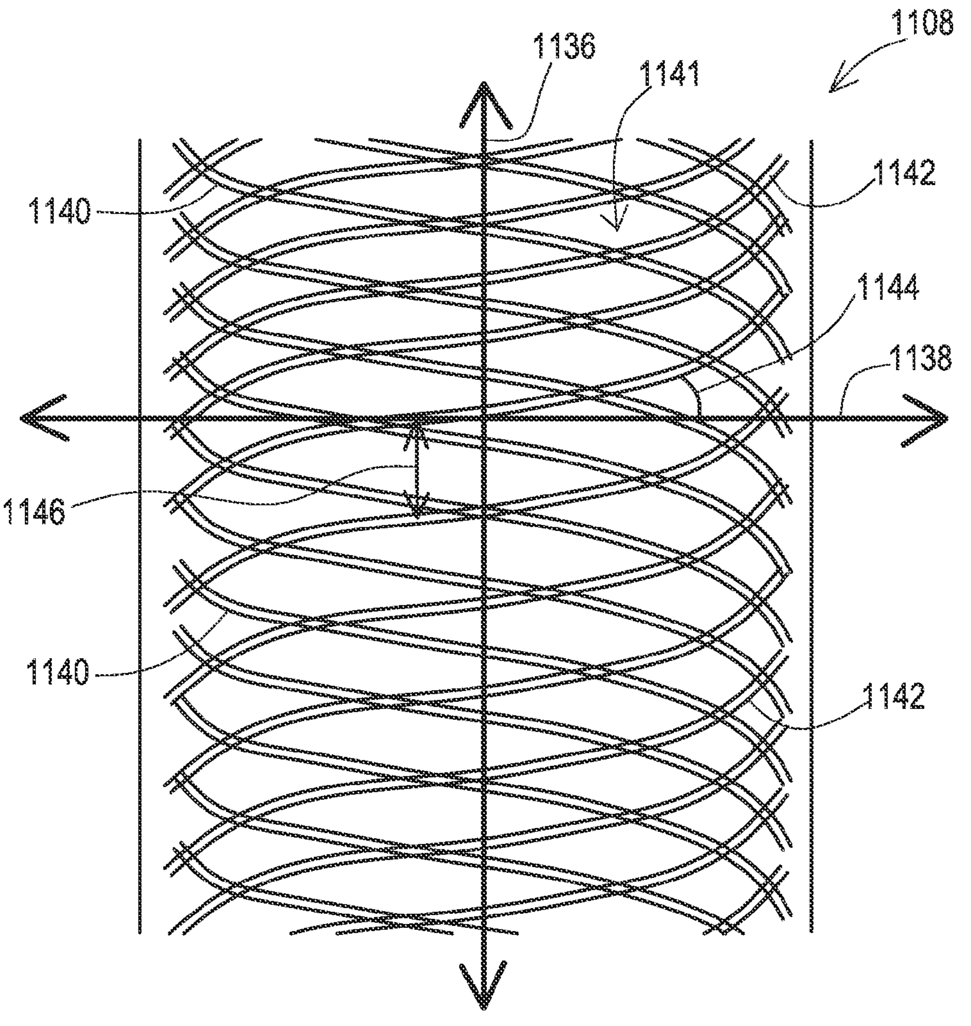
FIG. 2C shows an embodiment of the implantable lead with the shield revealed and with various parameters being specified.
Figure 2D:
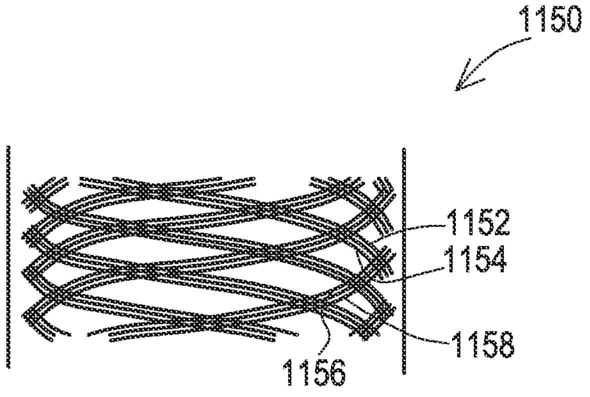
FIG. 2D shows an embodiment of the implantable lead with dual braid wire windings.
Figure 2E:
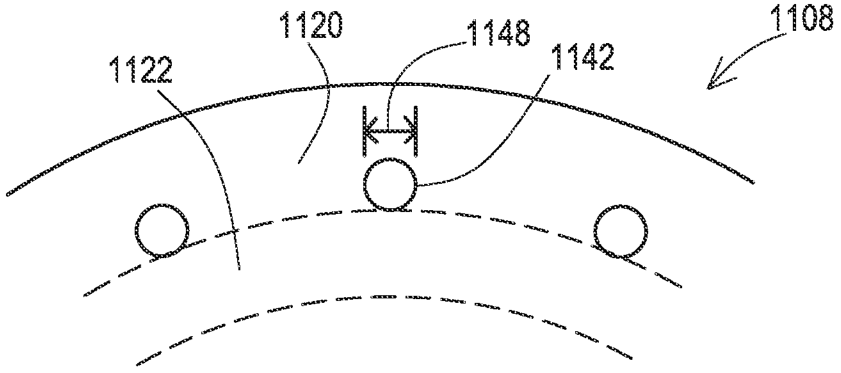
FIG. 2E shows an embodiment of the implantable lead with braid wires having a round cross-section.
Figure 2F:
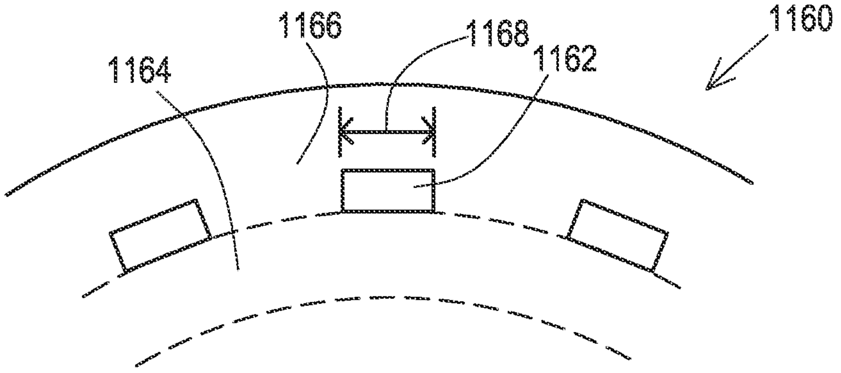
FIG. 2F shows an embodiment of the implantable lead with braid wires having a rectangular cross-section.
Figure 2G:
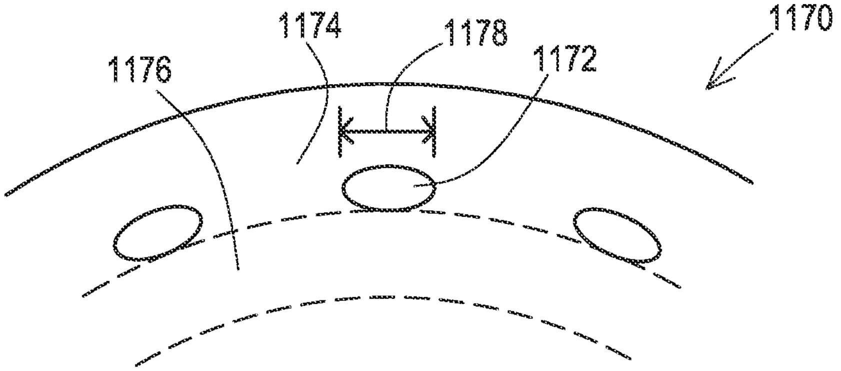
FIG. 2G shows an embodiment of the implantable lead with braid wires having an oval cross-section.
Figure 2H:
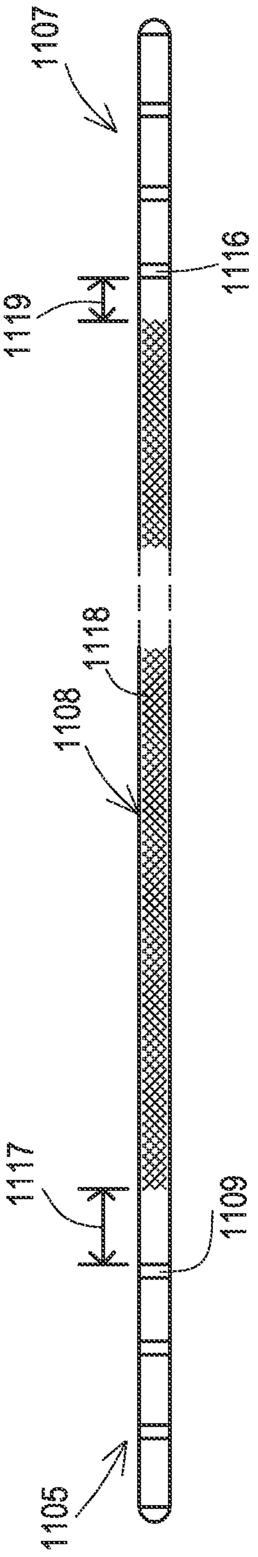
FIG. 2H shows an embodiment of the implantable lead with the lead terminating at a given spacing from a nearest connector and a nearest electrode at the proximal and distal ends.
Figure 3:
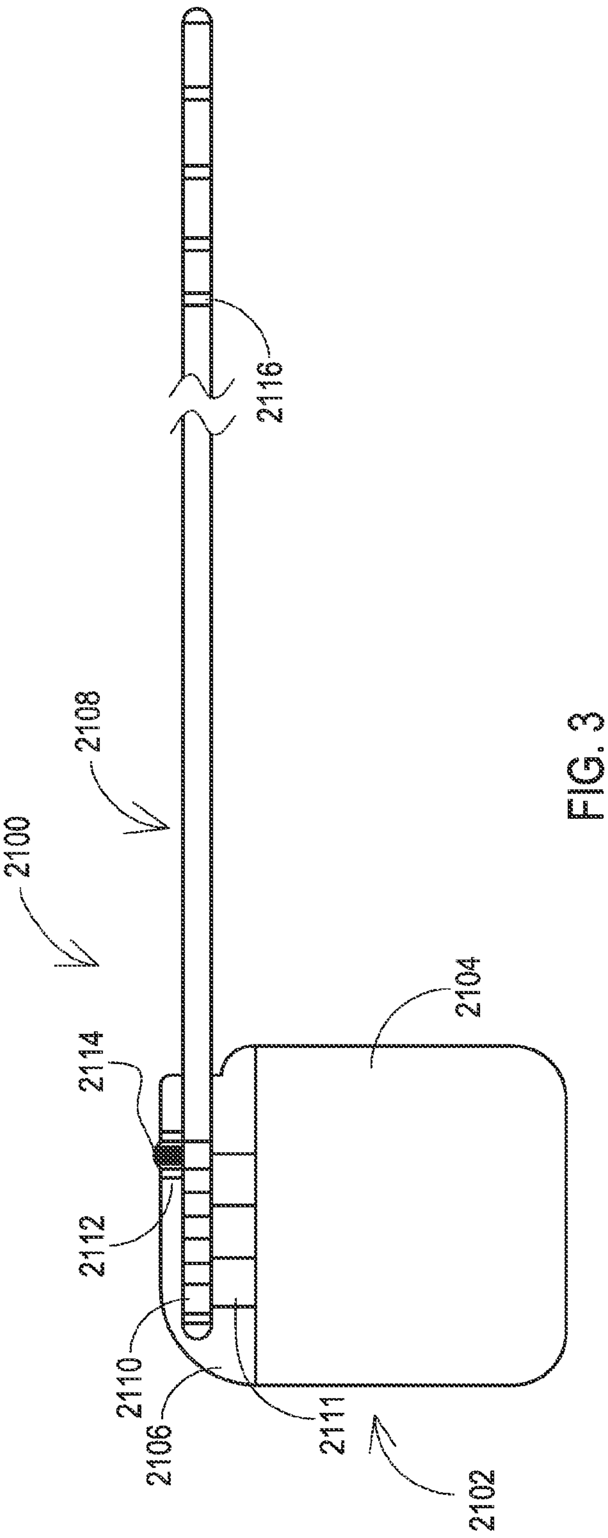
FIG. 3 shows an embodiment of an implantable medical system that includes an implantable medical device (IMD) coupled to a lead containing a shield.

For instance, shield details disclosed in relation to FIGS. 1-2H are also applicable to the shields of all embodiments disclosed in FIGS. 3-80C where such shield details may be desired. The examples of grounding a shield within a lead as disclosed in relation to FIGS. 3-15E are applicable to all embodiments disclosed herein where a grounded shield may be desired. The examples of shielding the extension and interconnecting the shielding of the lead to the extension as disclosed in relation to FIGS. 16-17G are applicable to all embodiments disclosed herein where inclusion of a shielded extension may be desired. The examples of terminating the shield as disclosed in relation to FIGS. 18-48 are applicable to all embodiments disclosed herein where terminating the shield within the lead body may be desired. The examples of rotationally coupling the lead body to a stylet as disclosed in relation to FIGS. 49-58 are applicable to all embodiments disclosed herein where such rotational coupling may be desired. The examples of markers for the lead as disclosed in relation to FIGS. 59-72 are applicable to all embodiments disclosed herein where such a marker may be desired. The examples of breaking the circumferential mechanical continuity of the shield as disclosed in FIGS. 73-76D are applicable to all embodiments disclosed herein where such a lack of continuity may be desired. The examples of guarding the termination of the shield as disclosed in FIGS. 77-80C are applicable to all embodiments disclosed herein where a guarded shield termination may be desired.

Embodiments disclosed in relation to FIGS. 1-2H provide for radio frequency (RF) shielding of an implantable lead that may be connected to an implantable medical device (IMD). A shield is present within the jacket of the implantable lead. The shield is designed to provide RF shielding while also providing various mechanical properties suitable for implantation.

FIG. 1 shows an example of an implantable medical system 1100 that includes an IMD 1102 coupled to a lead 1108. The IMD 1102 includes a metal can 1104, typically constructed of a medical grade titanium, such as grades 1-4, 5 or 9 titanium, or similar other biocompatible materials. The IMD 1102 includes a header 1106 typically constructed of materials such as polysulfone or polyurethane, that is affixed to the metal can 1104. The header 1106 is shown transparently for purposes of illustration. The header 1106 provides a structure for securing the lead 1108 to the IMD 1102 and for establishing electrical connectivity between circuitry of the IMD 1102 and electrodes of the lead 1108.

The lead 1108 includes electrodes 1116 on a distal end that are positioned at a stimulation site within a patient. The lead also includes connector rings 1110 on a proximal end that is positioned within the header 1106. The connector rings 1110 make physical contact with electrical connections 1111 within the header. The electrical connections 1111 may include a metal contact that the connector ring 1110 rests against upon being inserted into the header 1106 where a wire extends from the metal contact into the can 1104 where the circuitry is housed. Signals applied by the IMD 1102 to the connector rings 1110 are conducted through the lead 1108 to the electrodes 1116 to provide the stimulation therapy to the patient.

The lead 1108 is secured in the header 1106 such as by a set screw block 1112 within the header 1106 that allows at least one set screw 1114 to be tightened against at least one of the connector rings 1110. A shield 1118 such as the one discussed below with reference to FIGS. 2A and 2B is located within the lead 1108. The shield 1118 may or may not be grounded to the metal can 1104 at the IMD 1102 of FIG. 1 or at various points along the length of the lead. The shield 1118 may or may not be grounded through other mechanisms as well. For instance, the shield 1118 may be located within the lead 1108 at a small distance from the surface so that the shield 1118 will effectively capacitively couple to the tissue along the length of the lead to dissipate energy to the tissue over the length.

FIGS. 2A and 2B show an example of the lead 1108, where a shield 1118 is present. An outer jacket layer 1120 is shown transparently in FIG. 2A for purposes of illustrating the shield 1118. The shield 1118 blocks at least some RF energy from directly coupling to conductive filars 1124 that are present within the lead 1108. The conductive filars 1124 extend the length of the lead and interconnect the proximal connector rings 1110 to the distal electrodes 1116 so that stimulation signals are conducted from the proximal end to the distal end of the lead 1108.

As shown in FIG. 2A, the shield 1118 of this example is a braided metal wire. The metal wire may be constructed of various materials such as titanium, tantalum, niobium, platinum-iridium alloy, platinum, palladium, gold, stainless steel, and their alloys, or other metals. The metal braid wire may be a biocompatible metal, particularly for embodiments where a portion of the shield 1118 may be exposed for purposes of grounding. Biocompatible metals ensure that if the shield 1118 is exposed to tissue, either by design or due to wear on the lead 1108, the shield 1118 does not become a toxin to the patient.

As shown in FIG. 2B, the shield 1118 may be embedded within the jacket of the lead 1108. One manner of constructing the lead 1108 with the shield 1118 is to provide a jacket that includes an inner layer of insulation 1122 that isolates an inner region 1121 where the filars 1124 and any additional insulation layer 1126, such as polytetrafluoroethylene (PTFE) that may surround each filar 1124 are located. According to some embodiments, this inner layer 1122 may have a post-assembly thickness 1130 of at least 2 mils and may be significantly larger such as 5 or 6 mils depending upon size constraints for the lead 1108 and/or the size of the outer layer 1120. The shield 1118 may then reside on the outer portion of the inner layer 1122, and the jacket's outer layer of insulation 1120 may then enclose the shield 1118. The outer layer 1120 provides an overall lead diameter 1134. The outer jacket 1120 maybe added over the braid 1118, or it may be extruded over the braid.

For embodiments where it is desirable for the shield 1118 to RF couple to tissue, typically as capacitive coupling, either as an alternative to grounding at the can of the IMD or specific points along the length or in addition to grounding at the can or along the length, the entire outer jacket layer 1120 may be relatively thin, particularly for the portion passing over the braid wires of the shield 1118. According to the various embodiments a post-assembly thickness 1132 for the portion of the outer layer 1120 passing over a single braid wire may be on the order of 0.5 to 5 mils. The thickness of the outer layer 1120 over the shield 1118 is reduced by a braid wire diameter at points where braid wires intersect. Accordingly, the post-assembly thickness 1132 over the single wire may vary depending upon a chosen braid wire diameter so that adequate coverage also exists at the intersection points. Furthermore the thickness may be less than 0.5 mils, particularly where tissue in-growth is not of concern and in that case the outer layer 1120 could be omitted.

This thickness of the outer layer 1120 over the braid wires may also vary depending upon the type of metal used for the braid wires. For instance, it has been found that the thickness of the outer layer 1120 has less of an impact on the heating at the electrode when using a titanium braid wire than when using a tantalum wire with all else being equal. However, with an outer layer 1120 whose post-assembled thickness 1132 is on the lower side of the range, such as 2 mils or less, tantalum braid wires may allow for less heating at the electrodes than if titanium braid wires are used.

Where the shield 1118 grounds at the can 1104 and/or at one or more specific locations along its length, via a direct current coupling or a capacitive coupling, the shield 1118 may be located further from the outer surface of the lead 1108. This increased depth of the shield 1118 within the jacket may provide for a more durable lead 1108 in terms of protecting the braid wires in areas of high flexure and motion, such as in the lumbar spine.

The inner and outer jackets 1122, 1120 may be constructed of the same or similar materials such as various flexible polymers, examples of which are polyurethanes and silicones. Biocompatible materials may be used, especially for the outer layer 1120 when the outer layer 1120 has direct contact with body tissue. A lumen 1128 may be included in an inner region 1121, particularly for percutaneous leads 1108, to allow a stylet to be inserted for purposes of pushing and steering the lead into the desired position within the patient. For leads where an inner region 1121 is filled to define the lumen 1128, such as where filars 1124 are cables rather than the coils as shown, this inner region 1121 may be constructed of materials such as polyurethanes, silicones, polyetheretherketone (PEEK), nylon or other biocompatible polymer material.

FIG. 2C shows a view of the implantable lead 1108 where various parameters related to the braid wires can be seen. The inner layer of insulation 1122, as well as the outer layer 1120, defines an axial dimension 1136 that runs along the length of the lead 1108. Braid wires such as braid wires 1140, 1142 are braided around the inner layer 1122. A first set of braid wires including braid wire 1140 is wound around the inner layer 1122 in a first direction while a second set of braid wires including braid wire 1142 is wound around the inner layer 1122 in a second direction that is opposite the first. The braid wires of the first set and the braid wires of the second set weave together during the braiding with a braid wire of the first set passing over some wires and under others of the second set in a repeating pattern.

The weaving may use a particular pattern, such as passing over one, passing under one, passing over one, and so on or such as passing over two, passing under two, passing over two, and so on. With wires of larger diameter, or where wires are used in pairs, then a pattern of two-over-two-under helps reduce the stress on the wire as it weaves back and forth. If the wires are small and single, with a relatively large aperture between braid wires, then one-over-one-under works well. The wire stress is a factor to consider because implant leads flex continually with body motion and typically are expected to last many years.

The braiding has various parameters of interest. A first parameter is the braid angle 1144. Here, the braid angle 1144 is defined as the angle of the braid wire as measured transversely from the axial dimension 1136; however, others sometimes define it relative to the axis of the lead. So, as shown in FIG. 2C, the braid angle 1144 is measured between the braid wire and the transverse dimension 1138. According to various embodiments, the braid angle measured in this way is less than 60 degrees.

This braid angle 1144 has several implications. The braid angle 1144 is one factor in setting the maximum dimension of the braid aperture 1141 shown in FIG. 2C, and hence the degree of coverage formed by the braid wires. This braid angle 1144 is also a factor in relation to the degree of stiffness of the lead in flexure and the tendency of the braid wires to break during flexure. The braid angle is also a factor in the cohesion of the outer layer of insulation 1120 to the inner layer of insulation 1122, because when the aperture is of adequate size, cohesion occurs between the two layers 1120, 1122 through the aperture.

Another parameter of interest as shown in FIG. 2C is the axial spacing 1146 between adjacent wires of a set. According to various embodiments, the axial spacing 1146 has an upper limit equal to the lead diameter 1134. The axial spacing 1146 is also a factor in the aperture size, the axial stiffness, the bending stiffness, and the kink resistance.

Another parameter of interest, which is related to the braid angle 1144 and the axial spacing 1146, is the number of wires in each set. According to various embodiments, the first set of braid wires which are wound in the first direction includes at least three braid wires. Likewise, the second set of braid wires which are wound in the second direction includes at least three braid wires. These two sets of at least three braid wires each ensures that for the various ranges of parameters disclosed herein, the aperture 1141 has a transverse dimension that is sufficiently small to effectively shield the RF energy in the MRI spectrum, which typically spans from 43 MHz to 128 MHz.

The total number of braid wires is limited by the allowable axial and bend stiffness for the braid angle and braid wire size. In some examples, there may be as many as 16 braid wires in each set for a total of 32 braid wires. However, as shown in the example of FIG. 2C, each set includes six braid wires, where braid wire 1140 reappears on a given side of the lead 1108 after five other braid wires are wound. Likewise, braid wire 1142 reappears on the side of the lead 1108 after five other braid wires are wound.

FIG. 2D shows another lead embodiment 1150 that demonstrates another braid wire parameter of interest. In this example, the braid wires are paired so that two braid wires that are in contact wind around the inner layer 1122 instead of a single wire. For instance, dual braid wires 1152 and 1154 of a first set wound in a first direction are in contact as each winds around the inner layer 1122. Dual braid wires 1156 and 1158 of a second set wound in a second direction are in contact as each winds around the inner layer 1122.

The braid wires bundled together in this manner affect the stiffness of the lead 1108 as well as the aperture size. Bundling braid wires in this manner may provide coverage like that of wider dimensioned braid wires, such as rectangular braid wires, but without the increased bending stresses associated with the corners present on the rectangular braid wire.

FIG. 2E is an enlarged view of a portion of a lead 1108 to illustrate the cross-section of the braid wires. The view is a cross-section where the cut through the lead 1108 is taken at an angle perpendicular to the direction of travel of the topmost braid wire 1142 so as to provide a true cross-section of the topmost braid wire 1142. Here the topmost braid wire 1142 has a round cross-section and provides a braid wire diameter 1148. According to various embodiments, the braid wire diameter ranges from about 0.5 mils to about 2.5 mils. The braid wire diameter is measured as the dimension that faces outward from the inner layer 1122 as shown in FIG. 2E. The round cross-section lacks corners that may otherwise affect the bend stiffness of the lead 1108, but the round cross-section provides less coverage than other cross-sectional shapes that have a same height extending into the outer layer 1120 from the inner layer 1122.

FIG. 2F is an enlarged view of a portion of a lead 1160 to illustrate the cross-section of the braid wires. As in FIG. 2E, the view is a cross-section where the cut through the lead 1160 is taken at an angle perpendicular to the direction of travel of the topmost braid wire 1162 so as to provide a true cross-section of the topmost braid wire 1162. Here the braid wire 1162 has a rectangular cross-section and provides a braid wire width 1168. According to various embodiments, the braid wire width ranges from about 2 mils to about 5 mils. The braid wire width is measured as the dimension that faces outward from the inner layer 1164 as shown in FIG. 2F. The rectangular cross-section has corners that may affect the bend stiffness of the lead 1108 but provides more coverage than a round cross-sectional shape that has a same height extending into an outer layer 1166 from the inner layer 1164.

FIG. 2G is an enlarged view of a portion of a lead 1170 to illustrate the cross-section of the braid wires. As in FIG. 2E, the view is a cross-section where the cut through the lead 1170 is taken at an angle perpendicular to the direction of travel of the topmost braid wire 1172 so as to provide a true cross-section of the topmost braid wire 1172. Here the topmost braid wire 1172 has an oval cross-section and provides a braid wire major axis diameter 1178. According to various embodiments, the braid wire major axis diameter ranges from about 0.5 mils to about 4 mils. The braid wire major axis diameter is measured as the dimension that faces outward from the inner layer 1176 as shown in FIG. 2G. The oval cross-section lacks corners that may affect the bend stiffness of the lead 1108 but provides coverage similar to a rectangular cross-section that has a same height extending into an outer layer 1174 from the inner layer 1176.

In each of the examples of FIGS. 2E-2G, regardless of the cross-sectional shape and the material used, the braid wires have an ultimate tensile strength satisfactory for implantation. According to the various embodiments, this ultimate tensile strength is at least 150,000 pounds per square inch (150 ksi).

FIG. 2H shows the lead 1108 from end to end with the shield 1118 in view to illustrate the termination of the shield 1118 at the proximal end 1105 and the distal end 1107. The shield 1118 terminates prior to reaching the most distal connector 1109 of the proximal end 1105 and prior to reaching the most proximal electrode 1116 of the distal end 1107. Terminating the shield 1118 at a distance 1117 from the connector 1109 and at a distance 1119 from the electrode 1116 reduces the likelihood of RF energy that radiates from the end of the shield, leaking from the shield onto the conductor filars and then to the connector 1109 and/or electrode 1116. However, the shield termination distances 1117, 1119 are not too large so that adequate coverage over the filars 1124 is maintained.

The shield termination distance from the distal electrodes and proximal connectors may vary. According to the various embodiments, the distance may range from about 0.5 millimeters to about 10 centimeters depending upon the location of the lead 1108. For instance, if the distal tip is located in the brain or spinal column where intensities of RF energy are lower, then distance from the end of the shield 1118 to the nearest edge of the distal electrode may be from 0.5 mm up to about 10 cm, or from about 2 mm to 2 cm to further reduce electrode coupling and filar exposure. However, in other locations where the entire lead 1108 is just under the skin as for peripheral nerve stimulation, the distance from the end of the shield 1118 to the nearest edge of the distal electrode may be less than about 2 cm to prevent overexposure of the filars 1124. In these cases, the distance may be on the order of 2 mm or more to ensure that excessive RF coupling from the shield 1118 to the electrodes is avoided.

In one particular example, the lead 1108 is provided with a shield 1118 where the total lead diameter is 53.6 mils. The inner insulation layer 1122 has an as assembled inside diameter of 35 mils and an as assembled outside diameter of 50.19 mils for a total thickness of 5.89 mils or 5.39 mils to the inner edge of the braid wire. The outside insulation layer 1120 has an as assembled outside diameter of 53.6 mils and a total thickness of 3.41 mils, with 1.41 mils of thickness existing over braid wire intersection points and while the thickness over a single braid wire approaches 2.66 mils as the single braid wires approaches an intersection point where the single braid wire will pass under an intersecting braid wire. The braid wire is round in cross-section with a diameter of 1.25 mils and being embedded by about 0.5 mils into the inner layer 1122. Two sets of eight braid wires are provided for a total of sixteen braid wires, with the braid wires establishing a braid angle of 22 degrees with an axial spacing between adjacent braid wires of 7.5 mils. The shield 1118 terminates about 2 mm from the nearest edge of the distal electrode and proximal connector.

In another particular example, the lead 108 is provided with the specifications described in the preceding paragraph except that the shield gaps and depth the shield sinks into the inner insulation layer 1122 are different. Here, the shield 1118 terminates about 1 mm from the nearest edge of the distal electrode and proximal connector and the shield sinks 0.25 mil. As a result, the inner insulation thickness to the inner edge of the braid wire is 5.6 mils.

In another particular example, the lead 108 is provided with the specifications described in the preceding paragraph except insulation thicknesses, braid angle, and proximal shield gaps differ. In this example, the braid depth from the outer surface of the outer layer 1120 to the outer edge of a braid wire is about 2 mils at braid wire intersection points while the thickness over the braid wire approaches 3.25 mils as the single braid wire approaches an intersection point where the braid wire passes under an intersecting braid wire. The inner insulation layer 122 has an average thickness of 4.5 mils to the inner edge of the braid wire while the braid wire sinks into the inner insulation layer 1122 by about 0.25 mil. The shield 1118 terminates about 1.27 mm from the nearest edge of the distal electrode and terminates about 10 mm from the nearest edge of the proximal connector. The braid angle is about 23 degrees.

Embodiments disclosed in relation to FIGS. 3-10C provide for radio frequency (RF) grounding of a shield present within an implantable lead. The shield may be grounded in various ways such as to a can of an implantable medical device (IMD) or to a ground plate on a header of the IMD. The pathway for grounding may be a direct current pathway or be capacitively coupled. The pathway for grounding the shield may couple to the shield at a point along the lead that is external to the header of the IMD or may couple to the shield at a point within the header.

FIG. 3 shows an example of an implantable medical system 2100 that includes an IMD 2102 coupled to a lead 2108. The IMD 2102 includes a metal can 2104, typically constructed of a medical grade titanium, such as grades 1-4, 5 or 9 titanium, or similar other biocompatible materials. The IMD 2102 includes a header 2106 typically constructed of materials such as polysulfone or polyurethane, that is affixed to the metal can 2104. The header 2106 is shown transparently for purposes of illustration. The header 2106 provides a structure for securing the lead 2108 to the IMD 2102 and for establishing electrical connectivity between circuitry of the IMD 2102 and electrodes of the lead 2108.

The lead 2108 includes electrodes 2116 on a proximal end that are positioned at a stimulation site within a patient. The lead also includes connector rings 2110 on a proximal end that is positioned within the header 2106. The connectors 2110 make physical contact with electrical connections 2111 within the header. The electrical connections 2111 may include a metal contact that the electrode 2110 rests against upon being inserted into the header 2106 where a wire extends from the metal contact into the can 2104 where the circuitry is housed. Signals applied by the IMD 2102 to the electrodes 2110 are conducted through the lead 2108 to the electrodes 2116 to provide the stimulation therapy to the patient.

The lead 2108 is secured in the header 2106 such as by a set screw block 2112 within the header 2106 that allows at least one set screw 2114 to be tightened against at least one of the connectors 2110. The shield 2118 may be grounded by metal contacts provided along the lead to establish a ground pathway from the shield 2118 to the tissue. As another option, the shield 2118 may be located within the lead 2108 at a small distance from the surface so that the shield 2118 will effectively capacitively couple to the tissue along the length of the lead to dissipate energy to the tissue over the length.

Figure 4A:
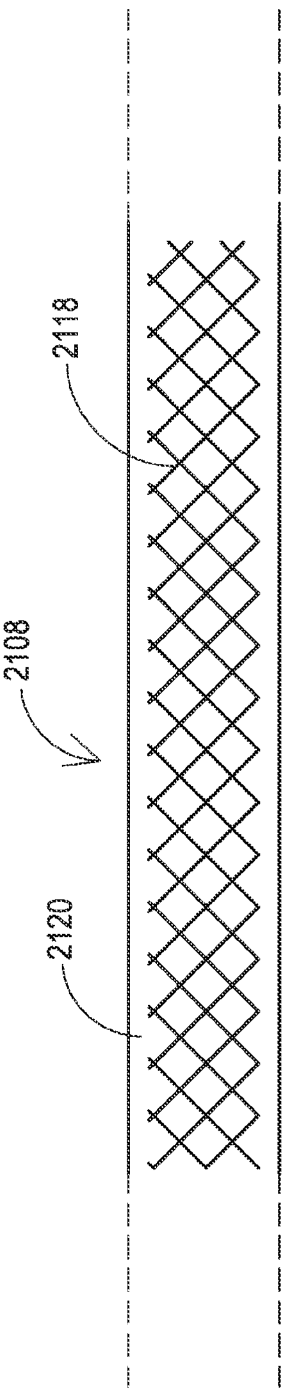
FIG. 4A shows an embodiment of an implantable lead with the shield revealed.
Figure 4B:
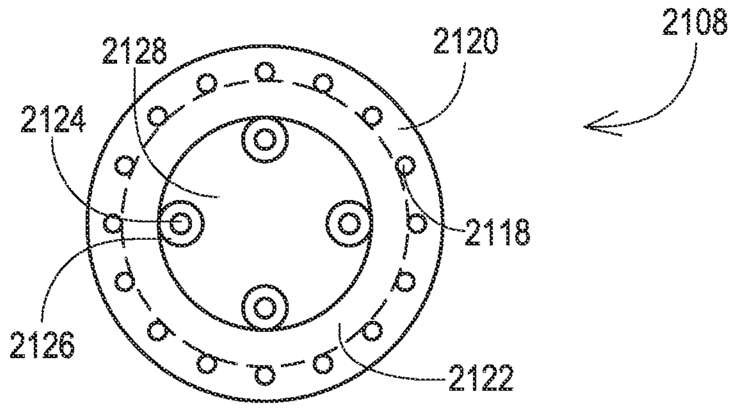
FIG. 4B shows the embodiment of the implantable lead in cross-section to reveal the shield and filars.

FIGS. 4A and 4B show an example of the lead 2108, where a shield 2118 is present. An outer jacket layer 2120 is shown transparently in FIG. 4A for purposes of illustrating the shield 2118. The shield 2118 blocks at least some RF energy from directly coupling to conductive filars 2124 that are present within the lead 2108. The conductive filars 2124 extend the length of the lead and interconnect the proximal connectors 2110 to the distal electrodes 2116 so that stimulation signals are conducted from the proximal end to the distal end of the lead 2108.

As shown in FIG. 4A, the shield 2118 of this example is a braided metal wire. The metal wire may be constructed of various materials such as titanium, tantalum, niobium, platinum-iridium alloy, platinum, palladium, gold, stainless steel, and their alloys, or other metals. It may be desired to utilize a biocompatible metal for the shield 2118, particularly for embodiments where a portion of the shield 2118 may be exposed for purposes of grounding. While the shield 2118 is shown as a braid, other shield configurations may be chosen particularly where flexibility is not an issue such as a foil strip wrapped about the lead 2108 in an overlapping manner or an outer layer 2120 that is heavily doped with conductive particles.

As shown in FIG. 4B, the shield 2118 may be embedded within the jacket of the lead 2108. One manner of constructing the lead 2108 with the shield 2118 is to provide an inner jacket 2122 that encloses the filars 2124 and any additional insulation layer 2126, such as polytetrafluoroethylene (PTFE) that may surround each filar 2124. The shield 2118 may then reside on the outer portion of the inner jacket 2122, and the outer jacket 2120 may then enclose the shield 2118. The outer jacket 2120 maybe added over the braid 2118, or it may be extruded over the braid.

For embodiments where it is desirable for the shield 2118 to RF couple to tissue, typically as a capacitive coupling, either as an alternative to grounding at the can of the IMD or in addition to grounding at the can, the amount of the outer jacket layer 2120 covering the shield 2118 may be relatively thin, such as on the order of 0.5 to 5 mils. Where the shield 2118 grounds at the can of the IMD and grounding via a capacitive coupling from the shield through the outer jacket

2120 directly to the tissue is of less significance, then the shield 2118 may be located further from the outer surface of the lead 2108.

The inner and outer jackets 2122, 2120 may be constructed of the same or similar materials such as various flexible and biocompatible polymers, examples of which are polyurethanes, and silicones. A lumen 2128 may be present inside of the inner jacket 2122 around which the insulated filars 2124 are coiled or otherwise positioned. The lumen 2128 may be useful, particularly for percutaneous leads 2108, to allow a stylet to be inserted for purposes of pushing and steering the lead 2108 into the desired position within the patient.

Figure 4C:
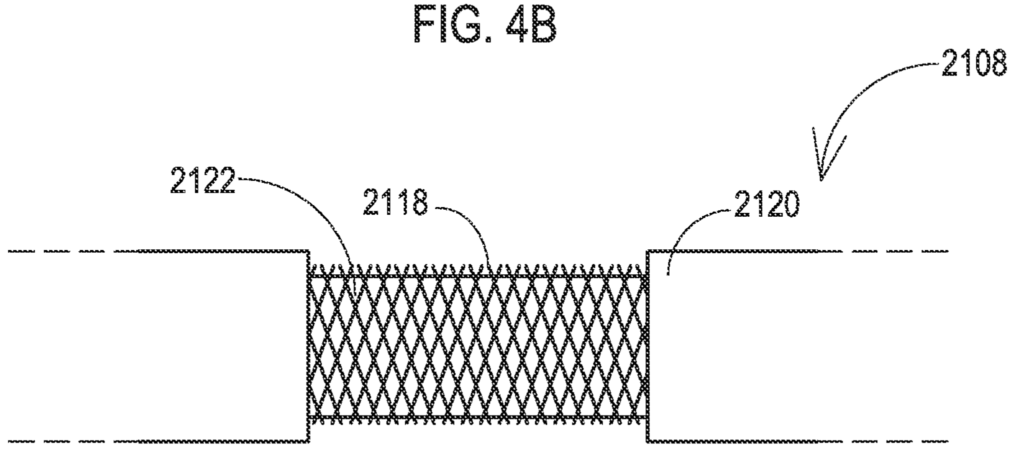
FIG. 4C shows an example of the implantable lead with a portion of the shield exposed near a proximal end of the implantable lead.

FIG. 4C shows one example of exposing the shield 2118 for purposes of grounding the shield 2118. In this example, the outer layer 2120 of the jacket has been removed at first point along the lead 2108 near the proximal end to expose the shield 2118 and the inner jacket 2122. For example, an excimer laser may be used to ablate the outer layer 2120. Physical contact may then be established between the shield 2118 and an electrode attached to the lead, a spring loaded connector or a connector block, a wire, or other direct current or capacitive coupling. For instance, a ground wire could be adhesively bonded with glue or tape in contact with the exposed shield 2118. Depending upon the embodiment, this first point along the lead where the shield 2118 is exposed may be located either inside or outside of the header of the IMD. Furthermore, depending upon the embodiment the coupling to the exposed shield 2118 may be a direct current coupling or a capacitive coupling, either providing a pathway for RF current to pass to ground.

Figure 4D:
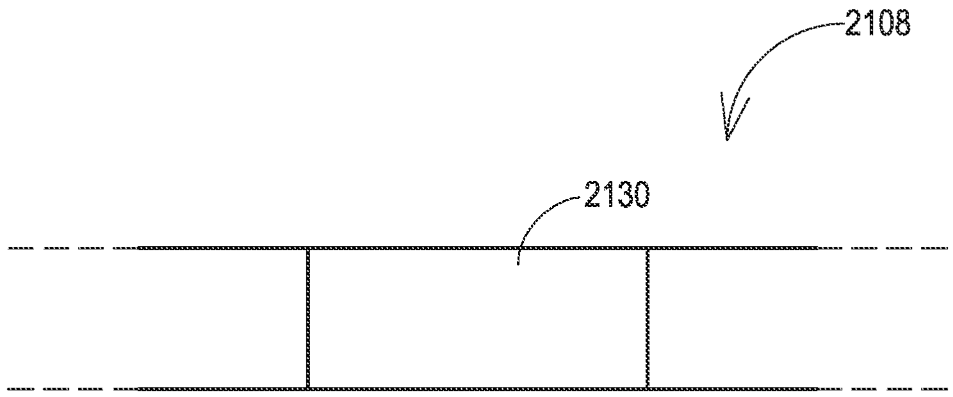
FIG. 4D shows an example of the implantable lead with an external electrode providing a coupling to the shield.

FIG. 4D shows another example of providing a pathway to ground the shield 2118. Here, an electrode 2130 is attached at the first point along the lead 2108 near the proximal end to provide a robust physical connection to a spring loaded connector, a connector block, a wire, or other direct current or capacitive coupling. Depending upon the embodiment, this first point along the lead where the electrode 2130 is positioned may be located either inside or outside of the header of the IMD. Furthermore, depending upon the embodiment a coupling to the electrode 2130 may be a direct current coupling or a capacitive coupling, either providing a pathway for RF current to pass to ground.

FIGS. 5A-5C show embodiments of grounding the shield to the can of the IMD by using a connector block mounted on the IMD and coupling a grounding path to the shield outside of a header of the IMD. The implantable medical system 2150 includes an IMD 2152 having a metal can 2154 and a header 2156. One or more leads 2164 extend from the header and pass through a connector block 2158 that is mounted to the can 2154.

The connector block 2158 includes features to ground the shield of the lead 2164 to the can 2154, such as a connector 2160 and a can attachment 2162. For instance, the connector block 2158 may be constructed of a biocompatible plastic or other non-conductor while the connector 2160 provides conduction to the can attachment 2162. The can attachment 2162 may be of various forms. For example, a wire that extends from the connector 2160 to the can 2154 where the can attachment 2162 is welded or otherwise affixed to the can 2154. As another example, the connector block 2158 may include a metal plate that contacts the metal can 2154 via a weld or other attachment.

FIG. 5B is a side view showing a pair of pass-through features of the connector block 2158 and a pair of leads 2164 having shields to be grounded. The connector block 2158 is shown in a cross-section so that a set screw 2168 is visible. The electrode or other contact for the shield of the lead 2164 is positioned within the pass-through 2166 such that the set screw 2168 and the electrode or other contact for the shield are aligned. The set screw 2168 is tightened against the electrode or other contact to establish the ground to the can 2154. The pass-through 2166 may be a slot through the connector block 2158 so that the lead 2164 can be lowered into the slot. As another option, the pass-through 2166 may be a bore through the connector block 2158 and the lead 2164 is fed through the bore.

FIG. 5C is a side view showing a pair of pass-through features of another embodiment of the connector block 2158 and a pair of leads 2164 having shields to be grounded. The connector block 2158 includes spring loaded connectors 2172. The electrode or other contact for the shield of the lead 2164 is positioned within the pass-through 2170 such that the spring loaded connector 2172 and the electrode or other contact for the shield are aligned. The electrode or other contact to the shield is forced within the spring loaded connector 2172 to establish the ground to the can 2154. As with the embodiment of FIG. 5B, the pass-through 2170 of this embodiment may be a slot through the connector block 2158 so that the lead 2164 can be lowered into the slot or may be a bore through the connector block 2158 where the lead 2164 is fed through the bore.

FIG. 6 shows one example of a spring loaded connector 2174. The spring loaded connector 2174 can open slightly when forced by insertion of the lead 2164 and then is biased back against the electrode or other contact of the lead 2164 once the lead is seated within the spring loaded connector 2174. Other spring loaded connector designs are also applicable.

Figure 7A:
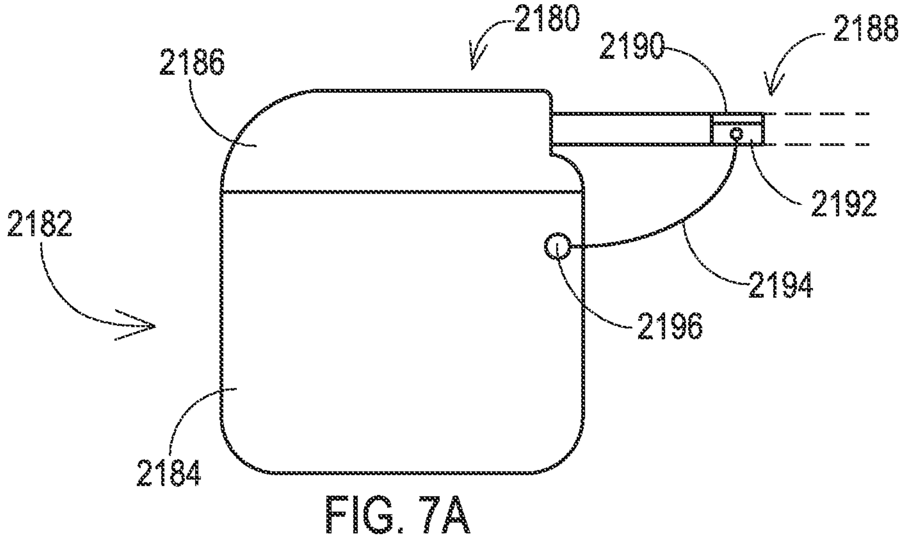
FIGS. 7A-7C show side views of embodiments of an implantable medical system where the shield is grounded with an external wire to the can over a direct current pathway.

FIG. 7A shows an implantable medical system 2180 where the shield of a lead 2188 is being grounded to a metal can 2184 of an IMD 2182 externally of the header 2186. Here, a direct current pathway is being provided between the shield and the metal can 2184. A spring loaded connector 2192 contacts an electrode 2190 on the lead 2188 where the electrode 2190 is in contact with the shield. A wire 2194 may be made from materials such as titanium, tantalum, platinum, stainless steel, nickel chromium, and alloys, and serves as a ground conductor. This wire 2194 is attached to the spring loaded connector 2192 by a weld or other bond. The wire 2194 extends from the spring loaded connector 2192 to the metal can 2184 where a weld 2196 or other bond such as with glue or tape attaches the wire 2194 to the metal can 2184.

Figure 7B:
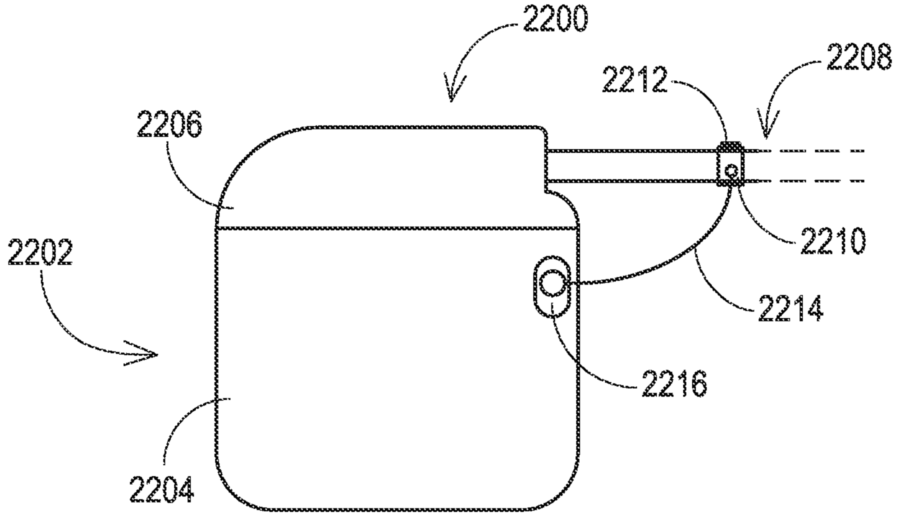

FIG. 7B shows an implantable medical system 2200 where the shield of a lead 2208 is being grounded to a metal can 2204 of an IMD 2202 externally of the header 2206. Here, a direct current pathway is also being provided between the shield and the metal can 2204. A metal connector block 2210 having a set screw 2212 contacts an electrode on the lead 2208 where the electrode is in contact with the shield. A wire 2214 serving as a ground conductor is attached to the connector block 2210 by a weld or other bond. The wire 2214 extends from the connector block 2212 to the metal can 2204 where glue 2216, such as a conductive epoxy or carbon filled polymer adhesive, or other bond such as a weld or tape attaches the wire 2214 to the metal can 2204.

Figure 7C:
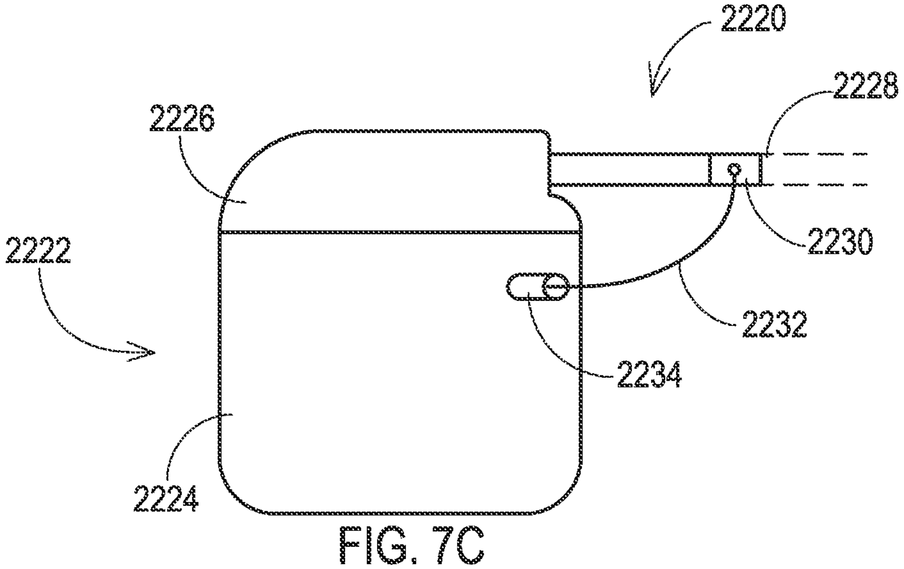

FIG. 7C shows an implantable medical system 2220 where the shield of a lead 2228 is being grounded to a metal can 2224 of an IMD 2222 externally of the header 2226. Here, a direct current pathway is also being provided between the shield and the metal can 2224. A coupling 2230 such as a ring electrode is in contact with the shield. A wire 2232 serving as a ground conductor is attached to the coupling 2230 by a weld or other bond. The wire 2232 extends from the coupling 2230 to the metal can 2224 where a crimp connector 2234 or other bond such as a weld or tape attaches the wire 2232 to the metal can 2224.

For the examples of FIGS. 7A-7C, various examples of connecting the grounding wire to the lead and to the can are disclosed. It will be appreciated that any combination of these and other examples of connections of the ground wire may be used to provide the direct current pathway that ultimately provides an RF ground from the shield to the metal can.

Figure 8A:
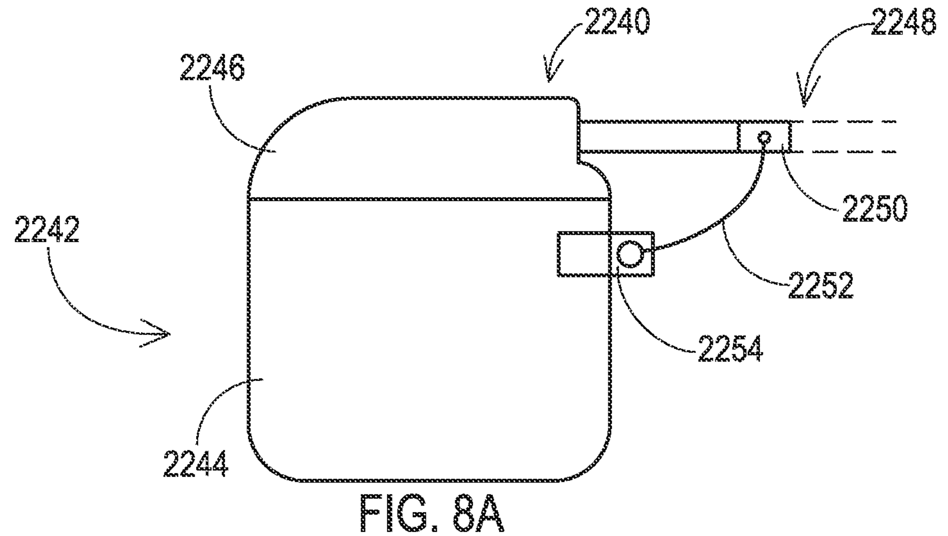
FIGS. 8A-8C show side views of embodiments of an implantable medical system where the shield is grounded with an external wire to the can over a capacitively coupled pathway.

FIG. 8A shows an implantable medical system 2240 where the shield of a lead 2248 is being grounded to a metal can 2244 of an IMD 2242 externally of the header 2246. Here, a capacitively coupled pathway is being provided between the shield and the metal can 2244. A coupling 2250 such as a spring loaded connector or a ring electrode contacts the lead 2248 and is in contact with the shield. A wire 2252 serving as a ground conductor is attached to the coupling 2250 by a weld or other bond. The wire 2252 extends from the coupling 2250 to nearby the metal can 2244 where a piece of tape 2254 or other tab affixed to the can 2244 attaches to the wire 2252. The tape 2254, such as double-sided tapes, epoxies, or polymer based adhesive, or other tab holds the wire in proximity to the metal can 2244 to establish a capacitive coupling between the wire 2252 and the can 2244.

Figure 8B:
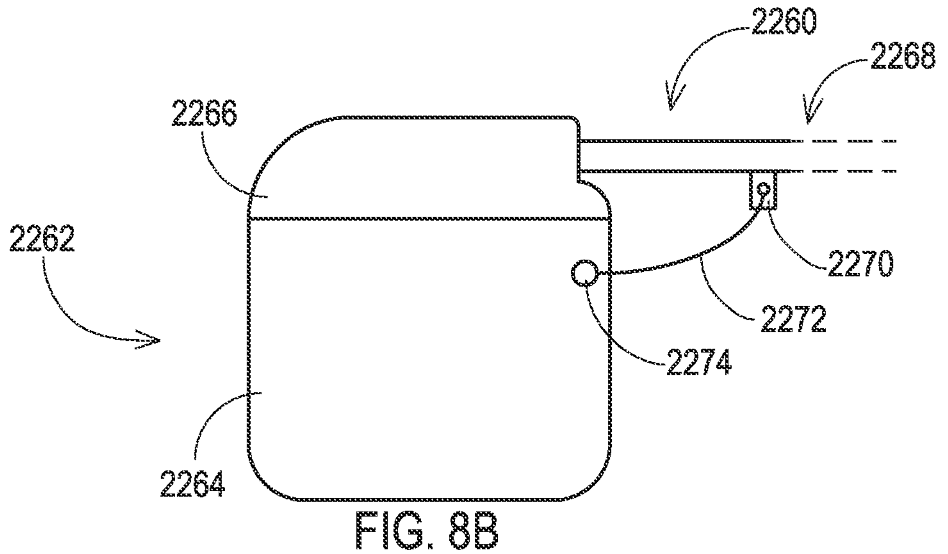

FIG. 8B shows an implantable medical system 2260 where the shield of a lead 2268 is being grounded to a metal can 2264 of an IMD 2262 externally of the header 2266. Here, a capacitively coupled pathway is being provided between the shield and the metal can 2264. A piece of tape 2270 or other tab contacts the lead 2268 at a point where the shield is present. A wire 2272 serving as a ground conductor is attached to the tab 2270 and is held nearby the lead 2268 and shield to establish a capacitive coupling between the wire 2272 and the shield. The wire 2272 extends from the tab 2270 to the metal can 2264 and is affixed to the metal can 2264 with a weld 2274 or other bond.

Figure 8C:
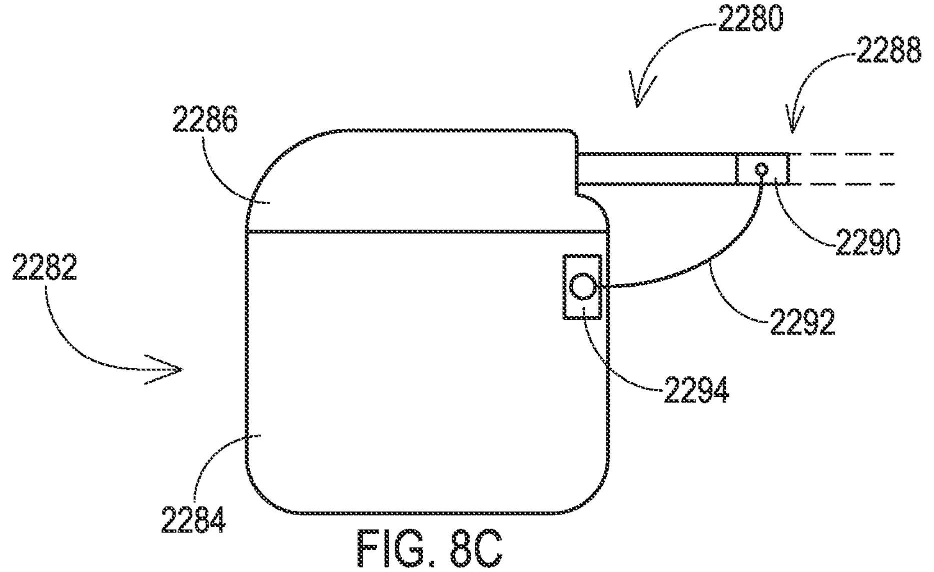

FIG. 8C shows an implantable medical system 2280 where the shield of a lead 2288 is being grounded to a metal can 2284 of an IMD 2282 externally of the header 2286. Here, a capacitively coupled pathway is being provided between the shield and the metal can 2284. A coupling 2290 such as a spring loaded connector or a ring electrode contacts the lead 2288 and is in contact with the shield. A wire 2292 serving as a ground conductor is attached to the coupling 2290 by a weld or other bond and extends from the coupling 2290 to nearby the metal can 2284. Non-conductive glue or another non-conductive bond 2294 to the can 2284 is present to adhere to the wire 2292 and hold the wire in proximity to the metal can 2284 to establish a capacitive coupling between the wire 2292 and the can 2284.

For the examples of FIGS. 8A-8C, various examples of connecting the grounding wire to the lead and to the can are disclosed, using combinations of direct current couplings and capacitive couplings. It will be appreciated that any combination of these and other examples of direct current coupling and capacitive coupling connections of the ground wire may be used to provide the capacitively coupled pathway that ultimately provides an RF ground from the shield to the metal can.

Figure 9A:
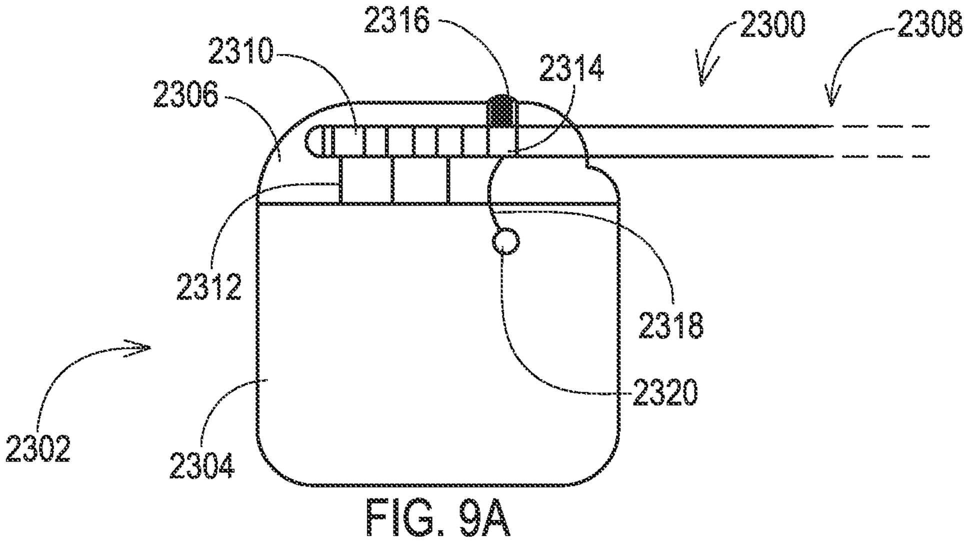
FIGS. 9A-9F show side views of embodiments of an implantable medical system where the shield is grounded within a header of the IMD to the can.

FIG. 9A shows an implantable medical system 2300 where the shield of a lead 2308 is being grounded to a metal can 2304 of an IMD 2302 within the header 2306. Proximal electrodes 2310 of the lead 2308 are electrically connected via wires 2312 to the IMD 2302. Here, a direct current coupled pathway is being provided between the shield and the metal can 2304. A coupling 2314 such as a spring loaded connector or a ring electrode contacts the lead 2308 and is in contact with the shield. A set screw 2316 may be present to further hold the proximal end of the lead 2308 in place within the header 2306. A wire 2318 serving as a ground conductor is attached to the coupling 2314 by a weld or other bond and extends from the coupling 2314 to the metal can 2304 where a weld 2320 or other bond holds the wire 2318 to the can 2304.

Figure 9B:
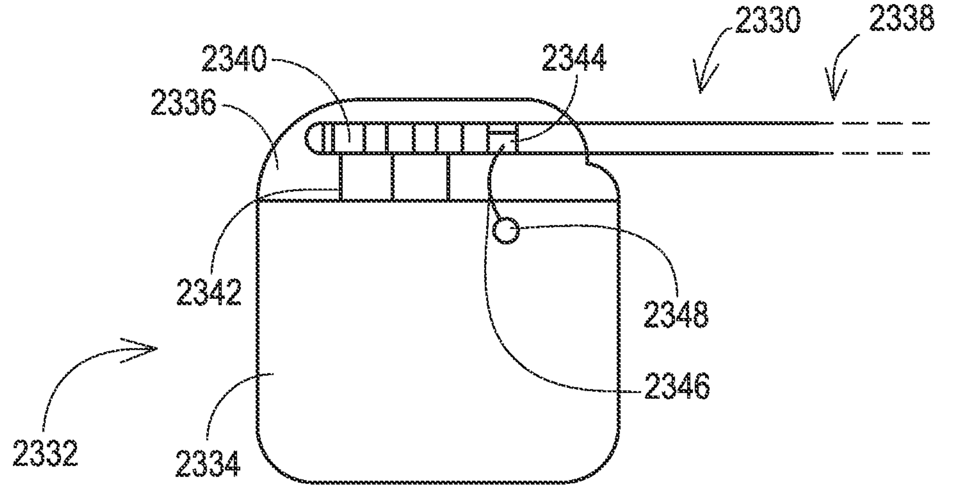

FIG. 9B shows an implantable medical system 2330 where the shield of a lead 2338 is being grounded to a metal can 2334 of an IMD 2332 within the header 2336. Proximal electrodes 2340 of the lead 2338 are electrically connected via wires 2342 to the IMD 2302. Here, a direct current coupled pathway is being provided between the shield and the metal can 2334. A coupling 2344 such as a spring loaded connector or a ring electrode contacts the lead 2338 and is in contact with the shield. A wire 2346 serving as a ground conductor is attached to the coupling 2344 by a weld or other bond and extends from the coupling 2344 to the metal can 2334 where a weld 2348 or other bond holds the wire 2346 to the can 2334.

Figure 9C:
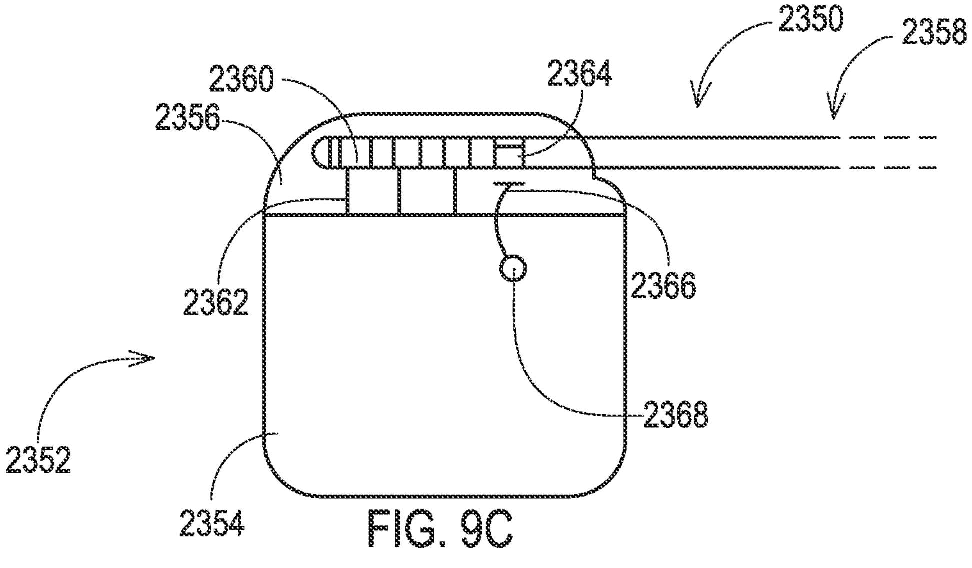

FIG. 9C shows an implantable medical system 2350 where the shield of a lead 2358 is being grounded to a metal can 2354 of an IMD 2352 within the header 2356. Proximal electrodes 2360 of the lead 2358 are electrically connected via wires 2362 to the IMD 2352. Here, a capacitively coupled pathway is being provided between the shield and the metal can 2354. A coupling 2364 such as a spring loaded connector or a ring electrode contacts the lead 2358 and is in contact with the shield. A wire 2366 serving as a ground conductor is capacitively coupled to the coupling 2364 within the header 2356 by the header structure holding the wire in proximity to the coupling 2364. The wire 2366 extends from the capacitive coupling to the metal can 2354 where a weld 2368 or other bond holds the wire 2366 to the can 2354.

Figure 9D:
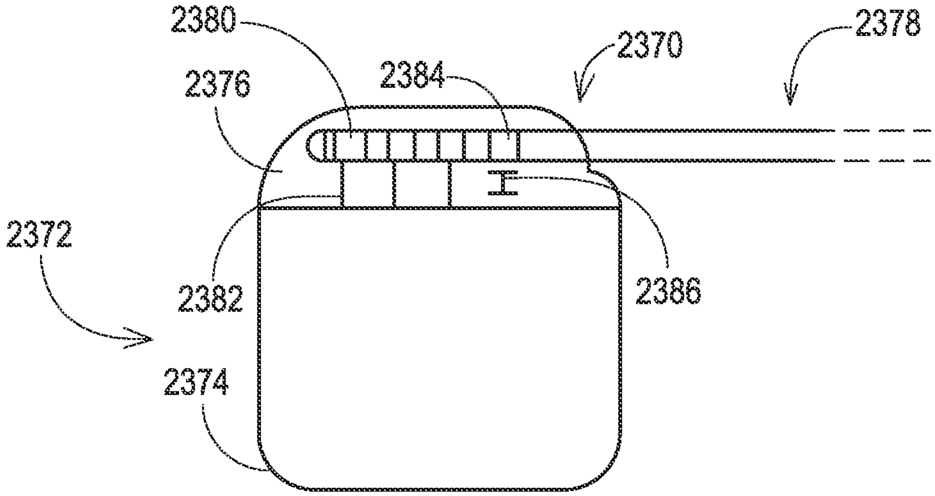

FIG. 9D shows an implantable medical system 2370 where the shield of a lead 2378 is being grounded to a metal can 2374 of an IMD 2372 within the header 2376. Proximal electrodes 2380 of the lead 2378 are electrically connected via wires 2382 to the IMD 2372. Here, a capacitively coupled pathway is being provided between the shield and the metal can 2374. A coupling 2384 such as a spring loaded connector or a ring electrode contacts the lead 2378 and is in contact with the shield. A wire 2386 serving as a ground conductor is capacitively coupled to the coupling 2384 within the header 2376 by the header structure holding the wire in proximity to the coupling 2384. The wire 2386 extends from the capacitive coupling toward the metal can 2374 and is capacitively coupled to the can 2374 within the header 2376 by the header structure holding the wire in proximity to the can 2374.

Figure 9E:
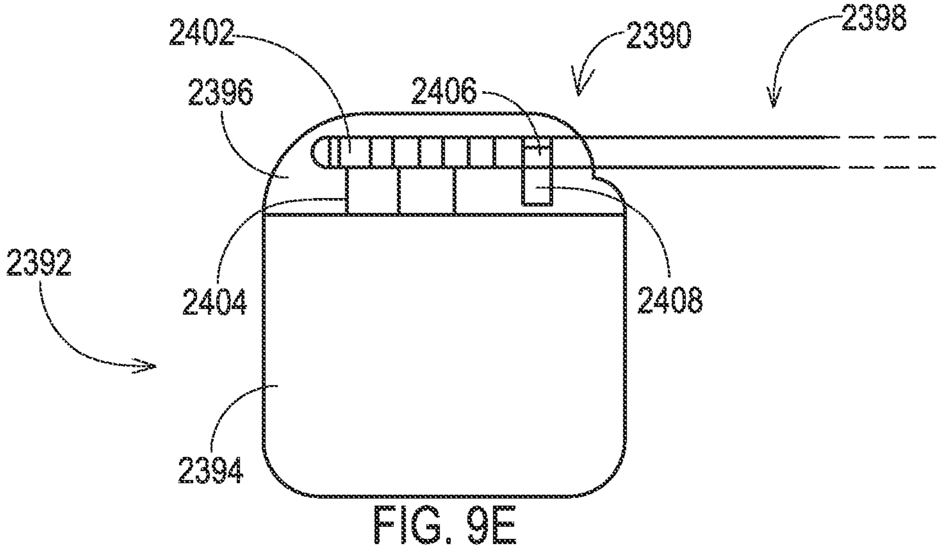

FIG. 9E shows an implantable medical system 2390 where the shield of a lead 2398 is being grounded to a metal can 2394 of an IMD 2392 within the header 2396. Proximal electrodes 2402 of the lead 2398 are electrically connected via wires 2404 to the IMD 2392. Here, a capacitively coupled pathway is being provided between the shield and the metal can 2394. A coupling 2406 such as a spring loaded connector or a ring electrode contacts the lead 2398 and is in contact with the shield. A shunt plate such as a tab 2408 or similar structure serving as a ground conductor extends from the coupling 2406 toward the can 2394 and is capacitively coupled to the can 2394 within the header 2396 by the header structure holding the tab 2408 in proximity to the can 2394.

Figure 9F:
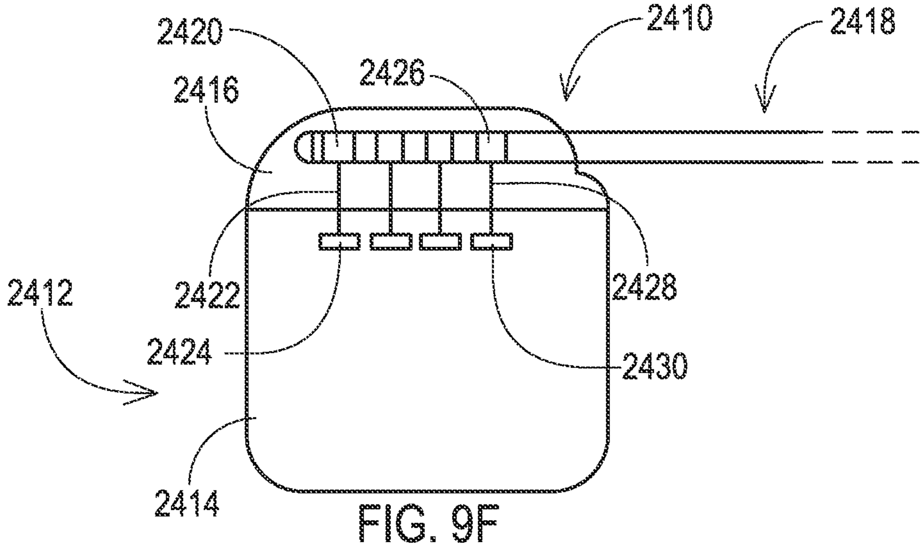

FIG. 9F shows an implantable medical system 2410 where the shield of a lead 2418 is being grounded to a metal can 2414 of an IMD 2412 within the header 2416. Proximal electrodes 2420 of the lead 2418 are electrically connected via wires 2422 to the IMD 2412. Within the can 2414, filter feed through (FFT) circuits 2424 are present to capacitively couple the wires 2422 to the metal can 2414 while allowing connection of the wires 2422 to stimulation circuits. The FFT circuits 2424 for the electrodes 2420 protects the IMD 2412 from electromagnetic background noise picked up by the filars, albeit potentially less noise due to the presence of the shield.

Here, a capacitively coupled pathway is being provided between the shield and the metal can 2414 also via an FFT circuit 2430. A coupling 2426 such as a spring loaded connector or a ring electrode contacts the lead 2418 and is in contact with the shield. A wire 2428 serving as a ground conductor extends from the coupling 2426 toward the can 2414 and terminates at the FFT circuit 2430 to provide the capacitive coupling between the shield and the can 2414.

As shown, the coupling 2426 to the shield may be an existing electrode of the lead 2418 that provides stimulation signals to a filar within the lead 2418. In that case, the FFT circuit 2430 may provide capacitive coupling to the can for both the filar and the shield. In such a case, it may be desirable to capacitively couple the shield to the coupling 2426 so that relatively low frequency stimulation signals are not present on the shield but induced RF current on the shield has a pathway to the FFT circuit 2430. For example, the outer jacket may separate the shield from the electrode by a separation on the order of 0.5-5 mils to allow an RF coupling to occur. As an alternative to using the same coupling and FFT circuit for both the shield and the filar, the shield may be provided a dedicated coupling 2426 and a dedicated FFT circuit 2430 that are independent of any electrodes and filars within the lead 2418.

For the examples of FIGS. 9A-9F, various examples of connecting the grounding conductor to the lead and to the can within the header are disclosed, using combinations of direct current couplings and capacitive couplings. It will be appreciated that any combination of these and other examples of direct current coupling and capacitive coupling connections of the ground conductor may be used to provide the capacitively coupled pathway that ultimately provides an RF ground from the shield within the header to the metal can. For instance, a capacitive coupling may be provided in any of the various embodiments at the coupling to the shield as discussed above in relation to FIG. 9F.

Figure 10A:
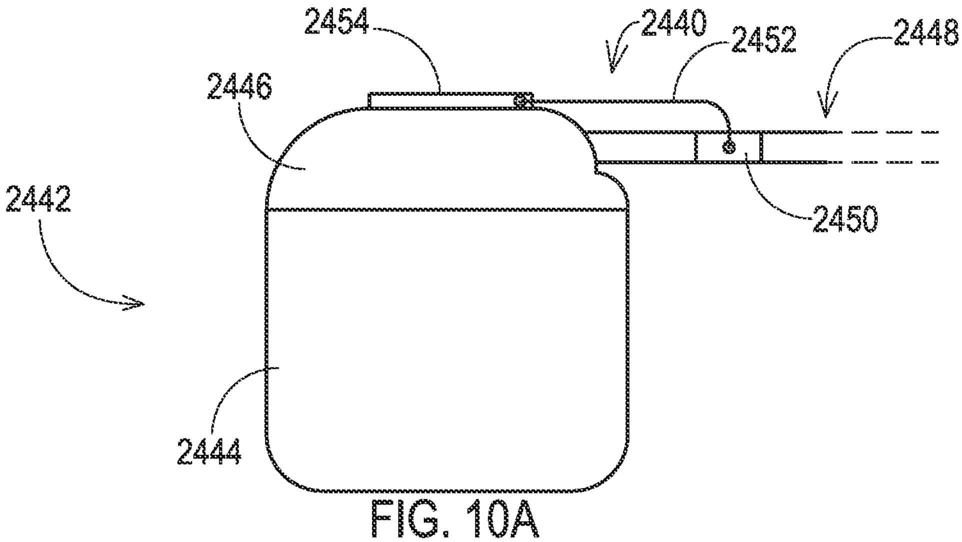
FIGS. 10A-10C show side views of embodiments of an implantable medical system where the shield is grounded to a ground plate on the header of the IMD.

FIG. 10A shows an implantable medical system 2440 where the shield of a lead 2448 is being grounded to a metal can 2444 of an IMD 2442 outside of the header 2446. Here, a ground pathway is being provided between the shield and a ground plate 2454 installed on the header 2446. The ground plate provides a relatively large surface area in comparison to an individual electrode and allows for safe dissipation of induced RF current on the shield in the same manner as grounding to the can 2444. A coupling 2450 such as a spring loaded connector or a ring electrode contacts the lead 2448 and is in contact with the shield. A wire 2452 that serves as a ground conductor is attached to the coupling 2450 by a weld or other bond and extends from the coupling 2450 to the ground plate 2454 where a weld or other bond holds the wire 2452 to the ground plate 2454.

Figure 10B:
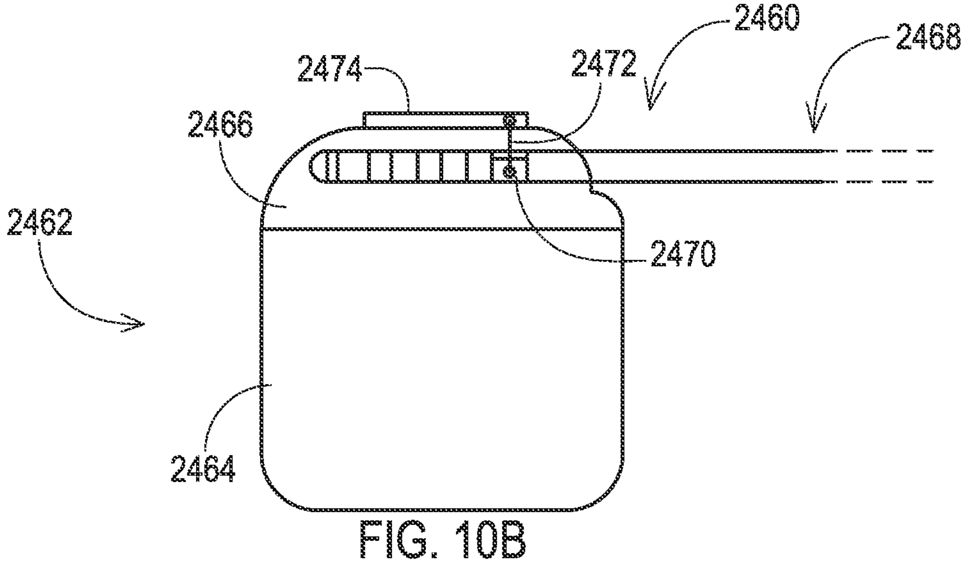

FIG. 10B shows an implantable medical system 2460 where the shield of a lead 2468 is being grounded to a metal can 2464 of an IMD 2462 within the header 2466. Here, a ground pathway is also being provided between the shield and a ground plate 2474 installed on the header 2466. A coupling 2470 such as a spring loaded connector or a ring electrode contacts the lead 2468 and is in contact with the shield. A wire 2472 that serves as a ground conductor is attached to the coupling 2470 by a weld or other bond and extends from the coupling 2470 to the ground plate 2474 where a weld or other bond holds the wire 2472 to the ground plate 2474.

Figure 10C:
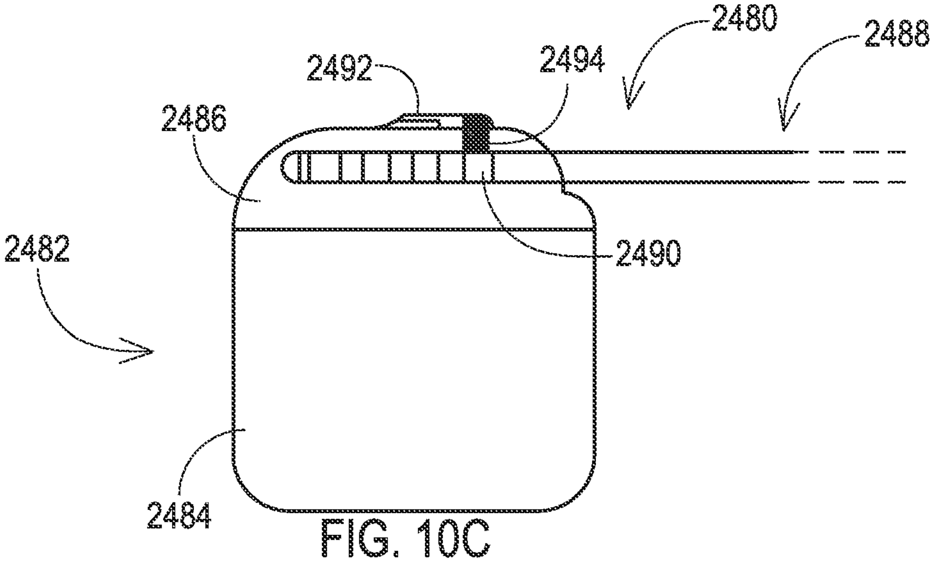

FIG. 10C shows an implantable medical system 2480 where the shield of a lead 2488 is being grounded to a metal can 2484 of an IMD 2482 within the header 2486. Here, a ground pathway is being provided between the shield and a connector block 2492 with a relatively large surface area that also acts as a ground plate installed on the header 2486. In this example, the connector block 2492 is a set screw block that uses a set screw 2494 to tighten against a coupling 2490 on the lead 2488. The coupling 2490 such as a ring electrode contacts the lead 2448 and is in contact with the shield. A set screw 2494 extends from the coupling 2490 and through the connector block 2492 and acts as a ground conductor to provide the ground pathway from the shield to the connector block 2492. Other conductive features may also be present within the connector block 2492 to contact the coupling 2490 and provide the RF ground pathway.

For the examples of FIGS. 10A-10C, various examples of connecting the grounding conductor to the lead and to the ground plate are disclosed. It will be appreciated that any combination of direct current coupling and capacitive coupling connections may be used to provide the pathway that ultimately provides an RF ground from the shield to the ground plate. For instance, a capacitive coupling may be provided in any of the various embodiments at the coupling to the shield as shown in FIGS. 10A-10C and as discussed above in relation to FIG. 9F. Likewise, a capacitive coupling may be present between a ground conductor extending from the coupling to the shield and the ground plate.

Embodiments disclosed in relation to FIGS. 11-15E also provide for radio frequency (RF) grounding of a shield present within an implantable lead. The shield may be grounded in various ways such as directly to tissue at one or more points along the lead body. The pathway for grounding may be a direct current pathway or be capacitively coupled. The pathway for grounding may utilize an exposed or nearly exposed shield at one or more points along the lead body, metal conductors attached to the lead at one or more points, a jacket with a conductive doping at one more points, and so forth.

Figure 11:
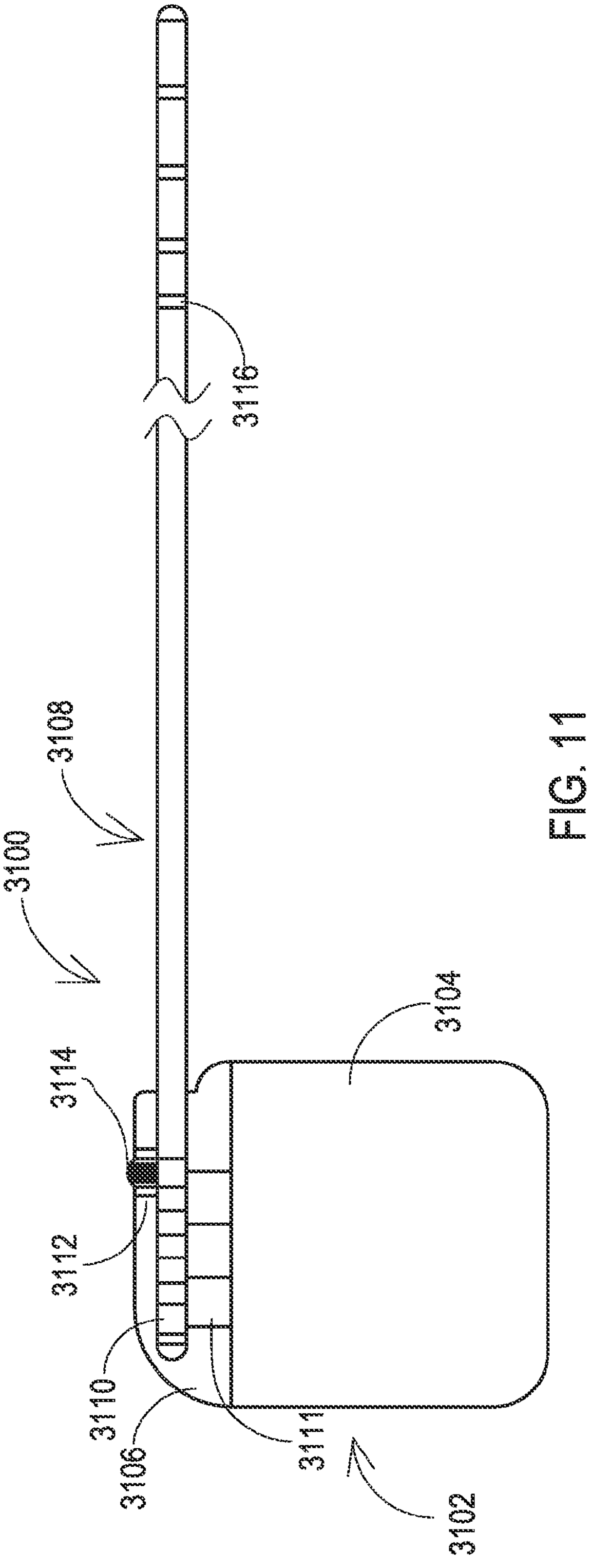
FIG. 11 shows an embodiment of an implantable medical system that includes an implantable medical device (IMD) coupled to a lead containing a shield.

FIG. 11 shows an example of an implantable medical system 3100 that includes an IMD 3102 coupled to a lead 3108. The IMD 3102 includes a metal can 3104, typically constructed of a medical grade titanium, such as grades 1-4, 5 or 9 titanium, or similar other biocompatible materials. The IMD 3102 includes a header 3106 typically constructed of materials such as polysulfone or polyurethane, that is affixed to the metal can 3104. The header 3106 is shown transparently for purposes of illustration. The header 3106 provides a structure for securing the lead 3108 to the IMD 3102 and for establishing electrical connectivity between circuitry of the IMD 3102 and electrodes of the lead 3108.

The lead 3108 includes electrodes 3116 on a distal end that are positioned at a stimulation site within a patient. The lead also includes connector rings 3110 on a proximal end that is positioned within the header 3106. The connector rings 3110 make physical contact with electrical connections 3111 within the header. The electrical connections 3111 may include a metal contact that the connector ring 3110 rests against upon being inserted into the header 3106 where a wire extends from the metal contact into the can 3104 where the circuitry is housed. Signals applied by the IMD 3102 to the connector rings 3110 are conducted through the lead 3108 to the electrodes 3116 to provide the stimulation therapy to the patient.

The lead 3108 is secured in the header 3106 such as by a set screw block 3112 within the header 3106 that allows at least one set screw 3114 to be tightened against at least one of the electrodes 3110. With the lead 3108 in place, the shield 3118 of the lead 3108 may then become grounded to the body along one or more points down the length of the lead from the IMD 3102.

Figure 12A:
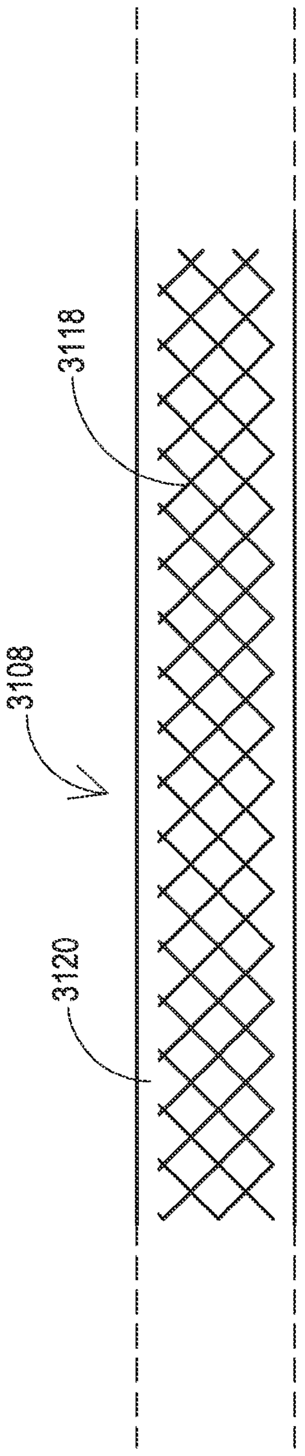
FIG. 12A shows an embodiment of an implantable lead with the shield revealed.
Figure 12B:
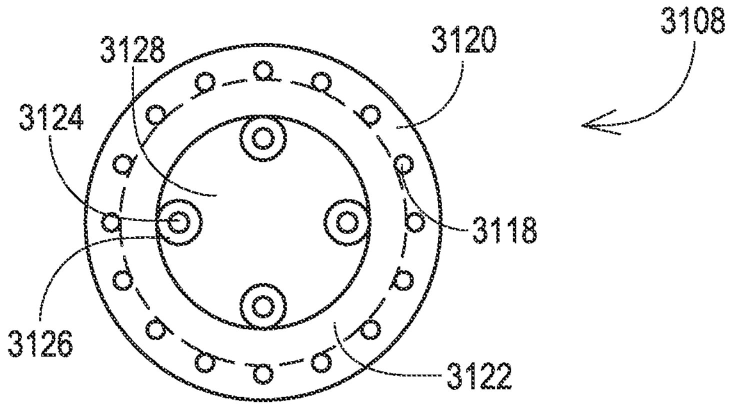
FIG. 12B shows the embodiment of the implantable lead in cross-section to reveal the shield and filars.

FIGS. 12A and 12B show an example of the lead 3108, where a shield 3118 is present. An outer jacket layer 3120 is shown transparently in FIG. 12A for purposes of illustrating the shield 3118. The shield 3118 blocks at least some RF energy from directly coupling to conductive filars 3124 that are present within the lead 3108. The conductive filars 3124 extend the length of the lead and interconnect the proximal electrodes 3110 to the distal electrodes 3116 so that stimulation signals are conducted from the proximal end to the distal end of the lead 3108.

As shown in FIG. 12A, the shield 3118 of this example is a braided metal wire. The metal wire may be constructed of various materials such as titanium, tantalum, niobium, platinum-iridium alloy, platinum, palladium, gold, stainless steel, and their alloys, or other metals. It may be desired to utilize a biocompatible metal for the shield 3118, particularly for embodiments where a portion of the shield 3118 may be exposed for purposes of grounding. While the shield 3118 is shown as a braid, other shield configurations may be chosen particularly where flexibility is not an issue such as a foil strip wrapped about the lead 3108 in an overlapping manner or an outer layer 3120 that is heavily doped with conductive particles.

As shown in FIG. 12B, the shield 3118 may be embedded within the jacket of the lead 3108. One manner of constructing the lead 3108 with the shield 3118 is to provide an inner jacket 3122 that encloses the filars 3124 and any additional insulation layer 3126, such as polytetrafluoroethylene (PTFE) that may surround each filar 3124. The shield 3118 may then reside on the outer portion of the inner jacket 3122, and the outer jacket 3120 may then enclose the shield 3118. The outer jacket 3120 maybe added over the braid 3118, or it may be extruded over the braid.

For embodiments where it is desirable for the shield 3118 to RF couple to tissue, typically as capacitive coupling, either as an alternative to grounding at the can of the IMD or in addition to grounding at the can, the amount of the outer jacket layer 3120 covering the shield 3118 may be relatively thin, such as on the order of 0.5 to 5 mils. Where the shield 3118 grounds at one or more specific locations along its length, via a direct current coupling or a capacitive coupling, the shield may be located further from the outer surface of the lead 3108 with additional features of the lead providing the coupling at the one or more specific locations as discussed below.

The inner and outer jackets 3122, 3120 may be constructed of the same or similar materials such as various flexible and biocompatible polymers, examples of which are polyurethanes, and silicones. A lumen 3128 may be included inside of the inner jacket 3122 around which the insulated filars 3124 are coiled or otherwise positioned. The lumen 3128 may be useful, particularly for percutaneous leads 3108, to allow a stylet to be inserted for purposes of pushing and steering the lead 3108 into the desired position within the patient.

Figure 12C:
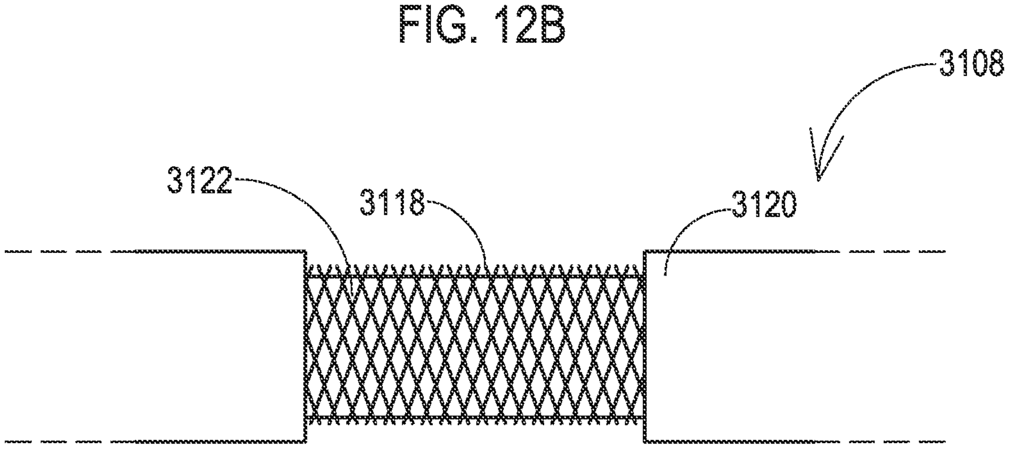
FIG. 12C shows an example of the implantable lead with a portion of the shield exposed at a point distant from the distal end of the lead.

FIG. 12C shows one example of exposing the shield 3118 at a particular point along the lead 3108 for purposes of grounding the shield 3118. In this example, the outer layer 3120 of the jacket has been removed at a first point along the lead 3108 distant from the distal end to expose the shield 3118 and the inner jacket 3122. For example, an excimer laser may be used to ablate the outer layer 3120. Physical contact may then be established between the shield 3118 and the tissue or between the shield 3118 and an electrode attached to the lead.

Figure 12D:
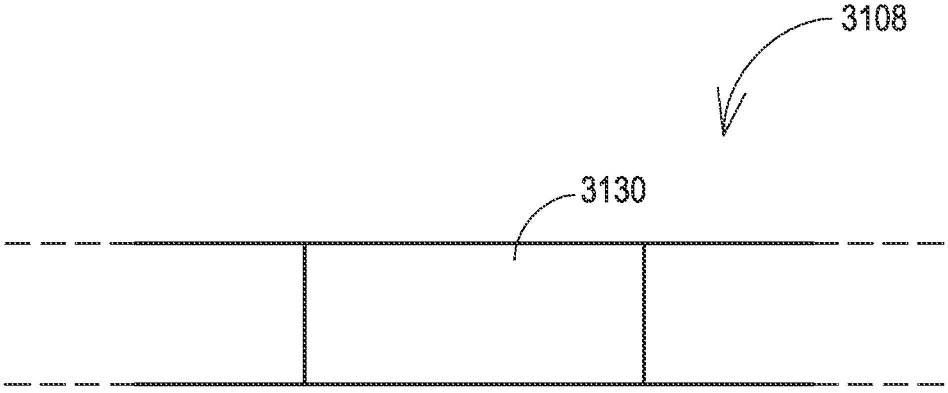
FIG. 12D shows an example of the implantable lead with an external electrode providing a coupling to the shield at a point distant from the distal end of the lead.

FIG. 12D shows another example of providing a pathway to ground the shield 3118. Here, a metal conductor, specifically a ring electrode 3130, is attached at the first point along the lead 3108 distant from the distal end to provide a robust physical connection to the tissue while avoiding tissue in-growth that may occur if the shield 3118 is exposed directly. Depending upon the embodiment, a coupling of the shield 3118 to the electrode 3130 may be a direct current coupling or a capacitive coupling, either providing a pathway for RF current to pass to ground. The ring electrode 3130 may be attached by methods such as crimping, clamping, welding, and the like.

Figure 12E:
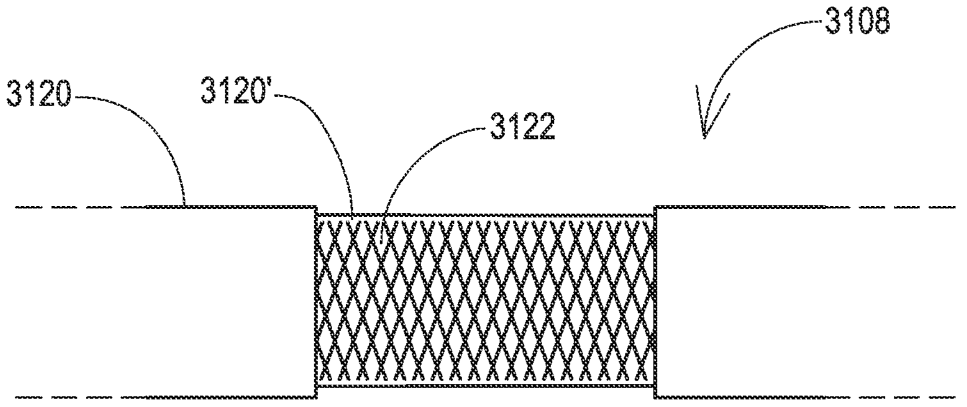
FIG. 12E shows an example of the implantable lead with a portion of the shield nearly exposed at a point distant from the distal end of the lead.

FIG. 12E shows an example of nearly exposing the shield 3118 at a particular point along the lead 3108 for purposes of grounding the shield 3118. In this example, the outer layer 3120 of the jacket has been almost entirely removed at a first point along the lead 3108 distant from the distal end to nearly expose the shield 3118 and the inner jacket 3122. Only a very thin layer 3120', on the order of about 0.5-5 mils, of the outer layer 3120 is remaining. Physical contact between the shield 3118 and the tissue is avoided so that tissue in-growth does not occur, and the shield 3118 capacitively couples to the tissue to provide the RF pathway to ground.

Figure 12F:
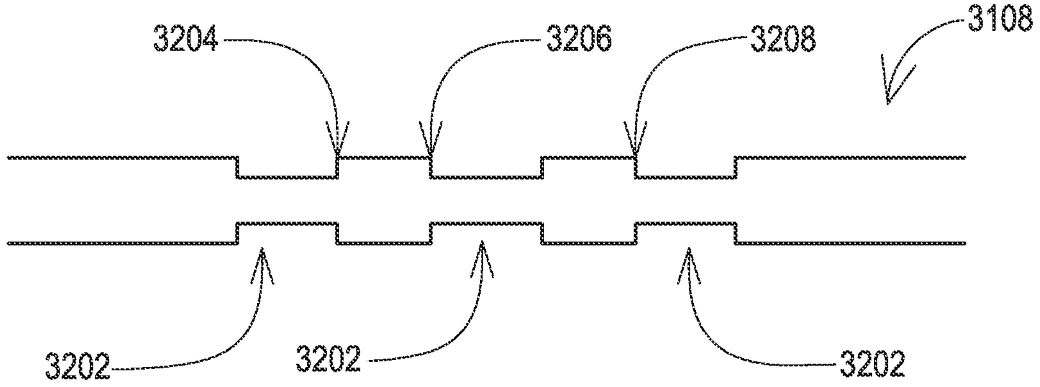
FIG. 12F shows an example of the implantable lead with a portion of the shield exposed or nearly exposed at a plurality of points distant from the distal end of the lead.

FIG. 12F shows an example of exposing, or nearly exposing, the shield 3118 at a plurality of points 3202 along the lead. At these points 3202, the outer layer 3120 has been at least partially ablated or otherwise removed to place the shield 3118 in closer proximity to the body tissue so that an RF pathway to ground is established. Where the shield 3118 is exposed, the RF pathway is a direct current coupling to the tissue. Where the shield 3118 is nearly exposed, the RF pathway is a capacitive coupling to the tissue.

Where multiple points of the RF pathway to ground are present, a particular separation of the multiple points is provided. A nearest edge-to-nearest edge distance between one point and an adjacent one is shown by the distance from edge 3204 to edge 3206. Where the outer layer is removed, the flexibility and strength of the lead is altered for the region including those points and this distance from edge 3204 to edge 3206 can be used to control the flexibility and strength.

Where multiple points of the RF pathway to ground are direct current couplings, another concern is current induced by the gradient magnetic fields present in a magnetic resonance (MR) scan. If the most proximal and most distal points of the direct current coupling are spaced too far apart, then the magnetic gradient may induce a dangerous current through the shield and produce a significant stimulation of tissue at those ground points along the lead. Therefore, choosing the nearest edge-to-nearest edge separation to fall within an illustrative range of 2 millimeters (mm) or more with a most proximal to most distal separation, such as edge 3204 to edge 3208, of about 40 centimeters (cm) or less may allow for flexibility of the lead in the region while maintaining small loops that prevent large magnetic gradient induced currents should the shield be exposed at the points 3202.

Figure 12G:
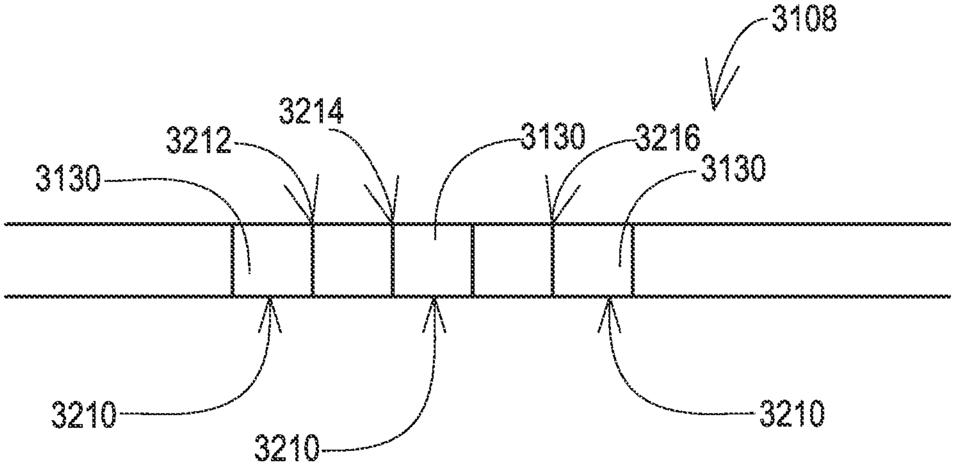
FIG. 12G shows an example of the implantable lead with a plurality of external electrodes providing a coupling to the shield at a plurality of points distant from the distal end of the lead.

FIG. 12G shows an example of coupling the shield 3118 to ground with a plurality of metal conductors such as rings 3130 at a plurality of points 3210 along the lead. At these points 3202, the outer layer 3120 has been at least partially ablated or otherwise removed to place the shield 3118 in close proximity with the metal conductors 3130 so that an RF pathway to ground is established through the metal conductors 3130. Where the shield 3118 is exposed to the metal conductors 3130, the RF pathway is a direct current coupling to the tissue. Where the shield 3118 is nearly exposed to the metal conductors 3130, the RF pathway is a capacitive coupling to the tissue.

As with the example of FIG. 12F, where multiple points of the RF pathway to ground are present, a particular separation of the multiple points is provided. A nearest edge-to-nearest edge distance between one point and an adjacent one is shown by the distance from edge 3212 to edge 3214. The flexibility and strength of the lead is altered for the region including those points, with the metal conductors 3130 limiting the bending in this region to essentially those sections of lead between the metal conductors 3130. Thus, in one example, a nearest edge-to-nearest edge distance may be maintained at or above 2 mm or 50% of the grounding ring length so that flexibility of the lead is maintained.

Also, where the shield 3118 is direct current coupled to the metal conductors 3130, a magnetic gradient induced current is of concern because the metal conductors 3130 have a direct current coupling to the tissue. In that case, the separation of the most proximal to the most distal may be kept within a range that prevents a large loop and avoids a large magnetic induced gradient current. In this particular example, the most proximal to the most distal distance, such as from edge 3212 to edge 3216, may be maintained at or below approximately 40 cm so that magnetic gradient induced currents are insignificant.

Figure 12H:
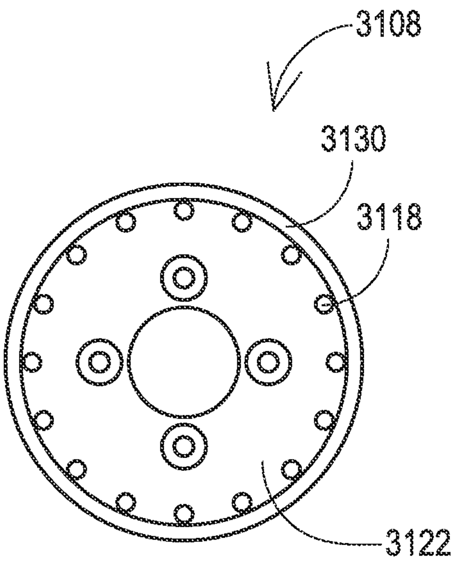
FIG. 12H shows the embodiment of the implantable lead in cross-section to reveal the shield and the external metal conductor in contact with the shield.

FIG. 12H shows a cross-section of the lead 3108 at a particular point where the outer jacket 3120 has been ablated or otherwise removed. In this example, the lead 3108 at this particular point includes a metal conductor 3130 with a direct current coupling to the shield 3118. The outer layer 3120 of the jacket has been removed to allow the metal conductor 3130, a ground ring as shown, to wrap around the lead and contact the shield 3118. The filars may be present within the inner jacket 3122 or any other inner layer as shown or within the lumen created by the inside wall of the inner jacket 3122 or any other inner layer as shown in FIG. 12B.

Figure 12J:
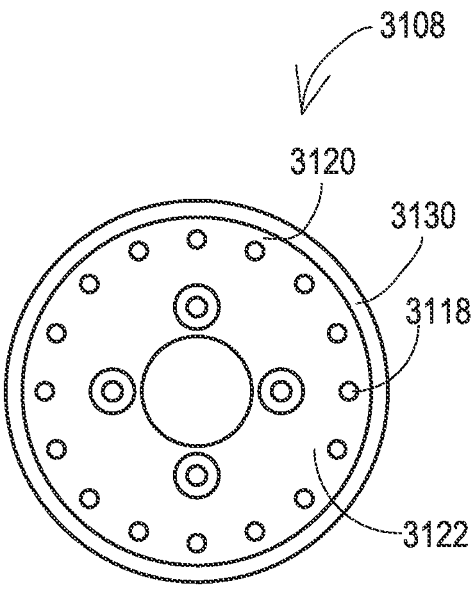
FIG. 12J shows the embodiment of the implantable lead in cross-section to reveal the shield and the metal conductor nearly contacting the shield.
Figure 12I:
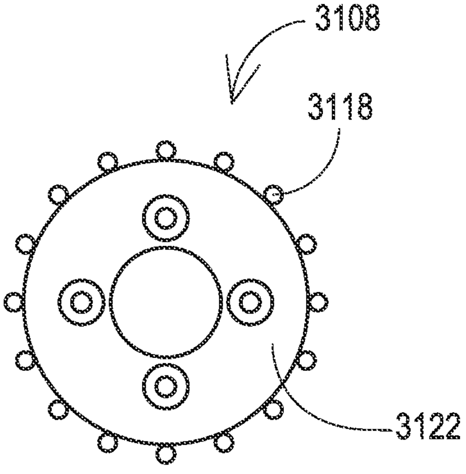
FIG. 12I shows the embodiment of the implantable lead in cross-section to reveal the exposed shield.

FIG. 12I shows a cross-section of the lead 3108 at a particular point where the outer jacket 3120 has been ablated or otherwise removed. In this example, the lead 3108 at this particular point has the shield 3118 exposed to tissue for a direct current coupling by entirely removing the outer layer 3120. The filars may be present within the inner jacket 3122 or any other inner layer as shown or within the lumen created by the inside wall of the inner jacket 3122 or any other inner layer as shown in FIG. 12B.

FIG. 12J shows a cross-section of the lead 3108 at a particular point where a portion of the outer jacket 3120 has been ablated or otherwise removed. In this example, the lead 3108 at this particular point includes a metal conductor 3130 with a capacitive coupling to the shield 3118. The outer layer 3120 of the jacket has been partially removed, with a remaining thickness of about 0.5 mils to 5 mils, to nearly expose the shield 3118. This allows the metal conductor 3130, a ground ring as shown, to wrap around the lead and capacitively couple with the shield 3118 at RF frequencies. The filars may be present within the inner jacket 3122 or any other inner layer as shown or within the lumen created by the inside wall of the inner jacket 3122 or any other inner layer as shown in FIG. 12B.

Figure 12K:
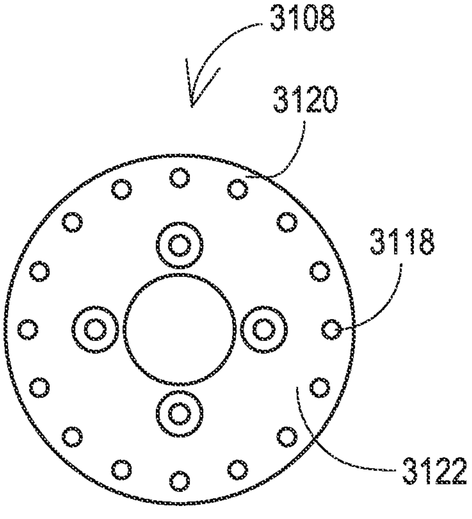
FIG. 12K shows the embodiment of the implantable lead in cross-section to reveal the nearly exposed shield.

FIG. 12K shows a cross-section of the lead 3108 at a particular point where a portion of the outer jacket 3120 has been ablated or otherwise removed. The outer layer 3120 of the jacket has been partially removed, with a remaining thickness of about 0.5 mils to 5 mils, to nearly expose the shield 3118. The shield 3118 capacitively couples to the tissue at RF frequencies. The filars may be present within the inner jacket 3122 or any other inner layer as shown or within the lumen created by the inside wall of the inner jacket 3122 or any other inner layer as shown in FIG. 12B.

Figure 13A:
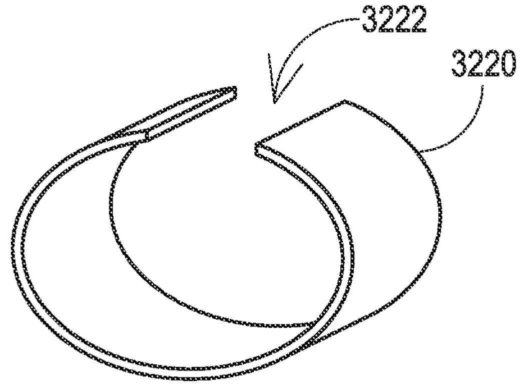
FIGS. 13A-13C show metal conductors of various types for attachment to a lead to provide a coupling to the shield.

FIG. 13A shows an example of a ring electrode 3220 that may be attached to a lead 3108 to form the RF pathway to ground from the shield 3118. The ring electrode may be constructed of platinum, platinum-iridium, titanium, tantalum, stainless steel, and other similar biocompatible metals. The ring electrode 3220 may have a gap 3222. The ring electrode 3220 may be sprung open to fit around the lead at the particular point where the jacket has been ablated, and the ring electrode 3220 is crimped back into a tightly fitting configuration. As another example, the ring electrode 3220 may be flat and then rolled into the ring shape about the lead. In some examples, the gap 3222 may close upon crimping while in other embodiments the gap 3222 may remain to some degree.

Figure 13B:
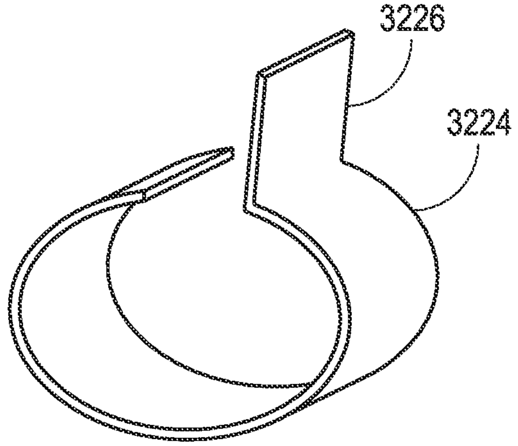

FIG. 13B shows an example of another ring electrode 3224 that may be attached to a lead 3108 to form the RF pathway to ground from the shield 3118. The ring electrode 3224 includes a tab 3226 that extends away from the lead to provide an additional surface area and extension into the tissue for adding grounding of the shield 3118. The ring electrode 3220 may be sprung open to fit around the lead at the particular point where the jacket has been ablated and the ring electrode 3220 is crimped back into a tightly fitting configuration. As in the previous example, the ring electrode 3224 may be flat and then rolled into the ring shape about the lead while maintaining a flat portion as the tab 3226.

Figure 13C:
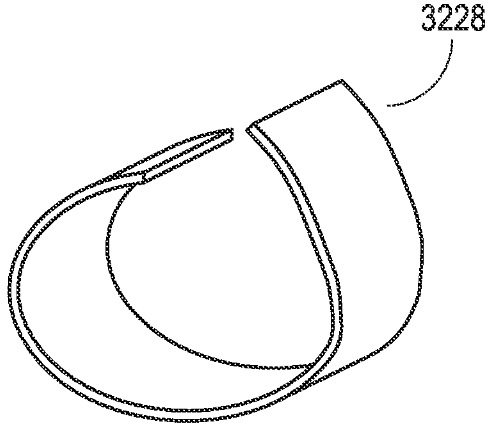

FIG. 13C shows an example of another ring electrode 3228 that may be attached to a lead 3108 to form the RF pathway to ground from the shield 3118. The ring electrode 3228 forms a helix. The ring electrode 3228 may be sprung open to fit around the lead at the particular point where the jacket has been ablated and the ring electrode 3228 is crimped back into a tightly fitting helical configuration. As in the previous examples, the ring electrode 3228 may be flat and then rolled into the helical ring shape about the lead.

Figure 13D:
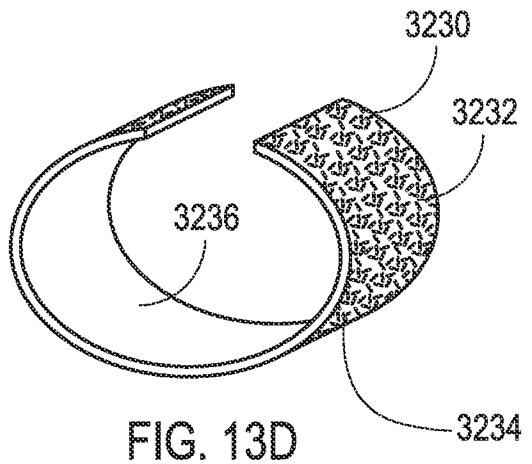
FIGS. 13D-13F show metal conductors having various configurations of non-conductive coatings for attachment to a lead to provide a coupling to the shield.

FIG. 13D shows an example of a ring electrode 3230 that may be attached to a lead 3108 to form the RF pathway to ground from the shield 3118. The ring electrode 3230 has an outer side 3234 that faces away from the shield 3118 and an inner side 3236 that faces toward the shield 3118 and may directly contact the shield 3118. In this example, the outer side 3234 has a non-conductive coating 3232 applied so that the outer side 3234 does not have a direct coupling to the tissue. The non-conductive coating may be of various types such as polyurethane, silicone or other biocompatible polymers.

The inner side 3236 may either have a direct current coupling or a capacitive coupling to the shield. With multiple ring electrodes 3230 in place on a lead, magnetic gradient induced current which is at a relatively low frequency is not a concern because the non-conductive coating 3232 prevents the relatively low frequency induced current from flowing to the tissue. Thus, the distance between adjacent electrodes is not limited by induced current concerns. Meanwhile, the high frequency RF induced current does ground to the tissue through the capacitive coupling provided by the non-conductive coating 3232.

Figure 13E:
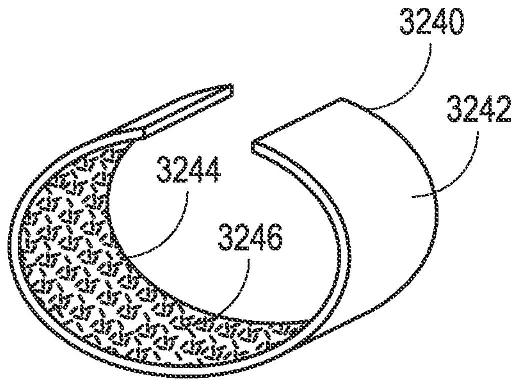

FIG. 13E shows an example of a ring electrode 3240 that may be attached to a lead 3108 to form the RF pathway to ground from the shield 3118. The ring electrode 3240 has an outer side 3242 that faces away from the shield 3118 and an inner side 3244 that faces toward the shield 3118 and may directly contact the shield 3118. In this example, the inner side 3244 has a non-conductive coating 3246 applied so that the inner side 3244 does not have a direct coupling to the shield 3118 even if the shield 3118 is entirely exposed to the ring electrode 3240. The non-conductive coating 3246 may be of the various types discussed above in the previous example.

The outer side 3242 may have a direct current coupling to the tissue. With multiple ring electrodes 3240 in place on a lead, magnetic gradient induced current is not a concern because the non-conductive coating prevents the relatively low frequency induced current from flowing from the shield 3118 to the ring electrode 3240. Thus, the distance between adjacent electrodes is not limited by induced current concerns. Meanwhile, the high frequency RF induced current does ground through the ring electrode 3240 to the tissue through the capacitive coupling provided by the non-conductive coating 3246.

Figure 13F:
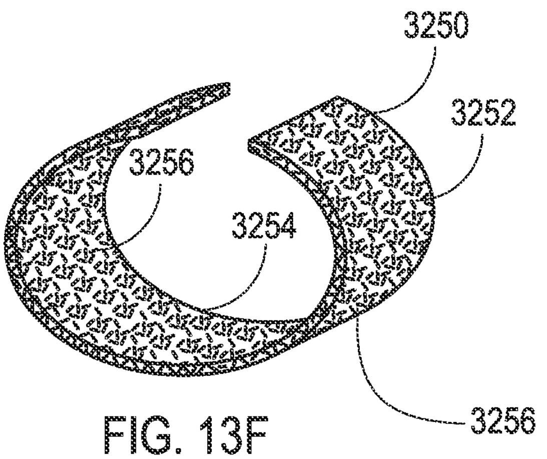

FIG. 13F shows an example of a ring electrode 3250 that may be attached to a lead 3108 to form the RF pathway to ground from the shield 3118. The ring electrode 3250 has an outer side 3252 that faces away from the shield 3118 and may directly contact the tissue and an inner side 3254 that faces toward the shield 3118 and may directly contact the shield 3118. In this example, both the inner side 3254 and the outer side 3252 have a non-conductive coating 3256 applied. The inner side 3254 does not have a direct current coupling to the shield 3118 even if the shield is entirely exposed to the ring electrode 3250. The outer side 3252 does not have a direct current coupling to the tissue even if in physical contact with the tissue. The non-conductive coating 3256 may be of the various types discussed above in the previous examples.

With multiple ring electrodes 3250 in place on a lead, magnetic gradient induced current is not a concern because the non-conductive coating prevents the relatively low frequency induced current from flowing from the shield 3118 to the ring electrode 3250. Thus, the distance between adjacent electrodes is not limited by induced current concerns. Meanwhile, the high frequency RF induced current does ground through the ring electrode 3250 to the tissue through the capacitive couplings on each side of the ring electrode 3250 provided by the non-conductive coating 3256.

While the examples of FIGS. 13A-13F show various shapes of ring electrodes, it will be appreciated that various other shapes are also applicable for metal conductors being attached to the lead to provide the RF ground pathway. Furthermore, while FIGS. 13D-13F show a particular ring electrode shape with a non-conductive coating, it will be appreciated that the non-conductive coating is applicable to either or both sides of any of the metal conductor configurations including those of FIGS. 13A-13C.

Figure 14A:
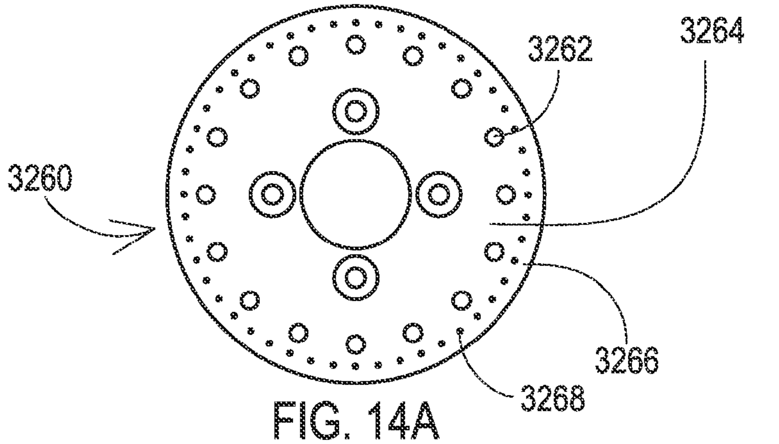
FIG. 14A shows the embodiment of the implantable lead in cross-section to reveal the shield and an outer doped jacket layer.

FIG. 14A shows a cross-section of a lead 3260 that includes an outer jacket layer 3266 that surrounds a shield 3262 and an inner jacket layer 3264. The outer jacket layer 3266 is doped with conductive particles 3268 at a particular point along the length of the lead. These conductive particles 3268 provide RF conductive qualities for the outer jacket layer 3266. Thus, the RF energy couples from the shield 3262 to the tissue through the doped outer jacket layer 3266. Examples of the conductive particles include carbon, tantalum, titanium, platinum, platinum-iridium, and other biocompatible conductive substances. The filars may be present within the inner jacket 3264 or any other inner layer as shown or within the lumen created by the inside wall of the inner jacket 3264 or any other inner layer like that shown in FIG. 12B.

Figure 14B:
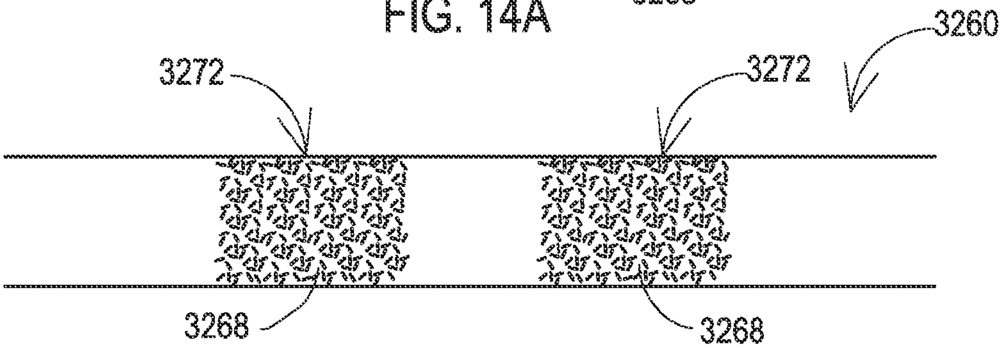
FIG. 14B shows the embodiment of the implantable lead with a plurality of points with the outer doped jacket layer.

FIG. 14B shows the lead 3260 with a plurality of points 3272 along the lead where the conductive particles 3268 are present within the outer layer 3266. The doped outer layer 3266 is exposed to create the RF pathway to ground from the outer layer 3266 to the tissue.

Figure 14C:
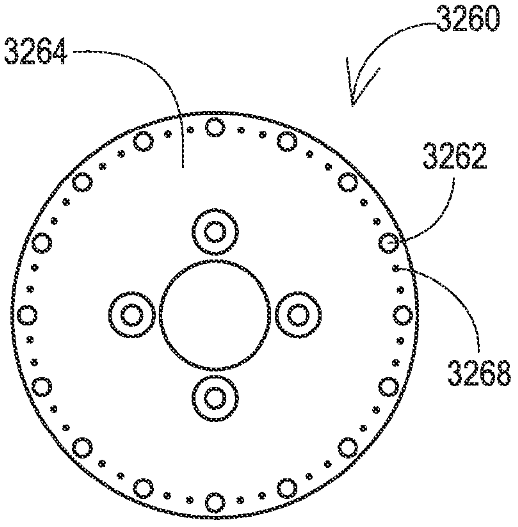
FIG. 14C shows an embodiment of the implantable lead in cross-section to reveal the shield and a doped jacket layer at the shield.

FIG. 14C shows a cross-section of a lead 3260 where the outer jacket layer 3266 that surrounds a shield 3262 has been removed via ablation or other technique to expose the shield 3262 and the inner jacket layer 3264. Here, the inner jacket layer 3264 is doped with conductive particles 3268 at least at the particular point(s) along the length of the lead where the outer layer 3266 has been removed. These conductive particles 3268 provide RF conductive qualities for the outer portion of the inner jacket layer 3264 where the shield 3262 is present. Thus, the RF energy couples from the shield 3262 to the tissue through the doped jacket layer 3264. The filars may be present within the inner jacket 3264 or any other inner layer as shown or within the lumen created by the inside wall of the inner jacket 3264 or any other inner layer like that shown in FIG. 12B.

Figure 14D:
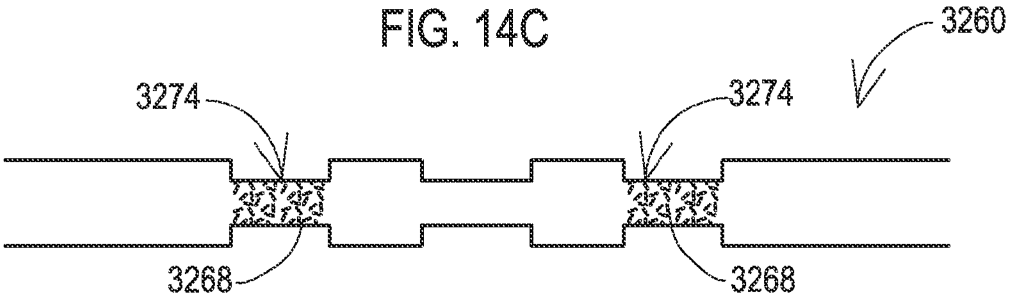
FIG. 14D shows the embodiment of the implantable lead with a plurality of points with the doped jacket layer at the shield.

FIG. 14D shows the lead 3260 with a plurality of points 3274 along the lead where the conductive particles 3268 are present within the inner layer 3264. The outer layer 3266 is removed at these points 3274 to expose the doped inner layer 3264 and to create the RF pathway to ground from the inner layer 3264 to the tissue.

Figure 15A:
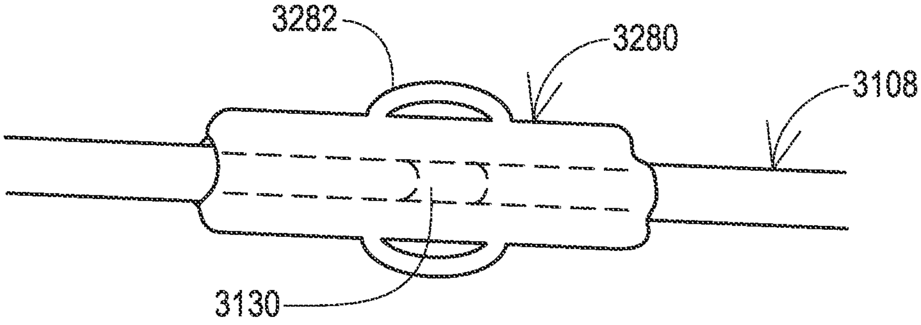
FIG. 15A shows an embodiment of the implantable lead having a lead anchor coupled to a metal conductor to provide the RF pathway to ground.
Figure 15B:
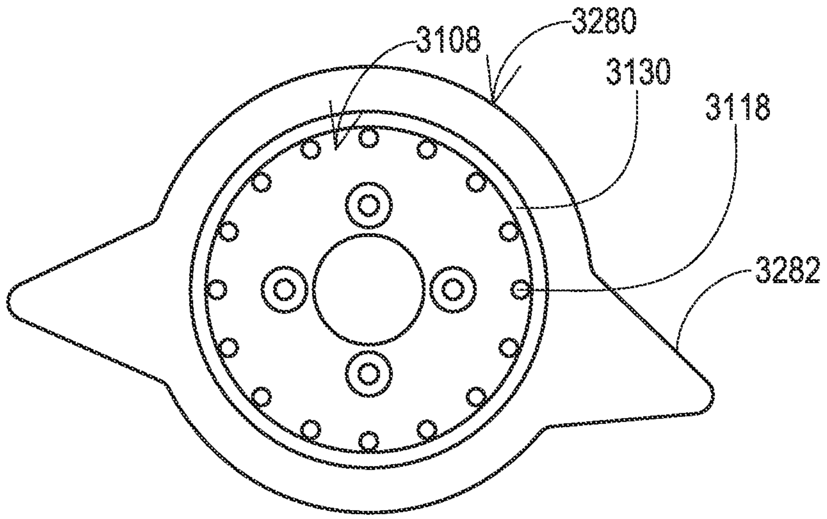
FIG. 15B shows the embodiment of the implantable lead in cross-section to reveal the shield, the metal conductor, and the lead anchor.
Figure 16:
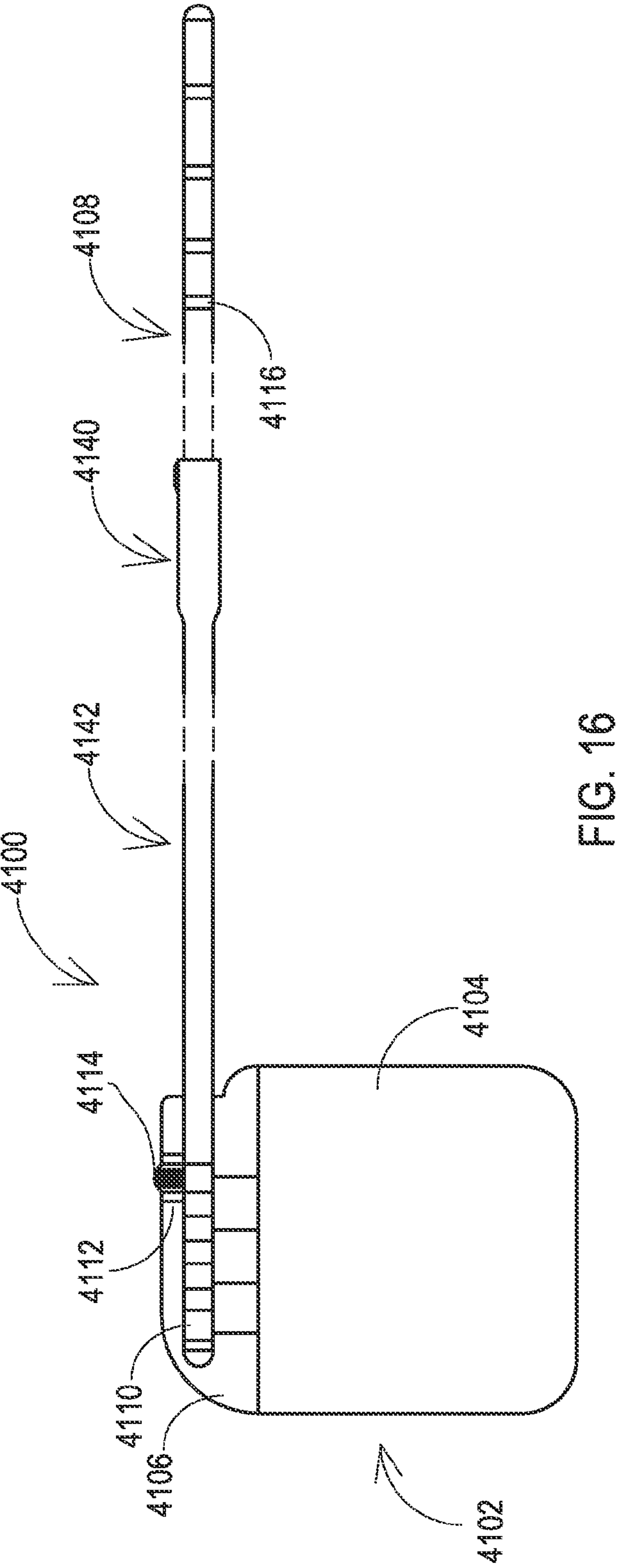
FIG. 16 shows an embodiment of an implantable medical system that includes an implantable medical device (IMD) coupled to an extension containing a shield which is coupled to a lead containing a shield.

FIGS. 15A and 15B show an example of an implantable medical lead 3108 where a lead anchor 3280 is attached. In this example, the lead anchor 3280 is an RF conductor to the tissue to provide the ground pathway for the shield 3118. In this particular example, the lead 3108 includes a ring electrode 3130 that is coupled to the shield 3118, either via a direct current coupling or a capacitive coupling. The lead anchor 3280 is constructed of metal or other conductor, or at least has a portion that is or conductive and directly contacts or nearly contacts the ring electrode 3130 and the tissue to ground the shield 3118 at RF frequencies. This ground pathway is secured in place via the conventional mounting of the lead anchor 3280 to the lead body and by the wings 3282 being sutured in place to the tissue. The filars may be present within the inner jacket or any other inner layer as shown or within the lumen created by the inside wall of the inner jacket or any other inner layer like that shown in FIG. 12B.

Figure 15C:
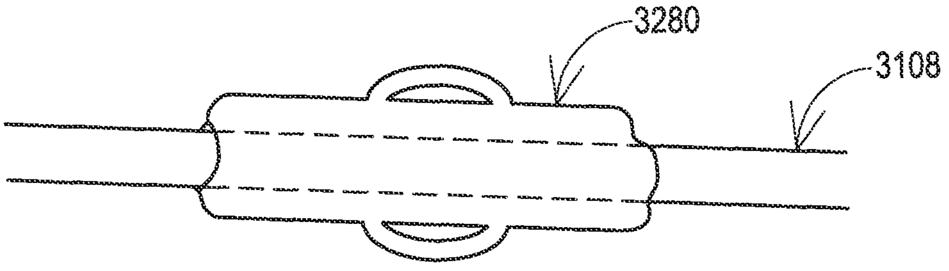
FIG. 15C shows an embodiment of the implantable lead having a lead anchor coupled directly to the shield to provide the RF pathway to ground.
Figure 15D:
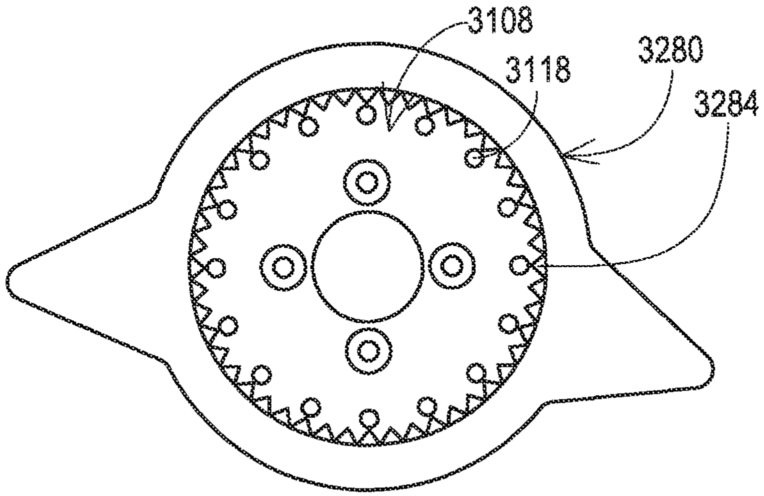
FIG. 15D shows the embodiment of the implantable lead in cross-section to reveal the shield and the lead anchor.

FIGS. 15C and 15D show another example of an implantable medical lead 3108 where a lead anchor 3280 is attached. In this example, the lead anchor 3280 is an RF conductor to the tissue to provide the ground pathway for the shield 3118. In this particular example, the lead 3108 does not have a ring electrode 3130 coupled to the shield 3118. However, as seen in FIG. 15D, the lead anchor has gripping teeth 3284 that sink into the outer layer of the jacket and either directly contact or nearly contact the shield 3118. The filars may be present within the inner jacket or any other inner layer as shown or within the lumen created by the inside wall of the inner jacket or any other inner layer like that shown in FIG. 12B.

Directly contacting the shield 3118 creates a direct current coupled RF pathway while nearly contacting the shield 3118 creates a capacitively coupled RF pathway. As with the previous example, the lead anchor 3280 is constructed of metal or other conductor, or at least has a portion that is conductive and contacts or nearly contacts the tissue to ground the shield 3118 at RF frequencies. This ground pathway is secured in place via the conventional mounting of the lead anchor to the lead body and by the wings 3282 being sutured in place to the tissue.

In these embodiments, the anchor may capacitively couple to the shield 3118 without teeth or rings being present, particularly where the depth of the shield within the outer layer 3120 is relatively small. For example, for depth of the shield 3118 of about 5 mils or less, the anchor may reside on the outer layer 3120 and capacitively couple to the shield 3118 to provide the RF pathway to ground.

Figure 15E:
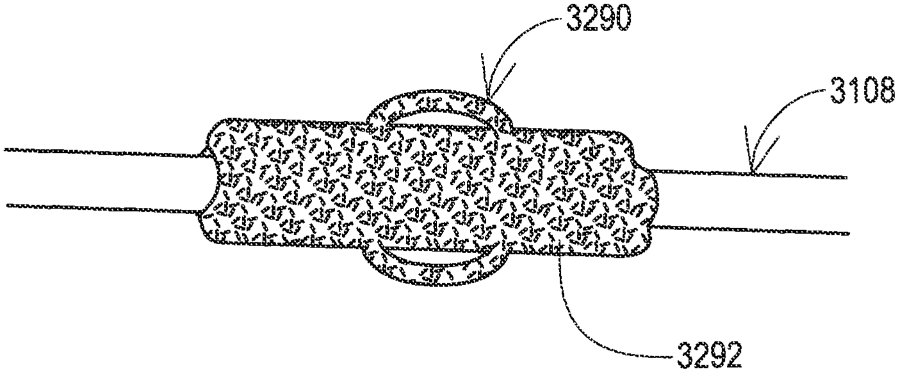
FIG. 15E shows an embodiment of the implantable lead having a lead anchor with a non-conductive coating.

FIG. 15E shows an example of an implantable medical lead 3108 where a lead anchor 3290 is attached. In this example, the lead anchor 3290 is an RF conductor to the tissue to provide the ground pathway for the shield 3118. However, in this particular example, lead anchor 3290 provides a capacitive coupling to ground by utilizing a non-conductive outer material or coating 3292 to contact the tissue. The lead anchor 3290 may have either a direct current coupling or capacitive coupling to the shield 3118, or ring electrode 3130 if any. The capacitive coupling to the tissue prevents the lead anchor 3290 from becoming a magnetic gradient induced current electrode, such as where other shield electrodes are present at other points along the lead 3108.

Utilizing an anchor to provide an RF pathway to ground, as shown in FIGS. 15A-15E, may also be useful considering that the typical mounting location of an anchor is at a point where the intensities of the RF fields change. For instance, an anchor may be positioned near the entry hole of the cranium where the lead 3108 is used for brain stimulation. The intensities of the field may change from one side of the entry hole to the other and providing the RF pathway to ground via an anchor near the entry hole may assist in dissipating energy received by the shield 3118 externally of the entry hole to prevent such energy from traveling through the shield 3118 and through the entry hole toward the shield termination which is closer to the stimulation electrodes.

Embodiments disclosed in relation to FIGS. 16-17G provide for shielding of both an implantable medical lead and an implantable lead extension. The two shields are interconnected with a radio frequency (RF) conductive path to maintain a continuity of the shielding along the length between the implantable medical device (IMD) and the stimulation site.

FIG. 16 shows an example of an implantable medical system 4100 that includes an IMD 4102 coupled to a lead 4108. The IMD 4102 includes a metal can 4104, typically constructed of a medical grade titanium, such as grades 1-4, 5 or 9 titanium, or similar other biocompatible materials. The IMD 4102 includes a header 4106 typically constructed of materials such as polysulfone or polyurethane, that is affixed to the metal can 4104. The header 4106 is shown transparently for purposes of illustration. The header 4106 provides a structure for securing the lead extension 4142 to the IMD 4102 and for establishing electrical connectivity between circuitry of the IMD 4102 and distal connectors of the lead extension 4142 that are located in a distal housing 4140.

The extension 4142 also includes ring connectors 4110 on a proximal end that is positioned within the header 4106. The ring connectors 4110 make physical contact with electrical connections within the header. The electrical connections may include a metal contact that the ring connector 4110 rests against upon being inserted into the header 4106 where a wire extends from the metal contact into the can 4104 where the circuitry is housed. Signals applied by the IMD 4102 to the ring connectors 4110 are conducted through the extension 4142 to the connectors within the housing 4140 to provide the stimulation signals to the lead 4108. The extension 4142 is secured in the header 4106 such as by a set screw block 4112 within the header 4106 that allows at least one set screw 4114 to be tightened against at least one of the ring connectors 4110.

The lead 4108 includes electrodes 4116 on a distal end that are positioned at a stimulation site within a patient. The lead 4108 also includes ring connectors on a proximal end that is positioned within the housing 4140. The ring connectors make physical contact with electrical connections within the housing 4140. The electrical connections may include a metal contact such as a Bal Seal® connector of the Bal Seal Engineering, Inc. of Foothill Ranch, Calif., another spring loaded connector, or a set screw block that the electrode rests against upon being inserted into the housing 4140. A wire extends from the metal contact of the housing 4140 into the extension 4142 to connect with the filars of the extension 4142. Signals applied by the IMD 4102 to the ring connectors 4110 are conducted through the extension 4142 and lead 4108 to the electrodes 4116 to provide the stimulation therapy to the patient.

The lead 4108 is secured in the housing 4140 such as by a set screw block within the housing 4140 that allows at least one set screw to be tightened against at least one of the electrodes. A shield 4144 of the extension and a shield 4118 of the lead 4108 that are discussed below with reference to FIGS. 17A-17G are present to prevent the induced RF current on the filars. The shields 4118, 4144 may be grounded at the IMD 4102 of FIG. 16 or at various grounding points established along the extension 4142 and/or lead 4108. As another option, the shield 4144 of the extension 4142 and/or the shield 4118 of the lead 4108 may be located within the extension 4142 or lead 4108 at a small distance from the surface so that the shields 4118, 4144 will effectively capacitively couple to the tissue along the length of the lead to dissipate energy to the tissue over the length. In any of these cases, continuity may be maintained between the shields 4118 and 4144 as discussed herein FIGS. 17A-17G show examples of the extension 4142 and lead 4108 where shields 4118, 4144 are present. The lead 4108 is inserted through an opening 4146 in the housing 4140 on the distal end of the extension 4142. Outer jacket layers 4120, 4141 for the lead 4108 and extension 4142 are shown transparently in FIG. 17A for purposes of illustrating the shields 4118, 4144. The shields 4118, 4144 block at least some RF energy from directly coupling to conductive filars that are present within the lead 4108 and extension 4142. The conductive filars extend the length of the extension 4142 and lead 4108 and interconnect the proximal connector rings 4110 of the extension 4142 to the distal electrodes 4116 of the lead 4108 so that stimulation signals are conducted to the stimulation site.

Figure 17A:
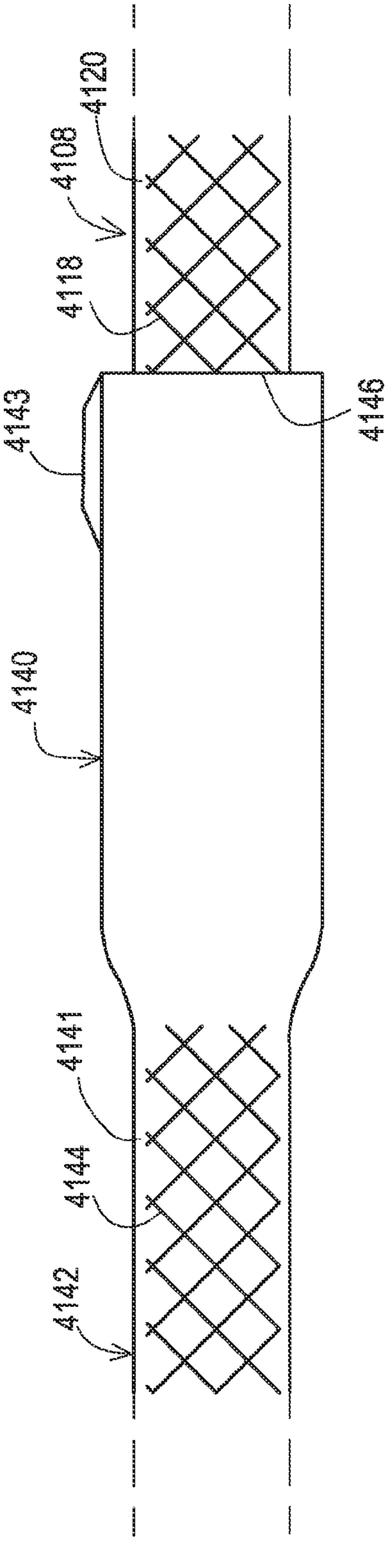
FIG. 17A shows an embodiment of an implantable extension coupled to an implantable lead with the shield of each revealed.

As shown in FIG. 17A, the shields 4118, 4144 of this example are braided metal wires. The metal wire may be constructed of various materials such as titanium, tantalum, niobium, platinum-iridium alloy, platinum, palladium, gold, stainless steel, and their alloys, or other metals. It may be desirable to utilize a biocompatible metal for the shields 4118, 4144, particularly for embodiments where a portion of the shields 4118, 4144 may be exposed for purposes of grounding. While the shield 4118 is shown as a braid, other shield configurations may be chosen particularly where flexibility is not an issue such as a foil strip wrapped about the lead 4108 in an overlapping manner or an outer layer 4120 that is heavily doped with conductive particles.

FIG. 17A also shows a set screw block 4143 present on the housing 4140. The set screw block 4143 may be used to fix the proximal end of the lead 4108 in place within the opening 4146 of the housing 4140 where a set screw is tightened against a connector ring on the lead 4108. Other manners of fixing the lead 4108 within housing 4140 may also be used.

Figure 17B:
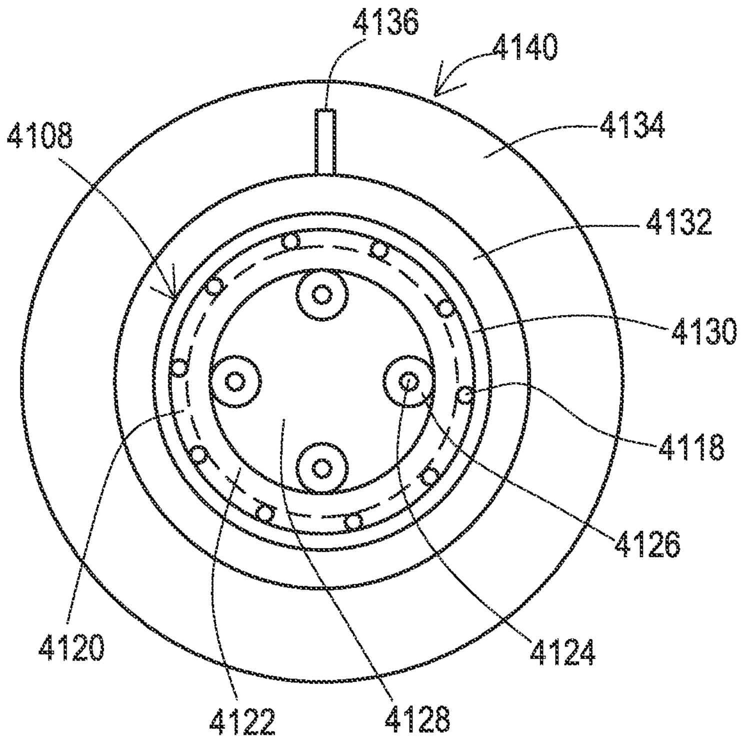
FIG. 17B shows an embodiment of a coupling of the implantable lead and extension in cross-section to reveal the shield, shield electrode, and filars of the lead and a shield connector and jumper wire of the lead extension.

FIG. 17B shows a coupling of the lead 4108 to the housing 4140 as a cross-section taken through the coupling of a shield connector 4132 to a shield electrode 4130. The shield 4118 of the lead 4108 may be embedded within the jacket of the lead 4108. One manner of constructing the lead 4108 with the shield 4118 is to provide an inner jacket 4122 that encloses the filars 4124 and any additional insulation layer 4126, such as polytetrafluoroethylene (PTFE) that may surround each filar 4124. The shield 4118 may then reside on the outer portion of the inner jacket 4122, and the outer jacket 4120 may then enclose the shield 4118. The outer jacket 4120 maybe added over the braid 4118, or it may be extruded over the braid.

For embodiments where it is desirable for the shield 4118 to RF couple to tissue, typically as a capacitive coupling, either as an alternative to or in addition to grounding at the can of the IMD or elsewhere, the amount of the outer jacket layer 4120 covering the shield 4118 may be relatively thin, such as on the order of 0.5 to 5 mils. Where the shield 4118 grounds at the can of the IMD and grounding via a capacitive coupling from the shield through the outer jacket 4120 directly to the tissue is of less significance, then the shield 4118 may be located further from the outer surface of the lead 4108.

The inner and outer jackets 4122, 4120 may be constructed of the same or similar materials such as various flexible and biocompatible polymers, examples of which are polyurethanes, and silicones. A lumen 4128 may be included inside of the inner jacket 4122 around which the insulated filars 4124 are coiled or otherwise positioned. The lumen 4128 may be useful, particularly for percutaneous leads 4108, to allow a stylet to be inserted for purposes of pushing and steering the lead 4108 into the desired position within the patient.

To provide a robust connection for the shield 4118, the shield electrode 4130 such as an electrode ring may be wrapped around the outer layer 4120 to contact the shield 4118 and provide a direct current coupling to the shield 4118. A direct current coupling between the shields avoids large variations in the characteristic impedance for the shielding from the extension 4142 to the lead 4108. Avoiding variations in the characteristic impedances may reduce the degree of RF reflection that occurs within the shield 4118, which in turn reduces the amount of RF heating that may occur via the stimulation electrodes.

The housing 4140 includes the shield connector 4132, such as a set screw block, a Bal Seal® connector, or another spring loaded connector. The shield connector 4132 of this embodiment is enclosed within a housing layer 4134 and contacts the shield electrode 4130 of the lead 4108. The housing layer 4134 may be constructed of various non-conductive materials such as polyurethane, polysulfone, nylon, silicone and polyetheretherketone (PEEK) and provides a relatively rigid structure similar to that provided by the header 4106 of the IMD 4102.

A shield jumper wire 4136 is included in this embodiment within the housing layer 4134. The shield jumper wire 4136 contacts the shield connector 4132 and extends from the shield connector 4132 into the housing layer 4134 and extends proximally to the shield 4144 within the extension 4142. The shield jumper wire 4136 may be welded, crimped, or otherwise affixed to the shield conductor 4132 and the shield 4144.

Figure 17C:
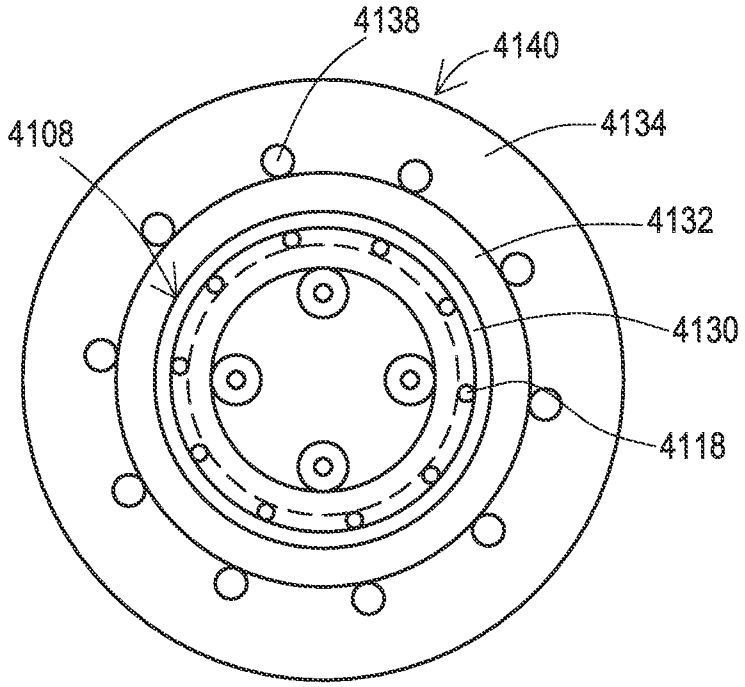
FIG. 17C shows an embodiment of a coupling of the implantable lead and extension in cross-section to reveal the shield, shield electrode, and filars of the lead and a shield connector and shield of the lead extension.

FIG. 17C shows an example similar to the example of FIG. 17B. The lead 4108 is constructed in the same manner. However, the housing 4140 utilizes a different construction. In the housing 4140, a housing shield 4138 is present and extends to the shield conductor 4132 where the housing shield 4138 contacts the shield connector 4132. No jumper wire is needed because the housing shield 4138 establishes continuity of the shielding from the shield connector 4132 to the shield 4144 present within the extension 4142.

The housing shield 4138 may be affixed to the shield connector 4132 in various ways. For instance, the housing shield 4138 may be welded or crimped to the shield connector 4132 to provide a direct current coupling. In some embodiments, the shield connector 4132 is distal relative to stimulation connectors of the housing 4140. In those cases, extending the housing shield 4138 through the housing 4140 to the shield connector 4132 provides additional shielding protection from RF induced currents.

Figure 17D:
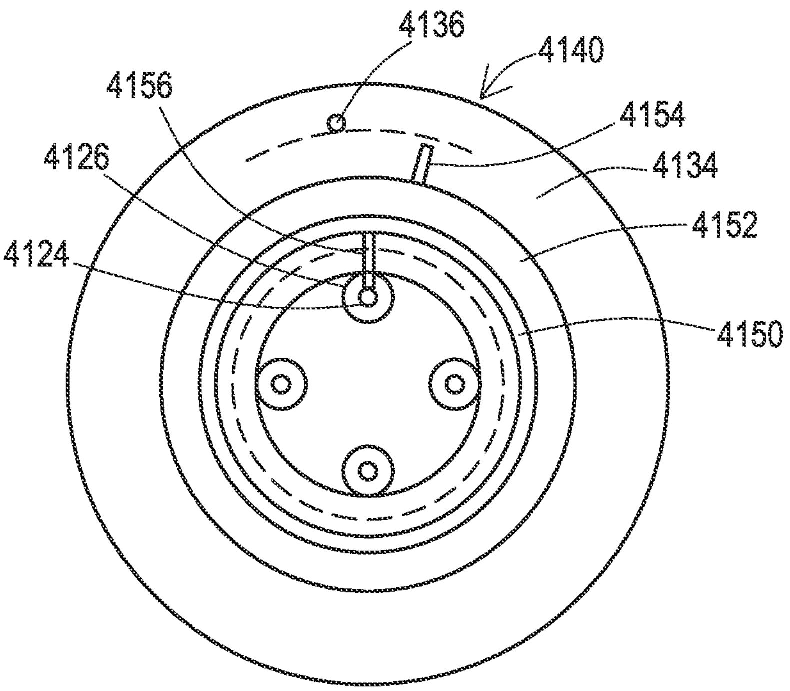
FIG. 17D shows an embodiment of a coupling of the implantable lead and extension in cross-section to reveal the filars, filar jumper, and filar electrode of the lead and a filar connector, filar jumper wire, and shield jumper wire of the lead extension.

FIG. 17D shows the lead 4108 coupled to the housing 4140 with a cross-section through a stimulation electrode coupling for embodiments of the housing 4140 that include a shield jumper wire 4136. The lead 4108 includes a stimulation connector 4150 and a stimulation jumper wire 4156 that interconnects the filar 4124 to the stimulation connector 4150. The housing 4140 includes a stimulation connector 4152 that contacts the stimulation connector 4150 to form a direct current coupling. A stimulation jumper wire 4154 of the housing 4140 contacts the stimulation connector 4152 and extends through the housing layer 4134 in the proximal direction to a corresponding filar within the extension 4142.

As shown in FIG. 17D, both the shield jumper wire 4136 and the stimulation jumper wire 4154 are present within the housing layer 4134. Separation between them is provided to avoid transferring significant RF energy being captured by the shields 4118, 4144 from the shield jumper wire 4136 to the stimulation jumper wire 4154. For instance, the separation may be in the range of 0.1 millimeters (mm) to 2.0 mm where the housing layer 4134 is constructed of polyurethane, polysulfone, nylon, and PEEK or has a dielectric property of between about 2 and 10.

Figure 17E:
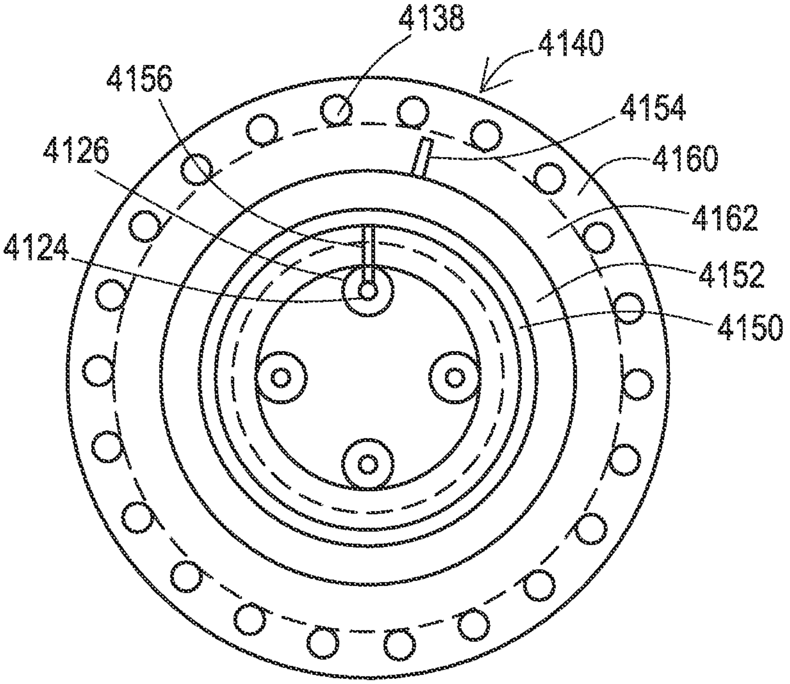
FIG. 17E shows an embodiment of a coupling of the implantable lead and extension in cross-section to reveal the filars, filar jumper wire, and filar electrode of the lead and a filar connector, filar jumper wire and shield of the lead extension.

FIG. 17E shows the lead 4108 coupled to the housing 4140 with a cross-section through a stimulation connector coupling for embodiments of the housing 4140 that include the housing shield 4138 extending through the housing 4140. The lead 4108 includes the stimulation connector 4150 and the stimulation jumper wire 4156 that interconnects the filar 4124 to the stimulation connector 4150. The housing 4140 includes the stimulation connector 4152 that contacts the stimulation connector 4150 to form a direct current coupling. The stimulation jumper wire 4154 of the housing 4140 contacts the stimulation connector 4152 and extends in the proximal direction to a corresponding filar within the extension 4142.

As shown in FIG. 17E, the housing shield 4138 and the stimulation jumper wire 4154 are present within different layers of housing material. The stimulation jumper wire 4154 is present within a housing inner layer 4162 while the housing shield 4138 is present about the housing inner layer 4162. A housing outer layer 4160 surrounds the housing shield 4138 and the housing inner layer 4162. The housing inner layer 4162 and the housing outer layer 4160 may be constructed of various non-conductive materials such as those discussed above for the housing layers 4134, and these layers 4160, 4162 may be the same or different non-conductive materials. Separation like that discussed above between the stimulation jumper wire 4154 and the housing shield 4138 is provided to avoid transferring significant RF energy being captured by the shields 4118, 4144 from the housing shield 4138 to the stimulation jumper wire 4154.

Figure 17F:
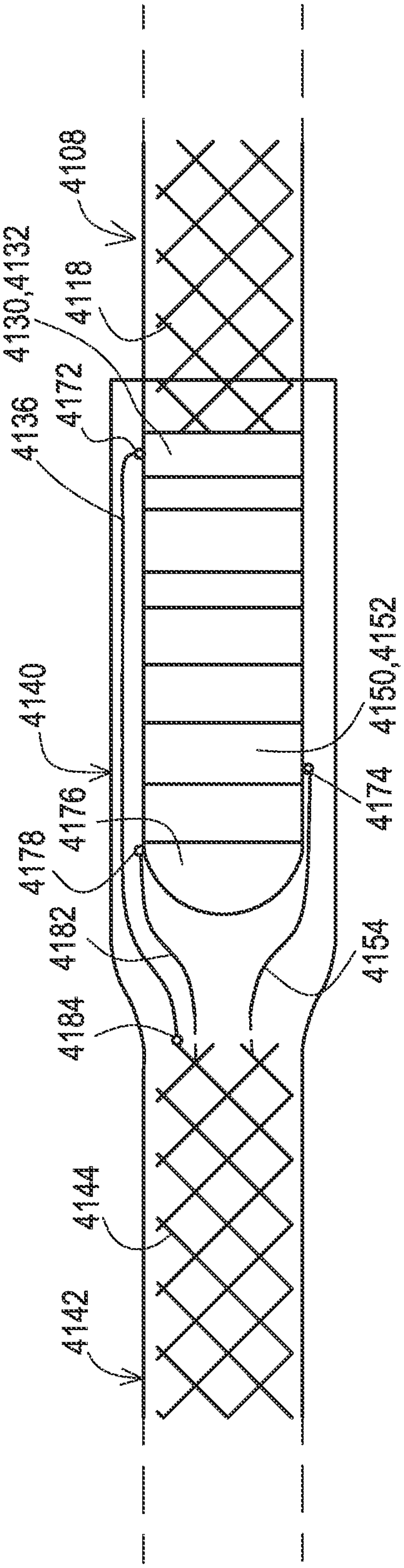
FIG. 17F shows an embodiment of an implantable extension coupled to an implantable lead where a jumper wire interconnects the two shields.
Figure 17G:
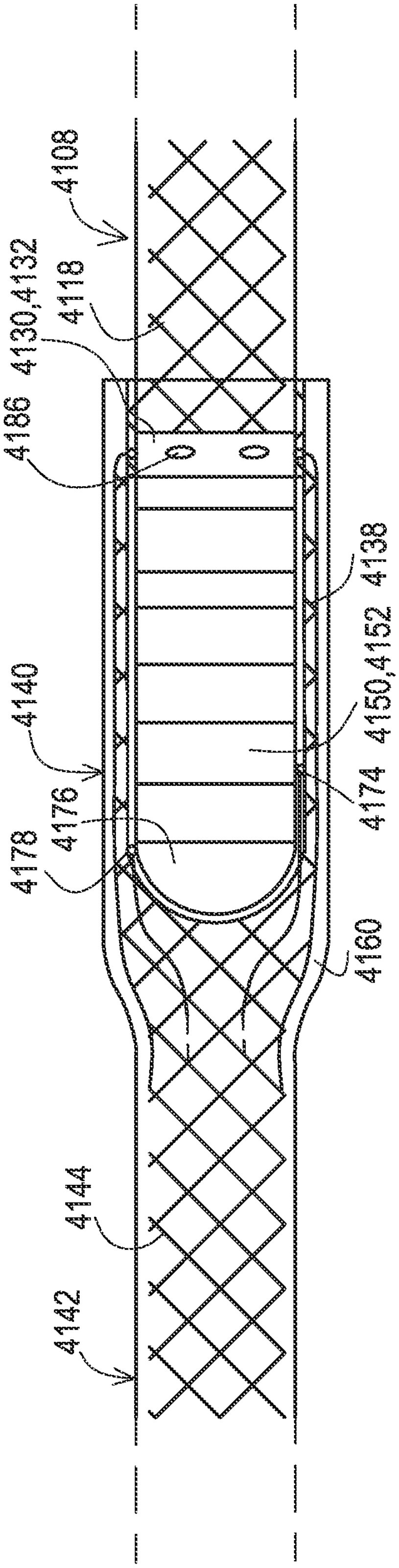
FIG. 17G shows an embodiment of an implantable extension coupled to an implantable lead where the shield of the extension extends to the shield connector of the extension to interconnect the two shields.

FIG. 17F shows an embodiment of the housing 4140 where the shield jumper wire 4136 is present. The shield jumper wire 4136 has an attachment point 4172 such as a weld or crimp to the shield connector 4132 where the shield electrode 4130 is seated. The shield jumper wire 4136 has another attachment point 4184 such as a weld or crimp to the shield 4144 of the extension 4142.

The stimulation jumper wires 4154, 4182 have attachment points 4174, 4178 such as a weld or crimp to the stimulation connectors 4152 where the stimulation electrodes 4150, 4176 are seated. Only two stimulation jumper wires 4154, 4182 are shown for purposes of clarity, and it will be appreciated that any number of stimulation connectors and corresponding stimulation jumper wires may be present within the housing 4140. As shown, separation is provided between the shield jumper wire 4136 and the stimulation jumper wires 4154, 4182 to avoid transferring RF energy to the stimulation jumper wires 4154, 4182.

FIG. 17G shows an embodiment of the housing 4140 where the housing shield 4138 is present. The housing shield 4138 has attachment points 4186 such as welds or crimps to the shield connector 4132 where the shield electrode 4130 is seated. The housing shield 4138 continues through the housing out layer 4160 while surrounding the housing inner layer 4162. The housing shield 4138 transitions to the extension shield 4144 upon reaching the junction of the housing 4140 to the body of the extension 4142. In other embodiments, the housing shield 4138 may be attached to the shield 4144 via welds or crimps rather than transitioning into the body of the extension 4142 as the shield 4144.

The stimulation jumper wires 4154, 4182 have attachment points 4174, 4178 to the stimulation connectors 4152 where the stimulation electrodes 4150, 4176 are seated. As shown, separation is provided between the housing shield 4138 and the stimulation jumper wires 4154, 4182 to avoid transferring RF energy to the stimulation jumper wires 4154, 4182.

Embodiments as disclosed in relation to FIGS. 18-29 provide for termination of a radio frequency (RF) shield present within an implantable medical lead for use with an implantable medical device (IMD). The shield may be terminated in various ways such as by terminating at an edge of a butt, scarf, or lap joint to an insulation extension. Furthermore, the shield termination may include features such as a ring attached at the shield termination point within the insulation, shield wires with folded over ends, or barbs between the insulation layers.

Figure 18:
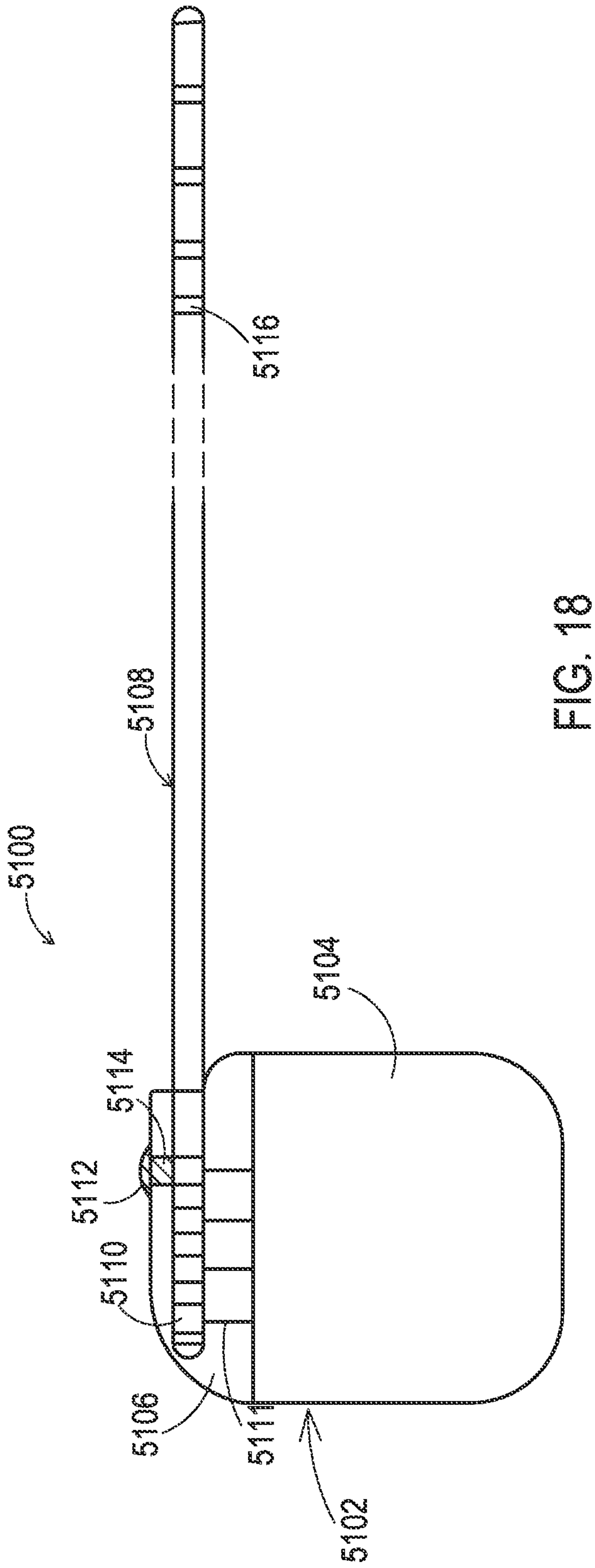
FIG. 18 shows an embodiment of an implantable medical system that includes an implantable medical device (IMD) coupled to a lead containing a shield.

FIG. 18 shows an example of an implantable medical system 5100 that includes an IMD 5102 coupled to a lead 5108. The IMD 5102 includes a metal can 5104, typically constructed of a medical grade titanium, such as grades 1-4, 5 or 9 titanium, or similar other biocompatible materials. The IMD 5102 includes a header 5106 typically constructed of materials such as polysulfone or polyurethane, that is affixed to the metal can 5104. The header 5106 is shown transparently for purposes of illustration. The header 5106 provides a structure for securing the lead 5108 to the IMD 5102 and for establishing electrical connectivity between circuitry of the IMD 5102 and electrodes of the lead 5108.

The lead 5108 includes electrodes 5116 on a distal end that are positioned at a stimulation site within a patient. The lead also includes connector rings 5110 on a proximal end that is positioned within the header 5106. The connector rings 5110 make physical contact with electrical connections 5111 within the header. The electrical connections 5111 may include a metal contact that the connector ring 5110 rests against upon being inserted into the header 5106 where a wire extends from the metal contact into the can 5104 where the circuitry is housed. Signals applied by the IMD 5102 to the connector rings 5110 are conducted through the lead 5108 to the electrodes 5116 to provide the stimulation therapy to the patient.

Figure 19A:
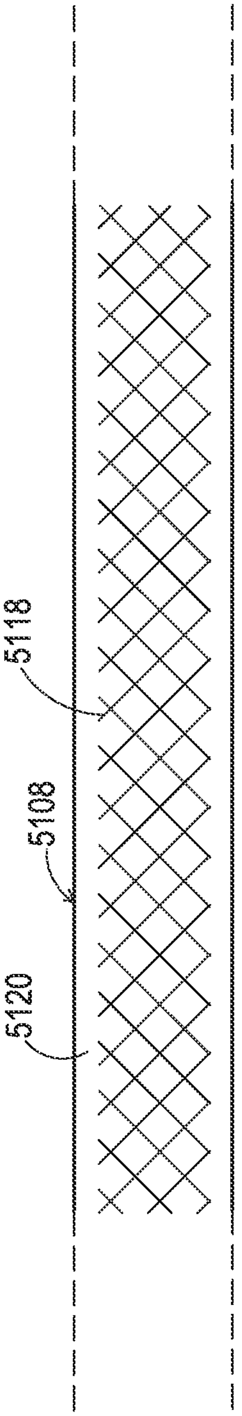
FIG. 19A shows an embodiment of an implantable lead with the shield revealed.
Figure 19B:
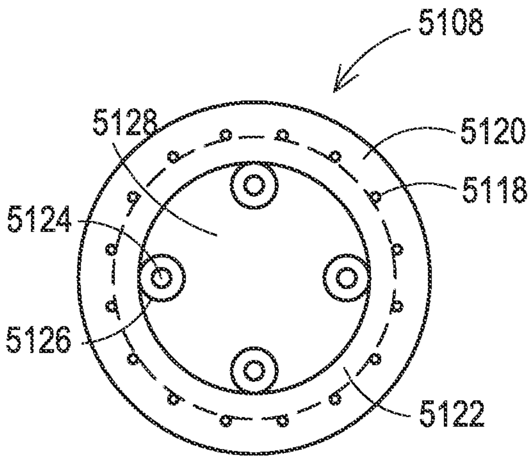
FIG. 19B shows the embodiment of the implantable lead in cross-section to reveal the shield and filars.

The lead 5108 is secured in the header 5106 such as by a set screw block 5112 within the header 5106 that allows at least one set screw 5114 to be tightened against at least one of the connector rings 5110. A shield 5118 as shown in FIGS. 19A and 19B may be grounded to the body along one or more points down the length of the lead from the IMD 5102 via ground rings and/or the shield 5118 may be grounded at the can 5104 of the IMD 5102 of FIG. 18. As another option, the shield 5118 may be located within the lead 5108 at a small distance from the surface so that the shield 5118 will effectively capacitively couple to the tissue along the length of the lead to dissipate energy to the tissue over the length.

Regardless of the manner of grounding, the shield 5118 terminates on one end near the proximal end and on the opposite end near the distal end of the lead 5108. At the termination point, shields having multiple metal wires such as braided shields are subject to fraying and shield wire migration. Preventing the shield wire from fraying and/or migrating to the tissue or to stimulation conductors within the lead 5108 may be desirable to prevent RF energy captured by the shield 5118 from being directed onto a small area of tissue via an electrode or exposed shield wire.

FIGS. 19A and 19B show an example of the lead 5108, where a shield 5118 is present. An outer insulation layer 5120 of a lead jacket is shown transparently in FIG. 19A for purposes of illustrating the shield 5118. The shield 5118 blocks at least some RF energy from directly coupling to conductive filars 5124 that are present within the lead 5108. The conductive filars 5124 extend the length of the lead and interconnect the proximal electrodes 5110 to the distal electrodes 5116 so that stimulation signals are conducted from the proximal end to the distal end of the lead 5108.

As shown in FIG. 19A, the shield 5118 of this example is a braided collection of metal wires. The metal wires may be constructed of various materials such as titanium, tantalum, niobium, platinum-iridium alloy, platinum, palladium, gold, stainless steel, and their alloys, or other metals. It may be desired to utilize a biocompatible metal for the shield 5118, particularly for embodiments where a portion of the shield 5118 may be exposed for purposes of grounding. While the shield 5118 is shown as a braid, other shield configurations may be chosen particularly where flexibility is not an issue such as a foil strip wrapped about the lead 5108 in an overlapping manner or an outer layer 5120 that is heavily doped with conductive particles.

As shown in FIG. 19B, the shield 5118 may be embedded within the jacket of the lead 5108. One manner of constructing the lead 5108 with the shield 5118 is to provide an inner insulation layer 5122 of the jacket that encloses the filars 5124 and any additional insulation layer 5126, such as polytetrafluoroethylene (PTFE) that may surround each filar 5124. The shield 5118 may then reside on the outer portion of the inner insulation layer 5122, and the outer insulation layer 5120 may then enclose the shield 5118. The outer jacket 5120 maybe added over the braid 5118, or it may be extruded over the braid.

For embodiments where it is desirable for the shield 5118 to RF couple to tissue, typically as a capacitive coupling, either as an alternative to grounding at the can 5104 of the IMD 5102 or at specific points along the lead 5108 or in addition to such grounds, the amount of the outer jacket layer 5120 covering the shield 5118 may be relatively thin, such as on the order of 0.5 to 5 mils. Where the shield 5118 grounds at one or more specific locations along its length, via a direct current coupling or a capacitive coupling, the shield 5118 may be located further from the outer surface of the lead 5108 with additional features of the lead providing the coupling at the one or more specific locations as discussed below.

The inner and outer insulation layers 5122, 5120 of the jacket may be constructed of the same or similar materials such as various flexible and biocompatible polymers, examples of which are polyurethane, and silicones. A lumen 5128 may be included inside of the inner jacket 5122 around which the insulated filars 5124 are coiled or otherwise positioned. The lumen 5128 may be useful, particularly for percutaneous leads 5108, to allow a stylet to be inserted for purposes of pushing and steering the lead 5108 into the desired position within the patient.

Figure 20:
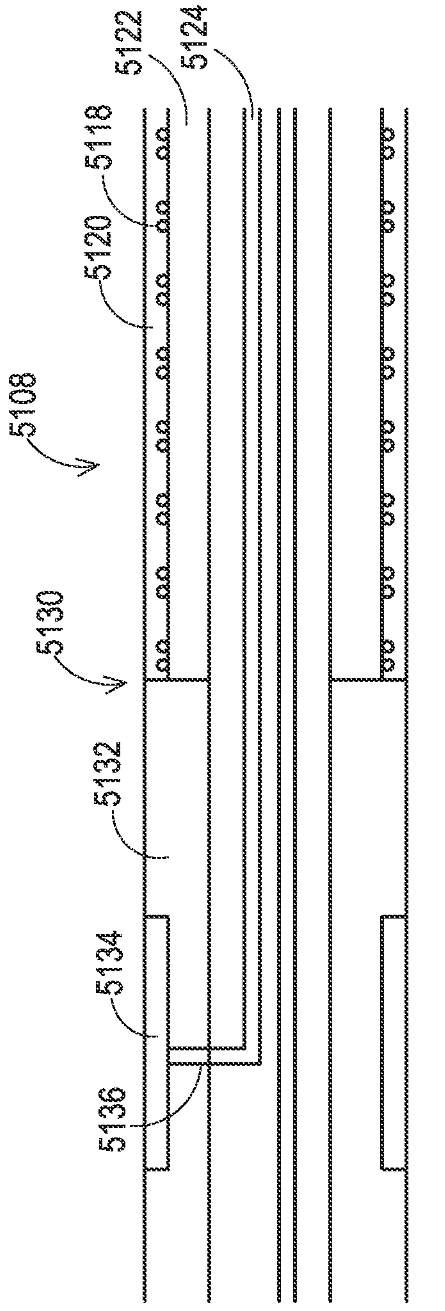
FIG. 20 shows an embodiment of the implantable lead where the shield terminates at a butt joint to an insulation extension.

FIG. 20 shows an embodiment of an implantable medical lead 5108 in cross-section with a cut taken down an axial centerline. The lead 5108 terminates at a butt joint 5130 where the inner insulation layer 5122, shield 5118, and outer insulation layer 5120 terminate. At this butt joint 5130, an insulation extension 5132 abuts and is bonded via RF heating, thermal, reflow, or similar processes to the blunt ends of the inner insulation layer 5122, outer insulation layer 5120, and shield 5118.

As shown in this example, the shield 5118 terminates at the butt joint 5130 rather than farther back within the jacket formed by the inner and outer insulation layers 5122, 5120. The insulation extension 5132 in this example extends the remainder of the lead 5108 where ring electrodes 5134 are located. The filars 5124 jumper to their respective ring electrodes via a filar jumper 5136. The lumen may be present with the filars 5124 being located about the lumen.

The material for the insulation extension 5132 may be selected to provide more or less stiffness than the inner and outer insulation layers 5122, 5120, depending upon which end of the lead the butt joint 5130 is located. For instance, where the electrode 5134 is on the proximal end of the lead 5108 and is being positioned within the header 5106 of the IMD 5102, the insulation extension 5132 may be constructed of a stiffer material. Where the electrode 5134 is on the distal end of the lead 5108 and is being steered to the stimulation site within the body, the insulation extension 5132 may be constructed of a more flexible material.

Using a stiffer material as the insulation extension 5132 on the proximal end aids in the insertion of the proximal end into the header 5106. As a particular example, the outer insulation 5120 may be constructed of polyurethane having a durometer 55D or similar rating while the insulation extension 5132 may be constructed of a polyurethane having a durometer 75D or similar rating.

Using a less stiff material as the insulation extension 5132 on the distal end aids in the positioning of the distal end at the stimulation site. As a particular example, the outer insulation 5120 may be constructed of polyurethane having a durometer 55D or similar rating while the insulation extension 5132 may be constructed of polyurethane having a durometer 80A or similar rating.

The gap between the termination of the shield 5118 at the butt joint 5130 and the nearest edge of the electrode 5134 is selected to avoid RF problems. In particular, the distance is selected so that RF coupling is avoided while the unshielded region of the filars 5124 is not overly exposed to RF. For MRI frequencies that typically range from 43 MHz to 128 MHz, a spacing of from 0.5 mm to 10 cm may be acceptable for these embodiments.

Figure 21:
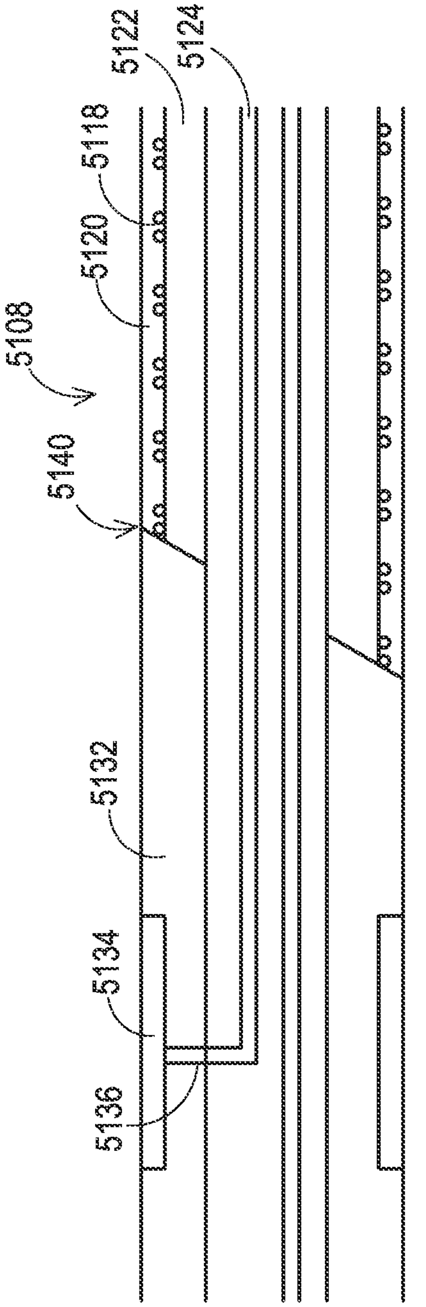
FIG. 21 shows an embodiment of the implantable lead where the shield terminates at a scarf joint to an insulation extension.

FIG. 21 shows another embodiment of an implantable medical lead 5108 in cross-section with a cut taken down an axial centerline. The lead 5108 terminates at a scarf joint 5140 where the inner insulation layer 5122, shield 5118, and outer insulation layer 5120 terminate at a wedged cut. At this scarf joint 5140, an insulation extension 5132 that has a complementary wedged cut abuts and is bonded to the wedged end of the inner insulation layer 5122, outer insulation layer 5120, and shield 5118 via RF heating, thermal, reflow or similar processes.

The scarf joint 5140 may be used rather than the butt joint 5130 of FIG. 20 because the scarf joint 5140 increases the bonding area. As shown in this example, the shield 5118 terminates at the scarf joint 5140 rather than farther back within the jacket formed by the inner and outer insulation layers 5122, 5120. The insulation extension 5132 in this example extends the remainder of the lead 5108 where ring electrodes 5134 are located. The filars 5124 jumper to their respective ring electrodes via a filar jumper 5136.

Similar to the previous embodiment of FIG. 20, the material for the insulation extension 5132 in this embodiment of FIG. 4 may be selected to provide more or less stiffness than the inner and outer insulation layers 5122, 5120, depending upon which end of the lead the scarf joint 5140 is located. For instance, where the electrode 5134 is on the proximal end of the lead 5108 and is being positioned within the header 5106 of the IMD 5102, the insulation extension 5132 may be constructed of a stiffer material such as polyurethane with a durometer 75D. Where the electrode 5134 is on the distal end of the lead 5108 and is being steered to the stimulation site within the body, the insulation extension 5132 may be constructed of a more flexible material such as polyurethane with a durometer 80A.

The gap between the termination of the shield 5118 at the butt joint 5130 and the nearest electrode 5134 is selected to avoid RF problems. In particular, the distance is selected so that RF coupling is avoided while the unshielded region of the filars 5124 is not overly exposed to RF. For MRI frequencies that typically range from 43 MHz to 128 MHz, spacing between the edge of the electrode 5134 nearest the scarf joint 5140 and the termination of the shield 5118 at the scarf joint 5140 may range from 0.5 mm to 10 cm for these embodiments. With the scarf joint 5140 of FIG. 21, the spacing between the termination of the shield 5118 and the electrode 5134 varies for different locations around the circumference of the scarf joint 5140, but the shortest spacing is maintained at 0.5 mm or above and the longest spacing is maintained at 10 cm or below.

Figure 22:
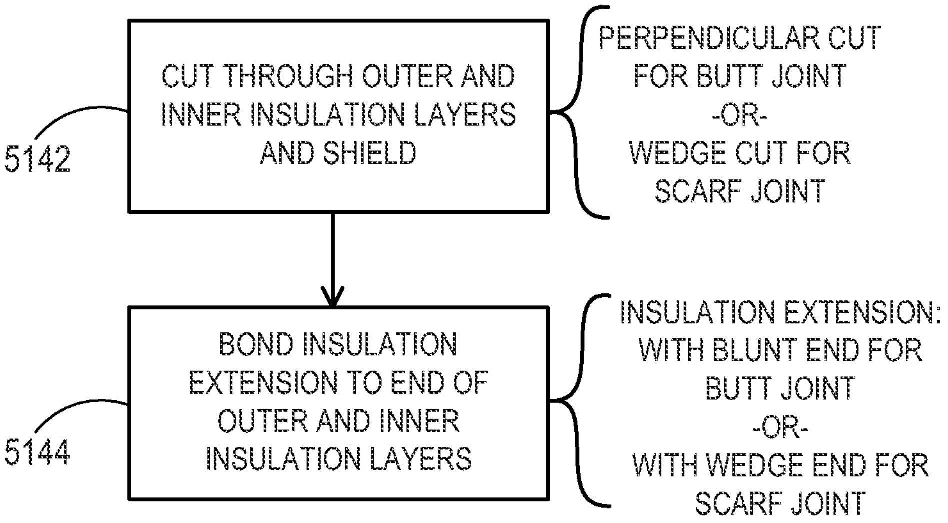
FIG. 22 shows one example of a set of steps to create the implantable lead of FIGS. 20 and 21.

FIG. 22 shows a set of steps to create the embodiments of FIGS. 20 and 21. Initially, a structure including the inner insulation layer 5122, outer insulation layer 5120, and shield 5118 may be provided. The shield 5118 has been braided over the inner insulation layer 5122 and then the outer insulation layer 5120 has been positioned and reflowed or otherwise bonded over the inner insulation layer 5122 and the shield 5118. To begin construction of the lead 5108 and the butt joint 5130 or scarf joint 5140, the structure is cut to size by making a cut through the insulation layers 5120, 5122 and the shield 5118 at a cutting step 5142. For a butt joint 5130, the cut is perpendicular to the axial dimension to create the blunt end. For a scarf joint 5140, the cut is at angle other than 90 degrees to the axial dimension to create the wedged end.

The insulation extension 5132 is also provided with a complementary end to bond to the lead 5108 to form the butt joint 5130 or scarf joint 5140. For the butt joint 5130, the insulation extension 5132 is cut perpendicular to the axial dimension to create the blunt end. For the scarf joint 5140, the insulation extension 5132 is cut at an angle other than 90 degrees to the axial dimension to create the wedged end. The two blunt ends for the butt joint 5130 are brought together and bonded at a bonding step 5144. Likewise, the two wedged ends for the scarf joint 5140 are brought together and bonded at the bonding step 5144.

Figure 23:
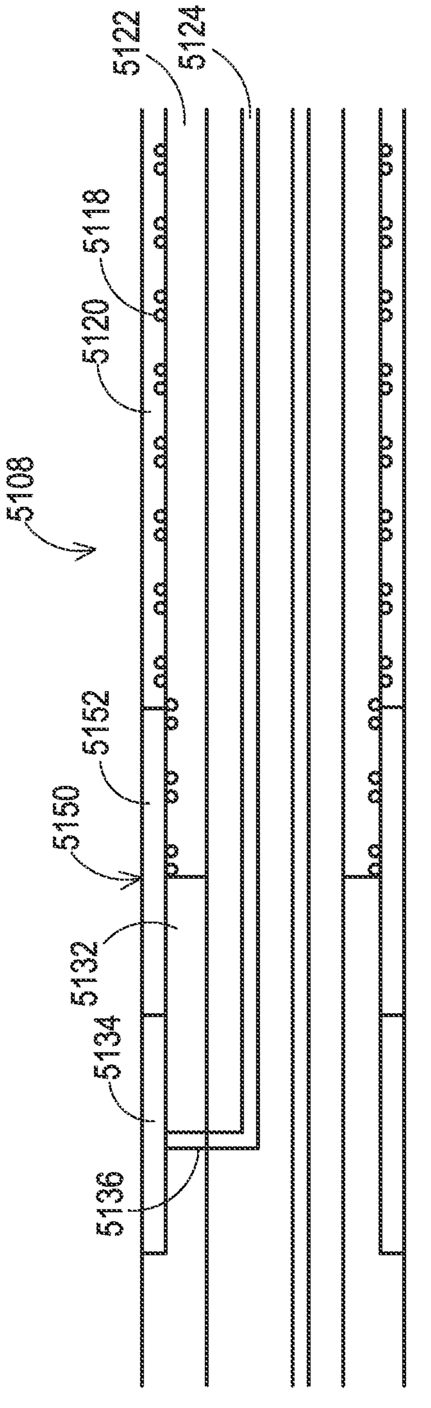
FIG. 23 shows an embodiment of the implantable medical lead where the shield terminates at a lap joint to an insulation extension.

FIG. 23 shows another embodiment of an implantable medical lead 5108 in cross-section with a cut taken down an axial centerline. The lead 5108 terminates at a lap joint 5150. The lap joint 5150 involves removing an end portion of the outer insulation layer 5120 and applying a replacement outer insulation layer 5152 onto the area of the shield 5118 and inner insulation layer 5122 where the outer insulation layer 5120 is missing. The replacement outer insulation layer 5152 also laps over a section of the insulation extension 5132 and may extend to the nearest electrode 5134.

As shown, the shield 5118 has been crimped down into the inner insulation layer 5122 at the region where the outer insulation layer 5120 has been removed. Doing so prevents the shield 5118 from bunching together during installation of the outer replacement insulation layer 5152. This may be especially the case where the replacement outer insulation layer 5152 is in the form of tubing that slides into place over the shield 5118 and inner insulation layer 5122 prior to attaching the insulation extension 5132. Where the replacement outer insulation layer 5152 is tubing, once being slid into place, it is reflowed or otherwise bonded to the inner insulation layer 5122. As an alternative, the replacement outer insulation layer 5152 may be injection molded into place.

As shown in this example, the shield 5118 terminates at the lap joint 5150 rather than farther back within the jacket formed by the inner and outer insulation layers 5122, 5120. The insulation extension 5132 in this example extends the remainder of the lead 5108 where ring electrodes 5134 are located. The filars 5124 jumper to their respective ring electrodes via a filar jumper 5136. The lumen may be present in some embodiments with the filars 5124 being located about the lumen.

In this embodiment the replacement outer insulation layer 5152 may be constructed of a material that differs in stiffness from the outer insulation layer 5120 depending upon which end of the lead 5108 the lap joint 5150 is located. For instance, where the electrode 5134 is on the proximal end of the lead 5108 and is being positioned within the header 5106 of the IMD 5102, the replacement outer insulation layer 5152 may be constructed of a stiffer material such as durometer 75D polyurethane. Where the electrode 5134 is on the distal end of the lead 5108 and is being steered to the stimulation site within the body, the replacement outer insulation layer 5152 may be constructed of a more flexible material such as 80A polyurethane.

In this embodiment, like that of the previous ones, the material for the insulation extension 5132 may also be selected to provide more or less stiffness than the inner and outer insulation layers 5122, 5120, depending upon which end of the lead the lap joint 5150 is located. For instance, where the electrode 5134 is on the proximal end of the lead 5108 and is being positioned within the header 5106 of the IMD 5102, the insulation extension 5132 may be constructed of a stiffer material such as durometer 75D polyurethane. Where the electrode 5134 is on the distal end of the lead 5108 and is being steered to the stimulation site within the body, the insulation extension 5132 may be constructed of a more flexible material such as 80A polyurethane.

The gap between the termination of the shield 5118 at the lap joint 5150 and the nearest electrode 5134 is also selected to avoid RF problems. For MRI frequencies, a spacing of from 0.5 mm to 10 cm may be acceptable for these embodiments.

Figure 24:
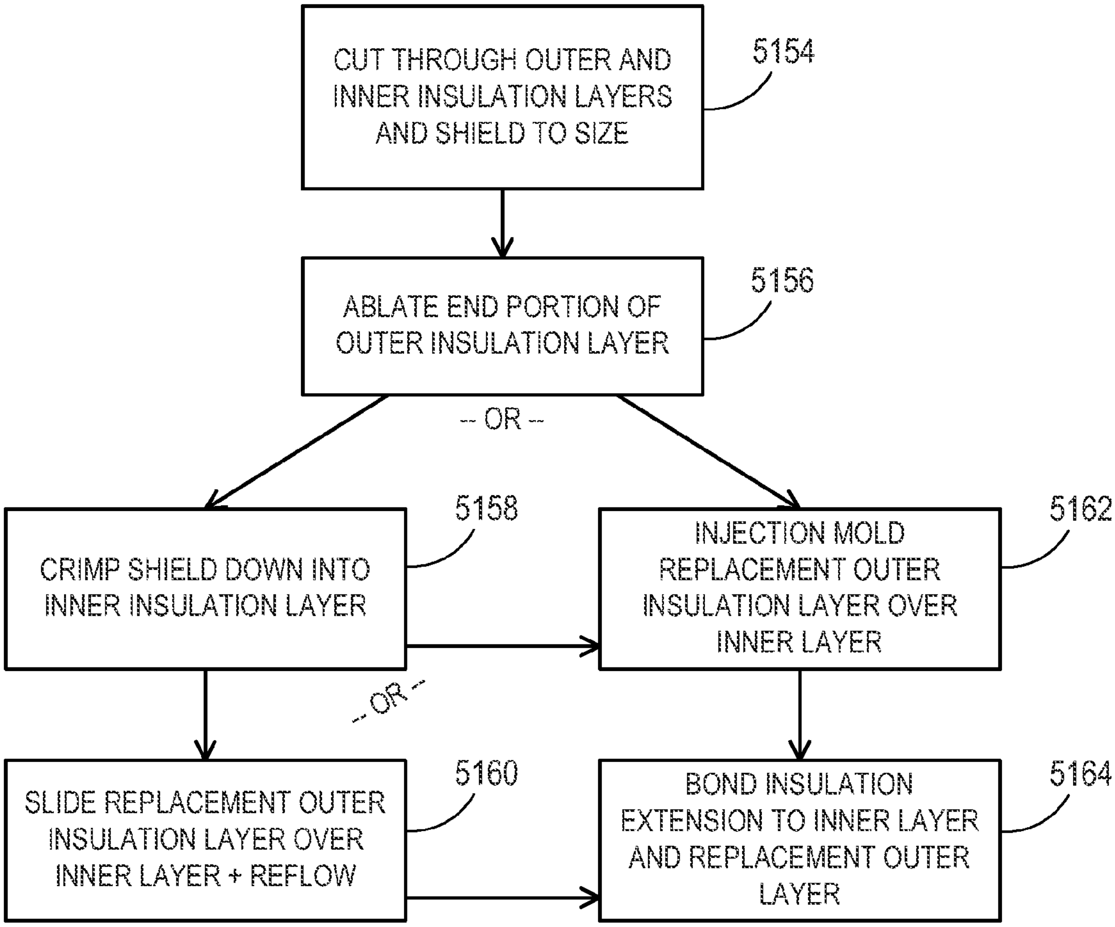
FIG. 24 shows one example of a set of steps to create the implantable lead of FIG. 23.

FIG. 24 shows one example of a set of steps that create the lap joint 5150 of FIG. 23. Initially, a structure including the inner insulation layer 5122, outer insulation layer 5120, and shield 5118 may be provided. The shield 5118 has been braided over the inner insulation layer 5122 and then the outer insulation layer 5120 has been positioned and reflowed or otherwise bonded over the inner insulation layer 5122 and the shield 5118. To begin construction of the lead 5108 and the lap joint 5150, the structure is cut to size by making a cut through the insulation layers 5120, 5122 and the shield 5118 at a cutting step 5154. For a lap joint 5150, this first cut is perpendicular to the axial dimension to create a blunt end.

Once cut to size, the outer insulation layer 5120 is then ablated by some distance to expose the shield 5118 and the inner insulation layer 5122 at an ablating step 5156. Ablation may be done using tools such as an excimer laser which can very precisely ablate to expose the shield 5118. The length of the outer insulation layer 5120 to be ablated may vary, but an illustrative range is from 0.25 centimeters (cm) to 5 cm.

Once ablation is complete, the next step may vary. The replacement outer insulation layer 5152 may be installed in various manners such as by reflowing tubing or by injection molding. If by injection molding, then the next step may be either a crimping step 5158 or an injecting step 5162. If by reflowing tubing, then it may be helpful to proceed to the crimping step 5158 after ablating.

At the crimping step 5158, the shield 5118 is crimped so as to sink down into the inner insulation layer 5122 at the area where the outer insulation layer 5120 has been removed. If a ring or other tool is used to crimp the shield 5118 into the inner insulation layer 5122, the ring or other tool may then be removed. Where the replacement outer insulation layer 5152 is being installed as tubing that is reflowed, then the next step is tubing step 5160. Where the replacement outer insulation layer 5152 is being installed by injection molding, then the next step is injecting step 5162.

At the tubing step 5160, the tubing is slid onto the inner insulation layer 5122 and over the shield 5118 at the area where the outer insulation layer 5120 has been removed and where the shield 5118 has been crimped down. The tubing extends beyond the end of the inner insulation layer 5122 so that it may eventually be bonded to the insulation extension 5132. The tubing is reflowed, RF heated, etc. to bond to the inner insulation layer 5122 and to the end of the outer insulation layer 5120 where the ablating stopped to form the replacement outer insulation layer 5152. Contemporaneously or sequentially, the insulation extension 5132 is bonded in place at the blunt end of the inner insulation layer 5122 and to the tubing of the replacement outer insulation layer 5152 that extends beyond the inner insulation layer 5122 at a bonding step 5164. This tubing may be reflowed, RF heated, etc. onto the insulation extension 5132.

Returning to the injecting step 5162, in the scenario where the replacement outer insulation layer 5152 is to be injection molded, then the injecting step 5126 takes place either after the ablating step 5156 or after the crimping step 5158. Material such as the desired polyurethane is injected onto the inner insulation layer 5122 and the shield 5118 to form the replacement outer insulation layer 5152. Contemporaneously, the insulation extension 5132 is bonded to the inner insulation layer 5122 and to the replacement outer insulation layer 5152 at the bonding step 5164.

Alternative manners of creating the lap joint 5150 may also be used. For instance, the structure of the outer insulation layer 5120, inner insulation layer 5122, and shield 5118 may be bonded to the insulation extension 5132 via a butt joint. Then, the area where the replacement outer insulation layer 5152 will be positioned that is currently occupied by the outer insulation layer 5120 is ablated. The insulation extension 5132 is also ablated at the same or similar depth as the outer insulation layer 5120. The replacement outer insulation layer 5152 may then be injection molded or shrunk into position at the ablation site.

Figure 25:
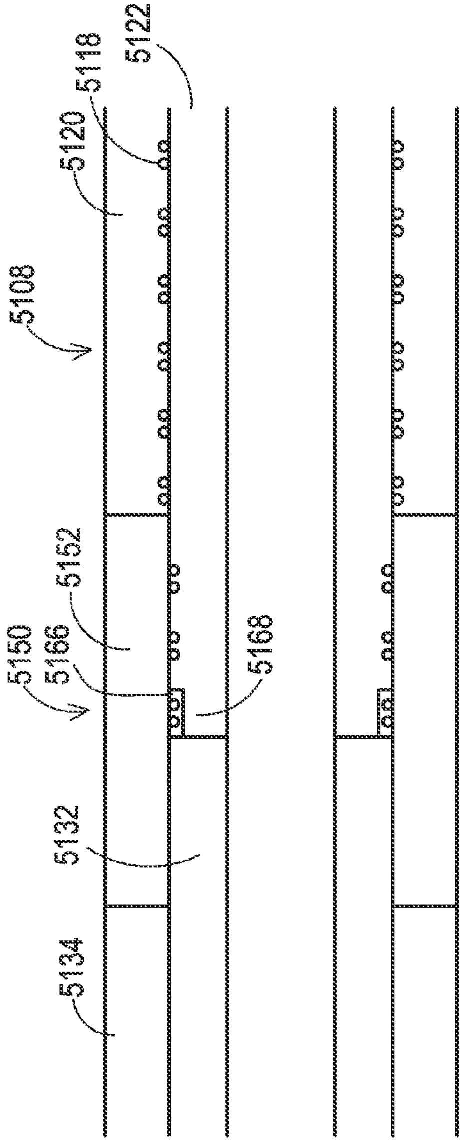
FIG. 25 shows an embodiment of the implantable medical lead where the shield terminates at a ring within a lap joint.

FIG. 25 shows an embodiment with an additional feature that may be included for the lap joint 5150. To further protect the termination of the shield 5118 from fraying or migrating, the wire ends of the shield 5118 may be capped with a ring 5166. The ring 5166 may be metal, plastic, or similar materials. In this example, a region 5168 of the inner insulation layer 5122 has been ablated to allow the ring to be positioned over the ends of the wires of the shield 5118.

Figure 26:
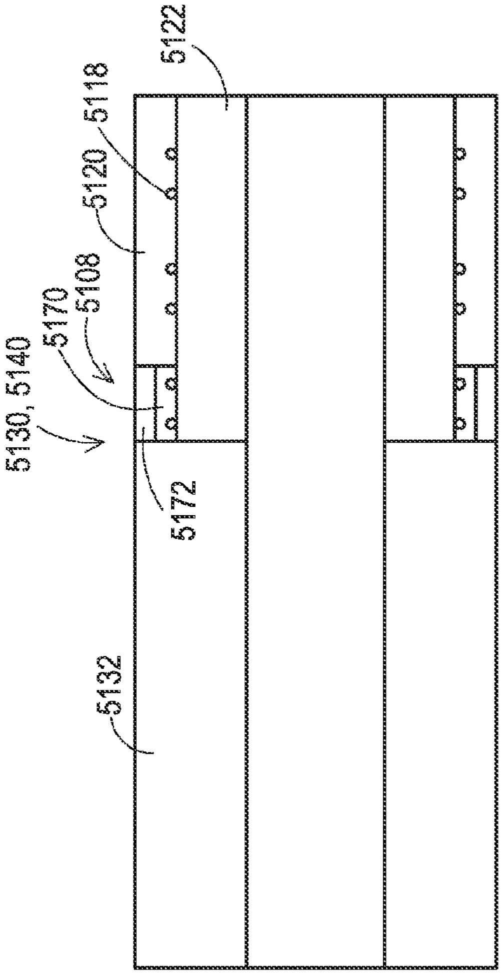
FIG. 26 shows an embodiment of the implantable medical lead where the shield terminates at a ring at a butt joint.

FIG. 26 shows an embodiment with an additional feature that may be included for the butt or scarf joints 5130, 5140. To further protect the termination of the shield 5118 from fraying or migrating, the wire ends of the shield 5118 may be capped with a ring 5170. Similar to the lap joint scenario, the ring 5170 may be metal, plastic, or similar materials. In this example, a region 5172 of the outer insulation layer 5120 has been ablated to allow the ring 5170 to be positioned over the ends of the wires of the shield 5118, and then this region 5172 may be filled using a reflow or injection molding of the polyurethane or other polymer.

Figure 27:
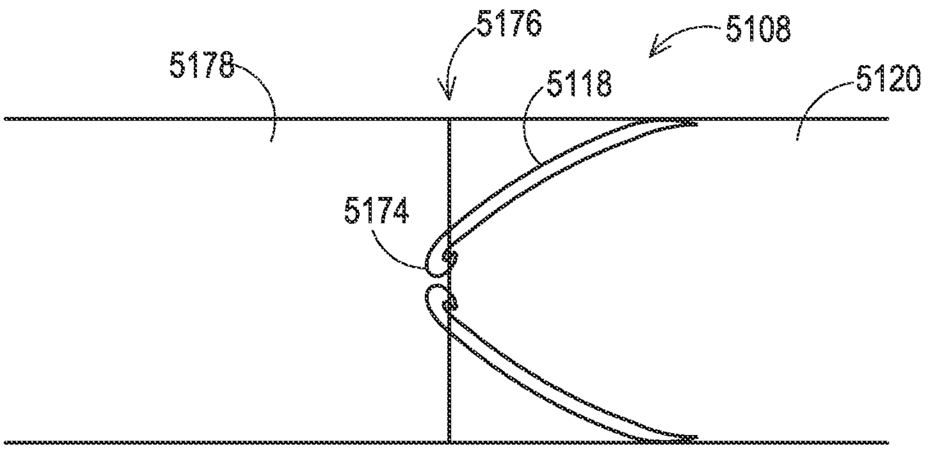
FIG. 27 shows an embodiment of the implantable medical lead where wires of the shield fold over individually at the termination point.

FIG. 27 shows an embodiment with an additional feature that may be included for a joint 5176, which may be of various types such as the butt, scarf, or lap joints 5130, 5140, and 5150. At the joint 5176, the outer insulation layer 5120 of the lead 5108 encounters another layer 5178. This layer 5178 may be the insulation extension 5132 and/or the replacement outer insulation layer 5152. In either case, wires of the shield 5118 may partially extend into the layer 5178. However, prior to bonding the layer 5178 to the layers 5120 or 5122, the ends of the wires of the shield 5118 may be individually folded over as shown in FIG. 27. In this manner, the folded over ends are less likely to fray and migrate.

Figure 28:
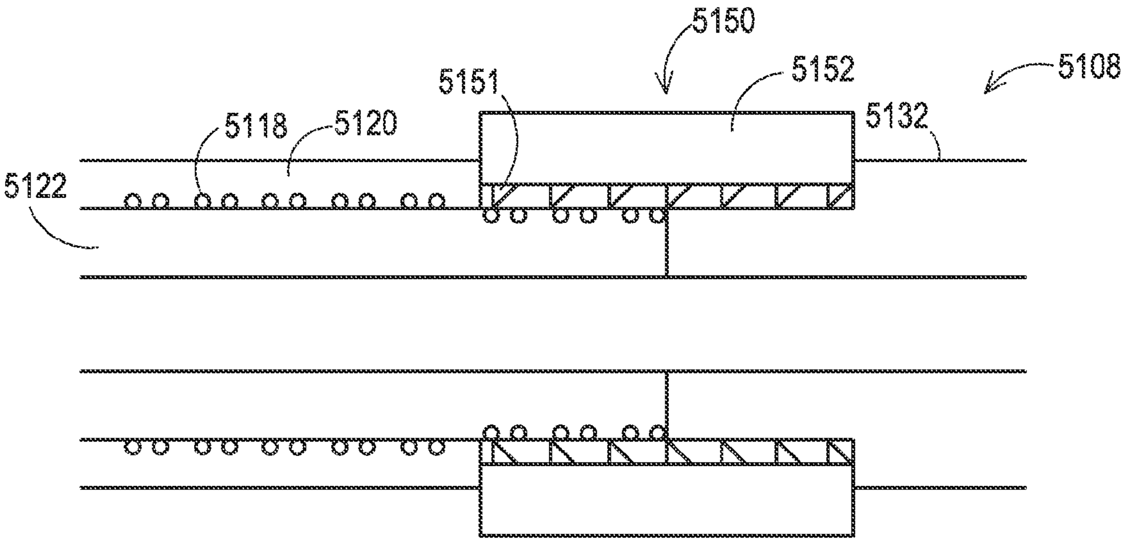
FIG. 28 shows an embodiment of the implantable medical lead where a joint at the shield termination includes a barbed connection to an inner insulation layer.

FIG. 28 shows an embodiment with another feature that may be included for a joint at the termination of the shield 5118 to assist in holding the bond between the inner insulation layer 5122 and the insulation extension 5132 in place. In this example, a lap joint 5150 is shown, but it will be appreciated that this feature may be applicable to other joints as well including butt and scarf joints 5130, 5140. Here, the replacement outer insulation layer 5152 may be tubing that is provided with barbs 5151 that extend toward the inner insulation layer 5122 and the shield 5118.

During reflow, the barbs may sink into the inner insulation layer 5122 as the inner insulation layer 5122 softens more so than the barbs 5151, and the replacement outer insulation layer 5152 descends into position. The barbs 5151 may also sink into the insulation extension 5132 once reflow or other bonding is attempted after the insulation extension 5132 has been inserted to provide extra grip between the replacement outer insulation layer 5152 and the insulation extension 5132. The barbs 5151 then provide extra grip between the inner insulation layer 5122 and the insulation extension 5132 particularly during axial tension. Rather than incorporating the barbs into the replacement outer tubing 5152 of the lap joint example, a separate barbed ring may be positioned on the inner insulation layer 5122 and then the replacement outer insulation layer 5152 is reflowed or otherwise bonded into place.

Figure 29:
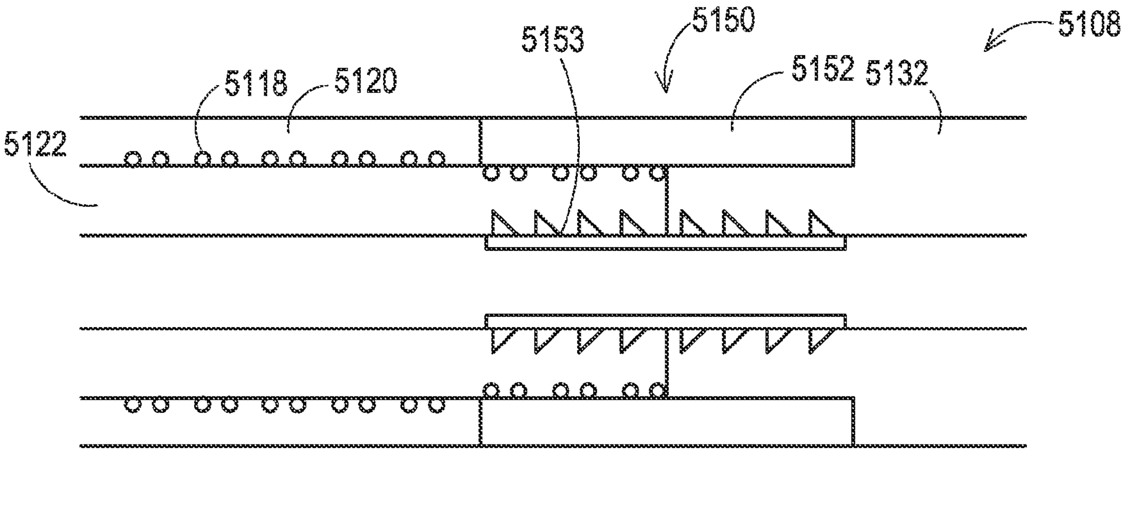
FIG. 29 shows an embodiment of the implantable medical lead where a joint at the shield termination includes a barbed connection to an inner insulation layer.

FIG. 29 shows an embodiment with another feature that may be included for a joint at the termination of the shield 5118 to assist in holding the bond between the inner insulation layer 5122 and the insulation extension 5132 in place. In this example, a lap joint 5150 is shown, but it will be appreciated that this feature may be applicable other joints as well including butt and scarf joints 5130, 5140. Here, a barbed ring 5153 is positioned inside of the inner insulation layer 5122 and is forced to expand radially until the barbs of the barbed ring 5153 sink into the inner insulation layer 5122. The barbs of the barbed ring 5153 may also sink into the inside of the insulation extension 5132. The barbed ring 5153 provides extra grip between the inner insulation layer 5122 and the insulation extension 5132 especially during axial tension. This barbed ring 5153 feature may also be used in conjunction with the barbs 5151 shown in FIG. 28.

Embodiments as disclosed in relation to FIGS. 30-48 also provide for termination of a radio frequency (RF) shield present within an implantable medical lead for use with an implantable medical device (IMD). The shield may be terminated in various ways such as by terminating at a joint to an insulation extension where one or more metal connectors are present in various configurations to provide a ground path for the shield. Furthermore, the shield termination may include features such as a shield wires with folded over ends, or barbs between the insulation layers.

Figure 30:
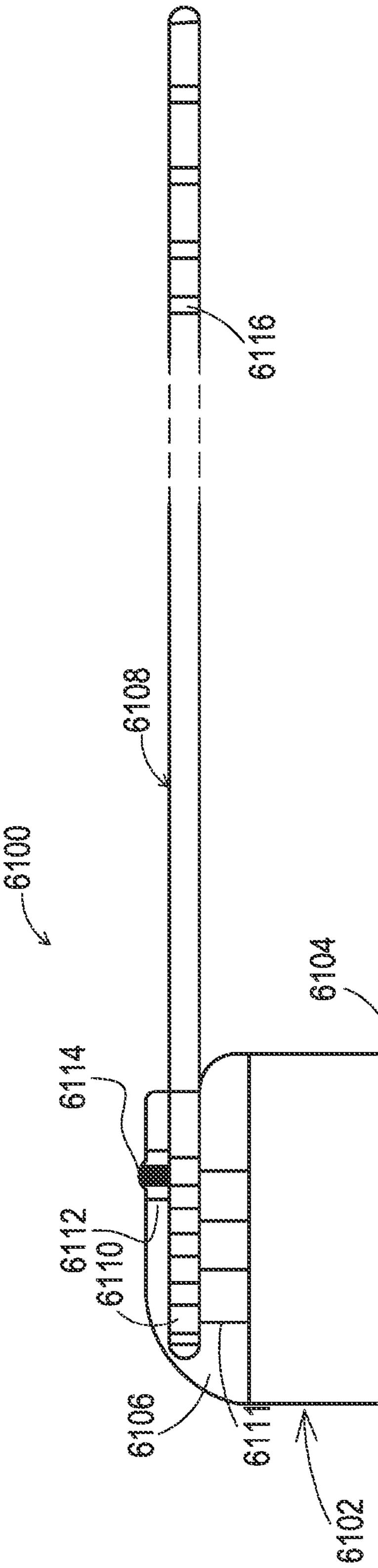
FIG. 30 shows an embodiment of an implantable medical system that includes an implantable medical device (IMD) coupled to a lead containing a shield.

FIG. 30 shows an example of an implantable medical system 6100 that includes an IMD 6102 coupled to a lead 6108. The IMD 6102 includes a metal can 6104, typically constructed of a medical grade titanium, such as grades 1-4, 5 or 9 titanium, or similar other biocompatible materials. The IMD 6102 includes a header 6106 typically constructed of materials such as polysulfone or polyurethane, that is affixed to the metal can 6104. The header 6106 is shown transparently for purposes of illustration. The header 6106 provides a structure for securing the lead 6108 to the IMD 6102 and for establishing electrical connectivity between circuitry of the IMD 6102 and electrodes of the lead 6108.

The lead 6108 includes electrodes 6116 on a distal end that are positioned at a stimulation site within a patient. The lead also includes ring connectors 6110 on a proximal end that is positioned within the header 6106. The ring connectors 6110 make physical contact with electrical connections 6111 within the header. The electrical connections 6111 may include a metal contact that the ring connector 6110 rests against upon being inserted into the header 6106 where a wire extends from the metal contact into the can 6104 where the circuitry is housed. Signals applied by the IMD 6102 to the ring connectors 6110 are conducted through the lead 6108 to the electrodes 6116 to provide the stimulation therapy to the patient.

The lead 6108 is secured in the header 6106 such as by a set screw block 6112 within the header 6106 that allows at least one set screw 6114 to be tightened against at least one of the ring connectors 6110. A shield 6118 as shown in FIGS. 31A and 31B may be grounded to the body along one or more points down the length of the lead from the IMD 6102 via ground rings and/or the shield 6118 may be grounded at the can 6104 of the IMD 6102 of FIG. 30.

Regardless of the manner of grounding, the shield 6118 terminates on one end near the proximal end and on the opposite end near the distal end of the lead 6108. At the termination point, shields having multiple metal wires such as braided shields are subject to fraying and shield wire migration. Preventing the shield wire from fraying and/or migrating to the tissue or to stimulation conductors within the lead 6108 may be desirable to prevent RF energy captured by the shield 6118 from being directed onto a small area of tissue via an electrode or exposed shield wire.

Figure 31A:
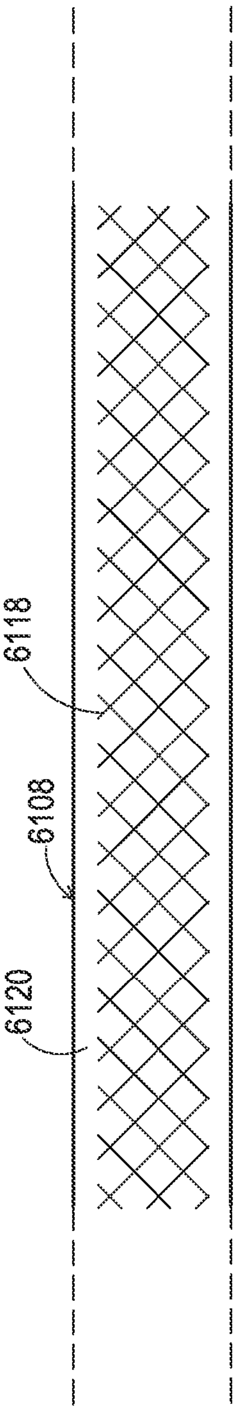
FIG. 31A shows an embodiment of an implantable lead with the shield revealed.
Figure 31B:
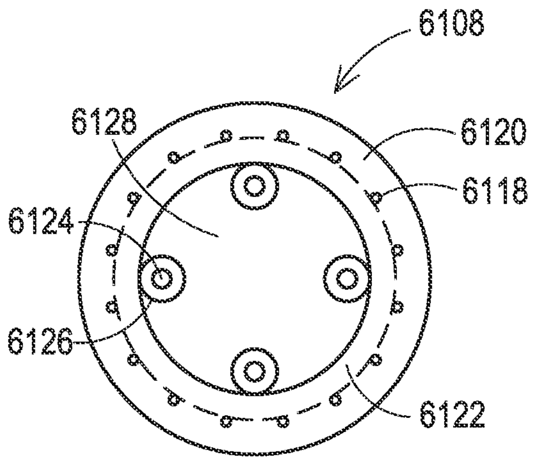
FIG. 31B shows the embodiment of the implantable lead in cross-section to reveal the shield and filars.

FIGS. 31A and 31B show an example of the lead 6108, where a shield 6118 is present. An outer insulation layer 6120 of a lead jacket is shown transparently in FIG. 31A for purposes of illustrating the shield 6118. The shield 6118 blocks at least some RF energy from directly coupling to conductive filars 6124 that are present within the lead 6108. The conductive filars 6124 extend the length of the lead and interconnect the proximal ring connectors 6110 to the distal electrodes 6116 so that stimulation signals are conducted from the proximal end to the distal end of the lead 6108.

As shown in FIG. 31A, the shield 6118 of this example is a braided collection of metal wires. The metal wires may be constructed of various materials such as titanium, tantalum, niobium, platinum-iridium alloy, platinum, palladium, gold, stainless steel, and their alloys, or other metals. It may be desired to utilize a biocompatible metal for the shield 6118, particularly for embodiments where a portion of the shield 6118 may be exposed for purposes of grounding. While the shield 6118 is shown as a braid, other shield configurations may be chosen particularly where flexibility is not an issue such as a foil strip wrapped about the lead 6108 in an overlapping manner or an outer layer 6120 that is heavily doped with conductive particles.

As shown in FIG. 31B, the shield 6118 may be embedded within the jacket of the lead 6108. One manner of constructing the lead 6108 with the shield 6118 is to provide an inner insulation layer 6122 of the jacket that encloses the filars 6124 and any additional insulation layer 6126, such as polytetrafluoroethylene (PTFE) that may surround each filar 6124. The shield 6118 may then reside on the outer portion of the inner insulation layer 6122, and the outer insulation layer 6120 may then enclose the shield 6118. The outer insulation layer 6120 may be added over the shield 6118 and shrunk in place or may be extruded over the shield 6118. The outer jacket 6120 maybe added over the braid 6118, or it may be extruded over the braid.

For embodiments where it is desirable for the shield 6118 to RF couple to tissue, typically as a capacitive coupling, in addition to grounding at the can or along the lead, the amount of the outer jacket layer 6120 covering the shield 6118 may be relatively thin, such as on the order of 0.5 to 5 mils. Where the shield 6118 grounds at one or more specific locations along its length, via a direct current coupling or a capacitive coupling, the shield 6118 may be located further from the outer surface of the lead 6108.

The inner and outer insulation layers 6122, 6120 of the jacket may be constructed of the same or similar materials such as various flexible and biocompatible polymers, examples of which are polyurethanes and silicones. A lumen 6128 may be included inside of the inner jacket 6122 around which the insulated filars 6124 are coiled or otherwise positioned. The lumen 6128 may be useful, particularly for percutaneous leads 6108, to allow a stylet to be inserted for purposes of pushing and steering the lead 6108 into the desired position within the patient.

Figure 32:
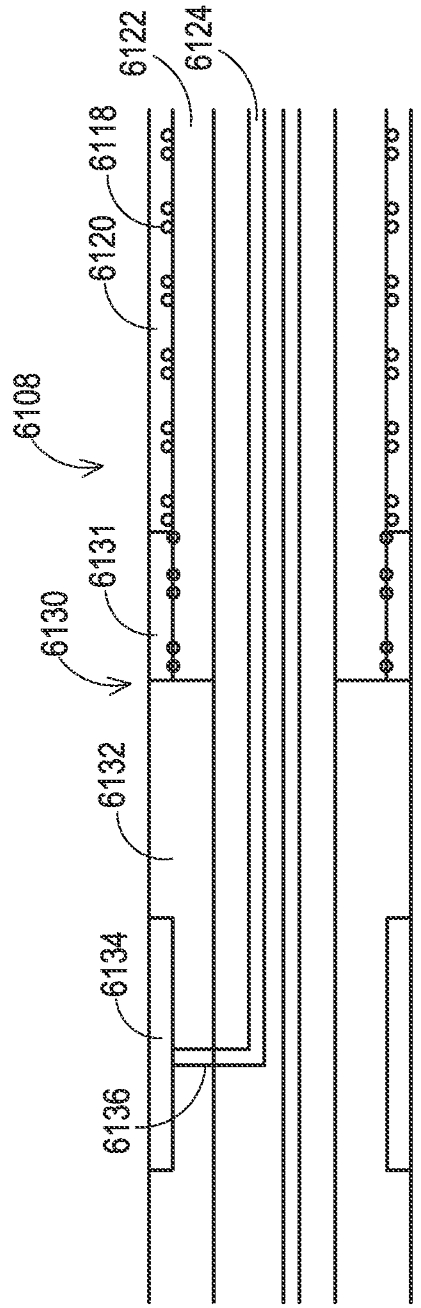
FIG. 32 shows an embodiment of the implantable lead where the shield terminates to a metal connector near a butt joint to an insulation extension.

FIG. 32 shows an embodiment of an implantable medical lead 6108 in cross-section with a cut taken down an axial centerline. The lead 6108 includes a butt joint 6130 where the inner insulation layer 6122 and shield 6118 terminate. The outer insulation 6120 terminates prior to the butt joint 6130 to expose the shield 6118 and inner insulation layer 6122. A metal connector 6131 is positioned over the shield 6118 and inner insulation layer 6122 and abuts the end of the outer insulation layer 6120. At the butt joint 6130, an insulation extension 6132 abuts and is bonded to the blunt end of the inner insulation layer 6122, shield 6118, and metal connector 6131 such as via reflow or injection molding.

As shown in this example, the shield 6118 terminates at the butt joint 6130 rather than farther back within the jacket formed by the inner and outer insulation layers 6122, 6120. The insulation extension 6132 in this example extends the remainder of the lead 6108 where ring connectors 6134 are located on the proximal end at a separate from the nearest connector ring ranging from about 0.5 millimeters to about 10 centimeters. The filars 6124 jumper to their respective ring connectors via a filar jumper 6136. The lumen may be present in some embodiments with the filars 6124 being located about the lumen.

The material for the insulation extension 6132 may be selected to provide a different amount of stiffness than the inner and outer insulation layers 6122, 6120. For instance, the insulation extension 6132 may be constructed of a stiffer material to aid in the insertion of the proximal end into the header 6106. As a particular example, the outer insulation 6120 may be constructed of polyurethane having a durometer 55D or similar rating while the insulation extension 6132 may be constructed of a polyurethane having a durometer 75D or similar rating.

The shield 6118 may be terminated with an exposed metal connector 6131 at a butt joint on the distal end so long as no terminating ground ring is present at the proximal end to thereby avoid stimulation induced by magnetic gradients. In such a case, the insulation extension may have a durometer rating similar to the outer layer 6120 but may instead be constructed of polyurethane having a durometer 80A or similar rating.

The metal connector 6131 is separated from the distal electrode by at least 0.5 mm up to 10 cm for some body locations, to avoid excessive RF coupling to the distal electrode, with 2 mm being one example of spacing that provides adequate filar coverage with insignificant coupling to the distal electrode. Where the distal end is located in a high RF intensity area such as just under the skin for peripheral nerve stimulation, then the distance may be kept smaller, such as less than 2 cm to avoid overexposure of the filars 6124.

Figure 33:
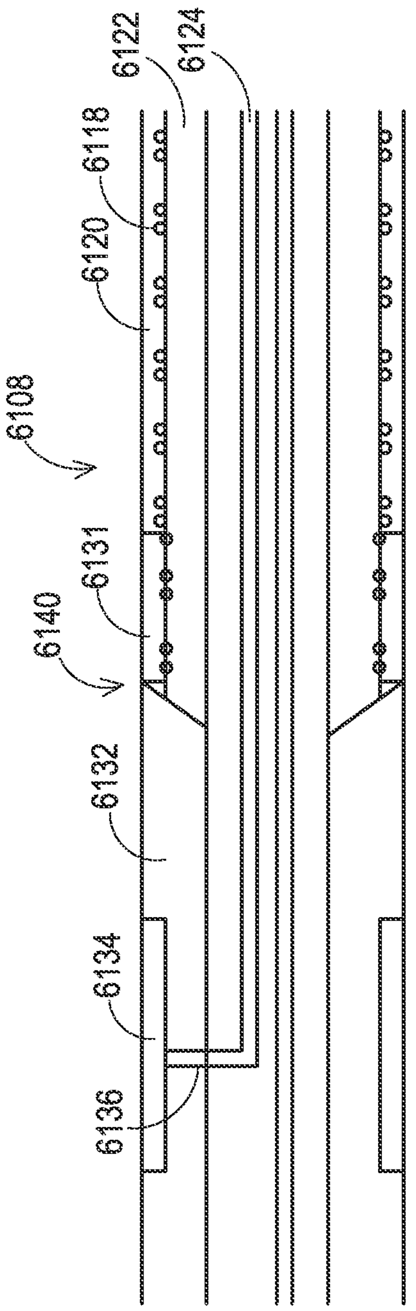
FIG. 33 shows an embodiment of the implantable lead where the shield terminates to a metal connector near a scarf joint to an insulation extension.

FIG. 33 shows another embodiment of an implantable medical lead 6108 in cross-section with a cut taken down an axial centerline. The lead 6108 terminates at a scarf joint 6140 where the inner insulation layer 6122 and shield 6118 terminate at a wedged cut. The outer insulation 6120 terminates prior to the scarf joint 6140 to expose the shield 6118 and inner insulation layer 6122. A metal connector 6131 is positioned over the shield 6118 and inner insulation layer 6122 and abuts the end of the outer insulation layer 6120. At this scarf joint 6140, an insulation extension 6132 that has a complementary wedged cut abuts and is bonded to the wedged end of the inner insulation layer 6122, shield 6118, and metal connector 6131 such as via reflow or injection molding.

The scarf joint 6140 may be used rather than the butt joint 6130 of FIG. 32 because the scarf joint 6140 has an increased bond area. As shown in this example, the shield 6118 terminates at the scarf joint 6140 rather than farther back within the jacket formed by the inner and outer insulation layers 6122, 6120. The insulation extension 6132 in this example extends the remainder of the lead 6108 where ring connectors 6134 are located on the proximal end. The filars 6124 jumper to their respective ring connectors via a filar jumper 6136.

Similar to the previous embodiment of FIG. 32, the material for the insulation extension 6132 in this embodiment of FIG. 33 may be selected to provide a different stiffness than the inner and outer insulation layers 6122, 6120. For instance, the insulation extension 6132 may be constructed of a stiffer material such as polyurethane with a durometer 75D.

The metal connector 6131 may be included on either the proximal or distal end to terminate the shield 6118 as discussed above. The separation of the metal connector 6131 to the distal electrode or proximal connector ring may also be in accordance with the separation as discussed above.

Figure 34:
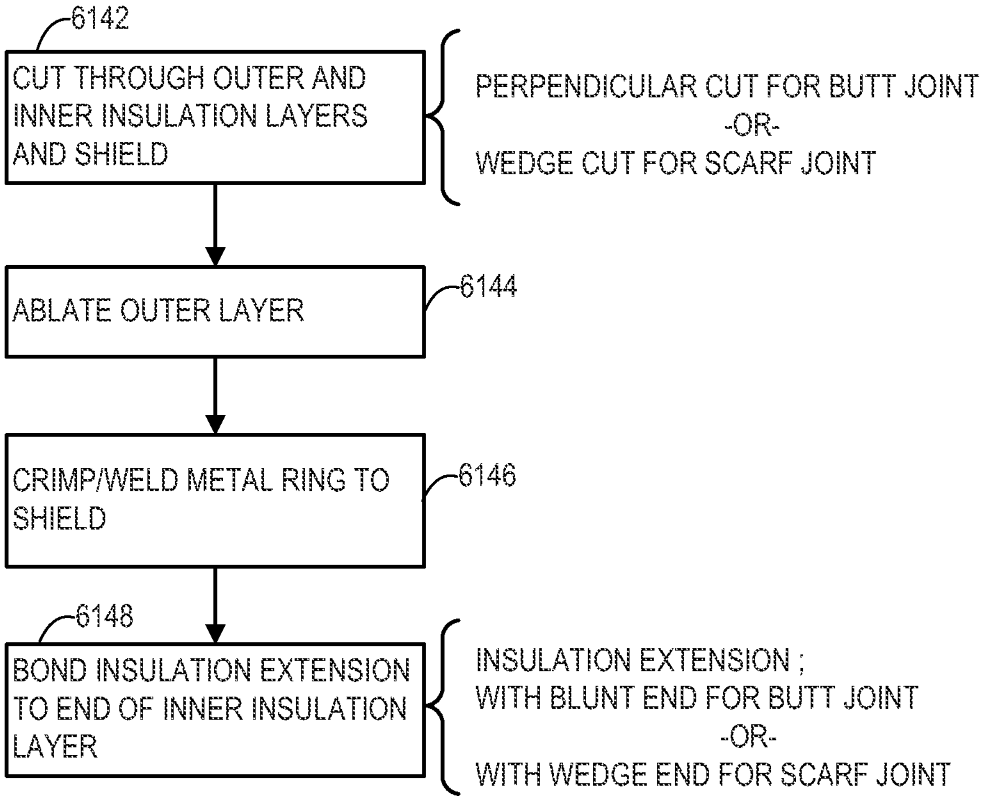
FIG. 34 shows one example of a set of steps to create the implantable lead of FIGS. 32 and 33.

FIG. 34 shows a set of steps to create the embodiments of FIGS. 32 and 33. Initially, a structure including the inner insulation layer 6122, outer insulation layer 6120, and shield 6118 may be provided. The shield 6118 has been braided over the inner insulation layer 6122 and then the outer insulation layer 6120 has been positioned and reflowed or otherwise bonded over the inner insulation layer 6122 and the shield 6118. To begin construction of the lead 6108 and the butt joint 6130 or scarf joint 6140, the structure is cut to size by making a cut through the insulation layers 6120, 6122 and the shield 6118 at a cutting step 6142. For a butt joint 6130, the cut is perpendicular to the axial dimension to create the blunt end. For a scarf joint 6140, the cut is at angle other than 90 degrees to the axial dimension to create the wedged end.

The end portion of the outer insulation layer 6120 is ablated to reveal the shield 6118 at ablating step 6144. The metal connector 6131, such as a ring connector, may then be crimped or welded onto the shield 6118 at crimping step 6146.

The insulation extension 6132 is bonded to the lead 6108 to form the butt joint 6130 or scarf joint 6140 at a bonding step 6148. For the butt joint 6130, the insulation extension 6132 is cut perpendicular to the axial dimension to create the blunt end. For the scarf joint 6140, the insulation extension 6132 is cut at an angle other than 90 degrees to the axial dimension to create the wedged end. The two blunt ends for the butt joint 6130 are brought together and bonded at a bonding step 6148. Likewise, the two wedged ends for the scarf joint 6140 are brought together and bonded at the bonding step 6148.

Figure 35:
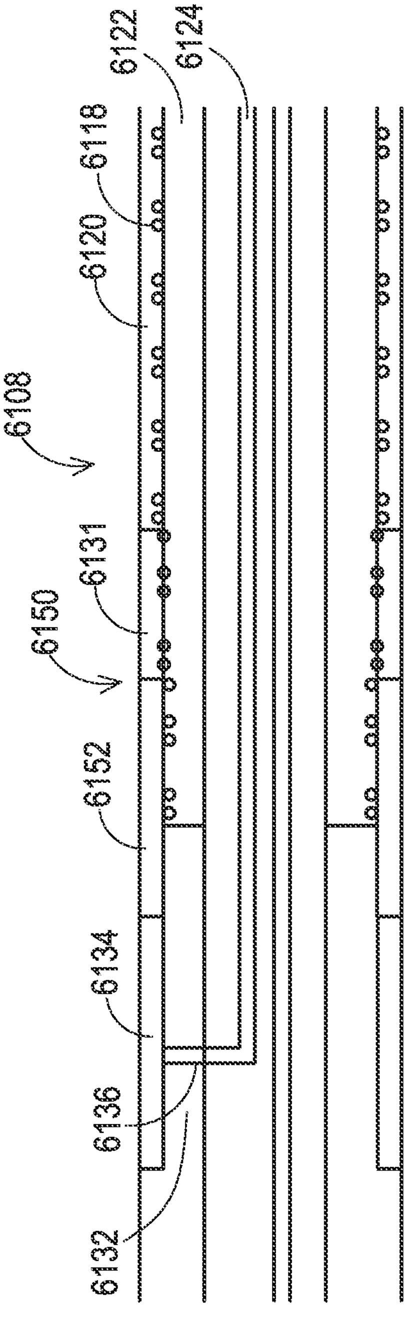
FIG. 35 shows an embodiment of the implantable medical lead where the shield terminates to a metal connector near a lap joint to an insulation extension.

FIG. 35 shows another embodiment of an implantable medical lead 6108 in cross-section with a cut taken down an axial centerline. The lead 6108 includes a lap joint 6150 where the inner insulation layer 6122 and the shield 6118 terminate. The lap joint 6150 involves removing an end portion of the outer insulation layer 6120 sufficient to allow space for the metal connector 6131 and a replacement outer insulation layer 6152 to lap over the area of the shield 6118 and inner insulation layer 6122 where the outer insulation layer 6120 is missing. The metal connector 6131 abuts the end of the outer insulation layer 6120. The replacement outer insulation layer 6152 abuts the metal connector 6131, laps over a section of the insulation extension 6132, and may extend to the nearest electrode 6134.

As shown, the shield 6118 has been crimped down into the inner insulation layer 6122 at the region where the outer insulation layer 6120 has been removed. Doing so prevents the shield 6118 from bunching together during installation of the outer replacement insulation layer 6152. This may be especially the case where the replacement outer insulation layer 6152 is in the form of tubing that slides into place over the shield 6118 and inner insulation layer 6122 prior to attaching the insulation extension 6132. Where the replacement outer insulation layer 6152 is tubing, once being slid into place, it is reflowed or otherwise bonded to the inner insulation layer 6122. As an alternative, the replacement outer insulation layer 6152 may be injection molded into place.

As shown in this example, the shield 6118 terminates at the lap joint 6150 rather than farther back within the jacket formed by the inner and outer insulation layers 6122, 6120. The insulation extension 6132 in this example extends the remainder of the lead 6108 where ring connectors 6134 are located at the proximal end. The filars 6124 jumper to their respective ring connectors via a filar jumper 6136. The lumen may be present in some embodiments with the filars 6124 being located about the lumen.

In this embodiment the replacement outer insulation layer 6152 may be constructed of a material that differs in stiffness from the outer insulation layer 6120. For instance, the replacement outer insulation layer 6152 may be constructed of a stiffer material such as durometer 75D polyurethane. In this embodiment, like that of the previous ones, the material for the insulation extension 6132 may also be selected to provide a different stiffness than the inner and outer insulation layers 6122, 6120. For instance, the insulation extension 6132 may also be constructed of a stiffer material such as durometer 75D polyurethane.

The metal connector 6131 may be included on either the proximal or distal end to terminate the shield 6118 as discussed above. The separation of the metal connector 6131 to the distal electrode or proximal connector ring may also be in accordance with the separation as discussed above.

Figure 36:
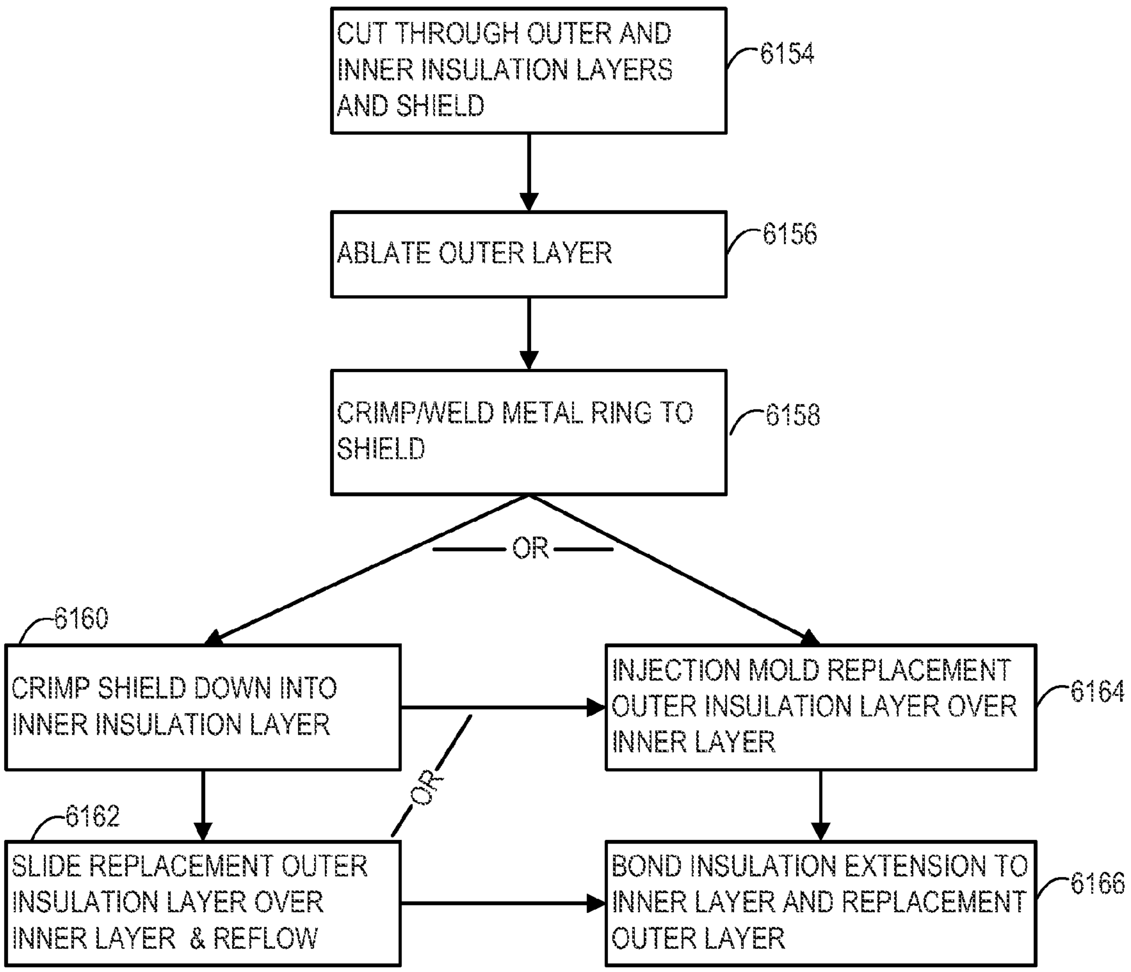
FIG. 36 shows one example of a set of steps to create the implantable lead of FIG. 35.

FIG. 36 shows one example of a set of steps that create the lap joint 6150 of FIG. 35. Initially, a structure including the inner insulation layer 6122, outer insulation layer 6120, and shield 6118 may be provided. The shield 6118 has been braided over the inner insulation layer 6122 and then the outer insulation layer 6120 has been positioned and reflowed or otherwise bonded over the inner insulation layer 6122 and the shield 6118. To begin construction of the lead 6108 and the lap joint 6150, the structure is cut to size by making a cut through the insulation layers 6120, 6122 and the shield 6118 at a cutting step 6154. For a lap joint 6130, this first cut is perpendicular to the axial dimension to create a blunt end.

Once cut to size, the outer insulation layer 6120 is then ablated by some distance to expose the shield 6118 and the inner insulation layer 6122 at an ablating step 6156. Ablation may be done using tools such as an excimer laser which can very precisely ablate to expose the shield 6118. The length of the outer insulation layer 6120 to be ablated is sufficient to allow for the metal connector 6131 as well as the amount of the replacement outer insulation layer 6152 that laps onto the inner insulation layer 6122. This length of ablation of the outer insulation layer 6120 may vary but an illustrative range is from 0.25 centimeters (cm) to 5 cm.

Once ablation is complete, the metal connector 6131 may then be put in position over the inner insulation layer 6122 and shield 6118. The metal connector 6131 is crimped or welded to the shield 6118 while abutting the end of the outer insulation layer 6120 at a crimping step 6158.

Once the metal connector 6131 is installed, the next step may vary. The replacement outer insulation layer 6152 may be installed in various manners such as by reflowing tubing or by injection molding. If by injection molding, then the next step may be either a crimping step 6160 or an injecting step 6164. If by reflowing tubing, then it may be helpful to proceed to the crimping step 6160 after ablating.

At the crimping step 6160, the portion of the shield 6118 that is exposed beyond the metal connector 6131 is crimped so as to sink down into the inner insulation layer 6122. If a ring or other tool is used to crimp the shield 6118 into the inner insulation layer 6122, the ring or other tool may then be removed. Where the replacement outer insulation layer 6152 is being installed as tubing that is reflowed, then the next step is tubing step 6162. Where the replacement outer insulation layer 6152 is being installed by injection molding, then the next step is injecting step 6164.

At the tubing step 6162, the tubing is slid onto the inner insulation layer 6122 and over the shield 6118 at the area where the outer insulation layer 6120 has been removed and where the shield 6118 has been crimped down. The tubing extends beyond the end of the inner insulation layer 6122 so that it may eventually be bonded to the insulation extension 6132. The tubing is reflowed or otherwise bonded to the inner insulation layer 6122 and to abut the end of the metal connector 6131. Contemporaneously, the insulation extension 6132 is bonded in place at the blunt end of the inner insulation layer 6122 and to the tubing of the replacement outer insulation layer 6152 that extends beyond the inner insulation layer 6122 at a bonding step 6166. This tubing may be reflowed or otherwise bonded onto the insulation extension 6132.

Returning to the injecting step 6164, in the scenario where the replacement outer insulation layer 6152 is to be injection molded, then the injecting step 6164 takes place either after the crimping step 6158 or after the crimping step 6160. Material such as the desired polyurethane is injected onto the inner insulation layer 6122 and the shield 6118 to form the replacement outer insulation layer 6152. Contemporaneously, the insulation extension 6132 is bonded to the inner insulation layer 6122 and to the replacement outer insulation layer 6152 at the bonding step 6166.

Alternative manners of creating the lap joint 6150 may also be used. For instance, the structure of the outer insulation layer 6120, inner insulation layer 6122, and shield 6118 may be bonded to the insulation extension 6130 via a butt joint. Then, the area where the metal connector 6131 and replacement outer insulation layer 6152 will be positioned that is currently occupied by the outer insulation layer 6120 is ablated. The insulation extension 6132 is also ablated at the same or similar depth as the outer insulation layer 6120. The metal connector 6131 may then be positioned, and the replacement outer insulation layer 6152 may then be injection molded or shrunk into position at the ablation site.

Figure 37:
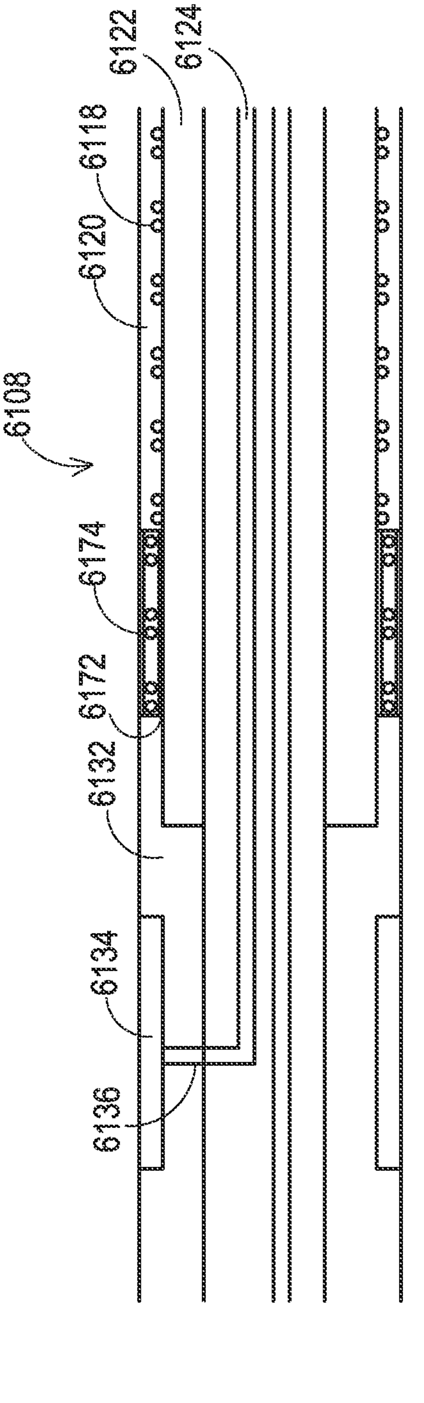
FIG. 37 shows an embodiment of the implantable medical lead where the shield terminates between a pair of metal connectors near a joint to an insulation extension.

FIG. 37 shows another embodiment of an implantable medical lead 6108 in cross-section with a cut taken down an axial centerline. The lead 6108 includes a joint between the inner insulation layer 6122 and the insulation extension 6132 where the inner insulation layer 6122 and the shield 6118 terminate. An inner metal connector 6172 is positioned around the inner insulation layer and an outer metal connector 6174 is positioned around the inner metal connector 6172. A portion of the shield 6118 is located between the inner metal connector 6172 and the outer metal connector 6174 such that a robust physical and electrical connection is established to the shield 6118.

In this example, the shield 6118 is braided after the inner metal connector 6172 has been positioned so that the braid of the shield 6118 laps over the inner metal connector 6172. The outer insulation layer 6120 terminates short of the end of the shield 6118 and inner insulation layer 6122. This may be achieved by ablating the outer insulation layer 6120 where it has been previously extruded over the shield and inner metal connector 6172.

As shown in this example, the shield 6118 terminates between the metal connectors 6172, 6174 rather than farther back within the jacket formed by the inner and outer insulation layers 6122, 6120. The insulation extension 6132 in this example extends the remainder of the lead 6108 where ring connectors 6134 are located at the proximal end. The filars 6124 jumper to their respective ring connectors via a filar jumper 6136. The lumen may be present in some embodiments with the filars 6124 being located about the lumen.

The metal connectors 6172, 6174 may be included on either the proximal or distal end to terminate the shield 6118 as discussed above. The separation of the metal connectors 6172, 6174 to the distal electrode or proximal connector ring may also be in accordance with the separation as discussed above for connector ring 6131.

Figure 38:
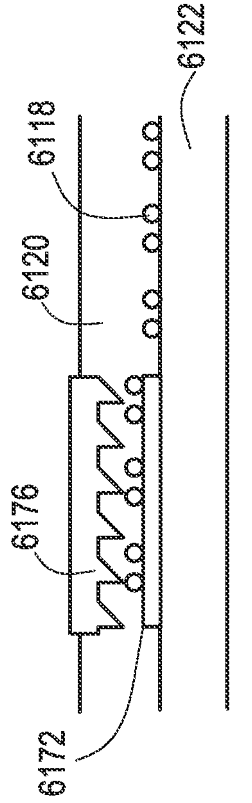
FIG. 38 shows an alternative embodiment where a top metal connector of the pair has sharp features to penetrate an outer insulation layer.

FIG. 38 shows an alternative manner of attaching the outer metal connector. Rather than ablate the outer insulation layer 6120 at the area where the shield 6118 and inner metal connector 6172 are located, an outer metal connector 6176 having features such as teeth that can penetrate through the outer insulation layer 6120 is used. The outer metal connector 6176 is crimped in place so that the features penetrate through the outer insulation layer 6120 to reach the shield 6118 and the inner metal connector 6172 and establish the physical and electrical connection.

Figure 39:
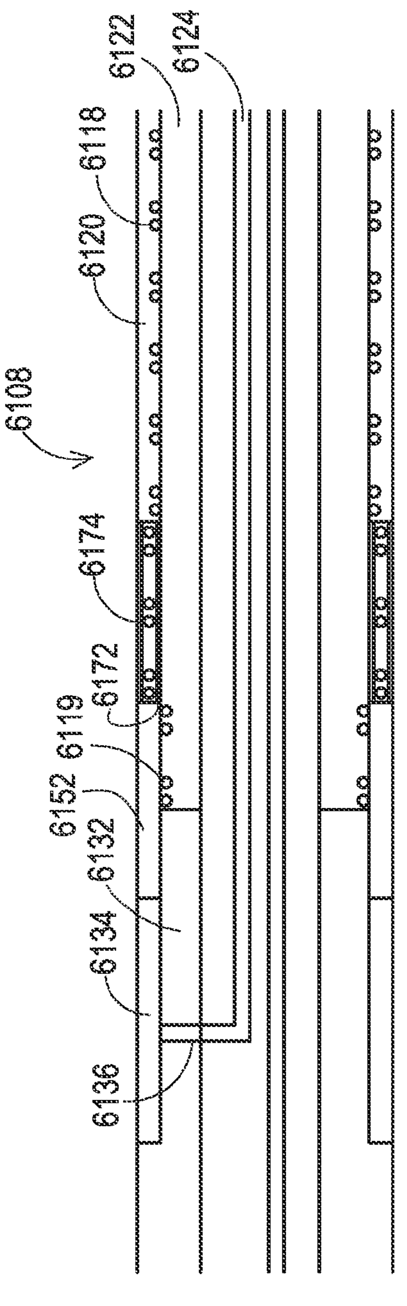
FIG. 39 shows an embodiment of the implantable medical lead where the shield terminates between a pair of metal connectors near a lap joint to an insulation extension.

FIG. 39 shows a similar embodiment to that of FIG. 37 where the lead includes the inner metal connector 6172 and the outer metal connector 6174. However, in this example, the shield 6118 does not terminate between the metal connectors 6172, 6174 but a portion 6119 of the shield 6118 continues beyond those connectors 6172, 6174 to extend over the remaining portion of the inner insulation layer 6122. This portion 6119 of the shield 6118 may be crimped into a sunken position within the inner insulation layer 6122.

A replacement outer insulation layer 6152 may be bonded over the portion 6119 of the shield 6118 to form a lap joint. The insulation extension 6132 may then be bonded to the inner insulation layer 6122 and the replacement outer insulation layer 6152. The insulation extension 6132 in this example extends the remainder of the lead 6108 where ring connectors 6134 are located at the proximal end. The filars 6124 jumper to their respective ring connectors via a filar jumper 6136. The lumen may be present in some embodiments with the filars 6124 being located about the lumen.

The metal connectors 6172, 6174 may be included on either the proximal or distal end to terminate the shield 6118 as discussed above. The separation of the metal connectors 6172, 6174 as well as any portion of the shield 6118 extending beyond the metal connectors 6172, 6174 to the distal electrode or proximal connector ring may also be in accordance with the separation as discussed above.

Figure 40:
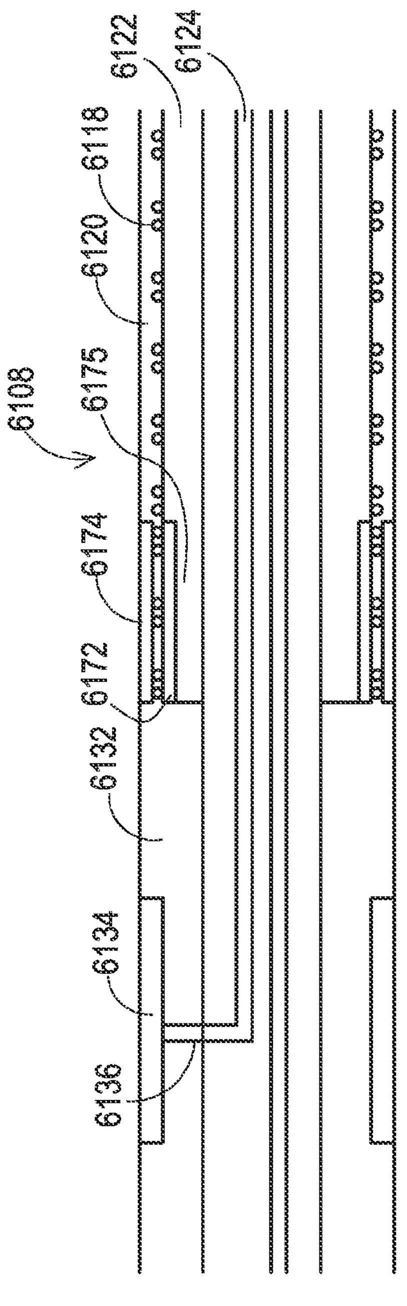
FIG. 40 shows an alternative embodiment of the implantable medical lead where an inner metal connector is mounted flush with an inner insulation layer.

FIG. 40 shows a similar embodiment to that of FIG. 37 where the lead includes the inner metal connector 6172 and the outer metal connector 6174. However, in this example, the inner metal connector 6172 does not wrap around the outside of the inner insulation layer 6122 but instead is embedded within the inner insulation layer 6122 so as to provide a flush surface for the shield 6118 to be braided upon. The shield 6118 is located between this inner metal connector 6172 and the outer metal connector 6174. In this example, the metal connectors 6172, 6174 together with the inner insulation layer 6122 form a butt joint with the insulation extension 6132.

The insulation extension 6132 is bonded to the inner insulation layer 6122 and abuts the metal connectors 6172, 6174. The insulation extension 6132 in this example extends the remainder of the lead 6108 where ring connectors 6134 are located at the proximal end. The filars 6124 jumper to their respective ring connectors via a filar jumper 6136. The lumen may be present in some embodiments with the filars 6124 being located about the lumen.

The metal connectors 6172, 6174 may be included on either the proximal or distal end to terminate the shield 6118 as discussed above. The separation of the metal connectors 6172, 6174 to the distal electrode or proximal connector ring may also be in accordance with the separation as discussed above.

Figure 41:
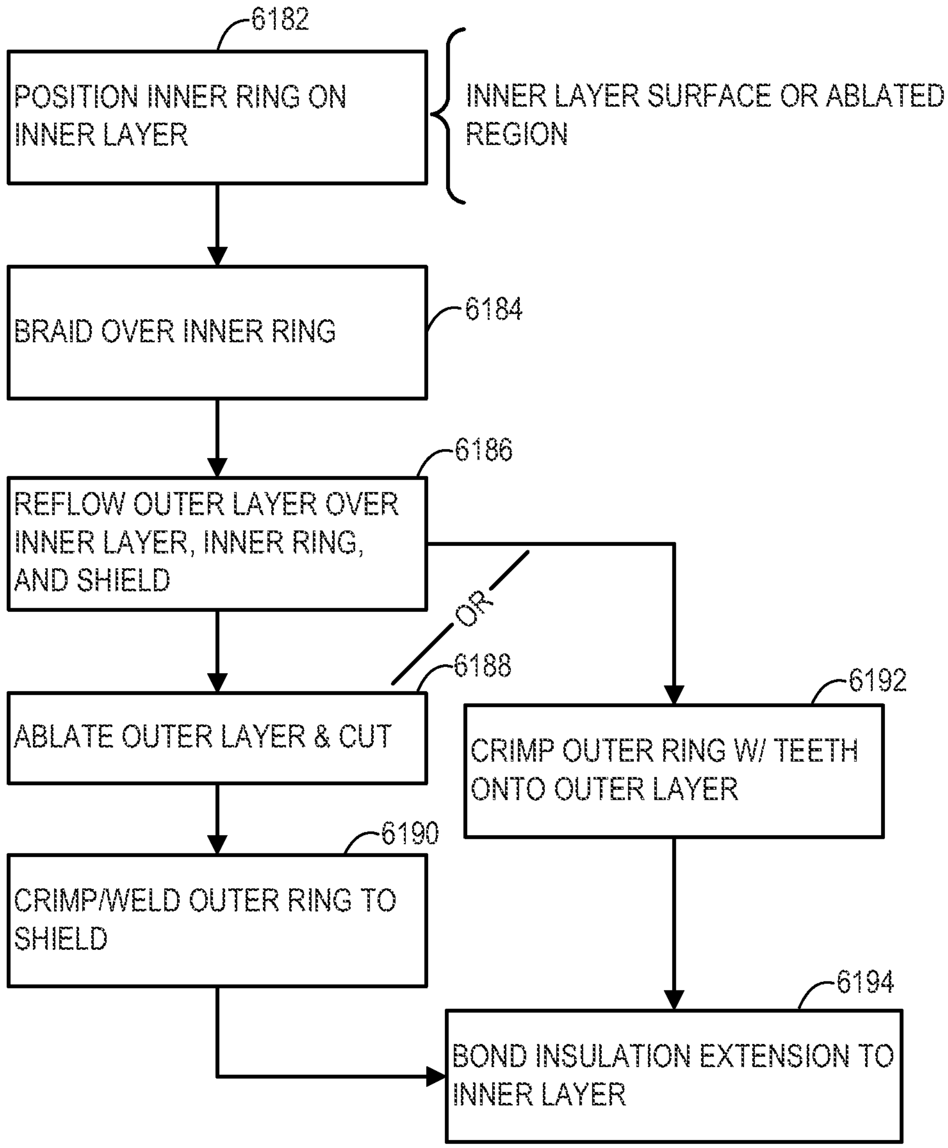
FIG. 41 shows one example of a set of steps to create the implantable lead of FIGS. 37-40.

FIG. 41 shows one example of a set of steps that create the shield termination of FIGS. 37-40. The inner metal connector 6172 is positioned on the inner insulation layer 6122 or embedded at the end at a connector step 6182. The shield 6118 is braided onto the inner insulation layer 6122 and over the inner metal connector 6172 at a braiding step 6184. The outer insulation layer 6120 is bonded by reflow or another process onto the inner insulation layer 6122 over the shield 6118 and over the inner metal connector 6172 such as by a reflowing step 6186.

At this point, preparation is made for the outer metal connector 6174. In one example, the outer insulation layer is ablated at an ablating step 6188 and then the outer metal connector is crimped or welded onto the exposed shield 6118 at the overlap to the inner metal connector 6172 at a crimping step 6190. Alternatively, the inner metal connector 6176 having the sharp features is crimped onto the outer insulation layer 6120 with the sharp features penetrating to the shield 6118 and the inner metal connector 6172 at a crimping step 6192. The insulation extension 6132 is then bonded to the inner insulation layer 6122 at a bonding step 6194.

Figure 42:
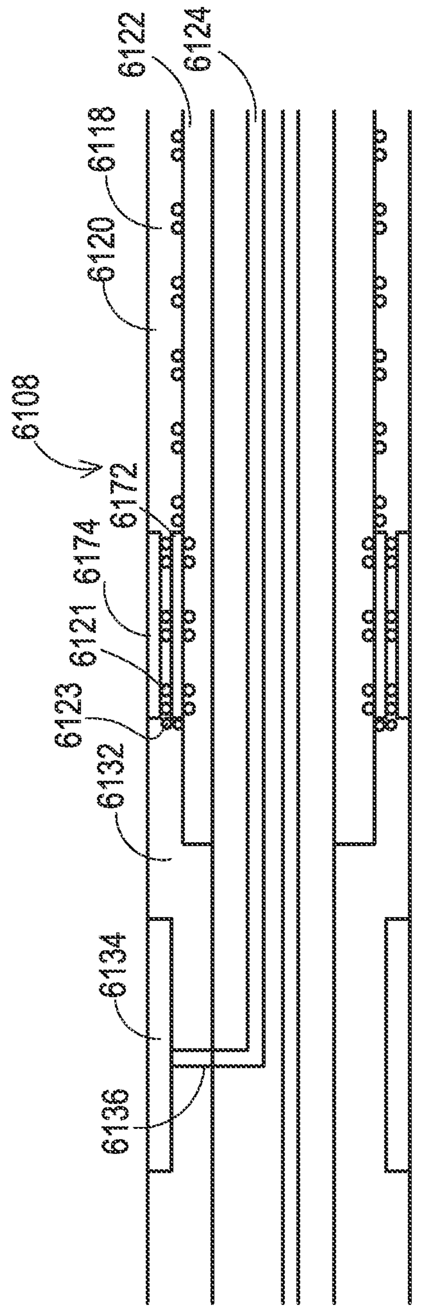
FIG. 42 shows an embodiment of the implantable medical lead where the shield folds over to terminate between a pair of metal connectors near a joint to an insulation extension.

FIG. 42 shows a similar embodiment to that of FIG. 37 where the lead includes the inner metal connector 6172 and the outer metal connector 6174. However, in this example, the inner metal connector 6172 does not wrap around the outside of the inner insulation layer 6122 prior to the shield 6118 being braided. Instead, the shield 6118 is braided over the inner insulation layer 6122 and the inner metal connector 6172 is then crimped or welded onto the shield 6118. The shield 6118 may be sunken into the inner insulation layer 6122 in the area where the inner metal connector 6172 is positioned.

The shield 6118 inverts as a whole at an inversion 6123 so that a portion 6121 of the shield 6118 laps over the inner metal connector 6172. The outer metal connector 6174 may then be crimped or welded in placed about the portion 6121 and the inner metal connector 6172. A robust electrical and physical termination of the shield 6118 occurs between the metal connectors 6172, 6174. The inversion 6123 may provide additional benefits for the shield 6118, such as reducing any RF energy leakage that might otherwise occur at a blunt end of the shield 6118.

The insulation extension 6132 is bonded to the inner insulation layer 6122 and abuts the metal connectors 6172, 6174. The insulation extension 6132 in this example extends the remainder of the lead 6108 where ring connectors 6134 are located at the proximal end. The filars 6124 jumper to their respective ring connectors via a filar jumper 6136. The lumen may be present in some embodiments with the filars 6124 being located about the lumen.

The metal connectors 6172, 6174 may be included on either the proximal or distal end to terminate the shield 6118 as discussed above. The separation of the metal connectors 6172, 6174 to the distal electrode or proximal connector ring may also be in accordance with the separation as discussed above.

Figure 43:
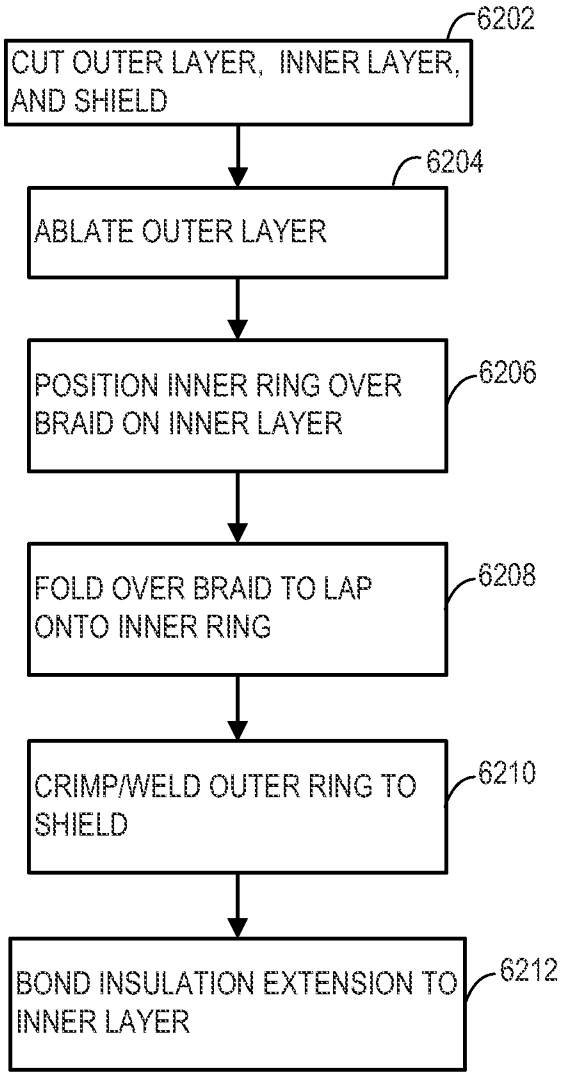
FIG. 43 shows one example of a set of steps to create the implantable lead of FIG. 42.

FIG. 43 shows one example of a set of steps that create the shield termination of FIG. 42. The outer insulation layer 6120, inner insulation layer 6122, and shield 6118 are cut to form a blunt end at a cutting step 6202. A portion of the outer insulation layer 6120 is then ablated to reveal the shield 6118 and inner insulation layer 6122 at an ablating step 6204. The inner metal connector 6172 is positioned on the shield 6118 and around the inner insulation layer 6122 with a portion of the shield 6118 and the inner insulation layer 6122 extending beyond the metal connector 6172 at a connector step 6206. The shield 6118 is inverted as a whole and lapped onto the inner metal connector at a folding step 6208.

At this point, the outer metal connector is crimped or welded onto the exposed shield 6118 at the overlap to the inner metal connector 6172 at a crimping step 6210. Alternatively, the outer metal connector 6176 having the sharp features is crimped onto the outer insulation layer 6120 with the sharp features penetrating to the shield 6118 and the inner metal connector 6172. The insulation extension 6132 is then bonded to the inner insulation layer 6122 at a bonding step 6212.

Figure 44:
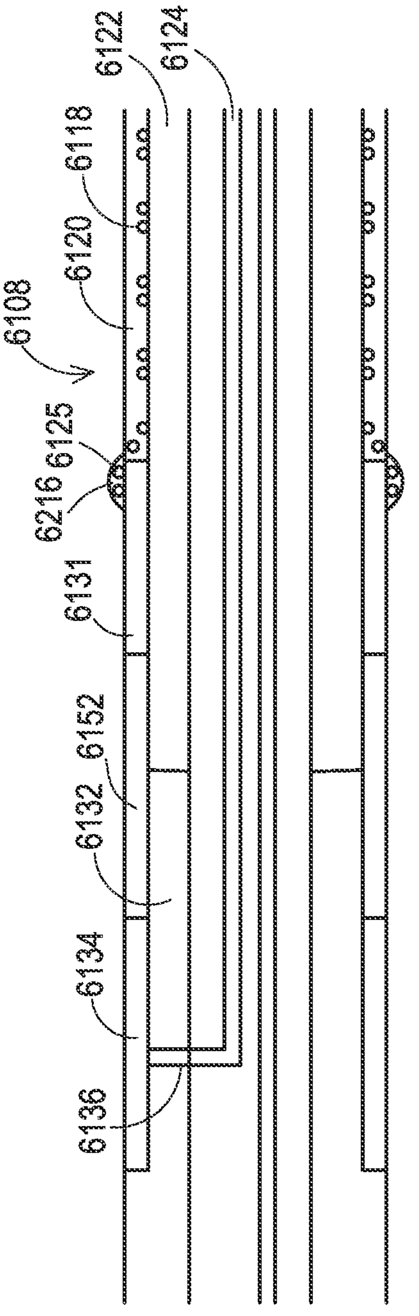
FIG. 44 shows an embodiment of the implantable medical lead where the shield laps onto a metal connector near a joint to an insulation extension.

FIG. 44 shows another embodiment of an implantable medical lead 6108 in cross-section with a cut taken down an axial centerline. The lead 6108 includes a joint between the inner insulation layer 6122 and the insulation extension 6132 where the inner insulation layer 6122 terminates. In this example, the shield 6118 does not remain braided upon the inner insulation layer 6122. Instead, a metal connector 6131 is positioned on the inner insulation layer 6122 and a portion 6125 of the shield 6118 is braided onto the metal connector 6131. The outer insulation layer 6120 is positioned over the braid 6118 up to the metal connector 6131 where the braid 6118 exits the outer insulation layer 6120 when lapping onto the metal connector 6131.

The portion 6125 may be exposed outside of the lead 6108 as a result of lapping onto the metal connector 6131. However, for embodiments where the metal connector 6131 is for insertion into the header 6106 of the IMD 6102, the exposure may occur immediately at the exit to the header 6106 or nearby the header seal. To the extent tissue in-growth is to be avoided in that area, an insulation ring 6216 of material the same as or similar to the outer insulation layer 6120 may be reflowed or otherwise bonded over the portion 6125.

As shown in this example, a replacement outer insulation layer 6152 may be present to form a lap joint between the inner insulation layer 6122 and the insulation extension 6132. The insulation extension 6132 in this example extends the remainder of the lead 6108 where ring connectors 6134 are located at the proximal end. The filars 6124 jumper to their respective ring connectors via a filar jumper 6136. The lumen may be present in some embodiments with the filars 6124 being located about the lumen.

The metal connector 6131 may be included on either the proximal or distal end to terminate the shield 6118 as discussed above. The separation of the metal connector 6131 to the distal electrode or proximal connector ring may also be in accordance with the separation as discussed above.

Figure 45:
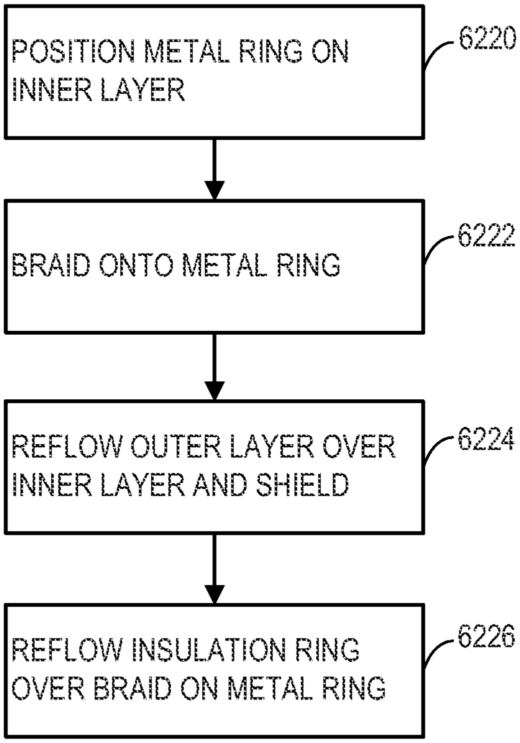
FIG. 45 shows one example of a set of steps to create the implantable lead of FIG. 44.

FIG. 45 shows one example of a set of steps that create the shield termination of FIG. 44. The metal connector 6131 is positioned on the inner insulation layer 6122 at a connector step 6220. The shield 6118 is braided onto the inner insulation layer 6122 and over the metal connector 6131 at a braiding step 6222. The outer insulation layer 6120 is bonded by reflow or another process onto the inner insulation layer 6122 over the shield 6118 up to the metal connector 6131 such as by a reflowing step 6224. The insulation ring 6216 may then be reflowed or injection molded over the braid portion 6125 on the metal connector 6131 at a bonding step 6226.

Figure 46:
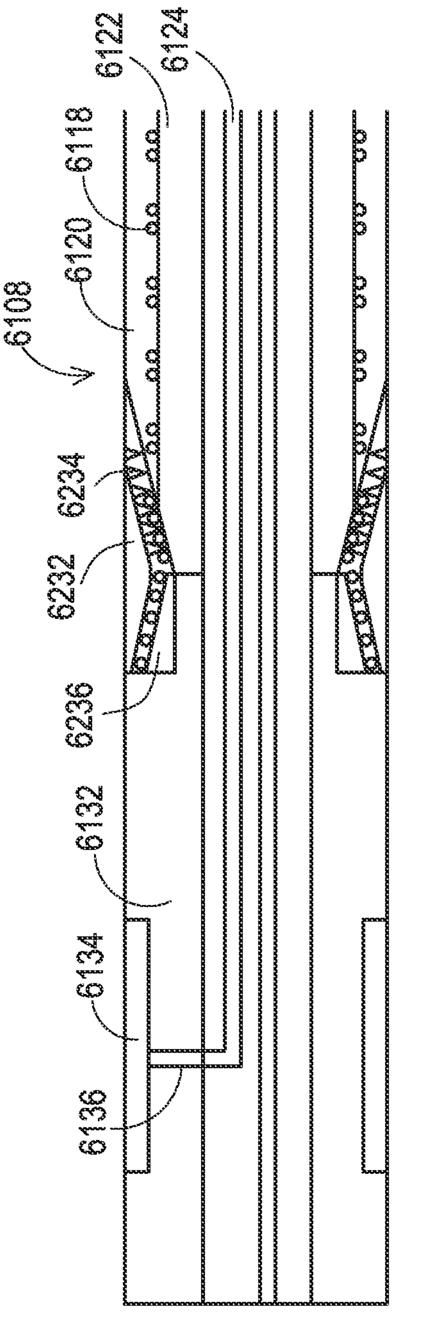
FIG. 46 shows an embodiment of the implantable medical lead where the shield exits the insulation layers at a taper and terminates between a pair of metal connectors.

FIG. 46 shows another embodiment of an implantable medical lead 6108 in cross-section with a cut taken down an axial centerline. The lead 6108 includes a joint between the inner insulation layer 6122 and the insulation extension 6132 where the inner insulation layer 6122 terminates. In this example, the shield 6118 does not remain braided upon the inner insulation layer 6122. Instead, a tapered ablation is created through the outer insulation layer 6120 and inner insulation layer 6122 and the shield 6118 exits the outer insulation layer 6120 and separates from the inner insulation layer 6122 at the taper.

A metal connector 6232 with a threaded taper 6234 is threaded onto the taper of the inner and outer insulation layers 6122, 6120. The threaded taper 6234 bites into the inner and outer insulation layers 6122, 6120 to provide a sturdy physical connection. The shield 6118 passes through the metal connector 6232 to an opposite side where an opposite taper is present. There, the shield 6118 terminates while being positioned firmly between the taper of the metal connector 6232 and a taper of an inner metal connector 6236 that is positioned about the insulation extension 6132.

The insulation extension 6132 in this example extends the remainder of the lead 6108 where ring connectors 6134 are located at the proximal end. The filars 6124 jumper to their respective ring connectors via a filar jumper 6136. The lumen may be present in some embodiments with the filars 6124 being located about the lumen.

The metal connectors 6232, 6236 may be included on either the proximal or distal end to terminate the shield 6118 as discussed above. The separation of the metal connectors 6232, 6236 to the distal electrode or proximal connector ring may also be in accordance with the separation as discussed above.

Figure 47:
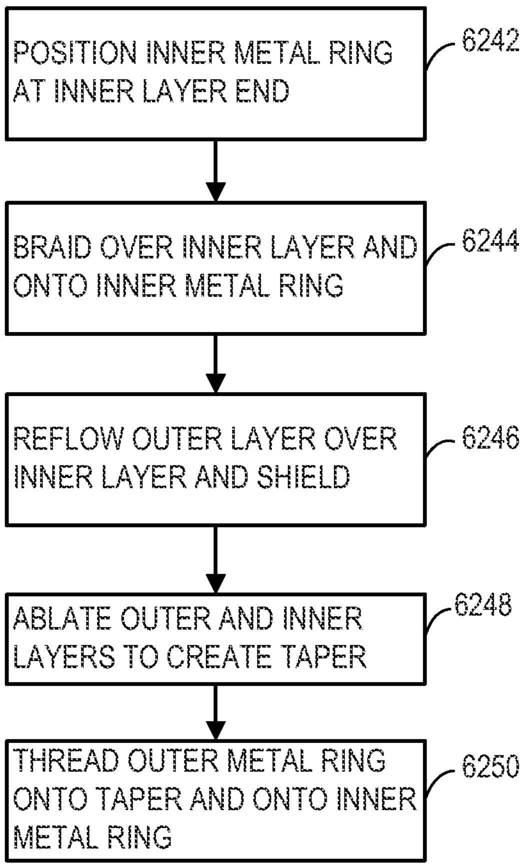
FIG. 47 shows one example of a set of steps to create the implantable lead of FIG. 46.

FIG. 47 shows one example of a set of steps that create the shield termination of FIG. 46. The inner metal connector 6236 is positioned at the end of the inner insulation layer 6122 at a connector step 6242. The shield 6118 is braided onto the inner insulation layer 6122 and over the inner metal connector 6236 at a braiding step 6244. The outer insulation layer 6120 is bonded by reflow or another process onto the inner insulation layer 6122 over the shield 6118 such as by a reflowing step 6246.

The inner and outer insulation layers 6122, 6120 are ablated to form the taper and expose the shield 6118 at an ablating step 6248. The outer metal connector 6232 is then placed into position over the inner metal connector 6236 and the taper of the inner and outer insulation layers 6122, 6120 at a connector step 6250. Here, the outer metal connector 6232 may be turned relative to the inner and outer insulation layers 6122, 6120 to sink the threaded taper 6234 into the inner and outer insulation layers 6122, 6120 while the outer metal connector 6232 firmly contacts the shield 6118 positioned against the inner metal connector 6236. The outer metal connector 6232 may be crimped or welded into place over the shield 6118 and the inner metal connector 6236.

Figure 48:
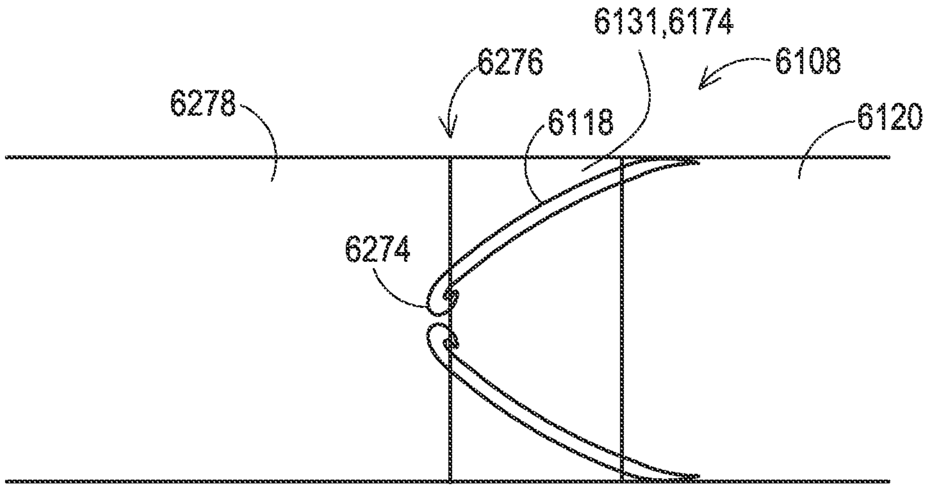
FIG. 48 shows an embodiment of the implantable medical lead where wires of the shield fold over individually at the termination point at a metal connector.

FIG. 48 shows an embodiment with an additional feature that may be included for a joint 6276, which may be of various types such as the butt, scarf, or lap joints 6130, 6140, and 6150. At the joint 6276, the outer metal connector 6131, 6174 of the lead 6108 encounters another layer 6278. This layer 6278 may be the insulation extension 6132 and/or the replacement outer insulation layer 6152. In either case, wires of the shield 6118 may partially extend into the layer 6278. However, prior to bonding the layer 6278 to the layer 6122, the ends of the wires of the shield 6118 may be individually folded over at areas 6274 as shown in FIG. 48. In this manner, the folded over ends are less likely to fray and migrate.

Embodiments as disclosed in relation to FIGS. 49-58 provide for rotation of a stylet within a lumen of an implantable medical lead by applying rotation directly to the implantable medical lead. The implantable medical lead has torsional stiffness and is rotationally coupled to the stylet. The torsional stiffness may be provided by features within the jacket of the lead body, such as a shield. The rotational coupling of the implantable medical lead to the stylet may be provided via features of the lead and/or stylet.

Figure 49:
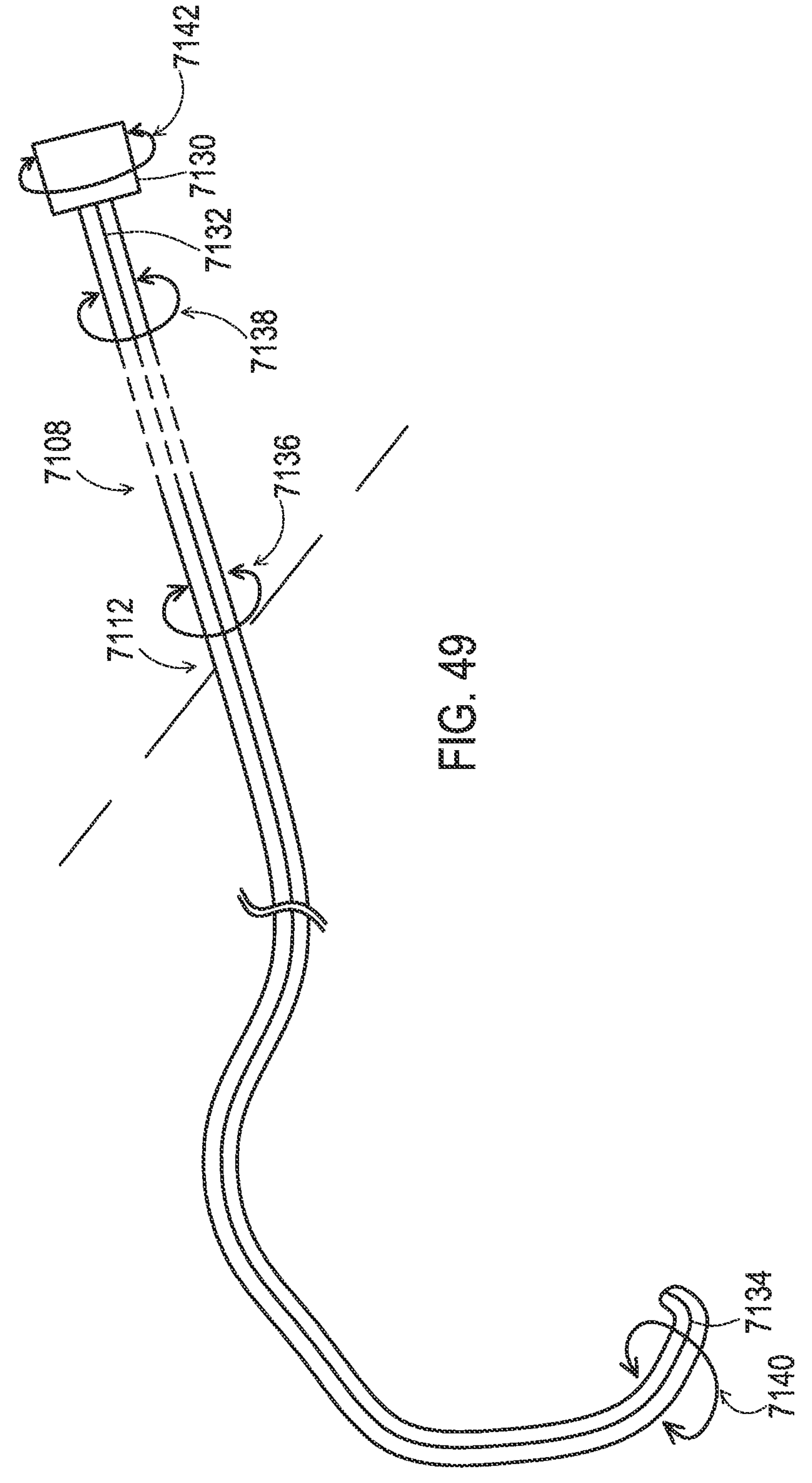
FIG. 49 shows a percutaneous implantation scenario of an embodiment of an implantable medical lead.

FIG. 49 shows a scenario where an implantable medical lead 7108 is being implanted within a patient. The lead 7108 enters the patient at an introduction site 7112 where an introduction needle provides a passageway into the body. The lead 7108 is shown transparently for purposes of illustration to reveal a stylet 7132 present within a lumen of the lead 7108. The stylet 7132, and specifically the bent tip 7134 of the stylet 7132, is used to steer the lead 7108 as the lead 7108 is being inserted in order to direct the distal end of the lead 7108 to the stimulation site which may be a significant distance from the introduction site 7112.

The bent tip 7134 is rotated in position by the stylet 7132 being rotated. The stylet 7132 may include a stylet hub 7130 on the proximal end. This stylet hub 7130 may engage the lead 7108 as discussed below. To rotate the stylet 7132 and the bent tip 7134, the doctor may apply rotation 7136 directly to the lead 7108 at the introduction site 7112 rather than reaching back to grasp the stylet hub 7130. The lead 7108 is torsionally stiff such that the rotation 7136 causes rotation along the length of the lead 7108 including rotation 7138 near the proximal end, rotation 7142 of the hub, and rotation 7140 near the distal end.

The stylet 7132 is rotationally coupled to the lead 7108 at one or more points. The rotational coupling may be near the proximal end or the distal end of the lead 7108, and this rotational coupling may be done in various ways as described below. Thus, the rotation 7136 being applied to the lead 7108 at the introduction site 7112 causes the stylet 7132 to rotate along the length to the bent tip 7134.

The stylet 7132 and stylet hub 7130 may be constructed of various materials. For example, the stylet may be constructed of steel, stainless steel, tungsten, beryllium, and their alloys which provides torsional rigidity. The stylet hub may be constructed of various materials such as nylon, polycarbonate, or other rigid engineering plastics.

Figure 50:
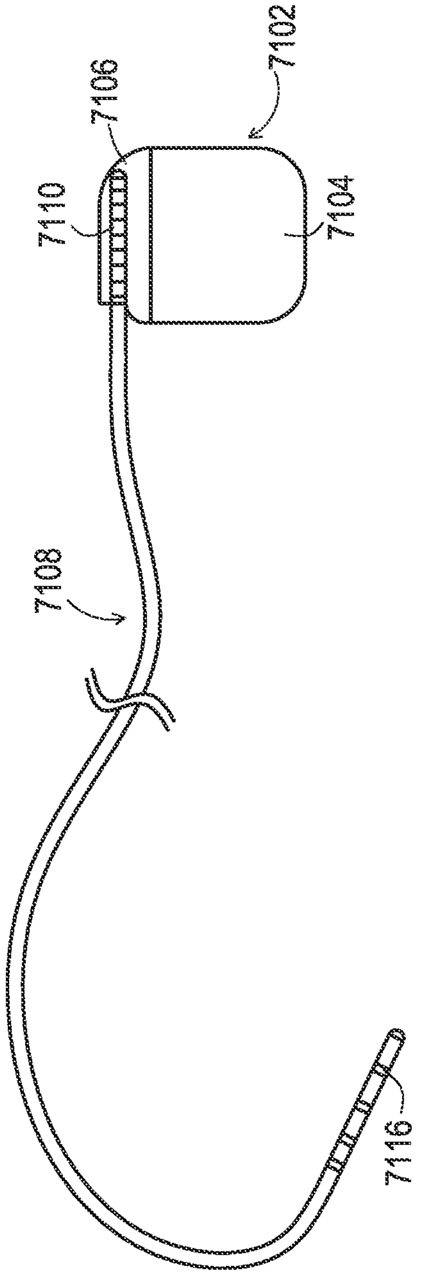
FIG. 50 shows an implantable medical system configuration resulting from the percutaneous implantation of FIG. 49.

FIG. 50 shows an implantable medical system in place once the lead 7108 has been directed to the stimulation site. The implantable medical system includes an IMD 7102 having a biocompatible case and a header 7106. The lead 7108 includes distal electrodes 7116 at the stimulation site that are used to provide the stimulation. The lead also includes proximal connectors 7110 that are fixed by a set screw or other mechanism within the header 7106 and are connected to electrical circuitry of the IMD 7102. The IMD 7102 produces stimulation signals that are provided to the connectors 7110. Filars within the lead 7108 carry the stimulation signals from the connectors 7110 to the electrodes 7116.

Figure 51:
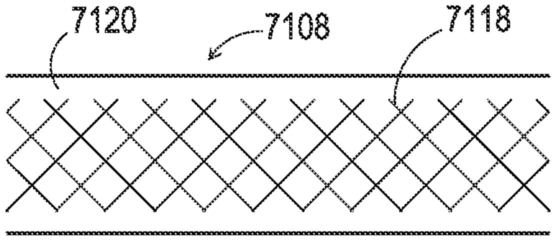
FIG. 51 shows an embodiment of the implantable medical lead that has a braided metal shield providing torsional stiffness.
Figure 52:
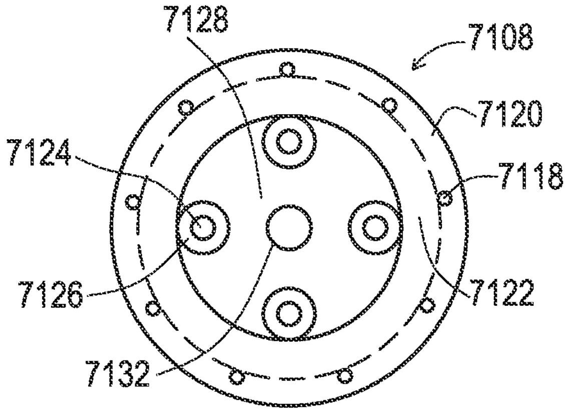
FIG. 52 shows a cross-section of an embodiment of the implantable medical lead where no rotational coupling exists to the stylet.

FIGS. 51 and 52 show an embodiment of the implantable medical lead 7108 where a shield 7118 is present that provides the torsional rigidity. An outer jacket layer 7120 is shown transparently in FIG. 51 for purposes of illustrating the shield 7118. The shield 7118 may be included for various reasons in addition to creating the torsional rigidity. For example, the shield 7118 may provide protection from unwanted RF energy. For instance, the lead 7108 may be a magnetic resonance imaging (MRI) safe lead that allows the patient to have an MRI scan without risking tissue damage due to induced RF currents in the filars of the lead 7108. The conductive filars 7124 extend the length of the lead 7108 and interconnect the proximal connectors 7110 to the distal electrodes 7116 so that stimulation signals are conducted from the proximal end to the distal end of the lead 7108.

As shown in FIG. 51, the shield 7118 of this example is a braided metal wire. The metal wire may be constructed of various materials such as titanium, tantalum, platinum, stainless steel, and their alloys, or other metals. It may be desired to utilize a biocompatible metal for the shield 7118, particularly for embodiments where a portion of the shield 7118 may be exposed for purposes of grounding. While the shield 7118 is shown as a braid, other shield configurations may be chosen such as a metal foil that is wrapped in an overlapping fashion. If shielding is not desired, then the foil may be more loosely wrapped and still provide torsional rigidity.

As shown in FIG. 52, the shield 7118 may be embedded within the jacket of the lead 7108. One manner of constructing the lead 7108 with the shield 7118 is to provide an inner jacket 7122 that encloses the filars 7124 and any additional insulation layer 7126 that may surround each filar 7124. The shield 7118 may then reside on the outer portion of the inner jacket 7122, and the outer jacket 7120 may then enclose the shield 7118.

The shield 7118 may ground to tissue via an RF coupling through the outer layer 7120 and/or via grounding to the can 7104 and/or to the tissue via ground rings. For embodiments where it is desirable for the shield 7118 to RF couple to tissue, the outer jacket layer 7120 may be relatively thin, such as on the order of 0.5 to 5 mils. Where the shield 7118 grounds at the can of the IMD and grounding via a RF coupling from the shield 7118 through the outer jacket 7120 directly to the tissue is of less significance, then the shield 7118 may be located further from the outer surface of the lead 7108. The outer jacket 7120 may be added over the shield 7118 by shrinking in place or by being extruded over the shield 7118.

The inner and outer jackets 7122, 7120 may be constructed of the same or similar materials such as various flexible and biocompatible polymers, examples of which are polyurethanes and silicones. The lumen 7128 is included in the inner jacket 7122, particularly for percutaneous leads 7108, to allow the stylet 7132 to be inserted for purposes of pushing and steering the lead into the desired position within the patient.

As shown in the cross-section of FIG. 52, at this particular point along the lead the stylet 7132 is free within the lumen 7128. The stylet 7132 has clearance relative to the lumen 7128. This clearance may aid in the insertion of the stylet 7132 into the lumen 7128.

Figure 53:
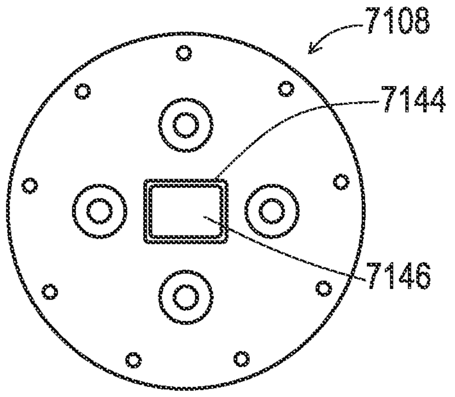
FIG. 53 shows a cross-section of an embodiment of the implantable medical lead where a square-shaped rotational coupling exists to the stylet.

FIG. 53 shows a cross-section at a point along an embodiment of the lead 7108 where a rotational coupling is established between the lead 7108 and the stylet 7132. At this point, the lumen 7128 of the lead 7108 has a portion forming a passageway 7144 that has a square cross-sectional shape rather than being round. As one example, this passageway 7144 may be created in the distal tip of the lead 7108, distal to the location of the distal electrodes. The stylet 7132 likewise has a shaft 7146 that has a square cross-sectional shape and that fits within the square shaped passageway 7144 of the lumen 7128. The position of the square shaped passageway 7144 may be such that when the stylet 7132 is fully inserted in the lead 7108, the square shaped shaft 7146 of the stylet 7132 mates to the square shaped passageway 7144 of the lumen 7128. The square shape effectively keys the stylet 7132 to the lead 7108 so that a rotational coupling is achieved.

Figure 54:
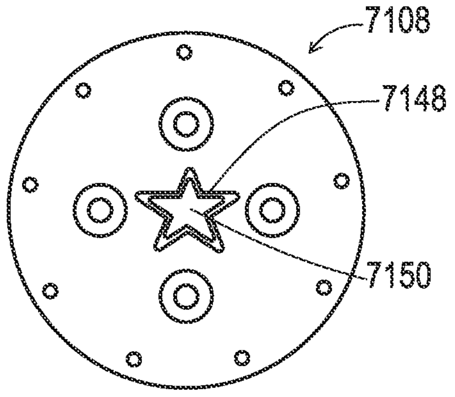
FIG. 54 shows a cross-section of an embodiment of the implantable medical lead where a star-shaped rotational coupling exists to the stylet.

FIG. 54 shows a cross-section at a point along another embodiment of the lead 7108 where a rotational coupling is established between the lead 7108 and the stylet 7132. At this point, the lumen 7128 of the lead has a particular portion forming a passageway 7148 that has a star cross-sectional shape rather than being round. As one example, this passageway 7148 may be created in the distal tip of the lead 7108, distal to the location of the distal electrodes. The stylet 7132 likewise has a shaft 7150 that has a star cross-sectional shape and that fits within the star shaped passageway 7148 of the lumen 7128. The position of the star shaped passageway 7148 may be such that when the stylet 7132 is fully inserted in the lead 7108, the star shaped shaft 7150 of the stylet 7132 mates to the star shaped passageway 7148 of the lumen 7128. The star shape effectively keys the stylet 7132 to the lead 7108 so that a rotational coupling is achieved.

Figure 55:
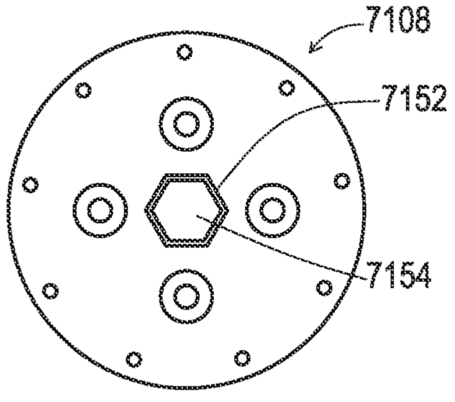
FIG. 55 shows a cross-section of an embodiment of the implantable medical lead where a hexagonal-shaped rotational coupling exists to the stylet.

FIG. 55 shows a cross-section at a point along another embodiment of the lead 7108 where a rotational coupling is established between the lead 7108 and the stylet 7132. At this point, the lumen 7128 of the lead has a particular portion forming a passageway 7152 that has a hexagonal cross-sectional shape rather than being round. As one example, this passageway 7152 may be created in the distal tip of the lead 7108, distal to the location of the distal electrodes. The stylet 7132 likewise has a shaft 7154 that has a hexagonal cross-sectional shape and that fits within the hexagonal shaped passageway 7152 of the lumen 7128. The position of the hexagonal shaped passageway 7152 may be such that when the stylet 7132 is fully inserted in the lead 7108, the hexagonal shaped shaft 7154 of the stylet 7132 mates to the hexagonal shaped passageway 7152 of the lumen 7128. The hexagonal shape effectively keys the stylet 7132 to the lead 7108 so that a rotational coupling is achieved.

The square, star, and hexagonal shapes are shown for purposes of illustration. It will be appreciated that any number of shaped engagements may be utilized to establish a rotational coupling between the lead 7108 and the stylet 7132. Furthermore, it will be appreciated that the coupling may occur at any point or multiple points along the lead 7108 where the torsional stiffness is present.

Figure 56:
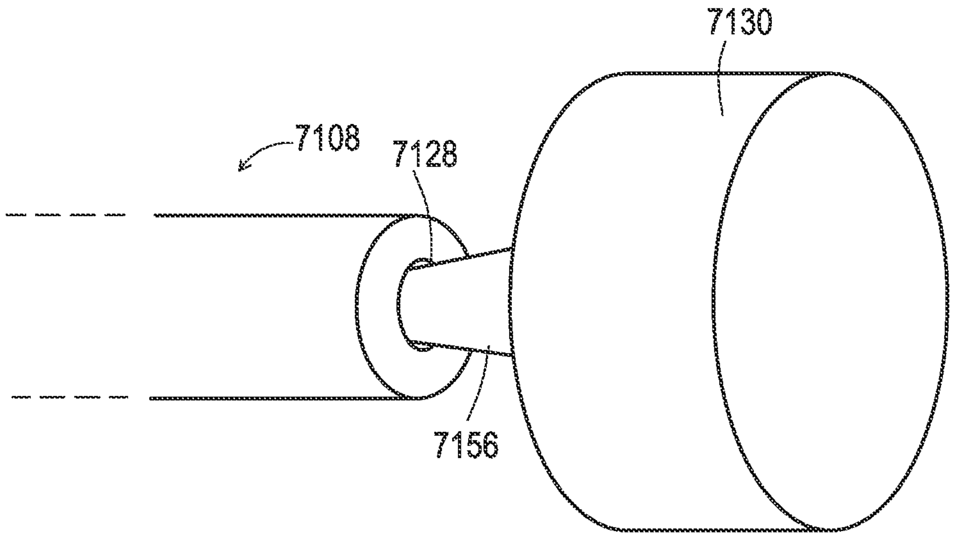
FIG. 56 shows a proximal end of an embodiment of the implantable medical lead achieving a rotational coupling with a tapered feature of a stylet hub.

FIG. 56 shows a side view of a proximal end of the lead 7108 with the lumen 7128 engaging an embodiment of the stylet hub 7130 in order to establish a rotational coupling between the stylet 7132 and the lead 7108. The stylet hub 7130 includes a tapered region 7156 that extends from the hub 7130 to the stylet 7132. This tapered region 7156 at a large diameter end has a diameter larger than that of the lumen 7128. As a result, the tapered region 7156 may be press fit into the lumen 7128 of the lead 7108 in order to produce a frictional fit that establishes a rotational coupling.

Figure 57:
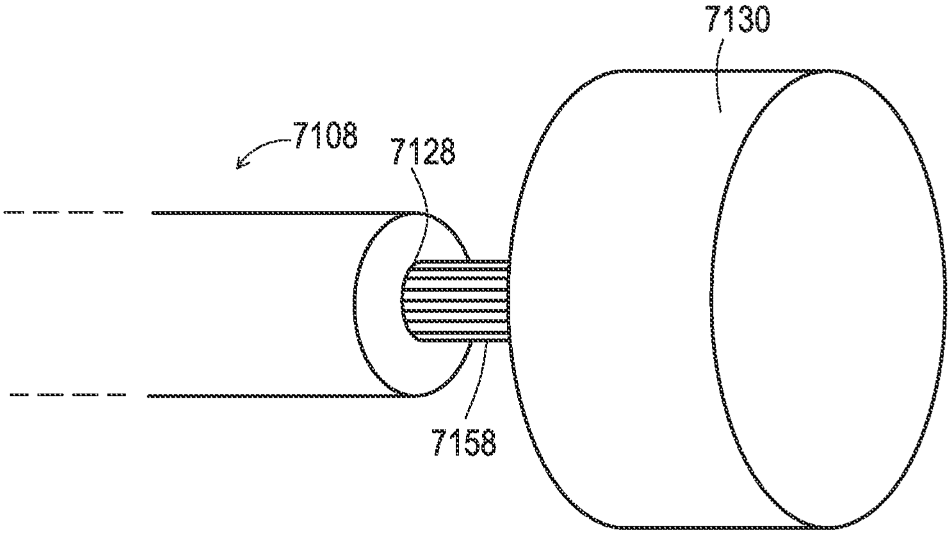
FIG. 57 shows a proximal end of an embodiment of the implantable medical lead achieving a rotational coupling with a splined feature of a stylet hub.

FIG. 57 shows a side view of a proximal end of the lead 7108 with the lumen 7128 engaging another embodiment of the stylet hub 7130 in order to establish a rotational coupling between the stylet 7132 and the lead 7108. The stylet hub 7130 includes a splined region 7158 that extends from the hub 7130 to the stylet 7132. The diameter created by the splined region 7158 may be greater than the diameter of the lumen 7128. This splined region 7158 may be press fit into the lumen 7128 of the lead 7108 in order to engage the splines with the lumen 7128 to establish a rotational coupling.

Figure 58:
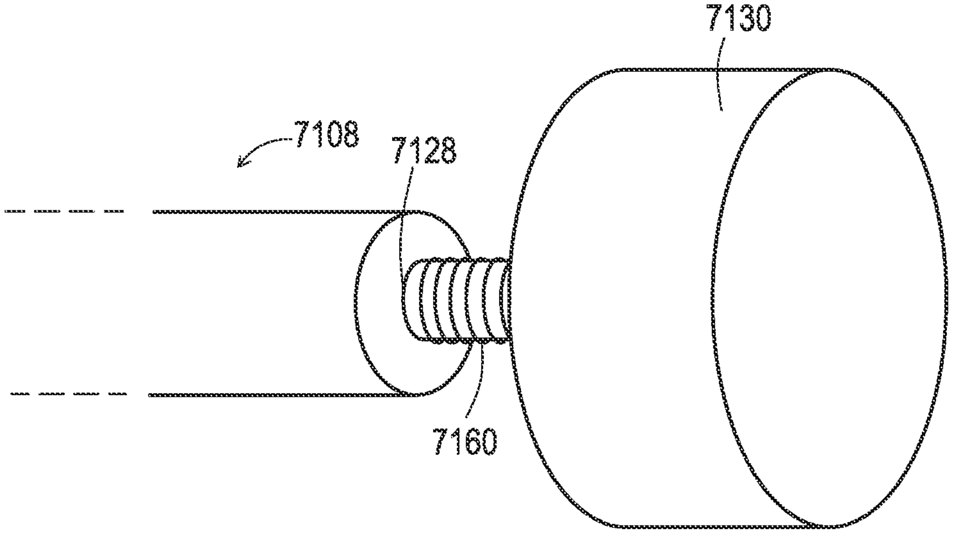
FIG. 58 shows a proximal end of an embodiment of the implantable medical lead achieving a rotational coupling with a threaded feature of a stylet hub.

FIG. 58 shows a side view of a proximal end of the lead 7108 with the lumen 7128 engaging another embodiment of the stylet hub 7130 in order to establish a rotational coupling between the stylet 7132 and the lead 7108. The stylet hub 7130 includes a threaded region 7160 that extends from the hub 7130 to the stylet 7132. The diameter created by the threaded region 7160 may be greater than the diameter of the lumen 7128. This threaded region 7160 may be screwed into the lumen 7128 of the lead 7108 in order to engage the threads with the lumen 7128 to establish a rotational coupling.

The tapered, splined, and threaded engagements of the hub 7130 to the lumen 7128 are shown for purposes of illustration. It will be appreciated that any number of hub features may be used to engage the lumen 7128 to provide the rotational coupling. It will be further appreciated that similar features may be used to allow the hub 7130 to instead engage the outer layer 7120 of the lead 7108 at the proximal end such as by having a taper, splines, or threads that surround the outer layer 7120 but with a smaller diameter than the outer layer 7120. These features face inward to engage the outer layer 7120 and establish the rotational coupling.

Embodiments as disclosed in relation to FIGS. 59-72 provide radiopaque markers that are added to implantable medical leads or to implantable medical devices (IMD) connected to the leads to identify the leads as being designed for safe application of a medical procedure such as an MRI scan. The radiopaque markers are visible on an X-ray or during fluoroscopy so that administering personnel can have a visual assurance that the lead is designed for safe application of the medical procedure of interest.

Figure 59:
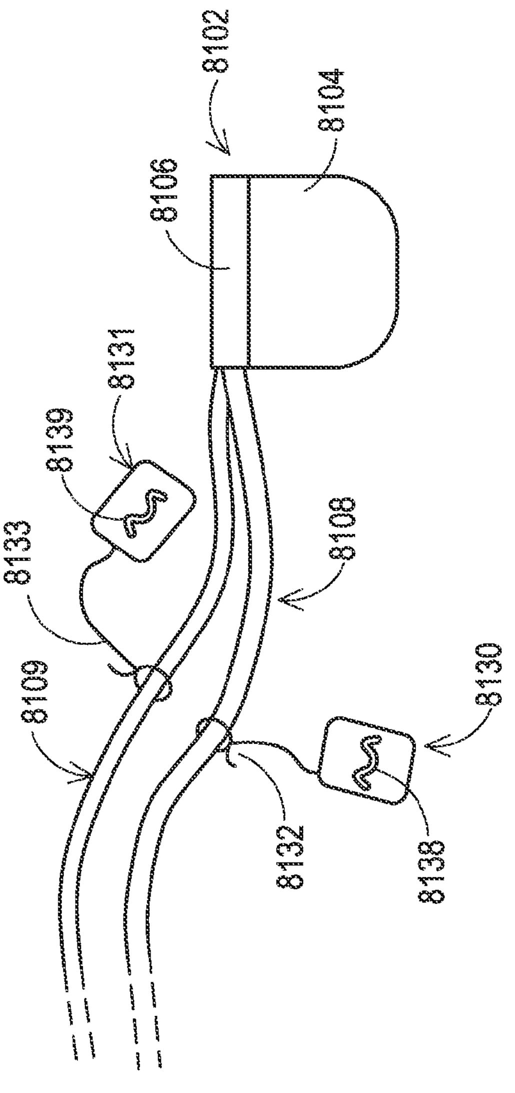
FIG. 59 shows an embodiment of an implantable medical system including an IMD and two leads, each with a radiopaque marker sutured to the lead.

FIG. 59 shows an embodiment of an implantable medical system that includes an IMD 8102 having a can 8104 that houses electronics and a header 8106. In this example, the IMD 8102 provides signals to a pair of implantable medical leads 8108, 8109 which are physically and electrically connected to the IMD 8102 via the header 8106.

Radiopaque markers 8130, 8131 are provided to identify the leads 8108, 8109 as being safe for a given procedure. In this particular example, the radiopaque markers 8130, 8131 are tags that are fixed directly to corresponding leads 8108, 8109. Sutures 8132 of the permanent type hold the tag 8130 to the lead 8108 while sutures 8133 hold the tag 8131 to the lead 8109. By individually tagging both leads 8108, 8109, the administering personnel can be assured that both leads are safe for the given procedure.

The tags 8130, 8131 may be added after the leads 8108, 8109 have been successfully implanted into the patient. For percutaneous leads, this is particularly desirable because the lead 8108, 8109 is inserted into the body of the patient via an introducer needle that lacks clearance for the tags 8130, 8131. Thus, once the leads 8108, 8109 are in position with the proximal ends of the leads being near the incision site and with the introducer needle removed, the tags 8130, 8131 can be inserted into a pocket made for the IMD 8102 and sutured in place by the doctor.

The tags 8130, 8131 may be constructed of a biocompatible material that has a density that is adequately radiopaque by being visible on an X-ray or during fluoroscopy. Examples of such materials include barium, tantalum, platinum, and platinum-iridium. The size of the tags 8130, 8131 may vary but when sized to have a length and width in the range of 0.25 to 5 centimeters and 0.01 to 0.2 inch thickness, the tag 8130, 8131 is adequately visible while being small enough to comfortably fit within or nearby the pocket near the IMD 8102.

When administering personnel wish to perform a given medical procedure such as an MRI, the personnel may take an X-ray or conduct fluoroscopy to look for the radiopaque marker. The IMD 8102 itself may need to also be designed for safety during a given medical procedure and may have its own internal or external radiopaque marker. Thus, placing the tags 8130, 8131 nearby the IMD 8102 may be desirable so that the tags of both the leads 8108, 8109 and the marker of the IMD 8102 are in the same field of view of an X-ray or during fluoroscopy.

In this example of FIG. 59, the tags 8130, 8131 include an aperture 8138, 8139 in the shape of a particular symbol. Due to the aperture 8138, 8139, this shape within the tag 8130, 8131 is visibly distinguishable on the X-ray or during fluoroscopy. Thus, this aperture 8138, 8139 may identify the safety aspects of the lead 8108, 8109 and/or the medical procedures that are safe to conduct. The shape of the apertures 8138, 8139 in FIG. 59 is a wave that represents that the leads 8108, 8109 are safe for an MRI scan conducted within normal operating parameters.

Figure 60:
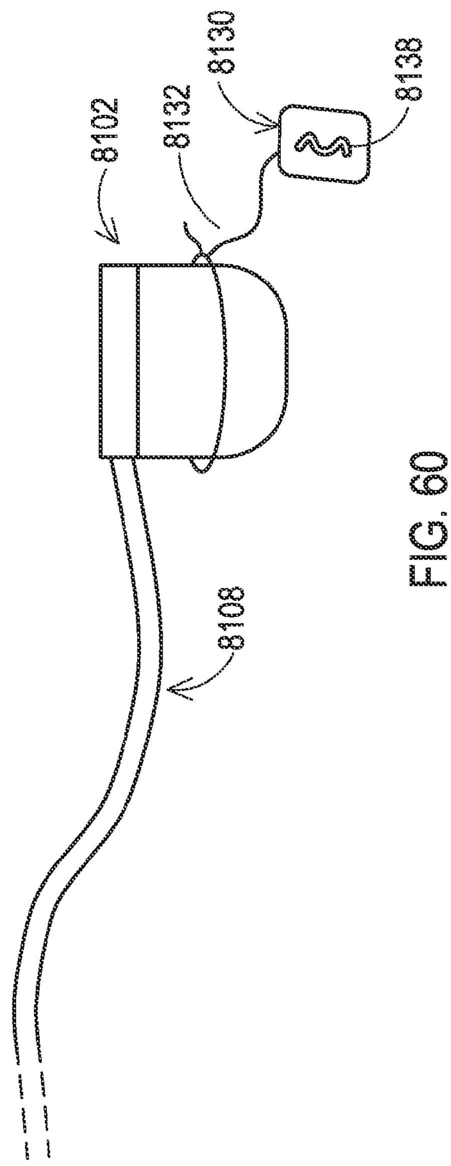
FIG. 60 shows an embodiment of an implantable medical system including an IMD and a lead, with a radiopaque marker sutured to the IMD case.

FIG. 60 shows a similar configuration for the radiopaque tag 8130. However, rather than the doctor suturing the tag 8130 to the lead 8108, the doctor connects the proximal end of the lead 8108 to the IMD 8102 that is placed into the pocket and sutures the tag 8130 to the IMD 8102. In the example shown, sutures 8132 extending from the tag 8130 are tied around the can 8104. It will be appreciated that the sutures 8132 could be tied to the IMD 8102 in other ways or to designated features of the IMD 8102.

Figure 61:
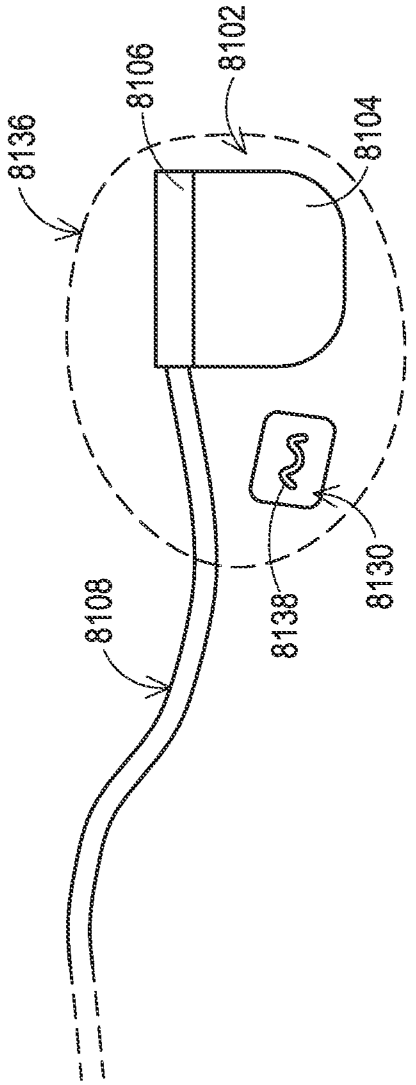
FIG. 61 shows an embodiment of an implantable medical system including an IMD and a lead, with a radiopaque marker placed loosely in a pocket nearby the IMD and lead.

FIG. 61 shows another example of placing the tag 8130 in close proximity to the IMD 8102 and lead 8108. However, in this example, the tag 8130 is not tied to either but is instead left loosely positioned within the pocket 8136 where the IMD 8102 is positioned. The pocket 8136 prevents the tag 8130 from migrating away from the position of the IMD 8102 so that the tag 8130 remains in the same field of view as the IMD 8102 and lead 8108 during an X-ray or fluoroscopy.

Figure 62:
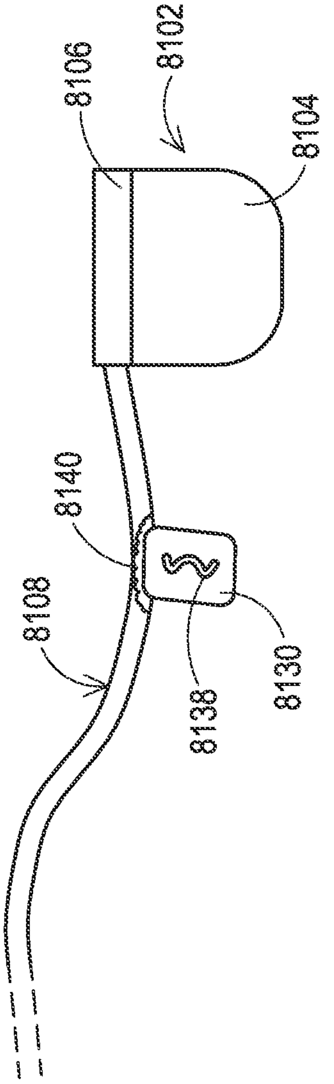
FIG. 62 shows an embodiment of an implantable medical system including an IMD and a lead, with a radiopaque marker glued to the lead.

FIG. 62 shows another example of placing the tag 8130 in close proximity to the IMD 8102 and the lead 8108. In this example, rather than suturing the tag 8130 to the lead 8108, the doctor may have chosen to bond the tag 8130 to the lead using a glue 8140. Examples of a glue suitable for bonding the tag 8130 to the lead 8108 include medical adhesives.

Figure 63:
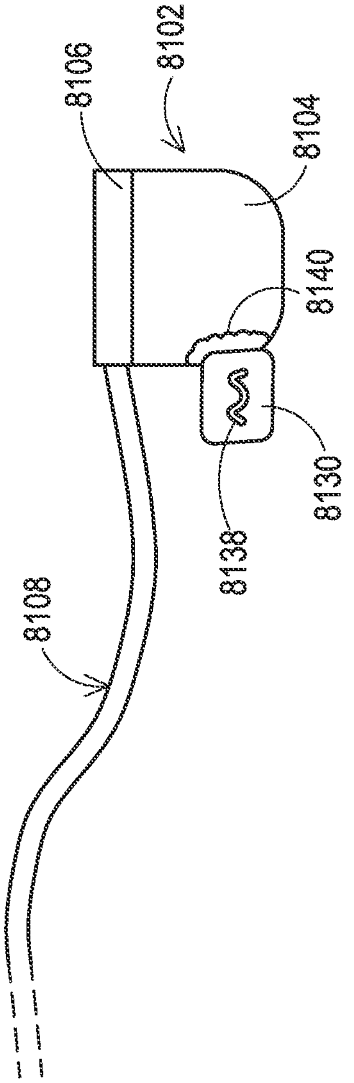
FIG. 63 shows an embodiment of an implantable medical system including an IMD and a lead, with a radiopaque marker glued to the IMD case.

FIG. 63 shows another example of placing the tag 8130 in direct proximity of the IMD 8102 by bonding the tag 8130 to the IMD 8102. Here, the tag 8130 is bonded to the IMD 8102 with the glue 8140. Examples of a glue suitable for bonding the tag 8130 to the IMD 8102 also include medical adhesives.

Figure 64:
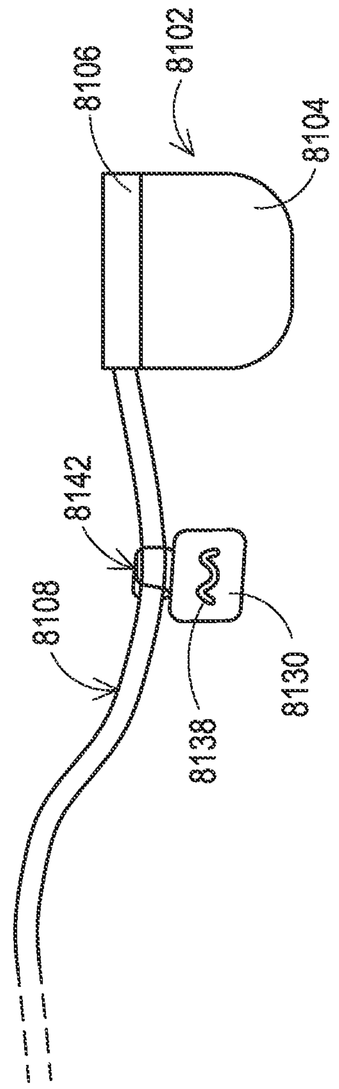
FIG. 64 shows an embodiment of an implantable medical system including an IMD and a lead, with a radiopaque marker clamped to the lead.

FIG. 64 shows another example of placing the tag 8130 in close proximity to the IMD 8102 and the lead 8108. In this example, the tag 8130 is attached to a clamp 8142, such as a U-shaped spring-loaded clamp or other clamp structures such as features that mechanically lock including detents. The clamp 8142 tightens against the lead 8108 to hold the tag 8130 in position relative to the lead 8108.

Figure 65:
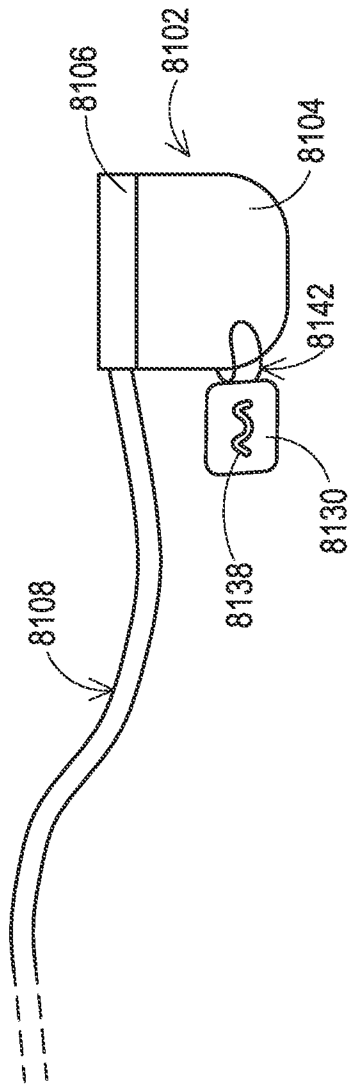
FIG. 65 shows an embodiment of an implantable medical system including an IMD and a lead, with a radiopaque marker clamped to the IMD case.

FIG. 65 shows another example of placing the tag 8130 in direct proximity to the IMD 8102. Here, the tag 8130 includes the clamp 8142 which is tightened against the can 8104 of the IMD 8102. The clamp 8142 could tighten against other portions of the IMD 8102 as well such as the header 8106. The clamp 8142 of FIG. 65 may be of the same types discussed above in relation to FIG. 64.

Figures 66, 67A, 67B:
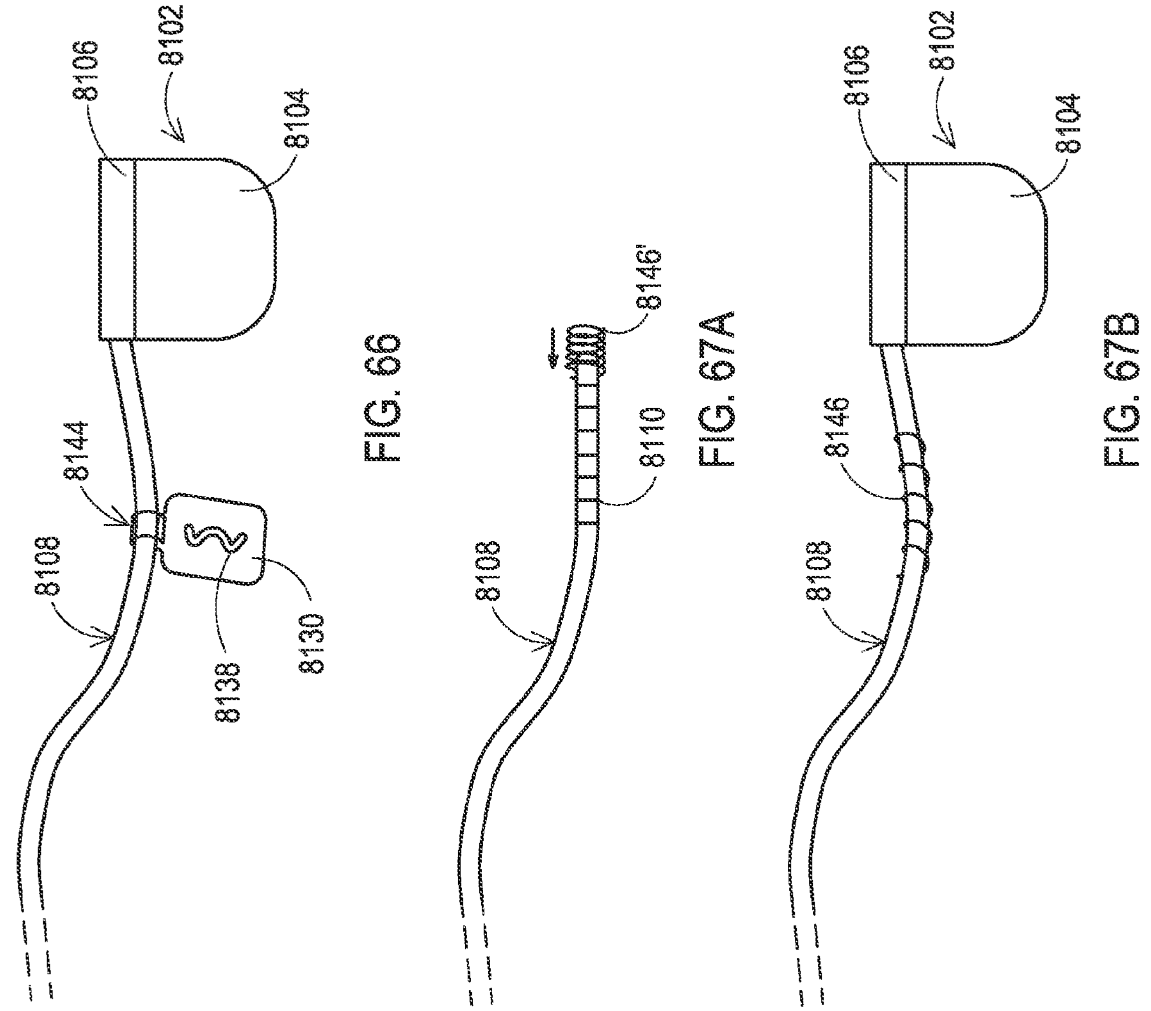
FIG. 66 shows an embodiment of an implantable medical system including an IMD and a lead, with a radiopaque marker crimped to the lead.
FIG. 67A shows an embodiment of an implantable medical system including a lead and a radiopaque coil being placed onto the lead in a radially expanded state.
FIG. 67B shows an embodiment of an implantable medical system including a lead and a radiopaque coil once placed onto the lead in a radially contracted state.

FIG. 66 shows another example of placing the tag 8130 in close proximity to the IMD 8102 and the lead 8108. In this example, the tag 8130 has an extension 8144 that forms a ring shape. Initially, the extension 8144 may be an open ring so that it easily fits onto the lead 8108. The extension 8144 may then be crimped to form a closed or nearly closed ring about the lead 8108 and to fix the tag 8130 relative to the lead 8108.

FIG. 67A shows an example of a radiopaque marker being installed on a lead where the radiopaque marker is not a tag. Instead, the radiopaque marker is a radiopaque coil 8146' that is in a radially expanded state produced by axially compressing the coil 8146'. The radially expanded state allows the coil 8146' to be placed about the lead 8108, with the lead 8108 traveling through the center of the coil in an axial direction. The coil 8146' is placed onto the proximal end of the lead 8108, shown here with connectors 8110, prior to the proximal end being inserted into the header 8106.

FIG. 67B shows the radiopaque coil 8146 in a radially contracted state. Here, once properly positioned along the lead 8108, the coil 8146 has been allowed to naturally expand axially to radially contract until the coil diameter meets that of the lead 8108 to fix the coil 8146 in place on the lead 8108. The lead 8108 is then connected to the IMD 8102, with the coil 8146 being located in proximity to the IMD 8102 in this example so as to be in the same field of view. The coil 8146 itself is the visible shape that indicates that the lead 8108 is safe for a particular medical procedure such as an MRI.

The radiopaque coil 8146 may be constructed of materials similar to the tag 8130. For instance, the coil 8146 may be constructed of barium, tantalum, platinum, and platinum-iridium. The size of the coil 8146 may vary but when sized in the range of 0.04 inch to 1.0 inch in length and from 2 mils to 0.10 inch in diameter when radially contracted, the coil 8146 is adequately visible while being small enough to comfortably fit within or nearby the pocket near the IMD 8102.

Figure 68A:
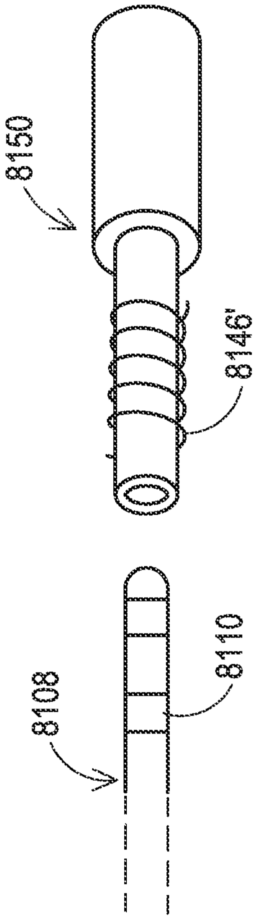
FIG. 68A shows the coil on an installation tool in the radially expanded state prior to placement on the lead.
Figure 68B:
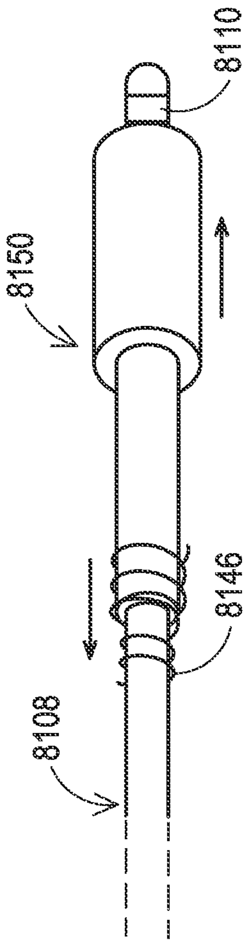
FIG. 68B shows the coil being placed onto the lead from the tool to achieve the radially contracted state.

FIGS. 68A and 68B show an example of a tool 8150 being used to place the coil 8146' in the radially expanded state onto the lead 8108 and to deposit the coil 8146 in the radially contracted state at the desired position on the lead 8108. The tool 8150 holds the coil 8146' in the radially expanded state by providing a larger diameter than the lead 8108 and while providing a passageway for the lead 8108.

As shown in FIG. 68B, the tool 8150 is positioned on the lead 8108 with the lead 8108 passing through the passageway of the tool 8150. The coil 8146' is pushed off of the tool 8150 until the coil 8146 has a radially contracted end about the lead 8108. The tool 8150 may then be pulled away from the lead 8108 to allow the remainder of the coil 8146' in the radially expanded state to slide off of the tool 8150 and onto the lead 8108 where the coil 8146 achieves the radially contracted state.

Figure 69A:
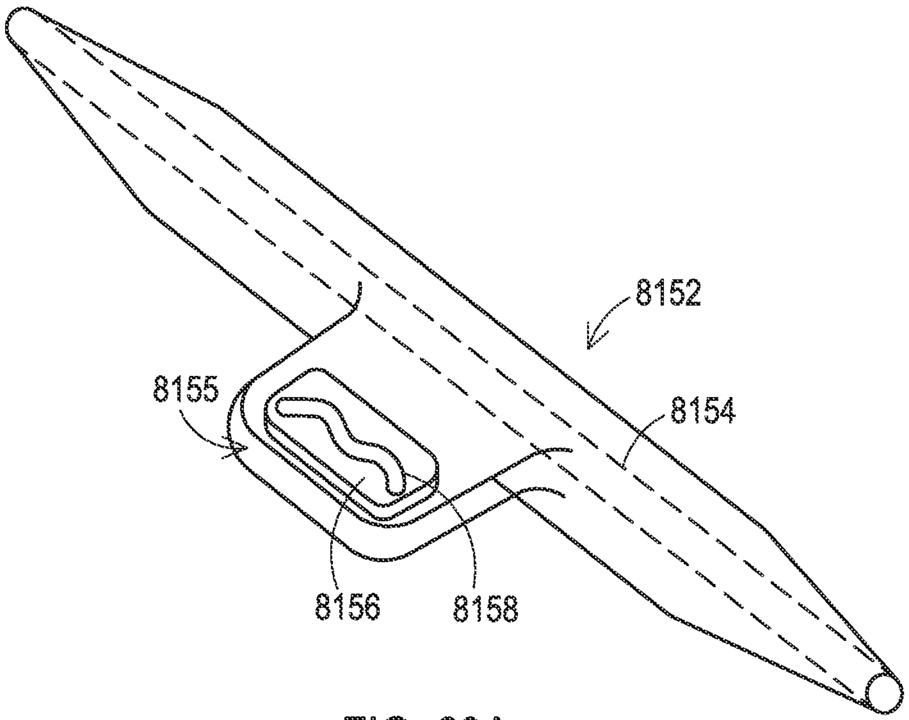
FIG. 69A shows an embodiment of a polymer structure that fits axially onto the lead and provides a radiopaque plate.
Figure 69B:
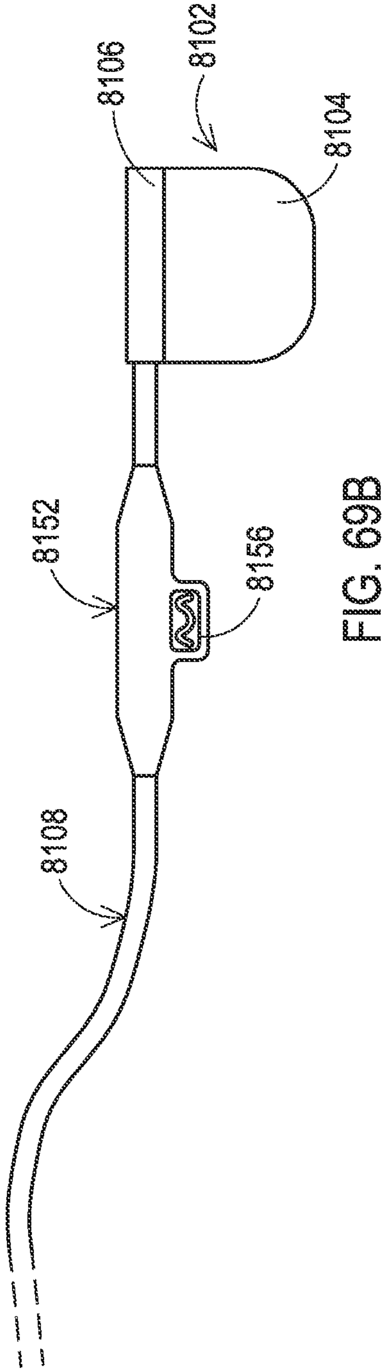
FIG. 69B shows an embodiment of an implantable medical system where the polymer structure of FIG. 69A is positioned on the lead.

FIG. 69A shows a polymer structure 8152 that may be used to place a radiopaque marker onto the lead 8108. FIG. 69B shows the polymer structure 8152 once positioned on the lead 8108. This polymer structure 8152 includes a cylindrical aperture 8154 that allows the lead 8108 to pass through. The cylindrical aperture 8154 may stretch to a larger diameter than the lead 8108 such as by using a conventional anchor deployment tool to position the polymer structure onto the lead 8108. The polymer structure 8152 may then be removed from the anchor tool to allow the polymer structure 8152 to contract onto the lead 8108.

The polymer structure 8152 includes an offset portion 8155. Within this offset portion 8155, a radiopaque plate 8156 is embedded. The radiopaque plate 8156 may include a symbol 8158 or other information to be conveyed to administering personnel. The radiopaque plate 8156 may be constructed of materials similar to the tag 8130. For instance, the plate 8156 may be constructed of barium, tantalum, platinum, and platinum-iridium. The size of the plate 8156 may vary but when sized in at about 0.040 inch in length/width and about 0.01 to 0.2 inch thick, the plate 8156 is adequately visible while being small enough to be contained within the polymer structure 8152.

The polymer structure 8152 of FIGS. 69A and 69B is similar to a lead anchor. However, this polymer structure 8152 lacks suture wings. Because the contraction of the cylindrical aperture 8154 holds the polymer structure in place, no sutures are needed.

The offset of the portion 8155 where the radiopaque plate 8156 is located provides for ease of removal of the polymer structure 8152 from the lead 8108. An axial cut can be made along the cylindrical aperture 8154 because the radiopaque marker does not surround the cylindrical aperture 8154. However, if ease of removal is not of concern, then embodiments may provide the radiopaque plate 8156 centered about the cylindrical aperture 8154.

Figure 69C:
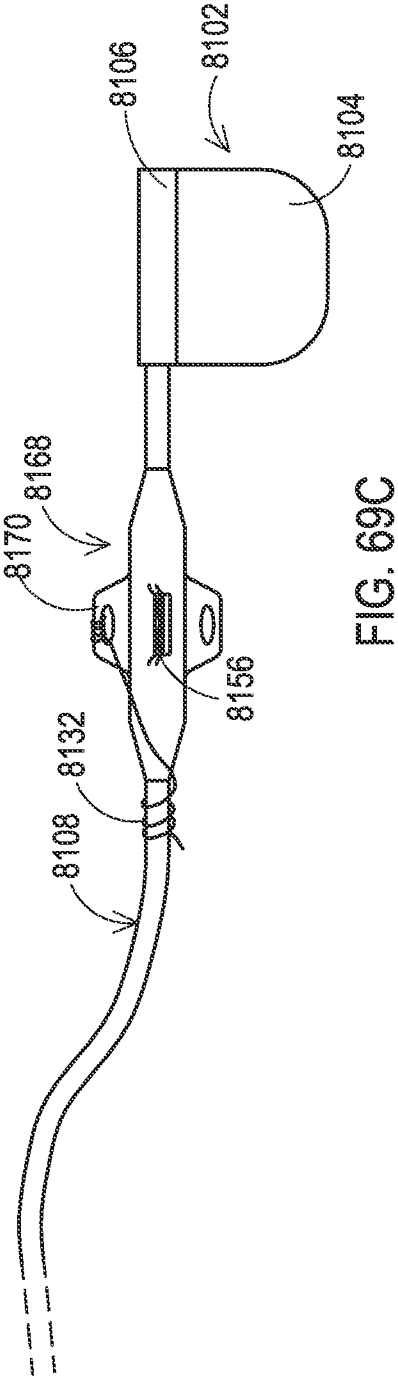
FIG. 69C shows an embodiment of an implantable medical system where an embodiment of a polymer structure that has an anchor format including suture wings and a radiopaque plate is sutured in place on the lead.

FIG. 69C shows a similar polymer structure 8168. However, the polymer structure 8168 is in the form of a lead anchor that includes suture wings 8170 while also including the radiopaque plate 8156. Rather than relying on the cylindrical aperture to contract onto the lead 8108, the lead anchor 8168 may additionally or alternatively have sutures 8132 that tie the suture wings 8170 to the lead 8108 to hold the polymer structure 8168 in place in proximity to the IMD 8102. The radiopaque plate 8156 may be centered about the lead 8108 within the polymer structure 8160 even where ease of removal is desired if the polymer structure 8160 is held in place by the sutures 8132 rather than a contracted state upon the lead 8108.

Figure 70A:
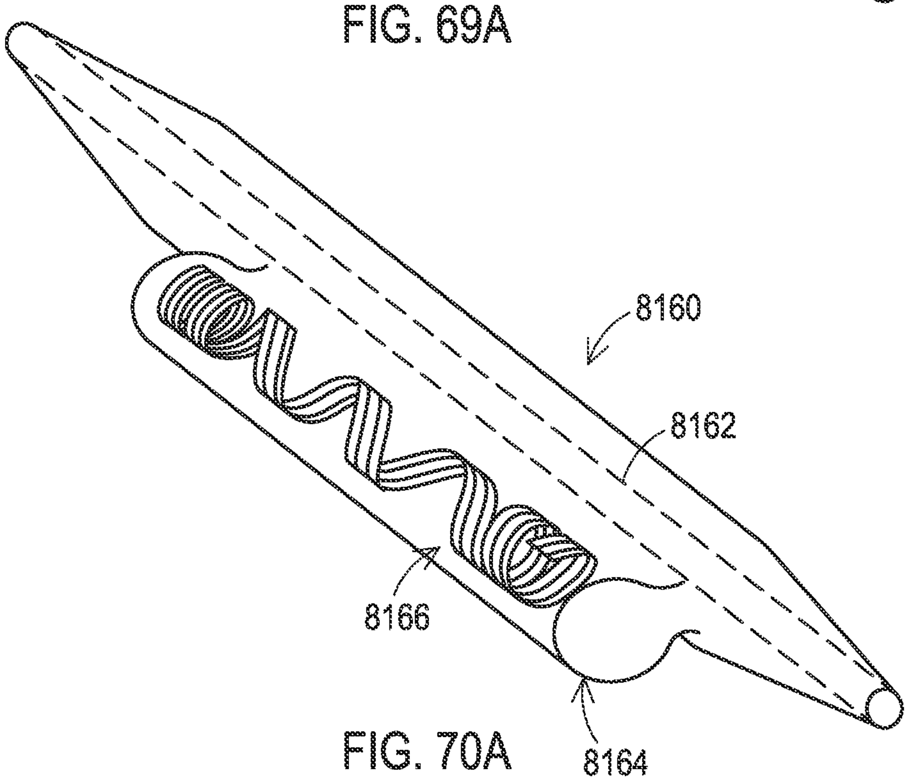
FIG. 70A shows an embodiment of a polymer structure that fits axially onto the lead and provides a radiopaque coil.
Figure 70B:
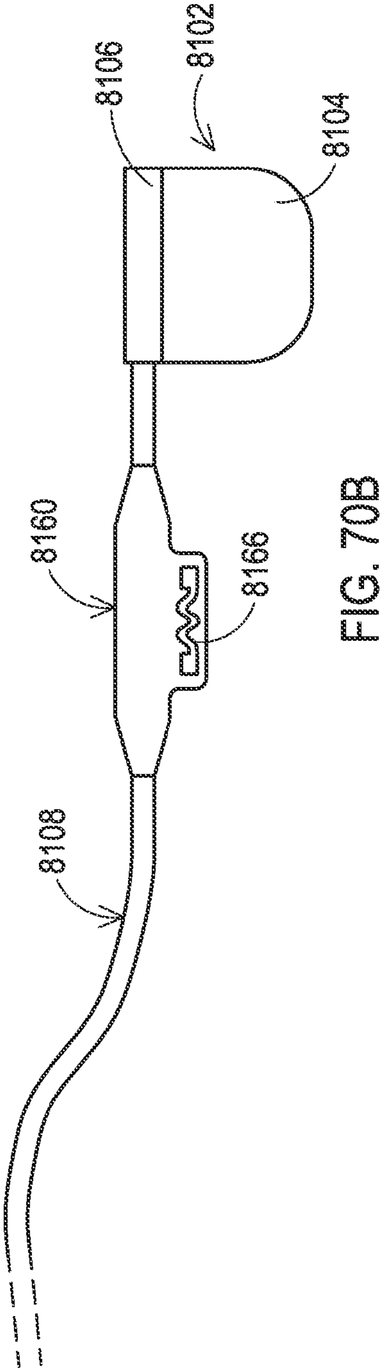
FIG. 70B shows an embodiment of an implantable medical system where the polymer structure of FIG. 70A is positioned on the lead.

FIG. 70A shows another polymer structure 8160 that may be used to place a radiopaque marker onto the lead 8108. FIG. 70B shows the polymer structure 8160 once positioned on the lead 8108. This polymer structure 8160 includes a cylindrical aperture 8162 that allows the lead 8108 to pass through. The cylindrical aperture 8162 may stretch to a larger diameter than the lead 8108 such as by using a conventional anchor deployment tool to position the polymer structure 8160 onto the lead 8108. The polymer structure 8160 may then be removed from the anchor tool to allow the polymer structure 8160 to contract onto the lead 8108.

The polymer structure 8160 includes an offset portion 8164. Within this offset portion 8164, a radiopaque coil 8166 is embedded. The radiopaque coil 8166 may form a symbol or other information to be conveyed to administering personnel. The radiopaque coil 8166 may be constructed of materials similar to the coil 8146. For instance, the coil 8166 may be constructed of barium, tantalum, platinum, and platinum-iridium. The size of the coil 8166 may vary but when sized in the range of 0.04 to 1.0 inch in length and 2 mils to 0.10 inch in wire diameter with an overall diameter of 0.020 to 0.5 inch, the coil 8166 is adequately visible while being small enough to be contained within the polymer structure 8160.

The polymer structure 8160 of FIGS. 70A and 70B is also similar to a lead anchor. However, this polymer structure 8160 lacks suture wings. Because the contraction of the cylindrical aperture 8162 holds the polymer structure 8160 in place, no sutures are needed.

The offset of the portion 8164 where the radiopaque coil 8166 is located provides for ease of removal of the polymer structure 8160 from the lead 8108. An axial cut can be made along the cylindrical aperture 8162 because the radiopaque marker does not surround the cylindrical aperture 8162. However, if ease of removal is not of concern, then embodiments may provide the radiopaque coil 8166 centered about the cylindrical aperture 8162.

Figure 70C:
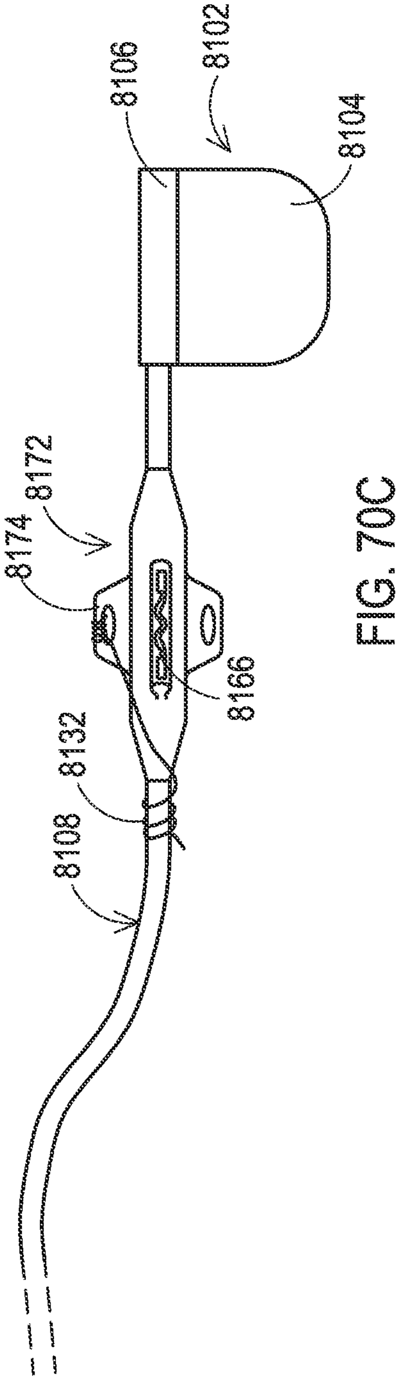
FIG. 70C shows an embodiment of an implantable medical system where an embodiment of a polymer structure that has an anchor format including suture wings and a radiopaque coil is sutured in position on the lead.

FIG. 70C shows a similar polymer structure 8172. However, the polymer structure 8172 is in the form of a lead anchor that includes suture wings 8174 while also including the radiopaque coil 8166. Rather than relying on the cylindrical aperture to contract onto the lead 8108, the lead anchor 8172 may additionally or alternatively have sutures 8132 that tie the suture wings 8174 to the lead 8108 to hold the polymer structure 8172 in place in proximity to the IMD 8102. The radiopaque coil 8166 may be centered about the lead within the polymer structure 8172 even where ease of removal is desired if the polymer structure 8172 is held in place by the sutures 8132 rather than a contracted state upon the lead 8108.

Figure 71:
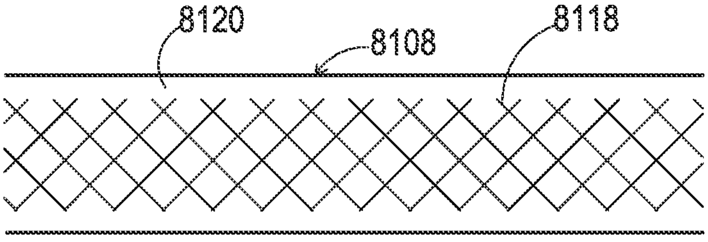
FIG. 71 shows an embodiment of the lead that includes a shield to provide safety during medical procedures such as an MRI scan.
Figure 72:
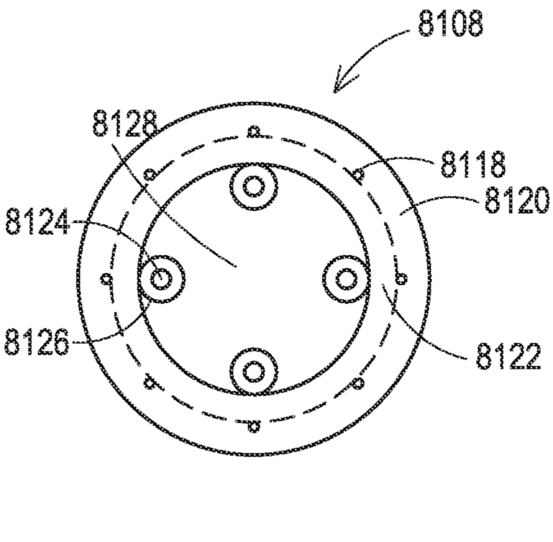
FIG. 72 shows the embodiment of FIG. 71 in cross-section to reveal the shield, filars, and lumen.

FIGS. 71 and 72 show an embodiment of the implantable medical lead 8108 where a shield 8118 is present. This shield 8118 may provide protection from RF energy that allows the lead 8108 to be conditionally MRI safe and thus eligible to carry the radiopaque marker for an MRI. An outer jacket layer 8120 is shown transparently in FIG. 71 for purposes of illustrating the shield 8118. The shield 8118 may provide protection from RF energy of an MRI that might otherwise cause tissue damage due to induced RF currents in the filars of the lead 8108. The conductive filars 8124 extend the length of the lead 8108 and interconnect the proximal connectors 8110 to the distal electrodes so that stimulation signals are conducted from the proximal end to the distal end of the lead 8108.

As shown in FIG. 71, the shield 8118 of this example is a braided metal wire. The metal wire may be constructed of various materials such as titanium, tantalum, niobium, platinum-iridium alloy, platinum, palladium, gold, stainless steel, and their alloys, or other metals. It may be desired to utilize a biocompatible metal for the shield 8118, particularly for embodiments where a portion of the shield 8118 may be exposed for purposes of grounding. While the shield 8118 is shown as a braid, other shield configurations may be chosen particularly where flexibility is not an issue such as a foil strip wrapped about the lead 8108 in an overlapping manner or an outer layer 8120 that is heavily doped with conductive particles.

As shown in FIG. 72, the shield 8118 may be embedded within the jacket of the lead 8108. One manner of constructing the lead 8108 with the shield 8118 is to provide an inner jacket 8122 that encloses the filars 8124 and any additional insulation layer 8126 that may surround each filar 8124. The shield 8118 may then reside on the outer portion of the inner jacket 8122, and the outer jacket 8120 may then enclose the shield 8118.

The shield 8118 may ground to tissue via an RF coupling through the outer layer 8120 and/or via grounding to the can 8104 and/or to the tissue via ground rings. For embodiments where it is desirable for the shield 8118 to RF couple to tissue, the outer jacket layer 8120 may be relatively thin, such as on the order of 0.5 to 5 mils. Where the shield 8118 grounds at the can 8104 of the IMD 8102 and grounding via a RF coupling from the shield 8118 through the outer jacket 8120 directly to the tissue is of less significance, then the shield 8118 may be located further from the outer surface of the lead 8108. The outer jacket 8120 may be added over the shield 8118 by shrinking in place or by being extruded over the shield 8118.

The inner and outer jackets 8122, 8120 may be constructed of the same or similar materials such as various flexible and biocompatible polymers, examples of which are polyurethanes and silicones. A lumen 8128 may be included inside of the inner jacket 8122 around which the insulated filars 8124 are coiled or otherwise positioned. The lumen 8128 may be useful, particularly for percutaneous leads 8108, to allow a stylet to be inserted for purposes of pushing and steering the lead 8108 into the desired position within the patient.

Embodiments as disclosed in relation to FIGS. 73-76D provide for reduced torsional stiffness of a shield present within an implantable medical lead for use with an implantable medical device (IMD). The torsional stiffness of the shield may be reduced in various ways such as by axially cutting the shield to form a slot that breaks the circumferential mechanical continuity of the shield. The slot may then be closed to re-establish the circumferential shielding continuity of the shield and to preserve the shielding function.

Figure 73:
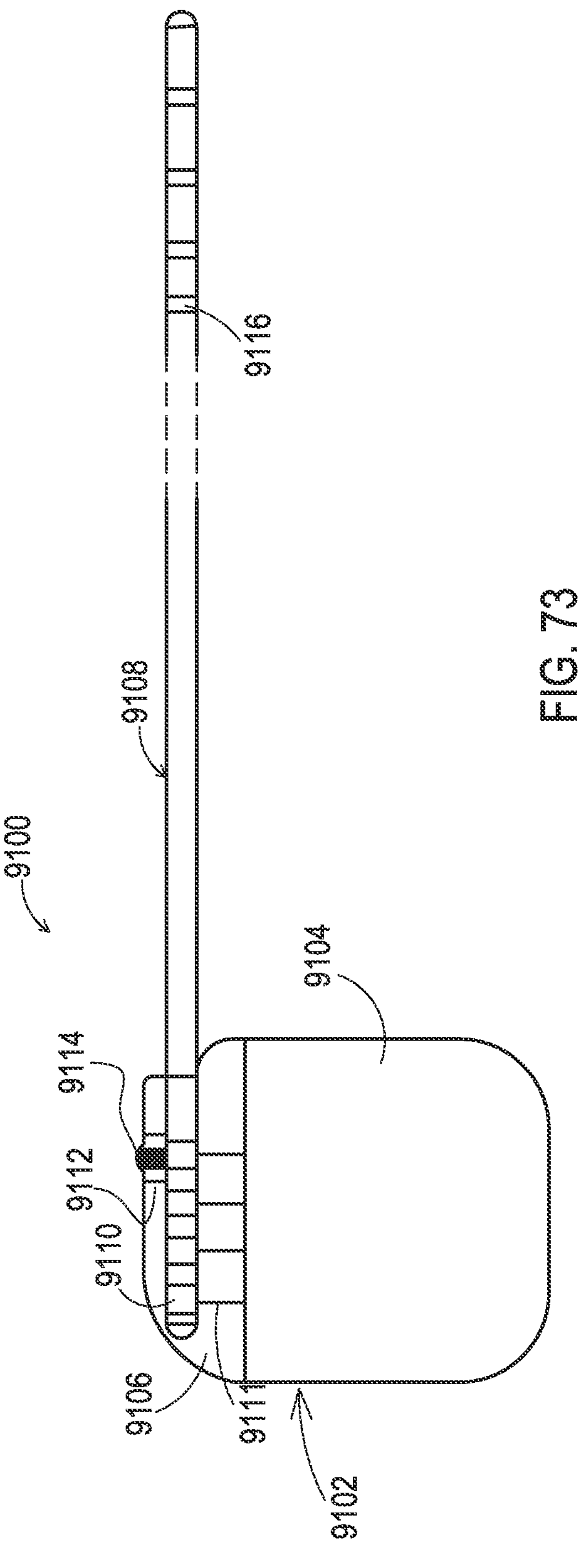
FIG. 73 shows an embodiment of an implantable medical system that includes an implantable medical device (IMD) coupled to a lead containing a shield.

FIG. 73 shows an example of an implantable medical system 9100 that includes an IMD 9102 coupled to a lead 9108. The IMD 9102 includes a metal can 9104, typically constructed of a medical grade titanium, such as grades 1-4, 5 or 9 titanium, or similar other biocompatible materials. The IMD 9102 includes a header 9106 typically constructed of materials such as polysulfone or polyurethane, that is affixed to the metal can 9104. The header 9106 is shown transparently for purposes of illustration. The header 9106 provides a structure for securing the lead 9108 to the IMD 9102 and for establishing electrical connectivity between circuitry of the IMD 9102 and electrodes of the lead 9108.

The lead 9108 includes electrodes 9116 on a distal end that are positioned at a stimulation site within a patient. The lead also includes connector rings 9110 on a proximal end that is positioned within the header 9106. The connector rings 9110 make physical contact with electrical connections 9111 within the header. The electrical connections 9111 may include a metal contact that the connector ring 9110 rests against upon being inserted into the header 9106 where a wire extends from the metal contact into the can 9104 where the circuitry is housed. Signals applied by the IMD 9102 to the connector rings 9110 are conducted through the lead 9108 to the electrodes 9116 to provide the stimulation therapy to the patient.

Figure 74A:
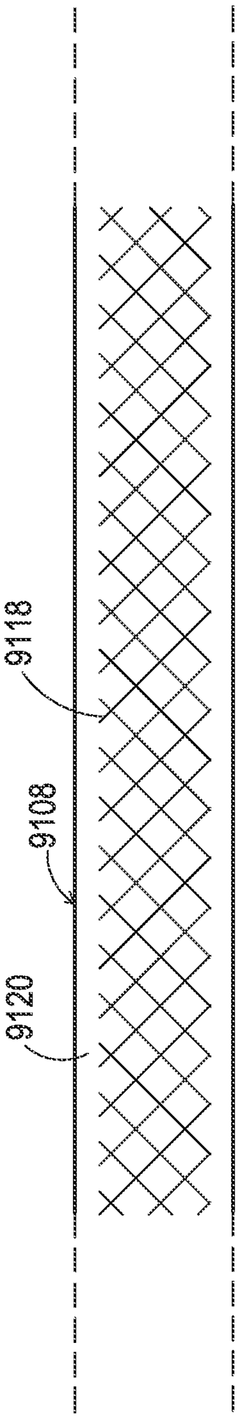
FIG. 74A shows an embodiment of an implantable lead with the shield revealed.
Figure 74B:
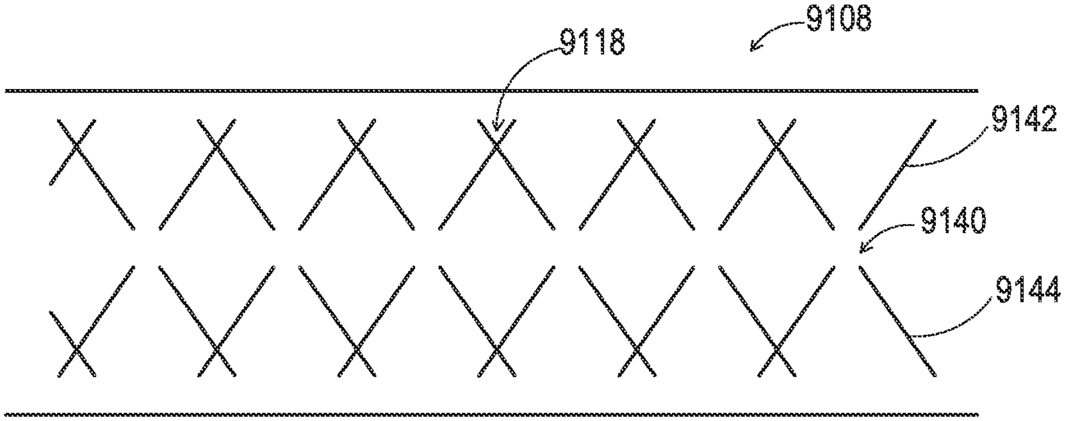
FIG. 74B shows an embodiment of an implantable lead with the shield having an axial cut that creates a slot.

The lead 9108 is secured in the header 9106 such as by a set screw block 9112 within the header 9106 that allows at least one set screw 9114 to be tightened against at least one of the connector rings 9110. A shield 9118 as shown in FIGS. 74A and 74B may be grounded to the body along one or more points down the length of the lead from the IMD 9102 via capacitive coupling through the jacket or via ground rings. The shield 9118 may also be grounded at the can 9104 of the IMD 9102 of FIG. 73.

Figure 75A:
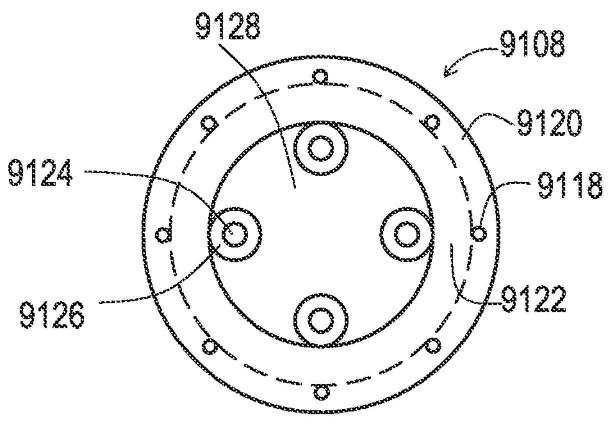

FIGS. 74A and 75A show an example of the lead 9108, where a shield 9118 is present. An outer insulation layer 9120 of a lead jacket is shown transparently in FIG. 74A for purposes of illustrating the shield 9118. The shield 9118 blocks at least some RF energy from directly coupling to conductive filars 9124 that are present within the lead 9108. The conductive filars 9124 extend the length of the lead and interconnect the proximal connector rings 9110 to the distal electrodes 9116 so that stimulation signals are conducted from the proximal end to the distal end of the lead 9108.

As shown in FIG. 74A, the shield 9118 of this example is a braided collection of metal wires. The metal wires may be constructed of various materials such as titanium, tantalum, niobium, platinum-iridium alloy, platinum, palladium, gold, stainless steel, and their alloys, or other metals. It may be desired to utilize a biocompatible metal for the shield 9118, particularly for embodiments where a portion of the shield 9118 may be exposed for purposes of grounding. While the shield 9118 is shown as a braid, other shield configurations may be chosen particularly where flexibility is not an issue such as a coiled configuration, foil strip wrapped about the lead 9108 in an overlapping manner or an outer layer 9120 that is heavily doped with conductive particles.

As shown in FIG. 75A, the shield 9118 may be embedded within the jacket of the lead 9108. One manner of constructing the lead 9108 with the shield 9118 is to provide an inner insulation layer 9122 of the jacket that encloses the filars 9124 and any additional insulation layer 9126, such as polytetrafluoroethylene (PTFE) that may surround each filar 9124. The shield 9118 may then reside on the outer portion of the inner insulation layer 9122, and the outer insulation layer 9120 may then enclose the shield 9118. The outer insulation layer 9120 may be added over the shield 9118 and shrunk in place or may be extruded over the shield 9118. The outer jacket 9120 maybe added over the braid 9118, or it may be extruded over the braid.

For embodiments where it is desirable for the shield 9118 to RF couple to tissue, typically as a capacitive coupling, in addition to grounding at the can 9104 or along the lead 9108, the amount of the outer jacket layer 9120 covering the shield 9118 may be relatively thin, such as on the order of 0.5 to 5 mils. Where the shield 9118 grounds at one or more specific locations along its length, via a direct current coupling or a capacitive coupling, the shield 9118 may be located further from the outer surface of the lead 9108.

The inner and outer insulation layers 9122, 9120 of the jacket may be constructed of the same or similar materials such as various flexible and biocompatible polymers, examples of which are polyurethanes and silicones. A lumen 9128 may be included inside of the inner jacket 9122 around which the insulated filars 9124 are coiled or otherwise positioned. The lumen 9128 may be useful, particularly for percutaneous leads 9108, to allow a stylet to be inserted for purposes of pushing and steering the lead 9108 into the desired position within the patient.

As shown, the shield 9118 has mechanical and shielding continuity about the circumference of the inner insulation layer 9122. This continuity is achieved by the wires of the braided shield 9118 being continuous. The circumferential shielding continuity exists because there are no non-conductive openings large enough to allow RF energy to easily pass through. The mechanical continuity produces a large increase in torsional stiffness over an unshielded lead, which may be beneficial in some respects but is detrimental in other respects.

The detrimental aspects may include difficulties twisting the lead during implant procedures due to high torsional stiffness. Twisting the lead 9108 may be beneficial when guiding the lead 9108 to the stimulation site and to the IMD 9102 and when wrapping excess lengths of the lead 9108 about the IMD 9102. Thus, in some instances, it may be desirable to provide a shielded implantable medical lead with reduced torsional stiffness.

Figure 75B:
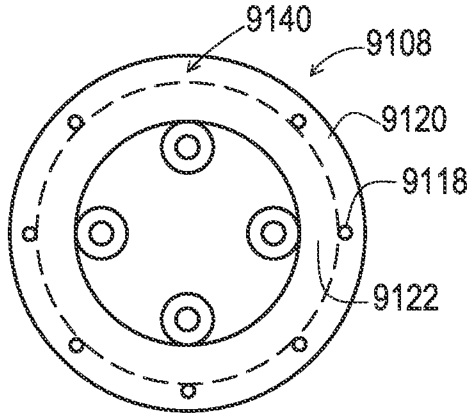

FIGS. 74B and 75B show the lead 9108 once the shield 9118 has been cut in an axial direction to create a slot 9140. A shield portion 9142 creates one edge of the slot 9140 while an opposing shield portion 9144 creates the opposite edge. The slot 9140 may be created by a single cut or by two cuts that are roughly parallel and result in a section of the shield 9118 being removed. The shield 9118 may be cut prior to applying the outer layer 9120 so that the outer layer 9120 does not need to be cut to cut the shield 9118.

The shield 9118 of FIG. 74B now lacks the circumferential mechanical continuity due to the slot 9140, and the torsional stiffness is reduced considerably as a result. However, the slot 9140 also breaks the circumferential shielding continuity because the slot 9140 has an axial dimension that allows RF energy to easily pass through the slot 9140. Therefore, to preserve the RF shielding function of the shield 9118, the slot 9140 is closed in one of various ways that re-establishes the circumferential shielding continuity while allowing the circumferential mechanical continuity to remain broken.

Figure 74C:
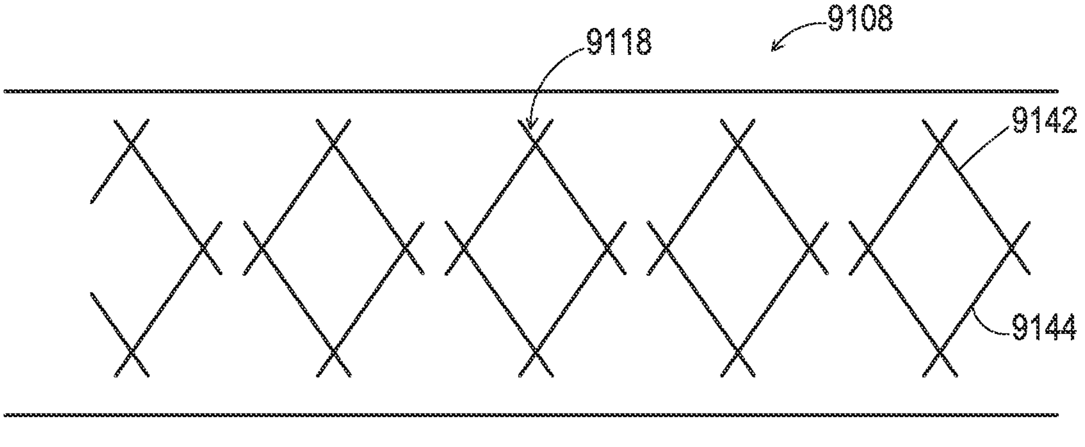
Figure 75C:
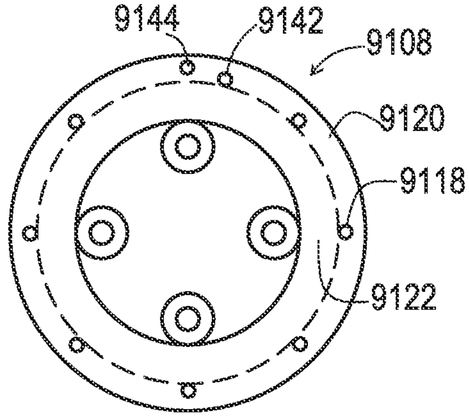

FIGS. 74C and 75C show one embodiment of the lead 9108 where the slot 9140 is closed to re-establish circumferential shielding continuity by closing the slot sufficiently relative to the wavelengths of RF energy so that the RF energy cannot easily penetrate the shield 9118 at the location of the slot 9140. In this example, the shield portion 9144 laps over the shield portion 9142 to close the slot 9140 from a shielding continuity standpoint. The shield portion 9144 may or may not contact the shield portion 9142 such that circumferential electrical continuity may or may not be re-established. However, either way, the shield portion 9144 is not bonded to the shield portion 9142 such that they remain mobile with respect to one another, thereby maintaining the break in the circumferential mechanical continuity.

The shield portion 9144 may be lapped onto the shield portion 9142 as a natural result of cutting the shield 9118, such as where the shield 9118 is loosely braided over the inner insulation layer 9122. The loose braiding provides an uncut shield diameter that is slightly larger than the diameter of the inner insulation layer 9122 such that cutting the shield 9118 to create the slot 9140 allows the shield portion 9144 to collapse onto the shield portion 9142. This collapse of the shield 9118 closes the slot 9140 while the shield diameter is reduced down to the diameter of the inner insulation layer 9122.

The outer insulation layer 9120 is then added over the shield 9118. The outer insulation layer 9120 is a polymer that holds the shield 9118 in place against the inner insulation layer 9122. However, the polymer of the outer insulation layer 9120 is compliant so that the shield portion 9144 can move relative to the shield portion 9142 upon application of torque to the lead 9108.

Figure 74D:
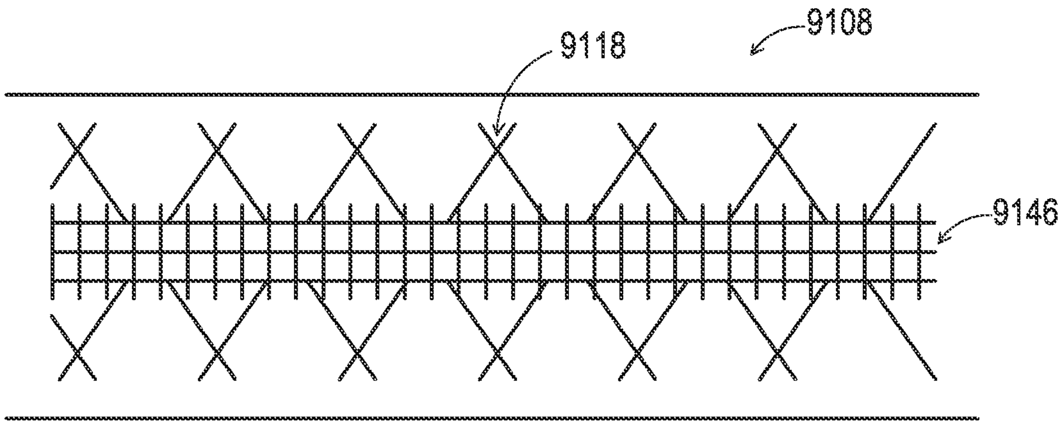
Figure 75D:
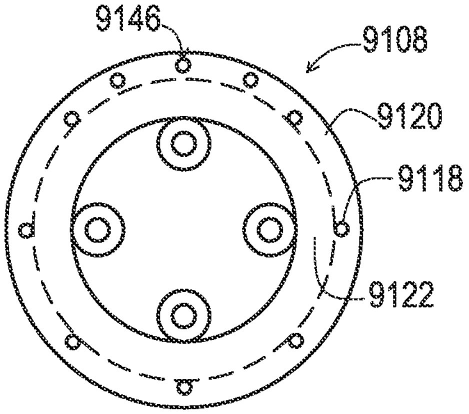

FIGS. 74D and 75D show another embodiment of the lead 9108 where the slot 9140 is closed to re-establish circumferential shielding continuity by closing the slot 9140 sufficiently relative to the wavelengths of RF energy so that the RF energy cannot easily penetrate the shield 9118 at the location of the slot 9140. In this example, the slot 9140 is closed by application of a shield patch 9146. The shield patch 9146 may be constructed similarly to the braided shield 9118, using the same or similar metal wire. In the example shown, the shield patch 9146 is a grid pattern, but it will be appreciated that other patterns may also be used such as where the grid includes U-shaped portions along the axial wires so that the U-shaped portions allow for axial extension of the lead 9108. The shield patch 9146 overlaps onto the shield 9118 on both sides of the slot 9140. The shield portion 9144 may or may not contact the shield portion 9142 such that circumferential electrical continuity may or may not be re-established. However, either way, the shield patch 9146 is not bonded to the shield 9118 such that the shield patch 9146 can move relative to the shield 9118 on either side of the slot 9140. As a result, the circumferential mechanical continuity of the shield 9118 remains broken.

Because the shield patch 9146 is being added to the lead 9108, the braided shield 9118 may be applied to the inner insulation layer 9122 in a close fitting manner as opposed to loosely braiding the shield 9118. Once the cut is complete, the shield patch 9146 may then be placed into position directly onto the shield 9118 and across the slot 9140.

The outer insulation layer 9120 is then added over the shield 9118 and the shield patch 9146. As in the embodiment of FIGS. 74C and 75C, the outer insulation layer 9120 is a polymer, and the outer insulation 9120 holds the shield 9118 in place against or close to the inner insulation layer 9122 and also holds the shield patch 9146 in place against or close to the shield 9118. However, the polymer of the outer insulation layer 9120 is compliant so that the shield patch 9146 can move relative to the shield 9118 on either or both sides of the slot 9140 upon application of an axial twisting moment to the lead 9108.

Figure 76A:
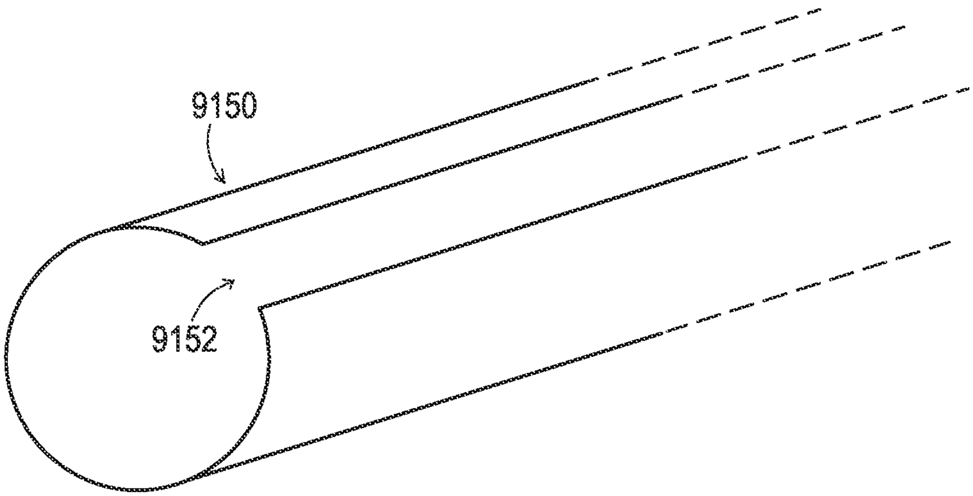

FIG. 76A shows a representation of a shield 9150 that may be used in an implantable medical lead 9108. The representation is a tube, and this tube is illustrative for multiple reasons. Where the shield 9150 is a braided shield, such as the shield 9118, the apertures are small relative to the wavelengths of the RF energy such that the braided shield 9118 is effectively a tube from the perspective of the RF energy. Where the shield 9150 is another configuration, such as a foil strip wrapped around the inner insulation layer 9122 in an overlapping fashion, the foil strip forms a true tube. In either case, a linear axial cut in the shield 9150 reduces torsional stiffness but appears as the slot 9152, which presents an opening that the RF energy may pass through.

Figure 76B:
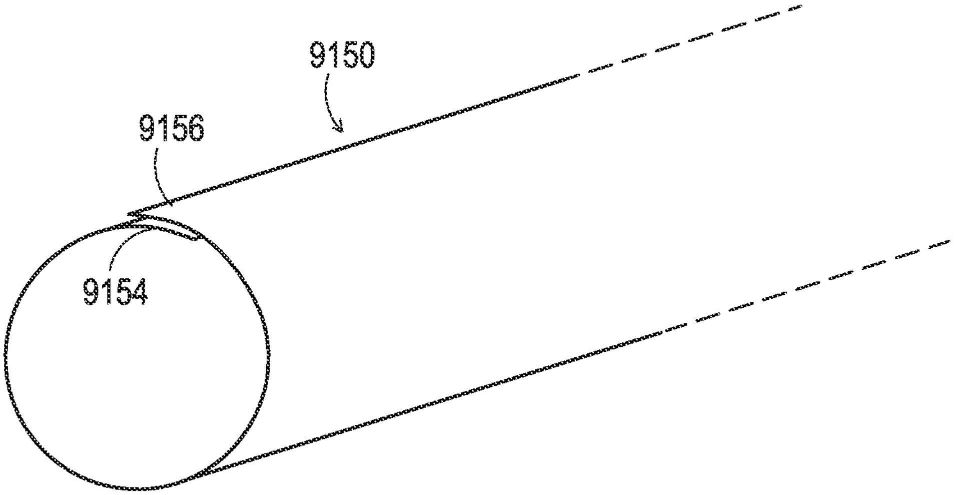

FIG. 76B shows a tubular representation of the shield 9150 that may correspond to a braided shield or other shield configuration such as an overlapping wrapped foil strip. Here, the shield 9150 uses the overlap technique such as that shown above in FIGS. 74C and 75C to close the slot 9152 formed by the linear axial cut. As can be seen, a shield portion 9156 on one side of the slot 9152 overlaps another shield portion 9154 on the opposite side of the slot 9152 and may or may not contact the shield portion 9154. Thus, the slot 9152 is effectively closed to establish shielding continuity across the slot 9152, but the shield portions 9154, 9156 may move relative to one another so that the mechanical continuity remains broken.

Figure 76C:
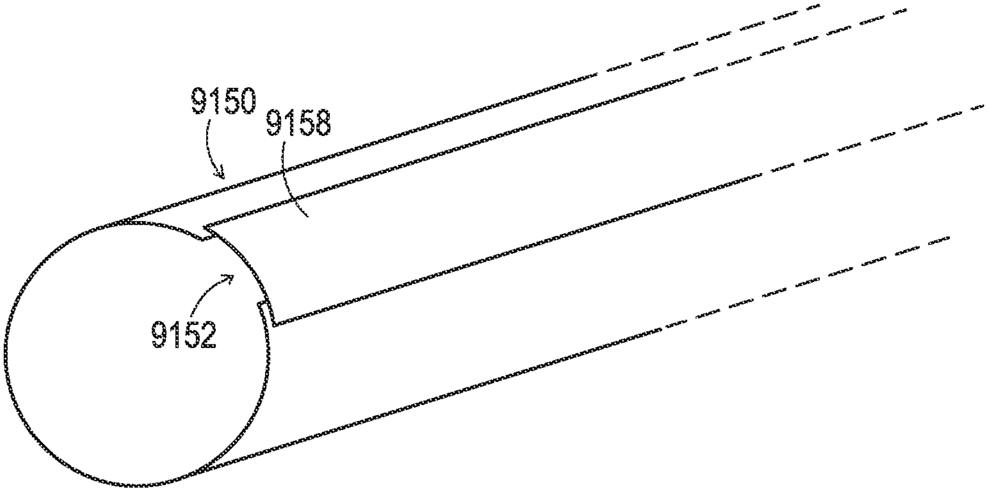

FIG. 76C shows a tubular representation of the shield 9150 that may also correspond to a braided shield or other shield configuration such as an overlapping wrapped foil strip. Here, the shield 9150 uses a shield patch technique such as that shown above in FIGS. 74D and 75D to close the slot 9152 formed by the linear axial cut. As can be seen, a shield patch 9158 reaches across the slot 9152 to overlap and may or may not physically contact the shield 9150 on both sides of the slot

9152. Thus, the slot 9152 is effectively closed to establish shielding continuity across the slot 9152, but the shield patch 9158 may move relative to the shield 9150 on either or both sides of the slot 9152 so that the mechanical continuity remains broken.

Figure 76D:
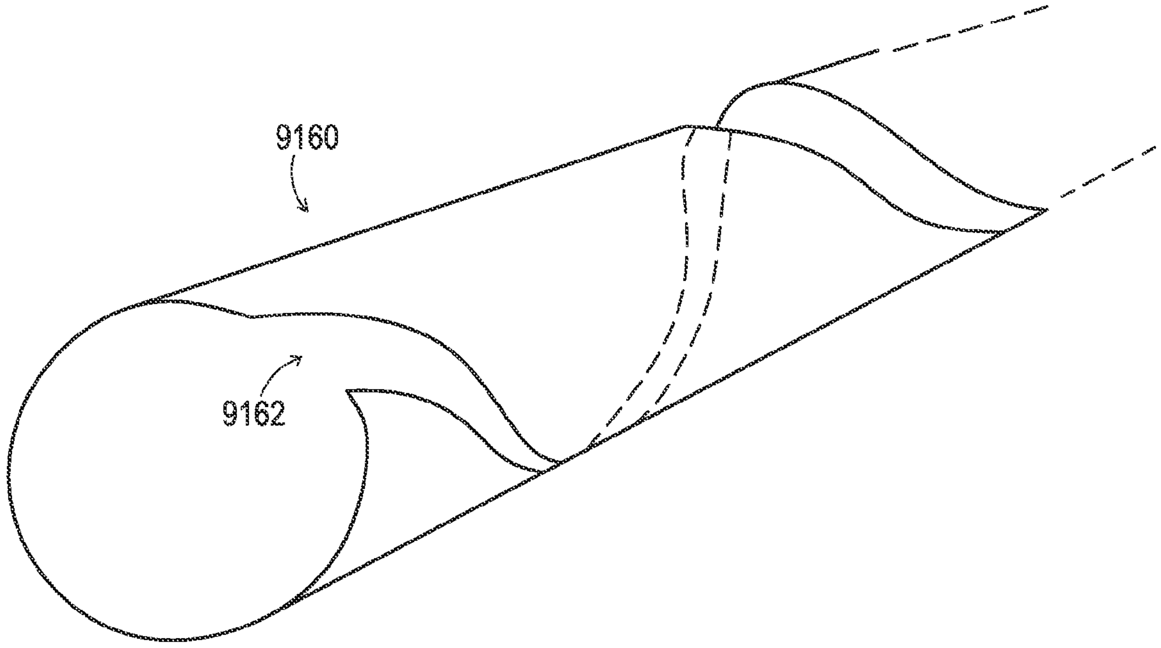

FIG. 76D shows a tubular representation of the shield 9160 that may correspond to a braided shield or other shield configuration such as an overlapping wrapped foil strip. Here, the shield 9160 has been cut axially using a helical cut rather than a linear cut to create a helical slot 9162. The slot 9162 breaks the circumferential mechanical continuity so as to reduce the torsional stiffness, but the slot 9162 also breaks the circumferential shielding continuity.

The slot 9162 may be closed using techniques discussed above. A shield patch may be wrapped around the helical slot 9162 to reach across the slot 9162 and achieve circumferential shielding continuity. Or, the shield 9160 may be given a larger diameter than the inner insulation layer upon which it is positioned so that upon creating the slot 9162, the shield 9160 may collapse to create an overlap along the helical slot 9162 to establish circumferential shielding continuity. This shield patch may be another piece of foil or may be a braided patch.

Embodiments as disclosed in relation to FIGS. 77-80C provide for guarding a termination of a shield to reduce coupling of RF energy from the termination of the shield to filars present within an implantable medical lead for use with an implantable medical device (IMD). The guarding of the termination of the shield may be done in various ways such as by inverting the shield near the termination such that a first portion of the shield separates the termination of the shield from inner layers of the lead. Other examples may involve including separate pieces of the shield to form first and second portions, where one portion separates the termination of the other portion from the inner layers of the lead.

Figure 77:
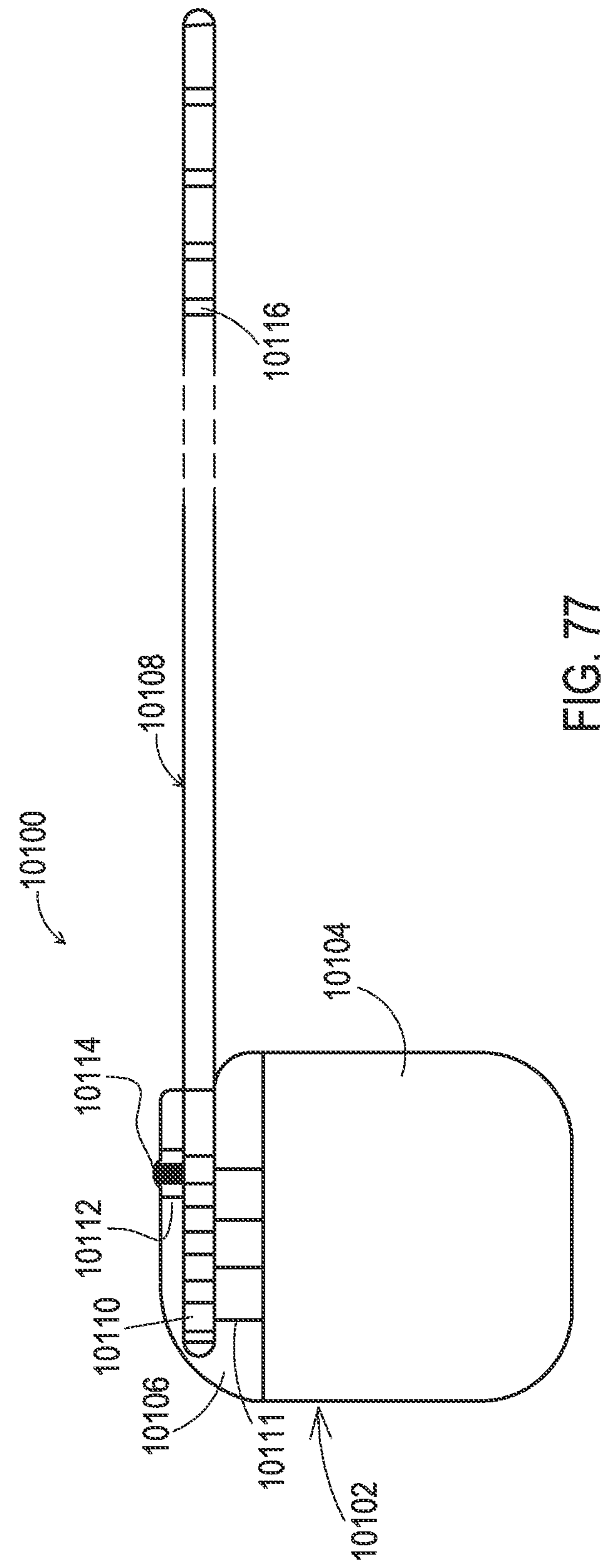

FIG. 77 shows an example of an implantable medical system 10100 that includes an IMD 10102 coupled to a lead 10108. The IMD 10102 includes a metal can 10104, typically constructed of a medical grade titanium, such as grades 1-4, 5 or 9 titanium, or similar other biocompatible materials. The IMD 10102 includes a header 10106 typically constructed of materials such as polysulfone or polyurethane, that is affixed to the metal can 10104. The header 10106 is shown transparently for purposes of illustration. The header 10106 provides a structure for securing the lead 10108 to the IMD 10102 and for establishing electrical connectivity between circuitry of the IMD 10102 and electrodes of the lead 10108.

The lead 10108 includes electrodes 10116 on a distal end that are positioned at a stimulation site within a patient. The lead 10108 also includes connector rings 10110 on a proximal end that is positioned within the header 10106. The connector rings 10110 make physical contact with electrical connections 10111 within the header. The electrical connections 10111 may include a metal contact that the connector ring 10110 rests against upon being inserted into the header 10106 where a wire extends from the metal contact into the can 10104 where the circuitry is housed. Signals applied by the IMD 10102 to the connector rings 10110 are conducted through the lead 10108 to the electrodes 10116 to provide the stimulation therapy to the patient.

The lead 10108 is secured in the header 10106 such as by a set screw block 10112 within the header 10106 that allows at least one set screw 10114 to be tightened against at least one of the connector rings 10110. A shield 10118 as shown in FIGS. 78A and 78B may be grounded to the body along one or more points down the length of the lead from the IMD 10102 via capacitive coupling through the jacket or via ground rings. The shield 10118 may also be grounded at the can 10104 of the IMD 10102 of FIG. 77.

FIGS. 78A and 78B show an example of the lead 10108, where a shield 10118 is present. An outer insulation layer 10120 of a lead jacket is shown transparently in FIG. 78A for purposes of illustrating the shield 10118. The shield 10118 blocks at least some RF energy from directly coupling to conductive filars 10124 that are present within the lead 10108. The conductive filars 10124 extend the length of the lead and interconnect the proximal connectors 10110 to the distal electrodes 10116 so that stimulation signals are conducted from the proximal end to the distal end of the lead 10108.

As shown in FIG. 78A, the shield 10118 of this example is a braided collection of metal wires. The metal wires may be constructed of various materials such as titanium, tantalum, niobium, platinum-iridium alloy, platinum, palladium, gold, stainless steel, and their alloys, or other metals. It may be desired to utilize a biocompatible metal for the shield 10118, particularly for embodiments where a portion of the shield 10118 may be exposed for purposes of grounding. While the shield 10118 is shown as a braid, other shield configurations may be chosen particularly where flexibility is not an issue such as a foil strip wrapped about the lead 10108 in an overlapping manner.

FIG. 78B is a cross-section that shows one example of construction of the lead 10108. In this embodiment, either the guard is not provided or the guard is not present at the area where the cross-section is taken. Thus, FIG. 78B shows the general construction of the lead 10108 without the specifics of the guard which are discussed below in relation to FIGS. 79A-79C and 80A-80C. The shield 10118 may be embedded within the jacket of the lead 10108. One manner of constructing the lead 10108 with the shield 10118 is to provide an inner insulation layer 10122 of the jacket that encloses the filars 10124 and any additional insulation layer 10126, such as polytetrafluoroethylene (PTFE) that may surround each filar 10124. The shield 10118 may then reside on the outer portion of the inner insulation layer 10122, and the outer insulation layer 10120 may then enclose the shield 10118. The outer insulation layer 10120 may be added over the shield 10118 and shrunk in place or may be extruded over the shield 10118.

For embodiments where it is desirable for the shield 10118 to RF couple to tissue along, typically as a capacitive coupling, in addition to grounding at the can 10104 or along the lead 10108, the entire outer jacket layer 10120 may be relatively thin, such as on the order of 0.5 to 5 mils. Where the shield 10118 grounds at one or more specific locations along its length, via a direct current coupling or a capacitive coupling, the shield 10118 may be located further from the outer surface of the lead 10108.

The inner and outer insulation layers 10122, 10120 of the jacket may be constructed of the same or similar materials such as various flexible and biocompatible polymers, examples of which are polyurethanes and silicones. A lumen 10128 may be included inside of the inner jacket 10122 around which the insulated filars 10124 are coiled or otherwise positioned. The lumen 10128 may be useful, particularly for percutaneous leads 10108, to allow a stylet to be inserted for purposes of pushing and steering the lead 10108 into the desired position within the patient.

FIG. 79A shows an embodiment of the implantable medical lead 10108 in an axial cross-section where termination of the shield 10118 is guarded to reduce coupling of RF energy to one or more filars 10124. FIG. 80A shows a radial cross-section of the same embodiment, with the cross section taken where the shield terminates. A single coiled filar 10124 is shown in this example but additional filars may be included and the filars may be of other forms such as linear cables rather than coils. In this example, the shield 10118 is one continuous shield of braided metal wires, but it will be appreciated that other shields may also be used such as the wrapped foil discussed above.

The shield 10118 of this example has an inversion 10136 near the distal end of the lead 10108. This inversion 10136 creates two sections to the shield 10118, a first portion 10119 that extends from the inversion 10136 back to the proximal end of the lead 10108 and a second portion 10121 that forms the distal termination of the shield 10118. The inversion 10136 creates a guard for the shield termination.

The second portion 10121 is separated from the inner insulation layer 10122 as well as the filars 10124 by the first portion 10119. The first portion 10119 is braided upon the inner insulation layer 10122 and then may be coated with the outer insulation layer 10120 with the second portion 10121 remaining uncoated. The inversion 10136 may then be created so that the second portion 10121 then laps onto the outer insulation layer 10120 so as to be separated from contact with the first portion 10119. The second portion 10121 may extend from the inversion 10136 toward the proximal end by various distances, for instance ranging from about ⅛ inch to about 1 inch, such that the second portion 10121 may be axially shorter than the first portion 10119 which extends to the proximal end or the second portion 10121 may also extend to the proximal end. The second portion 10121 may then be covered by an additional outer insulation layer 10117, made of the same or similar material as the outer insulation layer 10120, if it is desired that the second portion 10121 be physically isolated from the body tissue.

The thickness of the outer insulation layer 10120 at the inversion 10136 dictates the bend radius of the inversion 10136 where the second portion 10121 laps onto the outer insulation layer 10120. It may be desirable to have a bend radius that is sufficiently large, such as 0.002 inches, so that the inversion 10136 does not act as a shield termination from which RF might couple to the filars 10124. The lead diameter that is allowable for a given application may dictate the relative thicknesses of each of the layers and thus set an upper limit for the bend radius of the inversion 10136.

Prior to or contemporaneously with the addition of the outer insulation layer 10117, an extension 10132 to the outer insulation layer 10120 may be created to extend further toward the distal end where electrodes such as electrode 10130 are located. The extension 10132 may be constructed of the same or similar materials as that of the outer insulation layers 10117, 10120. The electrode 10130 has a filar jumper wire 10134 or the filar 10124 itself that extends through this extension 10132 and between the electrode 10130 and the filar 10124. Alternatively, the area where extension 10132 is shown may be created as a continuation of the outer insulation layer 10117.

FIG. 79B shows another embodiment of the implantable medical lead 10108 in an axial cross-section where termination of the shield 10118 is guarded to reduce coupling of RF energy to one or more filars 10124. FIG. 80B shows a radial cross-section of the same embodiment, with the cross section taken where the shield 10118 terminates. A quad coiled filar 10124 is shown in this example but additional or fewer filars may be included and the filars may be linear cables rather than coils. In this example, the shield 10118 is two separate pieces forming a first portion 10123 and a second portion 10125 of the shield 10118 made of braided metal wires. It will be appreciated that either or both pieces may be another form of a shield such as wrapped foil as discussed above.

The shield 10118 of this example has the first portion 10123 that is a separate piece that resides at the distal end of the lead 10108 and may extend toward the proximal end for a relatively short distance, for instance, in the range of about ⅛ inch to about 1 inch. The first portion 10123 is wrapped around the inner insulation layer 10122. An intervening layer of insulation 10115 then surrounds the first portion 10123.

The second portion 10125 of the shield 10118 is wrapped around the intervening layer of insulation 10115 and is therefore physically isolated from contact with the first portion 10123. The second portion 10125 then extends on to the proximal end of the lead 10108 and may therefore be axially longer than the first portion 10123. The outer insulation layer 10120 then surrounds the second portion 10125. As a result of this configuration, the first portion 10123 is located between the termination point at the second portion 10125 and the inner layers including the inner insulation layer 10122 and filars 10124.

Because there is no inversion in this embodiment of FIGS. 79B and 80B, the thickness of the layers 10115, 10120 may not be as large as the thickness of the outer insulation layer 10120 of the embodiment of FIGS. 79A and 80A where that thickness established the bend radius at the inversion 10136. As a result, the separation between the first portion 10123 and the second portion 10125 may be smaller than the separation between the first portion 10119 and the second portion 10121 of FIGS. 79A and 80A. For instance, the intervening insulation layer 10115 may have a thickness ranging from about 0.002 inches to about 0.006 inches to control the separation between the first portion 10123 and second portion 10125.

The outer insulation layer 10120 may be continued to extend on toward the distal end of the lead 10108, including filling the area where the electrode 10130 is located. Alternatively, prior to or contemporaneously with the addition of the outer insulation layer 10120, an extension layer from the outer insulation layer 10120 may be created to extend further toward the distal end where electrodes such as electrode 10130 are located. The extension may be constructed of the same or similar materials as that of the outer insulation layers 10117, 10120.

FIG. 79C shows another embodiment of the implantable medical lead 10108 in an axial cross-section where termination of the shield 10118 is guarded to reduce coupling of RF energy to one or more filars 10124. FIG. 80C shows a radial cross-section of the same embodiment, with the cross section taken where the shield 10118 terminates. A quad coiled filar 10124 is shown in this example but additional filars may be included and the filars may be other forms such as linear cables rather than coils. In this example, the shield 10118 is two separate pieces forming a first portion 10140 and a second portion 10142 of the shield 10118 made of braided metal wires, but it will be appreciated that either piece may be another form of a shield such as wrapped foil as discussed above.

The shield 10118 of this example has the first portion 10140 that is a separate piece that resides at the distal end of the lead 10108 and that has an inversion 10138 to establish a first sub-portion 10146 and a second sub-portion 10144. Both sub-portions 10144, 10146 may extend toward the proximal end of the lead 10108 for a relatively short distance in the range of about ⅛ inch to about 1 inch. The first sub-portion 10146 is wrapped around the inner insulation layer 10122. An intervening layer of insulation 10113 then surrounds the first sub-portion 10146.

The second portion 10142 of the shield 10118 is wrapped around the intervening layer of insulation 10113 and is therefore physically isolated from contact with the first sub-portion 10146. The second portion 10142 then extends on to the proximal end of the lead 10108 and is therefore axially longer than the first sub-portion 10146 and the second sub-portion 10144. The outer insulation layer 10120 then surrounds the second portion 10142. As a result of this configuration, the first sub-portion 10146 is located between the termination point at the second portion 10142 and the inner layers including the inner insulation layer 10122 and filars 10124.

The second sub-portion 10144 of the first portion 10140 laps onto the outer insulation layer 10120 as a result of the inversion 10138. The second sub-portion 10144 may then be covered by an additional outer insulation layer 10127, made of the same or similar material as the outer insulation layer 10120, if it is desired that the second sub-portion 10144 be physically isolated from the body tissue.

The thickness of both the intervening layer of insulation 10113 and the outer insulation layer 10120 at the inversion 10138 dictates the bend radius of the inversion 10138 where the second sub-portion 10144 laps onto the outer insulation layer 10120. It may be desirable to have a bend radius that is relatively large, such as about 0.002 inches, so that the inversion 10136 does not act as a shield termination from which RF might couple to the filars 10124. The lead diameter that is allowable for a given application may dictate the relative thicknesses of each of the layers and thus set an upper limit for the bend radius similar to the upper limit for the embodiment of FIGS. 79A and 80A.

The outer insulation layer 10127 may be continued to extend on toward the distal end of the lead 10108, including filling the area where the electrode 10130 is located. Alternatively, prior to or contemporaneously with the addition of the outer insulation layer 10127, an extension layer from the outer insulation layer 10120 may be created to extend further toward the distal end where electrodes such as electrode 10130 are located. The extension layer may be constructed of the same or similar materials as that of the outer insulation layers 10127, 10120.

While many embodiments have been particularly shown and described, it will be understood by those skilled in the art that various other changes in the form and details may be made therein without departing from the spirit and scope of the invention.

What is claimed is:

1. A method of shielding an implantable medical lead, comprising:

providing an inner layer of insulation establishing an axial dimension, the inner layer surrounding at least one conductive filar;

providing a shield over the inner layer of insulation, the shield comprising:

a plurality of metal wires forming a braid about the inner layer of insulation, a first set of the plurality being coiled in a first direction and a second set of the plurality being coiled in a second direction, the metal wires each having a dimension that faces outward from the inner layer within a range from 0.5 to 2.5 mils, the braid having a braid angle less than 60 degrees when measured transversely from the axial dimension, providing an outer layer of insulation over an entire length of the braid of the shield with the outer layer of insulation being adhered to the inner layer of insulation through openings within the braid formed by the metal wires;

providing at least one proximal electrode on a proximal end of the inner layer of insulation and at least one distal electrode on a distal end of the inner layer of insulation, with the at least one conductive filar establishing an electrical pathway between the at least one proximal electrode and the at least one distal electrode.

2. The method of claim 1, wherein the inner layer is a biocompatible material with a thickness of at least 2 mils.

3. The method of claim 1, wherein the shield ends on a distal end between 1 millimeter and 2 centimeters of a nearest edge of the at least one distal electrode.

4. The method of claim 1, wherein the shield comprises at least six metal wires forming the braid about the inner layer of insulation with at least three of the at least six wires being coiled in the first direction and at least three of the at least six wires being coiled in the second direction.

5. The method of claim 1, wherein a diameter of the outer layer establishes a lead diameter and wherein spacing in the axial dimension between adjacent wires coiled in the first direction is no greater than the lead diameter.

6. The method of claim 1, wherein the metal wires each have an ultimate tensile strength of at least 150 ksi.

7. The method of claim 1, wherein the metal wires have a cross-section in the shape of round, oval, or rectangular.

8. The method of claim 1, wherein the metal wires are a biocompatible material.

9. The method of claim 1, wherein the outer layer of insulation is a biocompatible material having a thickness over the metal wires of no greater than 4 mils.

10. The method of claim 1, wherein at least two metal wires of the first set are positioned in contact to form a pairing.

11. A method of shielding an implantable medical lead, comprising:

providing an inner layer of insulation establishing an axial dimension, the inner layer surrounding at least one conductive filar;

providing a shield over the inner layer of insulation, the shield comprising:

at least six metal wires forming a braid about the inner layer of insulation with at least three of the at least six wires forming a first set being coiled in the first direction and at least three of the at least six wires forming a second set being coiled in the second direction, the braid having a braid angle less than 60 degrees when measured transversely from the axial dimension, providing an outer layer of insulation over an entire length of the braid of the shield with the outer layer of insulation being adhered to the inner layer of insulation through openings within the braid formed by the metal wires;

providing at least one proximal electrode on a proximal end of the inner layer of insulation and at least one distal electrode on a distal end of the inner layer of insulation, with the at least one conductive filar establishing an electrical pathway between the at least one proximal electrode and the at least one distal electrode.

12. The method of claim 11, wherein the inner layer is a biocompatible material with a thickness of at least 2 mils.

13. The method of claim 11, wherein the shield ends on a distal end within 0.5 millimeters to 2 centimeters of a nearest edge of the at least one distal electrode.

14. The method of claim 11, wherein the shield comprises metal wires each having a dimension that faces outward from the inner layer within a range from 0.5 to 2.5 mils.

15. The method of claim 11, wherein a diameter of the outer layer establishes a lead diameter and wherein spacing in the axial dimension between adjacent wires coiled in the first direction is no greater than the lead diameter.

16. The method of claim 11, wherein the metal wires each have an ultimate tensile strength of at least 150 ksi.

17. The method of claim 11, wherein the metal wires have a cross-section in the shape of round, oval, or rectangular.

18. The method of claim 11, wherein the metal wires are a biocompatible material.

19. The method of claim 11, wherein the outer layer of insulation is a biocompatible material having a thickness over the metal wires of no greater than 4 mils.

20. The method of claim 11, wherein at least two metal wires of the first set are positioned in contact to form a pairing.

21. A method of shielding an implantable medical lead, comprising:

providing an inner layer of insulation establishing an axial dimension, the inner layer surrounding at least one conductive filar;

providing a shield over the inner layer of insulation, the shield comprising:

at least six metal wires forming a braid about the inner layer of insulation with at least three of the at least six wires being coiled in the first direction and at least three of the at least six wires being coiled in the second direction, the metal wires each having a dimension that faces outward from the inner layer within a range from 0.5 to 2.5 mils, providing an outer layer of insulation over an entire length of the braid of the shield with the outer layer of insulation being adhered to the inner layer of insulation through openings within the braid formed by the metal wires;

providing at least one proximal electrode on a proximal end of the inner layer of insulation and at least one distal electrode on a distal end of the inner layer of insulation, with the at least one conductive filar establishing an electrical pathway between the at least one proximal electrode and the at least one distal electrode.

22. The method of claim 21, wherein the inner layer is a biocompatible material with a thickness of at least 2 mils.

23. The method of claim 21, wherein the shield ends on a distal end within 1 millimeter of a nearest edge of the at least one distal electrode.

24. The method of claim 21, wherein the shield comprises at least six metal wires forming the braid about the inner layer of insulation with at least three of the at least six wires being coiled in the first direction and at least three of the at least six wires being coiled in the second direction.

25. The method of claim 21, wherein a diameter of the outer layer establishes a lead diameter and wherein spacing in the axial dimension between adjacent wires coiled in the first direction is no greater than a lead diameter.

26. The method of claim 21, wherein the metal wires each have an ultimate tensile strength of at least 150 ksi.

27. The method of claim 21, wherein the metal wires have a cross-section in the shape of round, oval, or rectangular.

28. The method of claim 21, wherein the metal wires are a biocompatible material.

29. The method of claim 21, wherein the outer layer of insulation is a biocompatible material having a thickness over the metal wires of no greater than 4 mils.

30. The method of claim 21, wherein at least two metal wires of the first set are positioned in contact to form a pairing.

31. A method of shielding an implantable medical lead, comprising:

providing an inner layer of insulation establishing an axial dimension, the inner layer surrounding at least one conductive filar;

providing a shield over the inner layer of insulation, the shield comprising:

a plurality of metal wires forming a braid about the inner layer of insulation, a first set of the plurality being coiled in a first direction and a second set of the plurality being coiled in a second direction, wherein spacing in the axial dimension between adjacent wires coiled in the first direction is no greater than a lead diameter and spacing in the axial dimension between adjacent wires coiled in the second direction is no greater than the lead diameter, providing an outer layer of insulation over an entire length of the braid of the shield with the outer layer of insulation being adhered to the inner layer of insulation through openings within the braid formed by the metal wires, a diameter of the outer layer establishing the lead diameter;

providing at least one proximal electrode on a proximal end of the inner layer of insulation and at least one distal electrode on a distal end of the inner layer of insulation, with the at least one conductive filar establishing an electrical pathway between the at least one proximal electrode and the at least one distal electrode.

32. The method of claim 31, wherein the inner layer is a biocompatible material with a thickness of at least 2 mils.

33. The method of claim 31, wherein the shield ends on a distal end within 1 millimeter to 2 centimeters of a nearest edge of the at least one distal electrode.

34. The method of claim 31, wherein the shield comprises at least six metal wires forming the braid about the inner layer of insulation with at least three of the at least six wires being coiled in the first direction and at least three of the at least six wires being coiled in the second direction.

35. The method of claim 31, wherein the metal wires each having a dimension that faces outward from the inner layer within a range from 0.5 to 2.5 mils.

36. The method of claim 31, wherein the metal wires each have an ultimate tensile strength of at least 150 ksi.

37. The method of claim 31, wherein the metal wires have a cross-section in the shape of round, oval, or rectangular.

38. The method of claim 31, wherein the metal wires are a biocompatible material.

39. The method of claim 31, wherein the outer layer of insulation is a biocompatible material having a thickness over the metal wires of no greater than 4 mils.

40. The method of claim 31, wherein at least two metal wires of the first set are positioned in contact to form a pairing.

41. A method of shielding an implantable medical lead, comprising:

providing an inner layer of insulation establishing an axial dimension, the inner layer being a biocompatible material and surrounding at least one conductive filar and having a thickness of at least 2 mils;

providing a shield over the inner layer of insulation, the shield comprising:

at least six metal wires forming a braid about the inner layer of insulation with at least three of the at least six wires being coiled in a first direction and at least three of the at least six wires being coiled in a second direction, the braid having a braid angle less than 60 degrees when measured transversely from the axial dimension, a spacing in the axial dimension between adjacent wires coiled in the first direction being no greater than a lead diameter, the metal wires each having a dimension that faces outward from the inner layer within a range from 0.5 to 2.5 mils;

the metal wires each having an ultimate tensile strength of at least 150 ksi, the metal wires having a cross-section in the shape of round, oval, or rectangular, the metal wires being a biocompatible material, providing a biocompatible outer layer of insulation over an entire length of the braid of the shield with the outer layer of insulation being adhered to the inner layer of insulation through openings within the braid formed by the metal wires, the outer layer having a thickness over the metal wires of no greater than 4 mils, a diameter of the outer layer establishing the lead diameter;

providing at least one proximal electrode on a proximal end of the inner layer of insulation and at least one distal electrode on a distal end, with the at least one conductive filar establishing an electrical pathway between the at least one proximal electrode and the at least one distal electrode, the shield ending on a proximal end within 0.5 millimeters to 10 centimeters of a nearest edge of the at least one proximal electrode and the shield ending on a distal end within 1 millimeter to 10 centimeters of a nearest edge of the at least one distal electrode.

42. An implantable medical lead, comprising:

an inner layer of insulation establishing an axial dimension, the inner layer surrounding at least one conductive filar;

a shield over the inner layer of insulation, the shield comprising:

a plurality of metal wires forming a braid about the inner layer of insulation, a first set of the plurality being coiled in first direction and a second set of the plurality being coiled in a second direction, the metal wires each having a dimension that faces outward from the inner layer within a range from 0.5 to 2.5 mils, the braid having a braid angle less than 60 degrees when measured transversely from the axial dimension, an outer layer of insulation over an entire length of the braid of the shield with the outer layer of insulation being adhered to the inner layer of insulation through openings within the braid formed by the metal wires; and at least one proximal electrode on a proximal end of the inner layer of insulation and at least one distal electrode on a distal end of the inner layer of insulation, with the at least one conductive filar establishing an electrical pathway between the at least one proximal electrode and the at least one distal electrode.

43. An implantable medical lead, comprising:

an inner layer of insulation establishing an axial dimension, the inner layer surrounding at least one conductive filar;

a shield over the inner layer of insulation, the shield comprising:

at least six metal wires forming a braid about the inner layer of insulation with at least three of the at least six wires forming a first set being coiled in the first direction and at least three of the at least six wires forming a second set being coiled in the second direction, the braid having a braid angle less than 60 degrees when measured transversely from the axial dimension, an outer layer of insulation over an entire length of the braid of the shield with the outer layer of insulation being adhered to the inner layer of insulation through openings within the braid formed by the metal wires;

at least one proximal electrode on a proximal end of the inner layer of insulation and at least one distal electrode on a distal end of the inner layer of insulation, with the at least one conductive filar establishing an electrical pathway between the at least one proximal electrode and the at least one distal electrode.

44. An implantable medical lead, comprising:

an inner layer of insulation establishing an axial dimension, the inner layer surrounding at least one conductive filar;

a shield over the inner layer of insulation, the shield comprising:

at least six metal wires forming a braid about the inner layer of insulation with at least three of the at least six wires being coiled in the first direction and at least three of the at least six wires being coiled in the second direction, the metal wires each having a dimension that faces outward from the inner layer within a range from 0.5 to 2.5 mils, an outer layer of insulation over an entire length of the braid of the shield with the outer layer of insulation being adhered to the inner layer of insulation through openings within the braid formed by the metal wires;

at least one proximal electrode on a proximal end of the inner layer of insulation and at least one distal electrode on a distal end of the inner layer of insulation, with the at least one conductive filar establishing an electrical pathway between the at least one proximal electrode and the at least one distal electrode.

45. An implantable medical lead, comprising:

an inner layer of insulation establishing an axial dimension, the inner layer surrounding at least one conductive filar;

a shield over the inner layer of insulation, the shield comprising:

a plurality of metal wires forming a braid about the inner layer of insulation, a first set of the plurality being coiled in a first direction and a second set of the plurality being coiled in a second direction, wherein spacing in the axial dimension between adjacent wires coiled in the first direction is no greater than a lead diameter and spacing in the axial dimension between adjacent wires coiled in the second direction is no greater than the lead diameter, an outer layer of insulation over an entire length of the braid of the shield with the outer layer of insulation being adhered to the inner layer of insulation through openings within the braid formed by the metal wires, a diameter of the outer layer establishing the lead diameter;

at least one proximal electrode on a proximal end of the inner layer of insulation and at least one distal electrode on a distal end of the inner layer of insulation, with the at least one conductive filar establishing an electrical pathway between the at least one proximal electrode and the at least one distal electrode.

46. An implantable medical lead, comprising:

an inner layer of insulation establishing an axial dimension, the inner layer being a biocompatible material and surrounding at least one conductive filar and having a thickness of at least 2 mils;

a shield over the inner layer of insulation, the shield comprising:

at least six metal wires forming a braid about the inner layer of insulation with at least three of the at least six wires being coiled in a first direction and at least three of the at least six wires being coiled in a second direction, the braid having a braid angle less than 60 degrees when measured transversely from the axial dimension, a spacing in the axial dimension between adjacent wires coiled in the first direction being no greater than a lead diameter, the metal wires each having a the dimension that faces outward from the inner layer within a range from 0.5 to 2.5 mils;

the metal wires each having an ultimate tensile strength of at least 150 ksi, the metal wires having a cross-section in the shape of round, oval, or rectangular, the metal wires being a biocompatible material, a biocompatible outer layer of insulation over an entire length of the braid of the shield with the outer layer of insulation being adhered to the inner layer of insulation through openings within the braid formed by the metal wires, the outer layer having a thickness over the metal wires of no greater than 4 mils, a diameter of the outer layer establishing the lead diameter;

at least one proximal electrode on a proximal end of the inner layer of insulation and at least one distal electrode on a distal end, with the at least one conductive filar establishing an electrical pathway between the at least one proximal electrode and the at least one distal electrode, the shield ending within 0.5 millimeters to 10 centimeters of a nearest edge of the at least one distal electrode.

47. A method of shielding an implantable medical lead, comprising:

providing an inner layer of insulation establishing an axial dimension, the inner layer surrounding at least one conductive filar;

providing a shield over the inner layer of insulation, the shield comprising a plurality of metal wires forming a braid about the inner layer of insulation, a first set of the plurality being coiled in a first direction and a second set of the plurality being coiled in a second direction, wherein at least two metal wires of the first set are positioned in contact to form a pairing;

providing an outer layer of insulation over the shield with the outer layer of insulation being adhered to the inner layer of insulation through openings within the braid formed by the metal wires such that the shield is entirely surrounded by a combination of the outer layer of insulation and inner layer of insulation;

providing at least one proximal electrode on a proximal end of the inner layer of insulation and at least one distal electrode on a distal end of the inner layer of insulation, with the at least one conductive filar establishing an electrical pathway between the at least one proximal electrode and the at least one distal electrode.

48. The method of claim 47, wherein the inner layer is a biocompatible material.

49. The method of claim 47, wherein the shield ends on a distal end between 1 millimeter and 2 centimeters of a nearest edge of the at least one distal electrode.

50. The method of claim 47, wherein the shield comprises at least six metal wires forming the braid about the inner layer of insulation with at least three of the at least six wires being coiled in the first direction and at least three of the at least six wires being coiled in the second direction.

51. The method of claim 47, wherein a diameter of the outer layer establishes a lead diameter and wherein spacing in the axial dimension between adjacent wires coiled in the first direction is no greater than the lead diameter.

52. The method of claim 47, wherein the metal wires each have an ultimate tensile strength of at least 150 ksi.

53. The method of claim 47, wherein the metal wires have a cross-section in the shape of round, oval, or rectangular.

54. The method of claim 47, wherein the metal wires are a biocompatible material.

55. The method of claim 47, wherein the outer layer of insulation is a biocompatible material having a thickness over the metal wires of no greater than 4 mils.

56. The method of claim 47, wherein at least two metal wires of the second set are positioned in contact to form a pairing.

57. The method of claim 47, wherein the inner layer provides a thickness of at least 2 mils.

58. The method of claim 47, wherein the shield ends from 1 millimeter to 10 millimeters from the proximal connector on the proximal end of the shield and from 1 millimeter to 10 millimeters from the distal electrode on the distal end of the shield.

59. The method of claim 47, wherein the shield ends 10 millimeters from the proximal connector on the proximal end of the shield and ends 1 millimeter from the distal electrode on the distal end of the shield.

60. An implantable medical lead, comprising:

an inner layer of insulation establishing an axial dimension, the inner layer surrounding at least one conductive filar;

a shield over the inner layer of insulation, the shield comprising a plurality of metal wires forming a braid about the inner layer of insulation, a first set of the plurality being coiled in a first direction and a second set of the plurality being coiled in a second direction, wherein at least one metal wire of the first set passes under multiple consecutive metals wires of the second set;

an outer layer of insulation over the shield with the outer layer of insulation being adhered to the inner layer of insulation through openings within the braid formed by the metal wires such that the shield is entirely surrounded by a combination of the outer layer of insulation and inner layer of insulation; and at least one proximal electrode on a proximal end of the inner layer of insulation and at least one distal electrode on a distal end of the inner layer of insulation, with the at least one conductive filar establishing an electrical pathway between the at least one proximal electrode and the at least one distal electrode.

* * * * *